United States Patent
Iijima et al.

(10) Patent No.: US 10,155,731 B2
(45) Date of Patent: *Dec. 18, 2018

(54) NITROGEN-CONTAINING SATURATED HETEROCYCLIC COMPOUND

(71) Applicants: MITSUBISHI TANABE PHARMA CORPORATION, Osaka-shi, Osaka (JP); SHANGHAI PHARMACEUTICALS HOLDING CO., LTD., Shanghai (CN)

(72) Inventors: Toru Iijima, Osaka (JP); Hiroshi Sugama, Osaka (JP); Takayuki Kawaguchi, Tokyo (JP); Jingkang Shen, Shanghai (CN); Guangxin Xia, Shanghai (CN); Jianshu Xie, Shanghai (CN); Miki Hirai, Osaka (JP)

(73) Assignees: MITSUBISHI TANABE PHARMA CORPORATION, Osaka-Shi, Osaka (JP); SHANGHAI PHARMACEUTICALS HOLDING CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/993,925

(22) Filed: Jan. 12, 2016

(65) Prior Publication Data
US 2016/0145220 A1    May 26, 2016

Related U.S. Application Data

(62) Division of application No. 14/005,512, filed as application No. PCT/JP2012/056750 on Mar. 15, 2012, now Pat. No. 9,278,944.

(30) Foreign Application Priority Data

Mar. 16, 2011 (JP) ................ 2011-058338

(51) Int. Cl.
| | |
|---|---|
| C07D 295/027 | (2006.01) |
| C07D 265/30 | (2006.01) |
| C07D 413/12 | (2006.01) |
| A61K 31/5377 | (2006.01) |
| A61K 31/5375 | (2006.01) |
| C07D 403/12 | (2006.01) |
| C07D 405/12 | (2006.01) |
| C07D 413/14 | (2006.01) |
| C07D 471/04 | (2006.01) |
| C07D 231/56 | (2006.01) |

(52) U.S. Cl.
CPC ......... C07D 265/30 (2013.01); C07D 231/56 (2013.01); C07D 403/12 (2013.01); C07D 405/12 (2013.01); C07D 413/12 (2013.01); C07D 413/14 (2013.01); C07D 471/04 (2013.01)

(58) Field of Classification Search
CPC .. C07D 295/02; C07D 265/30; C07D 413/12; C07D 413/14; C07D 295/027; A61K 31/5377; A61K 31/5355; A61K 31/5375
USPC ............. 544/168, 162, 124, 175; 514/239.5, 514/237.5, 237.2
See application file for complete search history.

(56) References Cited

U.S. PATENT DOCUMENTS

| | | | |
|---|---|---|---|
| 8,975,252 B2 * | 3/2015 | Akatsuka | C07D 209/08 514/230.5 |
| 9,556,159 B2 * | 1/2017 | Iijima | C07D 413/14 |
| 2004/0242592 A1 | 12/2004 | Alvaro et al. | |
| 2008/0194549 A1 | 8/2008 | Ehrhardt et al. | |
| 2008/0207630 A1 | 8/2008 | Eckl et al. | |
| 2008/0242662 A1 | 10/2008 | Nihonyanagi et al. | |
| 2009/0312304 A1 | 12/2009 | Breitenstein et al. | |
| 2010/0240644 A1 | 9/2010 | Akatsuka et al. | |
| 2011/0230457 A1 | 9/2011 | Berghausen et al. | |
| 2015/0232459 A1 | 8/2015 | Iijima et al. | |

FOREIGN PATENT DOCUMENTS

| | | | | |
|---|---|---|---|---|
| CA | 2690348 A1 * | 12/2008 | ........... | C07D 209/08 |
| WO | WO 03/015784 A1 | 2/2003 | | |
| WO | WO 2006/069788 A1 | 7/2006 | | |
| WO | WO 2006/100036 A1 | 9/2006 | | |
| WO | WO 2006/113376 A1 | 10/2006 | | |
| WO | WO 2006/128659 A2 | 12/2006 | | |
| WO | WO 2008/153182 A1 | 12/2008 | | |
| WO | WO 2011/076786 A1 | 6/2011 | | |

OTHER PUBLICATIONS

STN Registry database entry: CAS RN 1282600-96-7 (Entered STN: Apr. 19, 2011).*

(Continued)

*Primary Examiner* — Matthew P Coughlin
*Assistant Examiner* — Sagar Patel
(74) *Attorney, Agent, or Firm* — Birch, Stewart, Kolasch & Birch, LLP

(57) ABSTRACT

The present invention provides a nitrogen-containing saturated heterocyclic compound of the formula [I]:

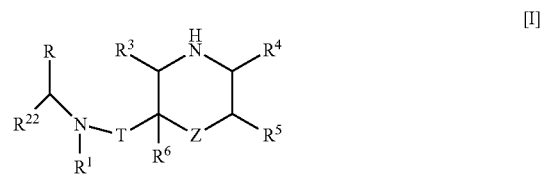

wherein $R^1$ is a cycloalkyl group and the like, $R^{22}$ is an optionally substituted aryl and the like, R is a lower alkyl and the like, T is a carbonyl group, Z is —O— and the like, and $R^3$ to $R^6$ are the same or different and a hydrogen atom and the like; or a pharmaceutically acceptable salt, that is useful as a renin inhibitor.

3 Claims, No Drawings

(56) References Cited

OTHER PUBLICATIONS

STN Registry database entry: CAS RN 1308143-41-0 (Entered STN: Jun. 9, 2011).*
STN Registry database entry: CAS RN 1305533-03-2 (Entered STN: Jun. 5, 2011).*
STN Registry database entry: CAS RN 1304061-38-8 (Entered STN: Jun. 1, 2011). (Year: 2011).*
International Search Report issued in PCT/JP2012/056750, dated May 29, 2012.
Written Opinion issued in PCT/JP2012/056750, dated May 29, 2012.

* cited by examiner

NITROGEN-CONTAINING SATURATED HETEROCYCLIC COMPOUND

CROSS REFERENCE TO RELATED APPLICATIONS

This application is a Divisional of copending application Ser. No. 14/005,512, filed on Sep. 16, 2013, which was filed as PCT International Application No. PCT/JP2012/056750 on Mar. 15, 2012, which claims the benefit under 35 U.S.C. § 119(a) to Patent Application No. 2011-058338, filed in Japan on Mar. 16, 2011, all of which are hereby expressly incorporated by reference into the present application.

TECHNICAL FIELD

The present invention relates to nitrogen-containing saturated heterocyclic compounds which are useful as a medicine, especially as a renin inhibitor, pharmaceutically acceptable salts and intermediates thereof.

BACKGROUND ART

Renin inhibitors are expected as a medicine for the prevention and/or treatment of diseases such as hypertension, heart failure, diabetic nephropathy and the like, and 3,4-substituted piperidine derivatives are disclosed for example (Patent Literature 1). But a morpholine derivative is not described in the literature.

Also WO 2008/153182 discloses some morpholine derivatives but they are compounds having a formula I wherein R is a hydrogen atom (Patent Literature 2).

CITATION LIST

Patent Literatures

Patent Literature 1: WO 06/069788 (US 2009/0312304A)
Patent Literature 2: WO 2008/153182 (US 2010/0240644A)

DISCLOSURE OF INVENTION

Technical Problem

The present invention provides novel nitrogen-containing saturated heterocyclic compounds having an excellent activity to inhibit renin.

Solution to Problem

In order to solve the problem, the inventors have extensively studied to find novel nitrogen-containing saturated heterocyclic compounds having an excellent activity to inhibit renin and finally completed the present invention.
The present invention is as follows;
1. A compound of the formula [I];

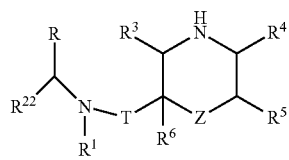

wherein $R^1$ is a cycloalkyl group or a non-substituted alkyl group;
$R^{22}$ is 1) an optionally substituted aryl group, 2) an optionally substituted tetrahydronaphthyl group, 3) an optionally substituted naphthylidinyl group, 4) an optionally substituted pyridyl group, 5) an optionally substituted pyrazolopyridyl group, 6) an optionally substituted indolyl group, 7) an optionally substituted benzofuranyl group, 8) an optionally substituted benzothienyl group, 9) an optionally substituted quinolyl group, 10) an optionally substituted cromanyl group, 11) an optionally substituted dihydrobenzofuranyl group, 12) an optionally substituted indazolyl group, 13) an optionally substituted pyrrolopyridinyl group, 14) an optionally substituted benzoisoxazolyl group, 15) an optionally substituted xanthenyl group, 16) an optionally substituted indolinyl group, 17) an optionally substituted quinazolinyl group, 18) an optionally substituted dihydroquinazolinyl group, 19) an optionally substituted furopyridyl group, 20) an optionally substituted dihydrofuropyridyl group, 21) an optionally substituted quinoxalinyl group, 22) an optionally substituted thienopyridyl group, 23) an optionally substituted dihydropyranopyridyl group, 24) an optionally substituted dihydrobenzothienyl group, 25) an optionally substituted dihydrothienopyridyl group, or 26) an optionally substituted imidazopyridinyl group;
R is a lower alkyl group or forms a ring by linking with $R^{22}$ on each terminal;
T is a carbonyl group;
Z is —O—, —NH— or a single bond;
$R^3, R^4, R^5$ and $R^6$ are the same or different, a hydrogen atom, an optionally substituted carbamoyl group or an optionally substituted alkyl group;
or a pharmaceutically acceptable salt thereof,
2. A compound of the formula [II]

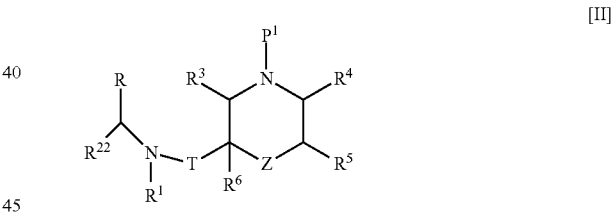

wherein $R^1$ is a cycloalkyl group or a non-substituted alkyl group;
$R^{22}$ is 1) an optionally substituted aryl group, 2) an optionally substituted tetrahydronaphthyl group, 3) an optionally substituted naphthylidinyl group, 4) an optionally substituted pyridyl group, 5) an optionally substituted pyrazolopyridyl group, 6) an optionally substituted indolyl group, 7) an optionally substituted benzofuranyl group, 8) an optionally substituted benzothienyl group, 9) an optionally substituted quinolyl group, 10) an optionally substituted cromanyl group, 11) an optionally substituted dihydrobenzofuranyl group, 12) an optionally substituted indazolyl group, 13) an optionally substituted pyrrolopyridinyl group, 14) an optionally substituted benzoisoxazolyl group, 15) an optionally substituted xanthenyl group, 16) an optionally substituted indolinyl group, 17) an optionally substituted quinazolinyl group, 18) an optionally substituted dihydoquinazolinyl group, 19) an optionally substituted furopyridyl group, 20) an optionally substituted dihydrofuropyridyl group, 21) an optionally substituted quinoxalinyl group, 22) an optionally substituted thienopyridyl group, 23) an optionally substituted dihydopyranopyridyl group, 24) an optionally substituted dihydrobenzothienyl group, 25) an optionally substituted dihydrothienopyridyl group, or 26) an optionally substituted imidazopyridinyl group;
R is a lower alkyl group or forms a ring by linking with $R^{22}$ on each terminal;
T is a carbonyl group;
$Z^1$ is —O—, —$NP^2$— or a single bond;
$R^3$, $R^4$, $R^5$ and $R^6$ are the same or different, a hydrogen atom, an optionally substituted carbamoyl group or an optionally substituted alkyl group;
$P^1$ is a protecting group and $P^2$ is a protecting group;
or a salt thereof.

The compound [I] of the present invention is explained in detail below.

The term "alkyl group" or "alkoxy group" in the present invention is exemplified by a straight or branched chain group having 1 to 10 carbon atoms, and groups having 1 to 6 carbon atoms are preferable, and groups having 1 to 4 carbon atoms are especially preferable. The term "lower alkyl group" or "lower alkoxy group" is exemplified by a straight or branched chain group having 1 to 6 carbon atoms, and groups having 1 to 4 carbon atoms are preferable.

The term "lower alkanoyl" is exemplified by a straight or branched chain group having 2 to 7 carbon atoms, and groups having 2 to 5 carbon atoms are preferable.

The term "cycloalkyl group" is exemplified by a cycloalkyl group having 3 to 8 carbon atoms, groups having 3 to 6 carbon atoms are preferable and groups having 3 to 4 carbon atoms are especially preferable.

The term "halogen atom" means a fluorine atom, a chlorine atom, a bromine atom and an iodine atom, and a fluorine atom, a chlorine atom and a bromine atom are especially preferable.

The term "an aryl group" is exemplified by a phenyl group, a naphthyl group and the like.

An example of substituents of the optionally substituted alkyl group in $R^3$ to $R^6$ includes a hydroxyl group, an optionally substituted alkoxy group, a carboxyl group, an optionally substituted carbamoyl group and the like.

An example of substituents of the optionally substituted aryl group, the optionally substituted tetrahydronaphthyl group, the optionally substituted naphthylidinyl group, the optionally substituted pyridyl group, the optionally substituted pyrazolopyridyl group, the optionally substituted indolyl group, the optionally substituted benzofuranyl group, the optionally substituted benzothienyl group, the optionally substituted quinolyl group, the optionally substituted cromanyl group, the optionally substituted dihydrobenzofuranyl group, the optionally substituted indazolyl group, the optionally substituted pyrrolopyridinyl group, the optionally substituted benzoisoxazolyl group, the optionally substituted xanthenyl group, the optionally substituted indolinyl group, the optionally substituted quinazolinyl group, the optionally substituted dihydoquinazolinyl group, the optionally substituted fulopyridyl group, the optionally substituted dihydrofulopyridyl group, the optionally substituted quinoxalinyl group, the optionally substituted thienopyridyl group, the optionally substituted dihydopyranopyridyl group, the optionally substituted dihydrobenzothienyl group, the optionally substituted dihydrothienopyridyl group and the optionally substituted imidazopyridinyl group includes an alkoxy group, an alkoxy group substituted with an alkoxy group, an alkoxy group substituted with an alkylcarbonylamino group, an alkoxy group substituted with an arylcarbonylamino group, an alkoxy group substituted with a heterocyclo-substituted carbonylamino group, an alkoxy group substituted with a cycloalkylcarbonylamino group, an alkoxy group substituted with an alkoxycarbonylamino group, an alkyl group substituted with an alkoxycarbonylamino group, an alkyl group substituted with an alkoxy group substituted with an alkoxy group, an alkoxy group substituted with an aryl group, a hydroxyl group, an alkyl group, an alkyl group substituted with an alkoxy group, an oxo group, a halogen atom, an alkoxy group substituted with a halogen atom, an alkyl group substituted with a halogen atom, an aryloxy group, an aryl group, an aryl group substituted with an alkoxy group, a heterocyclic group, a cyano group, a lower alkanoyl group, a carbamoyl group, a carbamoyl group substituted with an alkyl group and the like.

An example of substituents of the optionally substituted alkoxy group includes a hydroxyl group, an alkoxy group, a halogen atom, an alkoxy group substituted with a halogen atom, an amino group substituted with an alkylcarbonyl group, an amino group substituted with an arylcarbonyl group, a carbonylamino group substituted with a heterocyclo group, an amino group substituted with a cycloalkylcarbonyl, an amino group substituted with an alkoxycarbonyl group, an aryl group, an aryloxy group and the like.

An example of substituents of the optionally substituted carbamoyl group includes an alkyl group, an alkyl group substituted with a hydroxyl group, an alkyl group substituted with an alkoxy group, an alkyl group substituted with a phenyl group, a cycloalkyl group, a pyrrolidinyl group optionally substituted with a hydroxyalkyl group or an alkoxy-substituted alkyl group and the like.

An example of the heterocyclic group includes a pyridyl group, a pyrimidyl group, a furyl group, a thienyl group, a quinolyl group, a tetrahydroquinolyl group, a isoquinolyl group, a tetrahydroisoquinolyl group, an indolyl group, an indolinyl group, an indazolyl group, a benzofuranyl group, a benzothienyl group, a dihydrobenzofuranyl group, dihydrocromenyl group, a pyrrolopyridyl group, a benzoxadinyl group, a pyrazolyl group and the like.

The present invention includes the following inventions:
(a1) a compound [I] wherein $R^{22}$ is a group selected from
 1) an optionally substituted aryl group,
 2) an optionally substituted tetrahydronaphthyl group,
 3) an optionally substituted naphthylidinyl group,
 4) an optionally substituted pyridyl group,
 5) an optionally substituted pyrazolopyridyl group,
 6) an optionally substituted indolyl group,
 7) an optionally substituted benzofuranyl group,
 8) an optionally substituted benzothienyl group,
 9) an optionally substituted quinolyl group,
 10) an optionally substituted cromanyl group,
 11) an optionally substituted dihydrobenzofuranyl group,
 12) an optionally substituted indazolyl group,
 13) an optionally substituted pyrrolopyridinyl group,
 14) an optionally substituted benzoisoxazolyl group,
 15) an optionally substituted xanthenyl group,
 16) an optionally substituted indolinyl group,
 17) an optionally substituted quinazolinyl group,
 18) an optionally substituted dihydoquinazolinyl group,
 19) an optionally substituted furopyridyl group,
 20) an optionally substituted dihydrofuropyridyl group,
 21) an optionally substituted quinoxalinyl group,
 22) an optionally substituted thienopyridyl group,
 23) an optionally substituted dihydopyranopyridyl group,
 24) an optionally substituted dihydrobenzothienyl group,
 25) an optionally substituted dihydrothienopyridyl group, and
 26) an optionally substituted imidazopyridinyl group;

$R^1$ is a cyclopropyl group;
Z is —O— or —NH—; and
$R^3$, $R^4$, $R^5$ and $R^6$ are a hydrogen atom;
or a pharmaceutically acceptable salt thereof,
(a2) a compound wherein $R^{22}$ is a group selected from
 1) an optionally substituted phenyl group,
 2) an optionally substituted naphthyl group,
 3) an optionally substituted tetrahydronaphthy group,
 4) an optionally substituted naphthyldinyl group,
 5) an optionally substituted pyridyl group,
 6) an optionally substituted pyrazolopyridyl group,
 7) an optionally substituted indolyl group,
 8) an optionally substituted benzofuranyl group,
 9) an optionally substituted benzothienyl group,
 10) an optionally substituted quinolyl group,
 11) an optionally substituted cromanyl group,
 12) an optionally substituted dihydrobenzofuranyl group,
 13) an optionally substituted indazolyl group,
 14) an optionally substituted pyrrolopyridinyl group,
 15) an optionally substituted benzoisoxazolyl group,
 16) an optionally substituted xanthenyl group,
 17) an optionally substituted indolinyl group,
 18) an optionally substituted quinazolinyl group,
 19) an optionally substituted dihydoquinazolinyl group,
 20) an optionally substituted furopyridyl group,
 21) an optionally substituted dihydrofuropyridyl group,
 22) an optionally substituted quinoxalinyl group,
 23) an optionally substituted thienopyridyl group,
 24) an optionally substituted dihydopyranopyridyl group,
 25) an optionally substituted dihydrobenzothienyl group,
 26) an optionally substituted dihydrothienopyridyl group, and
 27) an optionally substituted imidazopyridinyl group;
$R^1$ is a cyclopropyl group;
Z is —O—; and
$R^3$, $R^4$, $R^5$ and $R^6$ are a hydrogen atom;
or a pharmaceutically acceptable salt thereof,
(a3) the compound of (a1) or (a2) above wherein $R^{22}$ is any group of 1) to 27) described below;
 1) a phenyl group optionally substituted with the same or different, one to four group(s) selected from a phenyl lower alkoxy group, a halogen atom, a lower alkyl group, a lower alkyl group substituted with a lower alkoxy group, a lower alkyl group substituted with a lower alkoxycarbonylamino group, a lower alkoxy group substituted with a lower alkoxy group, an aryl group substituted with a lower alkoxy group, a heterocyclic group, a cyano group and a lower alkoxy group,
 2) a naphthyl group optionally substituted with the same or different, one to six group(s) selected from a trihalogeno lower alkoxy group, a lower alkanoylamino lower alkoxy group, a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group, an aryl group substituted with a lower alkoxy group, a heterocyclic group, a cyano group and a lower alkoxy group,
 3) a tetrahydronaphthyl group optionally substituted with the same or different, one to six group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group,
 4) a naphthylidinyl group optionally substituted with the same or different, one to five group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group,
 5) a pyridyl group optionally substituted with the same or different, one to four group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group,
 6) a pyrazolopyridyl group optionally substituted with the same or different, one to four group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group,
 7) an indolyl group optionally substituted with the same or different, one to five group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group,
 8) a benzofuranyl group optionally substituted with the same or different, one to four group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group,
 9) a benzothienyl group optionally substituted with the same or different, one to four group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group,
 10) a quinolyl group optionally substituted with the same or different, one to four group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group,
 11) a cromanyl group optionally substituted with the same or different, one to five group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group,
 12) a dihydrobenzofuranyl group optionally substituted with the same or different, one to four group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group, 13) an indazolyl group optionally substituted with the same or different, one to five group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group, 14) a pyrrolopyridinyl group optionally substituted with the same or different, one to three group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group, 15) a benzoisoxazolyl group optionally substituted with the same or different, one to four group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group, 16) a xanthenyl group optionally substituted with the same or different, one to six group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group, 17) an indolinyl group optionally substituted with the same or different, one to five group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group, 18) a quinazolyl group optionally substituted with the same or different, one to five group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group, 19) a dihydroquinazolinyl group optionally substituted with the same or different, one to five group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group, 20) a furopyridyl group optionally substituted with the same or different, one to four group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group, 21) a dihydrofuropyridyl group optionally substituted with the same or different, one to four group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group, 22) a quinoxalinyl group optionally substituted with the same or different, one to five group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group, 23) a thienopyridyl group optionally substituted with the same or different, one to four group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group, 24) a dihydropyranopyridyl group optionally substituted with the same or different, one to four group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group, 25) a dihydrobenzothienyl group optionally substituted with the same or different, one to four group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group, 26) a dihydrothienopyridyl group optionally substituted with the same or different, one to four group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group, and 27) an imidazopyridinyl group optionally substituted with the same or different, one to four group(s) selected from a halogen atom, a lower alkyl group substituted with a lower alkoxy group, a lower alkyl group substituted with a lower alkoxycarbonylamino group, a lower alkyl group, a lower alkoxy group substituted with a lower alkoxy group, an aryl group substituted with a lower alkoxy group, a heterocyclic group, a cyano group and a lower alkoxy group, or a pharmaceutically acceptable salt thereof.

(a4) the compound of (a1) or (a2) above wherein $R^{22}$ is any group of 1) to 13) described below;

1) a phenyl group optionally substituted with the same or different, two or three groups selected from a phenyl lower alkoxy group, a halogen atom, a lower alkyl group substituted with a lower alkoxy group, a lower alkyl group substituted with a lower alkoxycarbonylamino group, a lower alkyl group, a lower alkoxy group substituted with a lower alkoxy group and a lower alkoxy group, 2) a naphthyl group optionally substituted with the same or different, one to three group(s) selected from a trihalogeno lower alkoxy group, a lower alkanoylamino lower alkoxy group, a halogen atom, an aryl group, an aryl group substituted with a lower alkoxy group, a heterocyclic group, a lower alkyl group and a lower alkoxy group substituted with a lower alkoxy group, 3) a tetrahydronaphthyl group optionally substituted with one or two group(s) selected from a halogen atom and a lower alkoxy group substituted with a lower alkoxy group, 4) an indolyl group optionally substituted with the same or different, one to three group(s) selected from a halogen atom, a cyano group, a lower alkoxy group, a lower alkoxy group substituted with an aryl group group, a lower alkyl group and a lower alkyl group substituted with a lower alkoxy group, 5) a benzofuranyl group optionally substituted with one or two group(s) selected from a halogen atom and a lower alkoxy group substituted with a lower alkoxy group, 6) a benzothienyl group optionally substituted with a lower alkoxy group substituted with a lower alkoxy group, 7) a quinolyl group optionally substituted with a lower alkoxy group substituted with a lower alkoxy group, 8) a cromanyl group optionally substituted with a lower alkoxy group substituted with a lower alkoxy group, 9) a dihydrobenzofuranyl group optionally substituted with one or two group(s) selected from a halogen atom and a lower alkoxy group substituted with a lower alkoxy group, 10) an indazolyl group optionally substituted with one or two group(s) selected from a halogen atom and a lower alkoxy group substituted with a lower alkoxy group, 11) a pyrrolopyridinyl group optionally substituted with one to three group(s) selected from a halogen atom, a lower alkyl group and a lower alkyl group substituted with a lower alkoxy group, 12) a pyrazolopyridyl group optionally substituted with one or two group(s) selected from a lower alkyl group substituted with a lower alkoxycarbnylamino group and a lower alkyl group, and 13) a pyridyl group optionally substituted with one or two group(s) selected from a lower alkoxy group, a lower alkyl group and a lower alkyl group substituted with a lower alkoxycarbnylamino group,
or a pharmaceutically acceptable salt thereof.

(a5) the compound of (a1) or (a2) above wherein $R^{22}$ is any group of 1) to 13) described below;

1) a phenyl group optionally substituted with two or three groups selected from a phenyl lower alkoxy group, a fluorine atom, a bromine atom, a chlorine atom, a lower alkyl group substituted with a lower alkoxy group, a lower alkyl group substituted with a lower alkoxycarbonylamino group, a lower alkyl group, a lower alkoxy group substituted with a lower alkoxy group and a lower alkoxy group, a phenyl group, 2) a naphthyl group optionally substituted with the same or different, one to three group(s) selected from a trihalogeno lower alkoxy group, a lower alkanoylamino lower alkoxy group, a fluorine atom, a bromine atom, a chlorine atom, a phenyl group, a phenyl group substituted with a lower alkoxy group, a pyridyl group, a furyl group, a thienyl group, a lower alkyl group and a lower alkoxy group substituted with a lower alkoxy group, 3) a tetrahydronaphthyl group optionally substituted with one or two group(s) selected from a fluorine atom, a bromine atom, a chlorine atom and a lower alkoxy group substituted with a lower alkoxy group, 4) an indolyl group optionally substituted with one to three group(s) selected from a fluorine atom, a bromine atom, a chlorine atom, a cyano group, a lower alkoxy group, a lower alkoxy group substituted with a phenyl group, a lower alkyl group and a lower alkyl group substituted with a lower alkoxy group, 5) a benzofuranyl group optionally substituted with one or two group(s) selected from a bromine atom, a chlorine atom, and a lower alkoxy group substituted with a lower alkoxy group, 6) a benzothienyl methyl group optionally substituted with a lower alkoxy group substituted with a lower alkoxy group, 7) a quinolyl group optionally substituted with a lower alkoxy group substituted with a lower alkoxy group, 8) a cromanyl group optionally substituted with a lower alkoxy group substituted with a lower alkoxy group, 9) a dihydrobenzofuranyl group optionally substituted with one or two group(s) selected from a bromine atom, a chlorine atom, and a lower alkoxy group substituted with a lower alkoxy group, 10) an indazolyl group optionally substituted with one or two group(s) selected from a fluorine atom, a bromine atom, a chlorine atom and a lower alkyl group substituted with a lower alkoxy group, 11) a pyrrolopyridinyl group optionally substituted with one or two group(s) selected from a fluorine atom, a bromine atom, a chlorine atom, a lower alkyl group and a lower alkyl group substituted with a lower alkoxy group, 12) a pyrazolopyridyl group optionally substituted with one or two group(s) selected from a lower alkyl group substituted with a lower alkoxycarbnylamino group and a lower alkyl group, and 13) a pyridyl group optionally substituted with one or two group(s) selected from a lower alkoxy group, a lower alkyl group and a lower alkyl group substituted with a lower alkoxycarbnylamino group,
or a pharmaceutically acceptable salt thereof.

(a6) the compound of (a1) or (a2) above wherein $R^{22}$ is any group of 1) to 13) described below;

1) a phenyl group optionally substituted with two or three groups selected from a methoxy group substituted with a phenyl group, an ethoxy group substituted with a phenyl group, a fluorine atom, a bromine atom, a chlorine atom, a methyl group, a propoxy group substituted with a methoxy group, a butyl group substituted with a methoxy group, a methoxycarbonylaminopropyl group and a methoxy group, 2) a naphthyl group optionally substituted with the same or different, one to three group(s) selected from trifluorobutoxy group, an acetylaminoethoxy group, a fluorine atom, a bromine atom, a chlorine atom, a phenyl group, a phenyl group substituted with a methoxy group, a pyridyl group, a furyl group, a thienyl group, a methyl group and a propoxy group substituted with a methoxy group, 3) a tetrahydronaphthyl group optionally substituted with one or two group(s) selected from a bromine atom, a chlorine atom and a propoxy group substituted with a methoxy group, 4) an indolyl group optionally substituted with one or two group(s) selected from a fluorine atom, a bromine atom, a chlorine atom, a cyano group, a methoxy group, a methoxy group substituted with a phenyl group, a methyl group and a propyl group substituted with a methoxy group, 5) a benzofuranyl group optionally substituted with one or two group(s) selected from a bromine atom, a chlorine atom, and a propoxy group substituted with a methoxy group,
6) a benzothienyl group optionally substituted with a propoxy group substituted with a methoxy group,
7) a quinolyl group optionally substituted with a propoxy group substituted with a methoxy group,
8) a cromanyl group optionally substituted with a propoxy group substituted with a methoxy group,
9) a dihydrobenzofuranyl group optionally substituted with one or two group(s) selected from a bromine atom, a chlorine atom, and a propoxy group substituted with a methoxy group,
10) an indazolyl group optionally substituted with one or two group(s) selected from a fluorine atom, a chlorine atom and a propyl group substituted with a methoxy group,
11) a pyrrolopyridinyl group optionally substituted with one or two group(s) selected from a bromine atom, a chlorine atom, a methyl group, an ethyl group, a propyl group substituted with a methoxy group
12) a pyrazolopyridyl group optionally substituted with one or two group(s) selected from a methoxycarbonylaminopropyl group and a methyl group, and
13) a pyridyl group optionally substituted with one or two group(s) selected from a methoxy group, an ethyl group and a methoxycarbonylaminopropyl group,
or a pharmaceutically acceptable salt thereof.

(a7) the compound of (a1) or (a2) above wherein $R^{22}$ is any group of 1) to 27) described below;
1) a phenyl group optionally substituted with one to three group(s) selected from a halogen atom, a trihalogeno lower alkyl group, a cyano group, a benzyloxy group, a lower alkoxy group, a dihalogeno lower alkoxy group, an aminocarbonyl group, a lower alkylaminocarbonyl group, di(lower alkyl)aminocarbonyl group, a lower alkylaminocarbonyl group substituted with a lower alkoxy group, a lower alkoxy group substituted with a lower alkoxy group, a lower alkyl group substituted with a lower alkoxy group, a lower alkyl group substituted with a lower alkoxycarbonylamino group and a lower alkyl group,
2) a naphthyl group optionally substituted with one or two group(s) selected from a lower alkoxy group substituted with a lower alkoxycarbonylamino group and a lower alkoxy group,
3) a tetrahydronaphthyl group optionally substituted with a lower alkoxy group,
4) a naphthylidinyl group,
5) a pyridyl group optionally substituted with one or two group(s) selected from a lower alkoxy group, a lower alkyl group and a lower alkyl group substituted with a lower alkoxycarbonylamino group,
6) a pyrazolopyridyl group optionally substituted with one or two group(s) selected from a lower alkyl group substituted with a lower alkoxy group, a lower alkyl group substituted with a lower alkoxycarbonylamino group and a lower alkyl group,
7) an indolyl group optionally substituted with one to three group(s) selected from a halogen atom, a lower alkyl group and a lower alkyl group substituted with a lower alkoxy group,
8) a benzofuranyl group optionally substituted with one or two group(s) selected from a lower alkyl group substituted with a lower alkoxy group and a lower alkoxy group substituted with a lower alkoxy group,
9) a benzothienyl group,
10) a quinolyl group optionally substituted with one or two group(s) selected from a halogen atom and a lower alkoxy group,
11) a cromanyl group,
12) a dihydrobenzofuranyl group optionally substituted with a lower alkoxy group substituted with a lower alkoxy group,
13) an indazolyl group optionally substituted with one to three group(s) selected from a halogen atom, a lower alkoxy group substituted with a lower alkoxy group, a lower alkyl group substituted with a lower alkoxycarbonylamino group, a trihalogeno lower alkyl group, a lower alkyl and a lower alkyl group substituted with a lower alkoxy group,
14) a pyrrolopyridinyl group optionally substituted with one to three group(s) selected from a halogen atom, a lower alkyl group, a lower alkyl group substituted with a lower alkoxycarbonylamino group and a lower alkyl group substituted with a lower alkoxy group,
15) a benzoisoxazolyl group optionally substituted with one or two group(s) selected from a lower alkyl group and a lower alkyl group substituted with a lower alkoxy group,
16) a xanthenyl group,
17) an indolinyl group optionally substituted with one or two group(s) selected from a halogen atom and a lower alkyl group substituted with a lower alkoxy group,
18) a quinazolyl group optionally substituted with one or two group(s) selected from a hydroxyl group and a lower alkoxy group substituted with a lower alkoxy group,
19) a dihydroquinazolyl group optionally substituted with an oxo group,
20) a furopyridyl group
21) dihydrofuropyridyl group
22) quinoxalinyl group,
23) a thienopyridyl group
24) a dihydropyranopyridyl group,
25) a dihydrobenzothienyl group,
26) a dihydrothienopyridyl group, and
27) an imidazopyridinyl group
or a pharmaceutically acceptable salt thereof.

(a8) the compound of (a1) or (a2) above wherein $R^{22}$ is any group of 1) to 27) described below;
1) a phenyl group optionally substituted with one to three group(s) selected from a fluorine atom, a bromine atom, a chlorine atom, a trifluoromethyl group, a cyano group, a benzyloxy group, a methoxy group, an ethoxy group, an isopropoxy group, difluoromethoxy group, an aminocarbonyl group, a methylaminocarbonyl group, a dimethylaminocarbonyl group, a methoxyethylaminocarbonyl group, a propoxy group substituted with a methoxy group, a butyl group substituted with a methoxy group, a methoxycarbonylaminopropyl group and a methoxy group;
2) a naphthyl group optionally substituted with one or two group(s) selected from an ethoxy group substituted with a methoxycarbonylamino group and a methoxy group
3) a tetrahydronaphthyl group optionally substituted with a methoxy group
4) a naphthylidinyl group,
5) a pyridyl group optionally substituted with one or two group(s) selected from a methoxy group, an ethyl group and a methoxycarbonylaminopropyl group,
6) a pyrazolopyridyl group optionally substituted with one or two group(s) selected from a butyl group substituted with a methoxy group, a methoxycarbonylaminopropyl group, and a methyl group,
7) an indolyl group optionally substituted with one to three group(s) selected from a chlorine atom, a methyl group and a propyl group substituted with a methoxy group, 8) a benzofuranyl group optionally substituted with one or two group(s) selected from a propyl group substituted with a methoxy group and a propoxy group substituted with a methoxy group, 9) a benzothienyl group, 10) a quinolyl group optionally substituted with one or two group(s) selected from a chlorine atom and a methoxy group, 11) a cromanyl group, 12) a dihydrobenzofuranyl group optionally substituted with a propoxy group substituted with a methoxy group, 13) an indazolyl group optionally substituted with one to three group(s) selected from a fluorine atom, a chlorine atom, a propoxy group substituted with a methoxy group, a propyl group substituted with a methoxycarbonylamino group, a trifluoromethyl group, a methyl group, a propyl group substituted with a methoxy group, a butyl group substituted with a methoxy group, 14) a pyrrolopyridinyl group optionally substituted with one to three group(s) selected from a fluorine atom, a chlorine atom, a methyl group, an ethyl group, a propyl group substituted with a methoxycarbonylamino group, a propyl group substituted with a methoxy group and a butyl group substituted with a methoxy group, 15) a benzoisoxazolyl group optionally substituted with one or two group(s) selected from a methyl group and a propyl group substituted with a methoxy group 16) a xanthenyl group, 17) an indolinyl group optionally substituted with one or two group(s) selected from a chlorine atom and a propyl group substituted with a methoxy group, 18) a quinazolinyl group optionally substituted with one or two group(s) selected from a hydroxyl group and a propoxy group substituted with a methoxy group, 19) a dihydroquinazolyl group optionally substituted with an oxo group, 20) a furopyridyl group, 21) a dihydrofuropyridyl group, 22) a quinoxalinyl group, 23) a thienopyridyl group, 24) a dihydropyranopyridyl group, 25) a dihydrobenzothienyl group, 26) a dihydrothienopyridyl group, and 27) an imidazopyridinyl group or a pharmaceutically acceptable salt thereof.

(a9) the compound of (a1) or (a2) above wherein the indolyl group of $R^{22}$ is any group of the next formulae:

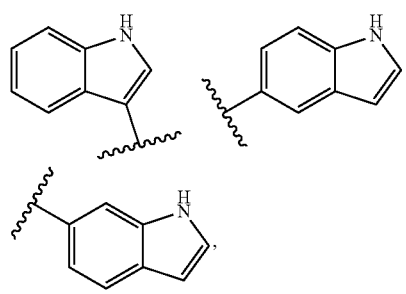

the benzofuranyl group of $R^{22}$ is any group of the next formulae:

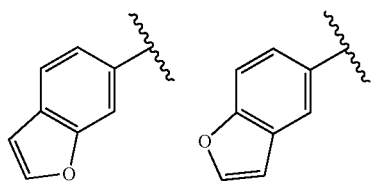 [SMILES: *c1ccc2ccoc2c1 ; *c1ccc2occc2c1]

the benzothienyl group of $R^{22}$ is any group of the next formulae:

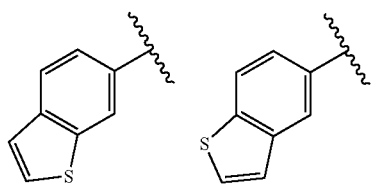 [SMILES: *c1ccc2ccsc2c1 ; *c1ccc2sccc2c1]

the quinolyl group of $R^{22}$ is any group of the next formulae:

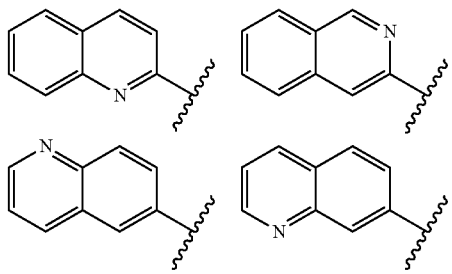

the naphthyl group of $R^{22}$ is any group of the next formulae:

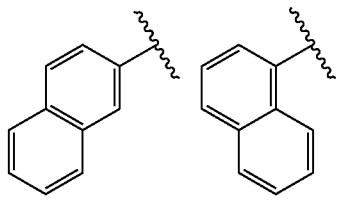

the tetrahydronaphthyl group of $R^{22}$ is any group of the next formulae:

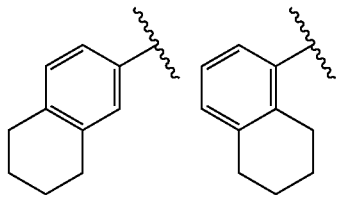

the cromanyl group of $R^{22}$ is any group of the next formulae:

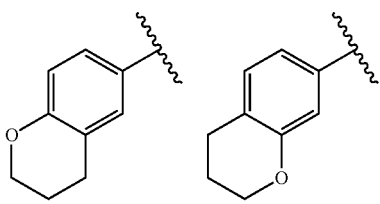 [SMILES: *c1ccc2c(c1)CCCO2 ; *c1ccc2c(c1)OCCC2]

the dihydrobenzofuranyl group of R$^{22}$ is any group of the next formulae:

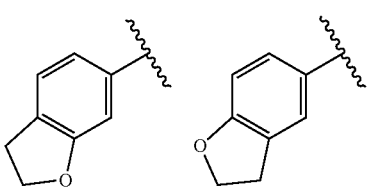 [SMILES: *c1ccc2c(c1)OCC2 ; *c1ccc2c(c1)CCO2]

the indazolyl group of R$^{22}$ is any group of the next formulae:

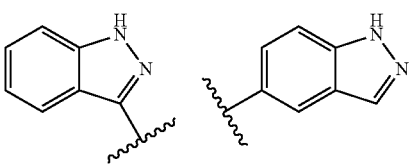

the pyrrolopyridinyl group of R$^{22}$ is any group of the next formulae:

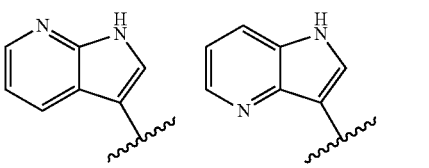

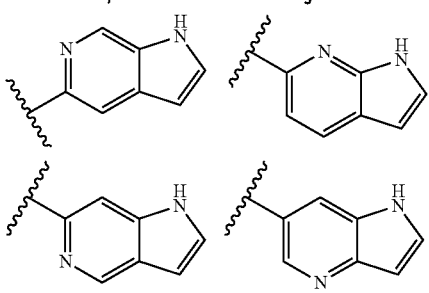

the naphthylidinyl group of R$^{22}$ is any group of the next formulae:

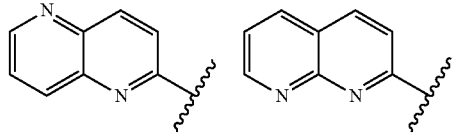

the benzoisoxazolyl group of R$^{22}$ is any group of the next formulae:

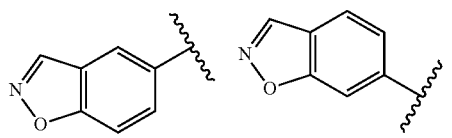

the xanthenyl group of R$^{22}$ is a group of the next formula:

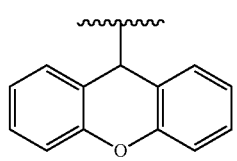 [SMILES: *C1c2ccccc2Oc2ccccc21]

the indolinyl group of R$^{22}$ is a group of the next formula:

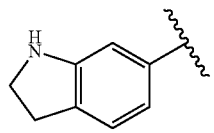 [SMILES: *c1ccc2c(c1)NCC2]

the quinazolinyl group of R$^{22}$ is a group of the next formula:

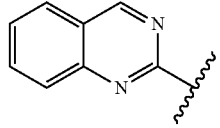 [SMILES: *c1ncc2ccccc2n1]

the quinoxalinyl group of R$^{22}$ is a group of the next formula:

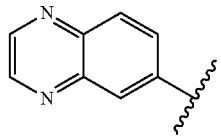 [SMILES: *c1ccc2nccnc2c1]

the furopyridyl group of R$^{22}$ is any group of the next formulae:

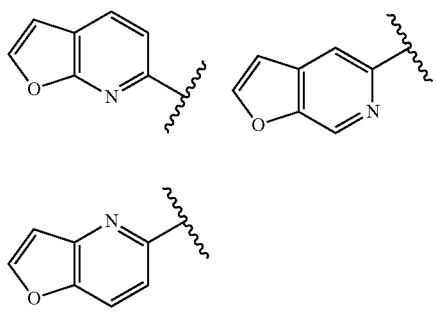

the dihydrofuropyridyl group of $R^{22}$ is any group of the next formulae:

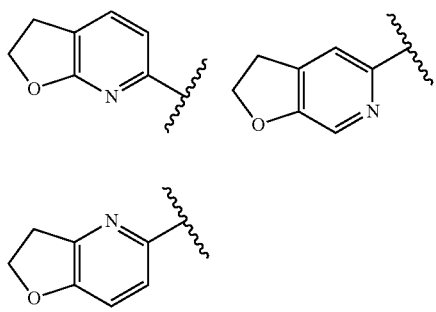

the imidazopyridyl group of $R^{22}$ is any group of the next formulae:

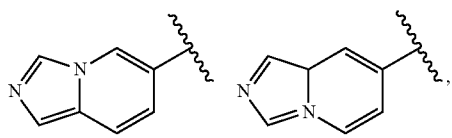

and the pyrazolopyridyl group of $R^{22}$ is any group of the next formulae:

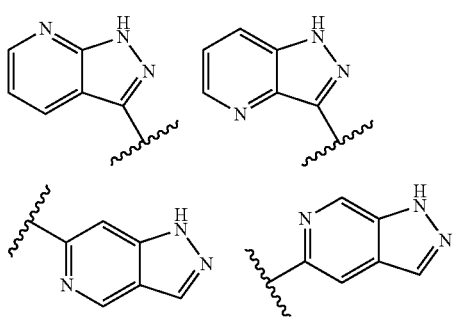

or a pharmaceutically acceptable salt thereof.
(a10) the compound of (a1) or (a2) above which is shown by the formula

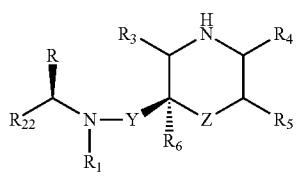

[I$^a$]

or a pharmaceutically acceptable salt thereof.
(b1) the compound described in any of (a1) to (a10) above, wherein $R^{22}$ of the compound [I] is selected from
   3) an optionally substituted naphthylidinyl group,
   4) an optionally substituted pyridyl group,
   5) an optionally substituted pyrazolopyridyl group,
   10) an optionally substituted cromanyl group,
   17) an optionally substituted quinazolinyl group,
   18) an optionally substituted dihydroquinazolinyl group,
   19) an optionally substituted furopyridyl group,
   20) an optionally substituted dihydrofuropyridyl group,
   21) an optionally substituted quinoxalinyl group,
   22) an optionally substituted thienopyridyl group,
   23) an optionally substituted dihydropyranopyridyl group,
   24) an optionally substituted dihydrobenzothienyl group, and
   25) an optionally substituted dihydrothienopyridyl group,
or a pharmaceutically acceptable salt thereof.
(c1) the compounds of (a1) above, which is shown by the formula [I$^{c1}$]:

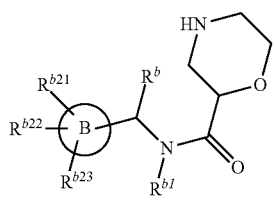

[I$^{c1}$]

wherein $R^b$ is lower alkyl,
$R^{b1}$ is cycloalkyl or alkyl,
the ring B is selected from
   1) an aryl group
   2) a tetrahydronaphthyl group,
   3) a naphthyldinyl group,
   4) a pyridyl group,
   5) a pyrazolopyridyl group,
   6) an indolyl group,
   7) a benzofuranyl group,
   8) a benzothienyl group,
   9) a quinolyl group
   10) a cromanyl group,
   11) a dihydrobenzofuranyl group,
   12) an indazolyl group
   13) a pyrrolopyridyl group,
   14) a benzoisoxazolyl group,
   15) a xanthenyl group,
   16) an indolinyl group,
   17) a quinazolinyl group
   18) a dihydroquinazolinyl group
   19) a furopyridyl group
   20) a dihydrofuropyridyl group
   21) a quinoxalinyl group, 22) a thienopyridyl group,
23) a dihydropyranopyridyl group,
24) a dihydrobenzothienyl group
25) a dihydrothienothienyl group and
26) an imidazopyridinyl group, $R^{b21}$ to $R^{b23}$ are the same of different, and a group selected from 1) hydrogen, 2) halogen, 3) alkyl optionally substituted with a group selected from halogen, alkoxy and alkoxycarbonylamino, 4) alkoxy optionally substituted with a group selected from alkoxy and alkoxycarbonylamino, 5) cyano, 6) carbamoyl optionally substituted with alkyl and 7) oxo, or a pharmaceutically acceptable salt thereof.

(c2) the compound of (c1), which is shown by the formula $I^{c2}$:

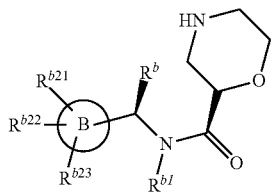

[$I^{c2}$]

wherein each symbol is the same as that of the formula $I^{c1}$ above, or a pharmaceutically acceptable salt thereof.

(c3) the compound of (c1) or (c2) above, wherein the ring B is a group selected from
1) an aryl group
4) a pyridyl group
5) a pyrazolopyridyl group
6) an indolyl group,
7) a benzofuranyl group
9) a quinolyl group
11) a dihydrobenzofuranyl group,
12) an indazolyl group,
13) a pyrrolopyridinyl group,
14) a benzoisoxazolyl group,
16) an indolinyl group,
17) a quinazolinyl group, and
18) a dihydroquinazolinyl group, or a pharmaceutically acceptable salt thereof.

(c4) the compound of (c1) or (c2) above, wherein the ring B is a group selected from
3) a naphthylidinyl group
4) a pyridyl group
5) a pyrazolopyridyl group
10) a cromanyl group,
17) a quinazolinyl group, and
18) a dihydroquinazolinyl group,
19) a furopyridyl group,
20) a dihydrofuropyridyl group
21) a quinoxalinyl group,
22) a thienopyridyl group,
23) a dihydropyranopyridyl group
24) a dihydrobenzothienyl group, and
25) a dihydrothienopyridyl group or a pharmaceutically acceptable salt thereof.

(c5) the compound of (c4) wherein the ring B is a group selected from
4) a pyridyl group,
5) a pyrazolopyridyl group,
17) a quinazolinyl group, and
18) a dihydroquinazolinyl group, or a pharmaceutically acceptable salt thereof.

(c6) the compound of (c4) wherein the ring B is a group selected from
4) a pyridyl group and
5) a pyrazolopyridyl group, or a pharmaceutically acceptable salt thereof.

(c7) the compound of (c4) wherein the ring B is a group of
5) a pyrazolopyridyl group, preferably 3-pyrazolopyridyl group, or a pharmaceutically acceptable salt thereof.

(c8) the compound of any of (c1) to (c7) wherein $R^{b1}$ is a cycloalkyl group or a pharmaceutically acceptable salt thereof.

(c9) the compound of (c8) wherein $R^{b1}$ is a cyclopropyl group or a pharmaceutically acceptable salt thereof.

(c10) the compound of any of (c1) to (c9) wherein $R^{b21}$ is a group selected from alkyl optionally substituted with alkoxy and alkoxycarbonylamino, and alkoxy optionally substituted with alkoxy and alkoxycarbamoyl, or a pharmaceutically acceptable salt thereof.

(C11) the compound of (c10) wherein $R^{b21}$ is a group selected from alkyl optionally substituted with alkoxy and alkoxycarbonylamino, and alkoxy optionally substituted with alkoxy and alkoxycarbamoyl, or a pharmaceutically acceptable salt thereof.

(c12) the compound of (c10) or (c11) wherein $R^{b21}$ to $R^{b23}$ are the same or different, and a group selected from hydrogen, alkyl and alkoxy, or a pharmaceutically acceptable salt thereof.

(d1) the compound of (1) selected from those described in examples, or a pharmaceutically acceptable salt thereof.

(d2) the compound of (d1) selected from those $IC_{50}$ values of which are described in Table 90-92, or a pharmaceutically acceptable salt thereof.

(d3) the compound of (d2) selected from those having $IC_{50}$ values less than 100 nM in Tables 90-92, or a pharmaceutically acceptable salt thereof.

(d4) the compound of (d2) selected from those having $IC_{50}$ values less than 10 nM in Tables 90-92, or a pharmaceutically acceptable salt thereof.

(d5) the compound of any of (d1) to (d5), which is shown by the formula $I^{c2}$, or a pharmaceutically acceptable salt thereof.

(d6) the compound of any of (d1) to (d5), which is selected from (c5), or a pharmaceutically acceptable salt thereof.

(d7) N-cyclopropyl-N-{1-[1-(4-methoxybutyl)-1H-pyrazolo[3,4-b]pyridin-3-yl]ethyl}morpholin-2-carboxamide;

methyl (3-{3-[1-{cyclopropyl(morpholin-2-ylcarbonyl)amino}ethyl]-1H-pyrazolo[3,4-b]pyridin-1-yl}propyl)carbamate;

methyl (3-{3-[1-{cyclopropyl(morpholin-2-ylcarbonyl)amino}ethyl]-6-methyl-1H-pyrazolo[3,4-b]pyridin-1-yl}propyl)carbamate;

methyl (3-{5-[1-{cyclopropyl(morpholin-2-ylcarbonyl)amino}ethyl]-2-methoxy pyridin-3-yl}propyl)carbamate;

methyl (3-{5-[1-{cyclopropyl(morpholin-2-ylcarbonyl)amino}ethyl]-2-ethylpyridin-3-yl}propyl)carbamate;

methyl (3-{4-[1-{cyclopropyl(morpholin-2-ylcarbonyl)amino}ethyl]-6-methoxy pyridin-2-yl}propyl)carbamate;

methyl (3-{4-[1-{cyclopropyl(morpholin-2-ylcarbonyl)amino}ethyl]-6-ethyl pyridin-2-yl}propyl)carbamate;

methyl (3-{4-[1-{cyclopropyl(morpholin-2-ylcarbonyl)amino}ethyl]-6-(2-methoxyethoxy)pyridin-2-yl}propyl)carbamate;

methyl (3-{4-[1-{cyclopropyl(morpholin-2-ylcarbonyl)amino}ethyl]-6-(3-methoxypropyl)pyridin-2-yl}propyl)carbamate; or methyl (3-{4-[1-{cyclopropyl(morpholin-2-ylcarbonyl)amino}ethyl]-6-(propan-2-yloxy)pyridin-2-yl}propyl)carbamate, or a pharmaceutically acceptable salt thereof.

(e1) a pharmaceutical composition comprising the compound of any of (1), (a1) to (a10), (b1), (c1) to (c12) and (d1) to (d7) or a pharmaceutically acceptable salt thereof.

(e2) a renin inhibitor comprising the compound of any of (1), (a1) to (a10), (b1), (c1) to (c12) and (d1) to (d7) or a pharmaceutically acceptable salt thereof.

(e3) a pharmaceutical composition for the treatment and/or prophylaxis of hypertension, cardiac failure, diabeti nephropathy and the like, comprising the compound of any of (1), (a1) to (a10), (b1), (c1) to (c12) and (d1) to (d7) or a pharmaceutically acceptable salt thereof.

(e4) the compound or the pharmaceutically acceptable salt thereof for use in renin inhibition, described in any of (1), (a1) to (a10), (b1), (c1) to (c12) and (d1) to (d7).

(e5) the compound or the pharmaceutically acceptable salt thereof for use in the treatment and/or prophylaxis of diseases resolved by renin-inhibition, described in any of (1), (a1) to (a10), (b1), (c1) to (c12) and (d1) to (d7).

(e6) the compound or the pharmaceutically acceptable salt thereof for use in the treatment and/or prophylaxis of hypertension, cardiac failure, diabetic nephropathy and the like, described in any of (1), (a1) to (a10), (b1), (c1) to (c12) and (d1) to (d7).

(e7) a method for inhibiting renin, comprising administration of the compound or the pharmaceutically acceptable salt thereof, described in any of (1), (a1) to (a10), (b1), (c1) to (c12) and (d1) to (d7).

(e8) a method for the treatment and/or prophylaxis of diseases resolved by renin-inhibition, comprising administration of the compound or the pharmaceutically acceptable salt thereof, described in any of (1), (a1) to (a10), (b1), (c1) to (c12) and (d1) to (d7).

(e9) a method for the treatment and/or prophylaxis of hypertension, cardiac failure, diabetic nephropathy and the like, comprising administration of the compound or the pharmaceutically acceptable salt thereof, described in any of (1), (a1) to (a10), (b1), (c1) to (c12) and (d1) to (d7).

The compound [I] of the present invention can be clinically used either in the free form or in the form of a pharmaceutically acceptable salt thereof. Examples of the pharmaceutically acceptable salt of the compound [I] include a salt with an inorganic acid such as hydrochloride, sulfate, phosphate or hydrobromide, or a salt with an organic acid such as acetate, fumarate, oxalate, citrate, methanesulfonate, benzenesulfonate, tosylate or maleate. Besides, when the compound [I] of the present invention has a carboxyl group(s) and the like in its molecule, examples of the pharmaceutically acceptable salt include, salts with a base such as alkaline metal (e.g., sodium salt, potassium salt) or alkaline earth metal (e.g., calcium salt).

The compound [I] of the present invention also includes a mixture of a stereoisomer such as a geometrical isomer, a tautomer and an enantiomer, and an isolated stereoisomer thereof. In the compound [I] of the present invention, (R)-configuration is preferable for an asymmetric carbon atom of the morpholine ring having the substituent, T, from the view of renin-inhibition. From the view of renin-inhibition, (R)-configuration is also preferable for an asymmetric carbon atom which is substituted with R.

The present invention also includes an intramolecular salt, a hydrate, a pharmaceutically acceptable solvate and a crystal polymorph of the compound [I]. Additionally it should be understood that the compound [I] of the present invention is not limited to the compounds described in the examples below but includes whole the compounds of the formula [I] and pharmaceutically acceptable salts thereof.

Accordingly the compound of the present invention or the pharmaceutically acceptable salts thereof may be useful as an agent for prevention and/or treatment of hypertension, cardiac failure, diabetic nephropathy and the like, and can be advantageous as a medicine due to its low toxicity.

The compound [I] of the present invention or a pharmaceutically acceptable salt thereof can be either orally or parenterally administered, and can be formulated into a conventional pharmaceutical preparation such as tablets, granules, capsules, powders, injections or inhalants etc.

The dose of the compound [I] of the present invention or a pharmaceutically acceptable salt thereof may vary in accordance with the administration routes, and the ages, body weights and conditions of the patients, but usually it is in the range of about 0.001 to 500 mg/kg, preferably in the range of about 0.1 to 100 mg/kg.

The compound [I] of the present invention can be prepared by the following methods but should not be construed to be limited thereto.

Method for Preparing the Compound [I]

The compound [I] of the present invention or the pharmaceutically acceptable salt thereof can be prepared by deprotecting $P^1$ of the compound of the formula [II];

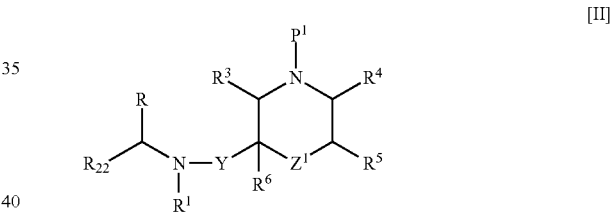

[II]

wherein $P^1$ is a protecting group and the other symbols are the same as defined above, and converting the product to a pharmaceutically acceptable salt thereof, if necessary.

Method for Preparing the Compound [II]

The compound [II] can be prepared by reacting a carboxylic compound of the formula [III]:

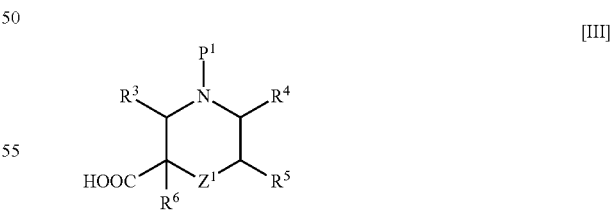

[III]

wherein the symbols are the same as defined above, or an activated derivative thereof with an amine compound of the formula [IV];

$(R^{22}RCH)R^1NH$ [IV]

wherein the symbols are the same as defined above.

The compound of the present invention has two or more asymmetric carbon and the reaction product may be obtained as a mixture of diastereoisomers. Such a mixture of diastereoisomers can be separated and purified by a usual method, a silica gel column chromatography for example.

Reaction in the Method for Preparing the Compound [I]

Examples of the protecting group shown as $P^1$ or $P^2$ include a usual amino-protecting group such as a tert-butoxycarbonyl group, a benzyloxycarbonyl group, 4-methoxy benzyloxycarbonyl group, a benzyl group, a 4-methoxybenzyl group, an acetyl group, a benzoyl group, a tosyl group and the like.

The protecting group $P^1$ and $P^2$ of the compound [II] can be deprotected by treating with acid or base or catalytic reduction or a deprotecting agent in a suitable solvent or without solvent. As an acid, an inorganic acid such as hydrochloric acid, sulfuric acid and the like, and an organic acid such as acetic acid, trifluoroacetic acid, methanesulfonic acid, p-toluenesulfonic acid and the like can be preferably used. As a base, an inorganic base (e.g., an alkali metal hydride such as sodium hydride, an alkali metal carbonate such as sodium carbonates and potassium carbonates, an alkali metal amide such as sodium amides and lithium amide, an alkali metal alkoxide such as sodium methoxide, an alkali metal such as sodium, and an alkali metal hydroxide such as sodium hydroxide, potassium hydroxide etc.) and the like can be preferably used. As a deprotecting agent, zinc bromide and trimethylsilane trifluoromethanesulfonate etc. can be used. The catalytic reduction can be carried out by preferably using palladium carbon, palladium hydroxide carbon, platinum oxide and the like as a catalyst under hydrogen atmosphere. Examples of the solvent include any solvent which does not disturb the reaction, such as methanol, ethanol, isopropyl alcohol, 1,4-dioxane, diethyl ether, tetrahydrofuran, methylene chloride, chloroform, dichloroethane, ethyl acetate, toluene, and a mixture thereof. The acid or the base described above can be used as the solvent. The reaction can be suitably carried out at from −78° C. to a boiling temperature of the solvent.

Reaction in the Method for Preparing the Compound [II]

The compound [II] can be prepared by a condensation reaction of a carboxylic acid compound [III] and an amine compound [IV] in a suitable solvent or without a solvent.

The condensation reaction can be carried out by a conventional condensation reaction in the presence of a condensing agent, or reacting an activated derivative of the compound [III] (e.g., an acid halide, a mixed acid anhydride, an activated ester and the like) with the compound [IV], after the compound [III] is converted to the reactive derivative thereof. Examples of the condensing agent include N,N-dicyclohexylcarbodiimide (DCC), 1-ethyl-3-(3-dimethylaminopropyl)carbodiimide (EDC) or hydrochloride thereof, carbonyldiimidazole (CDI), diphenylphosphoryl azide (DPPA), diethyl cyanophosphonate (DEPC) and the like, and among them DCC, EDC or its hydrochloride is preferable.

When the reactive derivative of the compound [III] is used, the reactive derivative can be reacted with the compound [IV] in a suitable solvent or without a solvent in presence of an acid scavenger if necessary, after the compound [III] is converted to an acid halide using a halogenating agent (e.g., thionyl chloride, thionyl bromide, oxalyl chloride and the like), a mixed acid anhydride using chlorocarbonate ester (e.g., methyl chlorocarbonate, ethyl chlorocarbonate, isobutyl chloroformate and the like) or acid chloride (2,4,6-trichlorobenzoyl chloride and the like), or an activated ester of N-hydroxylamine compound (1-hydroxysuccinimide, 1-hydroxybenzotriazole and the like) or of phenol compound (p-nitrophenol and the like) or a lower alcohol ester (methyl ester, ethyl ester and the like). In a method converting to an acid halide, an addition of catalyst such as dimethylformamide and the like can accelerate the reaction. As an acid scavenger, an inorganic base or an organic base is used when necessary, and examples of an inorganic base include sodium carbonate, potassium carbonate, cesium carbonate, sodium bicarbonate, sodium hydroxide, potassium hydroxide, lithium hydroxide and the like and examples of an organic base include triethylamine, tributylamine, diisopropylethylamine, 1,8-diazabicyclo[5,4,0]undeca-7-ene, N,N-diethylaniline, pyridine, lutidine, colidine and the like. In the present reaction, triethylamine, diisopropylethylamine, pyridine and the like are preferably used as an acid scavenger. When the acid scavenger is used in this reaction, acid scavenger is used as the solvent.

In the condensing reaction shown above, it can be conducted or accelerated by adding 4-aminopyridine and the like When using a solvent in the condensing reaction above, any inert solvent which does not disturb the reaction can be used and examples of the solvents include chloroform, dichloromethane, dichloroethane, toluene, diethyl ether, tetrahydrofuran, dioxane, 1,2-dimethoxyethane, ethyl acetate, amide-related solvent (N,N-dimethylformamide, N,N-dimethylacetamide, 1,3-dimethyl-2-imidazolidinon etc.), pyridine, 2,6-lutidine, water and the like, and a mixture thereof can be also used. Among them, chloroform, tetrahydrofuran, dioxane, N,N-dimethylformamide, N,N-dimethylacetamide, and a mixture of chloroform and N,N-dimethylformamide etc. are preferred.

Usually the condensation reaction above can be carried out at a temperature from −20° C. to a reflux temperature of the solvent and if necessary, it can be carried out at a lower temperature which is suitably selected.

Examples of the compounds [I] of the present invention prepared by the methods illustrated above are shown below, but the present invention should not be construed to be limited thereto.

EXAMPLES

Example 1

(2R)—N-Cyclopropyl-N-{1-[4-(3-methoxypropoxy)-1-benzofuran-6-yl]ethyl}morpholine-2-carboxamide [Ex(1-1), Ex(1-2)]

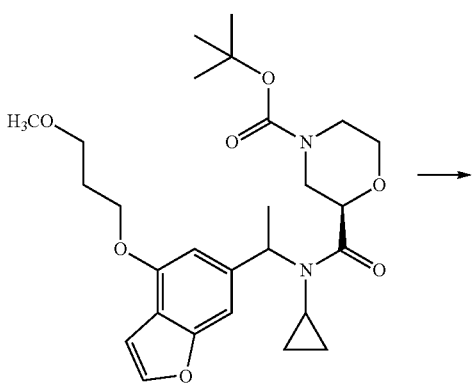

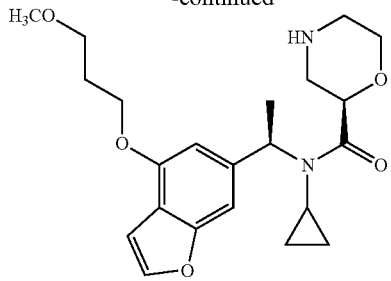

Ex(1-1)

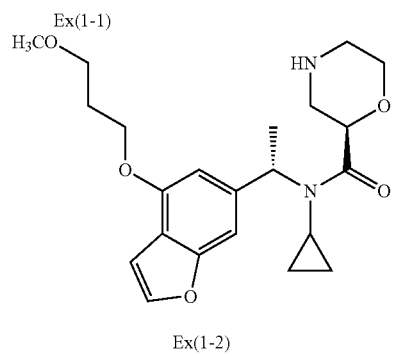

Ex(1-2)

To a solution of tert-butyl (2R)-2-[(cyclopropyl {1-[4-(3-methoxypropoxy)-1-benzofuran-6-yl]ethyl}amino)carbonyl]morpholine-4-carboxylate (200 mg) and 2,6-lutidine (0.142 mL) in chloroform (4 mL) was added trimethylsilyltriflate (0.180 mL) under ice-cooling, and the mixture was stirred at the same temperature for 30 minutes. Then, thereto was added aqueous saturated sodium hydrogen carbonate solution under ice-cooling, and the mixture was extracted with ethyl acetate. The organic layer was washed with saturated saline, dried over magnesium sulfate, and then concentrated under reduced pressure. The resulting residue was purified by silica gel column chromatography (eluent: chloroform/methanol/ammonia water=200/2/1) to give (2R)—N-cyclopropyl-N-{(1R)-1-[4-(3-methoxypropoxy)-1-benzofuran-6-yl]ethyl}morpholine-2-carboxamide [Ex(1-1)] (12.5 mg) and (2R)—N-cyclopropyl-N-{(1S)-1-[4-(3-methoxypropoxy)-1-benzofuran-6-yl]ethyl}morpholine-2-carboxamide [Ex(1-2)] (20.2 mg) as a colorless oil.

APCI-MS m/z: 403 [M+H]+.

Example 2

(2R)—N-{(1R)-1-[3-Chloro-1-(3-methoxypropyl)-1H-indol-6-yl]ethyl}-N-cyclopropylpiperazine-2-carboxamide [Ex(2-1)]

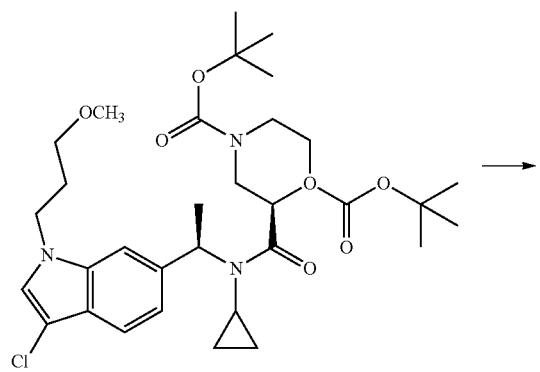

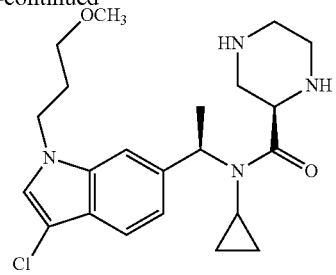

Ex(2-1)

To a solution of di-tert-butyl (2R)-2-{[{(1R)-1-[3-chloro-1-(3-methoxypropyl)-1H-indol-6-yl]ethyl}(cyclopropyl)amino]carbonyl}piperazine-1,4-dicarboxylate (44.0 mg) and 2,6-lutidine (0.050 mL) in dichloromethane (1.0 mL) was added trimethylsilyltriflate (0.051 mL) under ice-cooling, and the mixture was stirred at the same temperature for 1 hour. Then, thereto were added aqueous saturated sodium hydrogen carbonate solution and methanol (2.0 mL) under ice-cooling, and the mixture was extracted with chloroform. The organic layer was washed with saturated saline, dried over magnesium sulfate, and then concentrated under reduced pressure. The resulting residue was purified by NH-silica gel column chromatography (eluent: ethyl acetate→ethyl acetate/methanol=5/1) to give (2R)—N-{(1R)-1-[3-chloro-1-(3-methoxypropyl)-1H-indol-6-yl]ethyl}-N-cyclopropylpiperazine-2-carboxamide [Ex(2-1)] (25.4 mg) as a colorless oil.

APCI-MS m/z: 419/421 [M+H]+.

Example 3

(2R)—N—Cyclopropyl-N-{(1R)-1-[1-(3-methoxypropyl)-3-methyl-1H-indazol-6-yl]ethyl}-morpholine-2-carboxamide hydrochloride [Ex(3-1)]

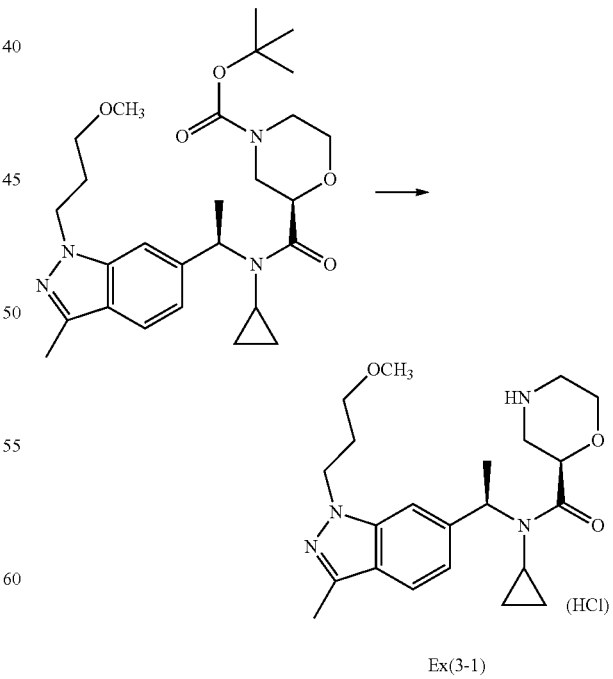

Ex(3-1)

To a solution of tert-butyl (2R)-2-[(cyclopropyl{(1R)-1-[1-(3-methoxypropyl)-3-methyl-1H-indazol-6-yl]ethyl}amino)carbonyl]morpholine-4-carboxylate (44.4 mg)

in chloroform (2.0 mL) was added 4-normal hydrogen chloride-dioxane solution (0.75 mL) under ice-cooling, and the mixture was stirred at room temperature for 20 hours. The reaction solution was concentrated under reduced pressure, and the resulting residue was dissolved in water (1 mL), and then washed with diethyl ether. The aqueous layer was freeze-dried to give (2R)—N-cyclopropyl-N-{(1R)-1-[1-(3-methoxypropyl)-3-methyl-1H-indazol-6-yl]ethyl}morpholine-2-carboxamide hydrochloride [Ex(3-1)] (25 mg) as a colorless powder.

APCI-MS m/z: 401 [M+H]$^+$.

Example 4

(2R)—N-{1-[4-Chloro-1-(3-methoxypropyl)-3-methyl-1H-indazol-6-yl]ethyl}-N-cyclopropyl morpholine-2-carboxamide [Ex(4-1), Ex(4-2)]

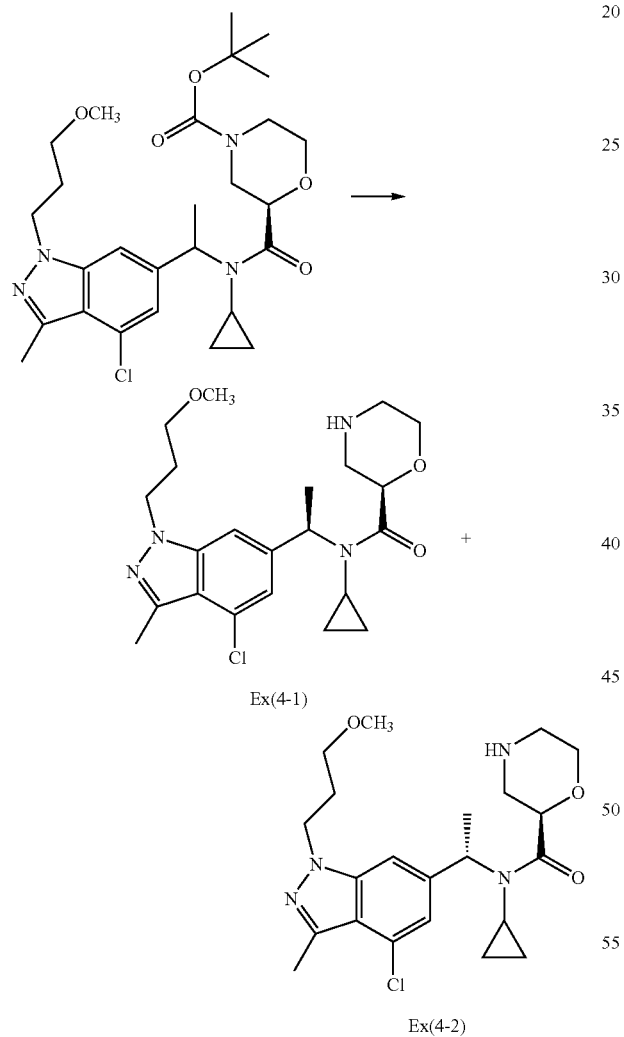

Ex(4-1)

Ex(4-2)

To a solution of tert-butyl (2R)-2-{[{1-[4-chloro-1-(3-methoxypropyl)-3-methyl-1H-indazol-6-yl]ethyl}(cyclopropyl)amino]carbonyl}morpholine-4-carboxylate (146 mg) in chloroform (2.0 mL) was added 4-normal hydrogen chloride-dioxane solution (2.0 mL) under ice-cooling, and the mixture was stirred at room temperature for 3 hours. The reaction solution was concentrated under reduced pressure, and then thereto was added aqueous saturated sodium hydrogen carbonate solution under ice-cooling, and the mixture was extracted with chloroform. The organic layer was washed with saturated saline, dried over magnesium sulfate, and then concentrated under reduced pressure. The resulting residue was purified by silica gel column chromatography (eluent: chloroform/methanol/ammonia water=500/10/1) to give (2R)—N-{(1R)-1-[4-chloro-1-(3-methoxypropyl)-3-methyl-1H-indazol-6-yl]ethyl}-N-cyclopropylmorpholine-2-carboxamide [Ex(4-1)] (50.2 mg) and (2R)—N—{(1S)-1-[4-chloro-1-(3-methoxypropyl)-3-methyl-1H-indazol-6-yl]ethyl}-N-cyclopropylmorpholine-2-carboxamide [Ex(4-2)] (18.4 mg) as a colorless oil.

APCI-MS m/z: 435/437 [M+H]$^+$.

Example 5A (2R)—N-{1-[3-Bromo-4-methoxy-5-(3-methoxypropoxy)phenyl]ethyl}-N-cyclopropylmorpholine-2-carboxamide [Ex(5-1), Ex(5-2)]

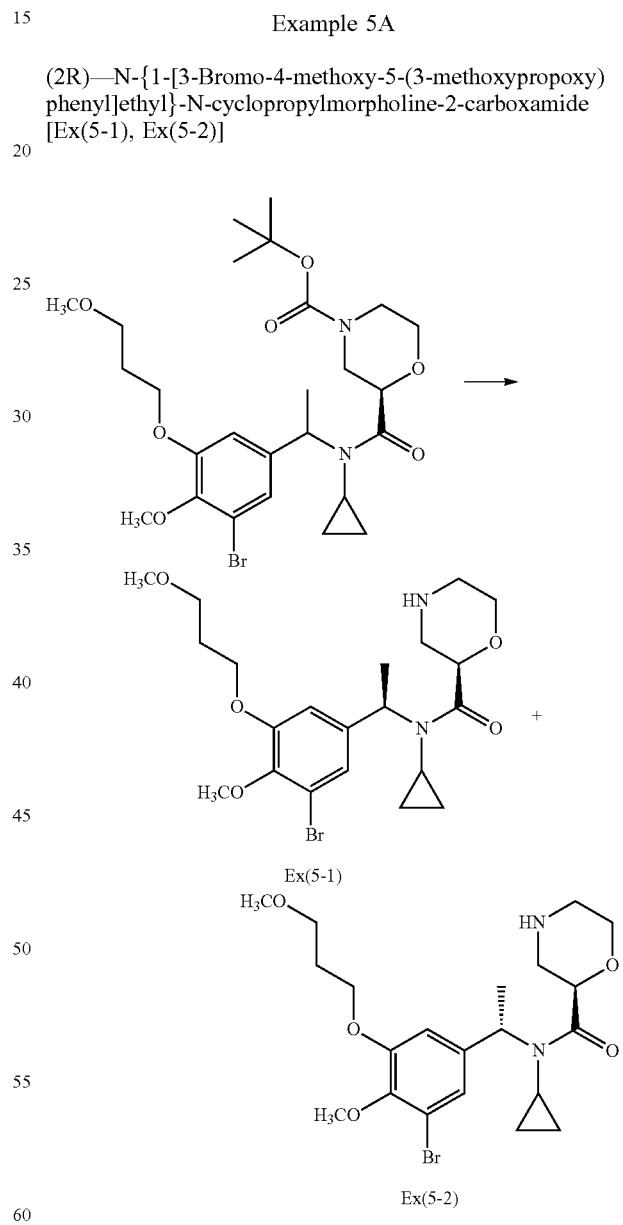

Ex(5-1)

Ex(5-2)

To a solution of tert-butyl (2R)-2-{[{1-[3-bromo-4-methoxy-5-(3-methoxypropoxy)-phenyl]ethyl}(cyclopropyl)amino]carbonyl}morpholine-4-carboxylate (135 mg) in dichloromethane (2 mL) was added trifluoroacetic acid (2 mL), and the mixture was stirred at room temperature for 30 minutes. The reaction solution was concentrated under reduced pressure, and to the resulting residue was added chloroform, and the mixture was filtered through (Bond-Elute: registered trademark) (NH₂). The filtrate was concentrated under reduced pressure, and the resulting residue was purified by NH-silica gel column chromatography (eluent: ethyl acetate/methanol/ammonia water=200/10/1) to give (2R)—N-{(1R)-1-[3-bromo-4-methoxy-5-(3-methoxypropoxy)phenyl]ethyl}-N-cyclopropylmorpholine-2-carboxamide [Ex(5-1)] (53.7 mg) and (2R)—N-{(1S)-1-[3-bromo-4-methoxy-5-(3-methoxypropoxy)phenyl]ethyl}-N-cyclopropylmorpholine-2-carboxamide [Ex(5-2)] (30.5 mg) as a colorless oil.

APCI-MS m/z: 471/473[M+H]⁺.

Example 5B

Methyl

{3-[3-((1-{cyclopropyl[(2R)-morpholin-2-ylcarbonyl]amino}ethyl)-1H-pyrrolo[2,3-b]-pyridin-1-yl]propyl}carbamate

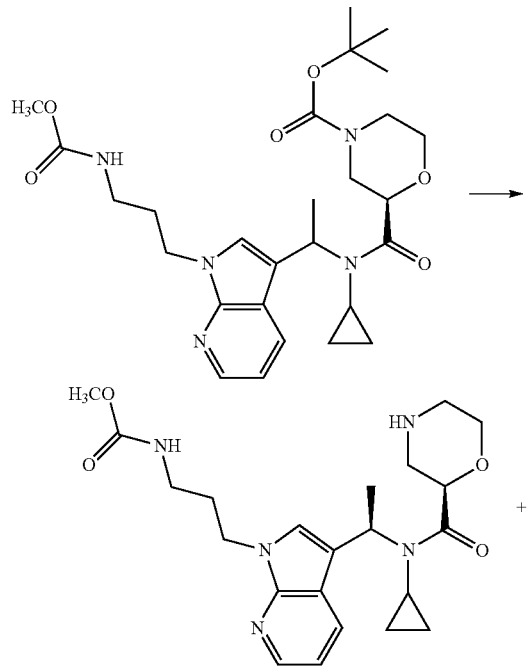

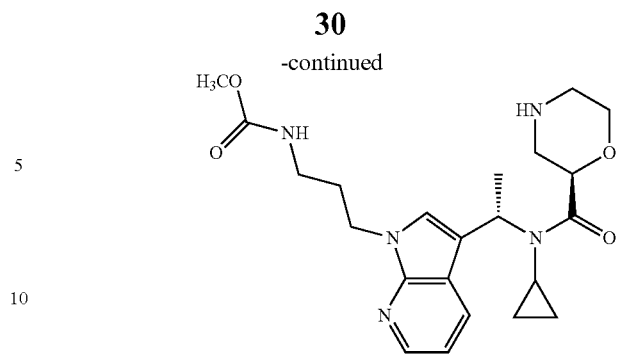

To a solution of t-butyl (2R)-2-({cyclopropyl[1-(1-{3-[(methoxycarbonyl)amino]propyl}-1H-pyrrolo[2,3-b]pyridin-3-yl)ethyl]amino}carbonyl)morpholin-4-carboxylate (116 mg) and 2,6-lutidine (0.077 mL) in dichloromethane (2 mL) was added trimethylsilyltriflate (0.099 mL) under ice-cooling, and the mixture was stirred at the same temperature for 1 hour. Then, thereto were added aqueous sodium hydrogen carbonate solution and methanol (2.0 mL) under ice-cooling, and the mixture was extracted with chloroform. The organic layer was washed with saturated saline, dried over magnesium sulfate, and then concentrated under reduced pressure. The resulting residue was purified by NH-silica gel column chromatography (eluent: ethyl acetate→ethyl acetate/methanol=9/1) to give methyl {3-[3-(1-cyclopropyl[(2R)-morpholin-2-ylcarbonyl]amino ethyl)-1H-pyrrolo[2,3-b]pyridin-1-yl]propyl}carbamate (50 mg) as a colorless oil. Methyl {3-[3-(1-cyclopropyl[(2R)-morpholin-2-ylcarbonyl]amino ethyl)-1H-pyrrolo[2,3-b]pyridin-1-yl]propyl}carbamate (40 mg) was separated by CHIRALPAK IC (eluent: n-hexane/ethanol/diethylamine=50/50/0.1; instrument: Waters 302 (600E system)) into diastereomers to give methyl {3-[3-((1R)-1-cyclopropyl[(2R)-morpholin-2-ylcarbonyl]amino-ethyl)-1H-pyrrolo[2,3-b]pyridin-1-yl]propyl}carbamate (18 mg) as a colorless oil and methyl {3-[3-((1S)-1-{cyclopropyl[(2R)-morpholin-2-ylcarbonyl]amino}ethyl)-1H-pyrrolo[2,3-b]pyridin-1-yl]propyl}carbamate (18 mg) as a colorless oil.

APCI-MS m/z: 430 [M+H]⁺.

Examples 6 to 160

The following nitrogen-containing saturated heterocyclic compounds, etc. were prepared in the similar manner to the above Examples 1 to 5. Each symbol of Methods A to C refers to each method according to the following method of Examples.

Method A: Examples 1, 2
Method B: Examples 3, 4
Method C: Example 5A

TABLE 1

| EX. No. | Chemical formula | a | MW | b | c | d | e |
|---|---|---|---|---|---|---|---|
| 6 | 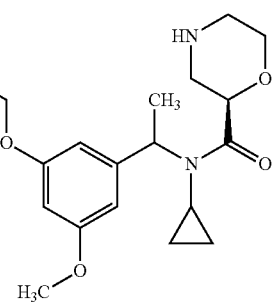 | | 392.4928 | B | 393 | [M + H]+ | O |

TABLE 1-continued

| EX. No. | Chemical formula | a | MW | b | c | d | e |
|---|---|---|---|---|---|---|---|
| 7 | | HCl | 360.8826 | B | 325 | [M + H]+ | P |
| 8 | | HCl | 360.8826 | B | 325 | [M + H]+ | P |
| 9 | | HCl | 428.9538 | B | 393 | [M + H]+ | O |

TABLE 2

| | | a | MW | b | c | d | e |
|---|---|---|---|---|---|---|---|
| 10 | | HCl | 436.9808 | B | 401 | [M + H]+ | P |

TABLE 2-continued

| # | Structure | Salt | MW | Class | MS | Ion | Notes |
|---|-----------|------|-----|-------|-----|-----|-------|
| 11 | 3-(3-methoxypropoxy)phenyl; N-cyclopropyl; α-methyl; morpholine-2-carboxamide | HCl | 398.928 | B | 363 | [M + H]+ | P |
| 12 | 3,5-dimethoxyphenyl; N-cyclopropyl; α-methyl; morpholine-2-carboxamide | HCl | 370.8744 | B | 335 | [M + H]+ | O |
| 13 | 3,4-dimethoxyphenyl; N-cyclopropyl; α-methyl; morpholine-2-carboxamide | | 334.4134 | A | 335 | [M + H]+ | O |

TABLE 3

| # | Structure | Salt | MW | Class | MS | Ion | Notes |
|---|-----------|------|-----|-------|-----|-----|-------|
| 14 | 3,4-dimethoxyphenyl; N-cyclopropyl; α-methyl; morpholine-2-carboxamide | | 334.4134 | A | 335 | [M + H]+ | O |
| 15 | 3,4-dimethoxyphenyl; N-cyclopropyl; α-ethyl; morpholine-2-carboxamide | | 348.4402 | A | 349 | [M + H]+ | O |
| 16 | 3,4-dimethoxyphenyl; N-cyclopropyl; α-ethyl; morpholine-2-carboxamide | | 348.4402 | A | 349 | [M + H]+ | O |

TABLE 3-continued
| | | | | | | |
|---|---|---|---|---|---|---|
| 17 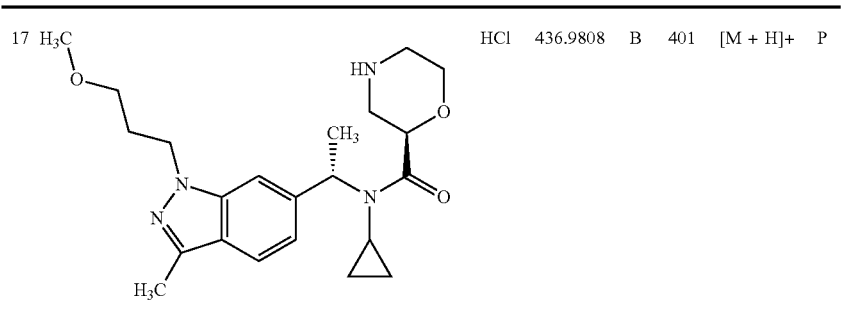 | HCl | 436.9808 | B | 401 | [M + H]+ | P |
TABLE 4
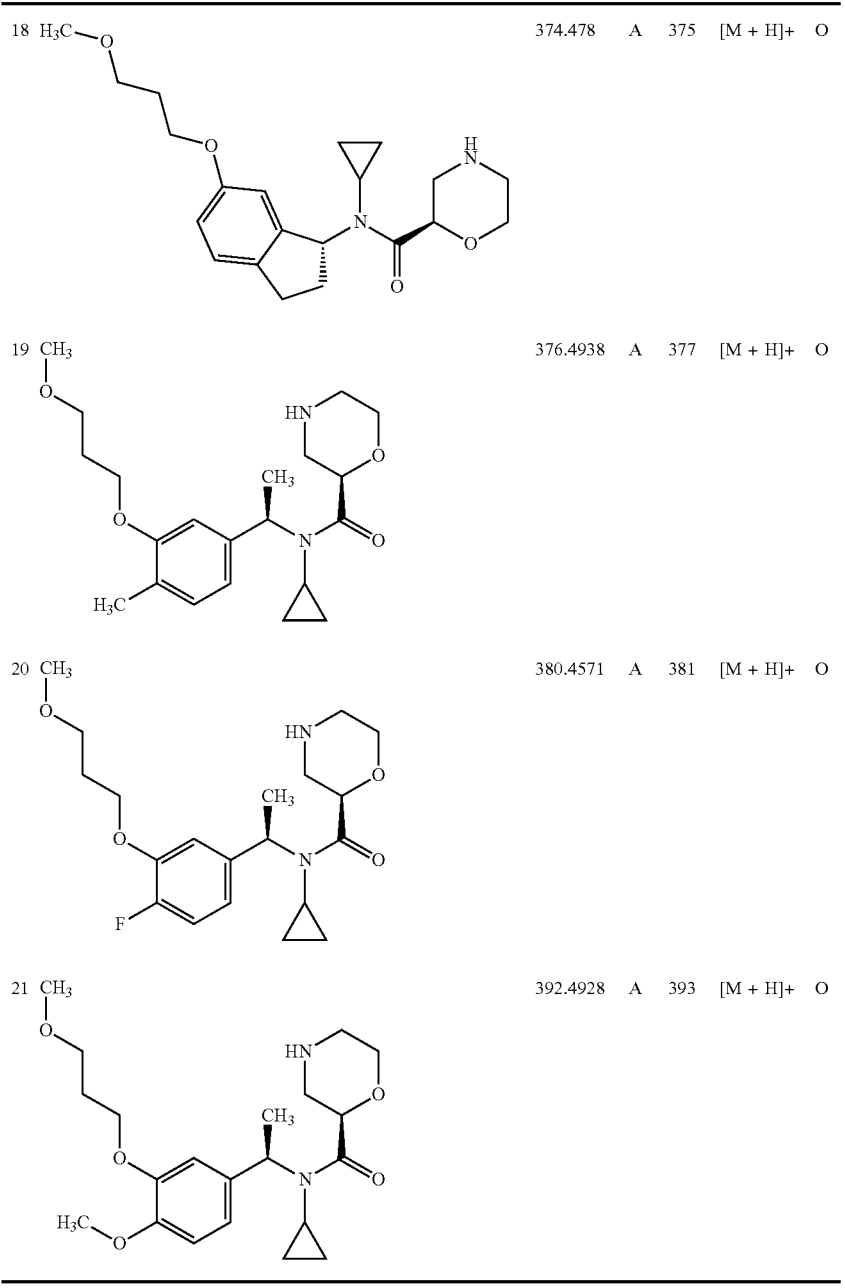
| | | | | | | |
|---|---|---|---|---|---|---|
| 18 | | 374.478 | A | 375 | [M + H]+ | O |
| 19 | | 376.4938 | A | 377 | [M + H]+ | O |
| 20 | | 380.4571 | A | 381 | [M + H]+ | O |
| 21 | | 392.4928 | A | 393 | [M + H]+ | O |

TABLE 5

| # | Structure | Mass | | m/z | | |
|---|---|---|---|---|---|---|
| 22 | 3-(3-methoxypropoxy)-4-methylphenyl derivative with (S)-methyl, N-cyclopropyl, morpholine-2-carboxamide | 376.4938 | A | 377 | [M + H]+ | O |
| 23 | 3-(3-methoxypropoxy)-4-fluorophenyl derivative with (S)-methyl, N-cyclopropyl, morpholine-2-carboxamide | 380.4571 | A | 381 | [M + H]+ | O |
| 24 | 3-(3-methoxypropoxy)-4-methoxyphenyl derivative with (S)-methyl, N-cyclopropyl, morpholine-2-carboxamide | 392.4928 | A | 393 | [M + H]+ | O |
| 25 | 3-(3-methoxypropoxy)-5-methylphenyl derivative with (S)-methyl, N-cyclopropyl, morpholine-2-carboxamide | 376.4938 | A | 377 | [M + H]+ | O |

TABLE 6

| # | Structure | Mass | | m/z | | |
|---|---|---|---|---|---|---|
| 26 | 3-(3-methoxypropoxy)-5-methylphenyl derivative with (S)-methyl, N-cyclopropyl, morpholine-2-carboxamide | 376.4938 | A | 377 | [M + H]+ | O |

TABLE 6-continued

| 27 | [structure: 6-(3-methoxypropoxy)-indanyl N-cyclopropyl morpholine-2-carboxamide] | 374.478 | A | 375 | [M + H]+ | O |

| 28 | [structure: 3-chloro-1-(3-methoxypropyl)-indol-6-yl (S)-ethyl N-cyclopropyl morpholine-2-carboxamide] | 419.95 | A | 420/422 | [M + H]+ | O |

| 29 | [structure: 3-chloro-1-(3-methoxypropyl)-indol-6-yl (S)-ethyl N-cyclopropyl morpholine-2-carboxamide, alternate stereochem] | 419.95 | A | 420/422 | [M + H]+ | O |

TABLE 7

| 30 | [structure: 3-chloro-1-(3-methoxypropyl)-indol-6-yl (S)-ethyl N-cyclopropyl piperazine-2-carboxamide] | 418.9659 | A | 419/421 | [M + H]+ | O |

TABLE 7-continued
| | | | | | | |
|---|---|---|---|---|---|---|
| 31 | 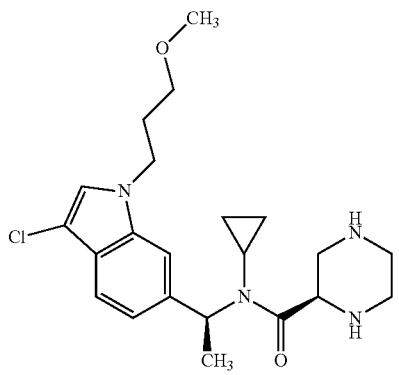 [SMILES: COCCCn1cc(Cl)c2ccc([C@H](C)N(C(=O)[C@H]3CNCCO3)C3CC3)cc21] | | 418.9659 | A | 419/421 [M + H]+ | O |
| 32 | 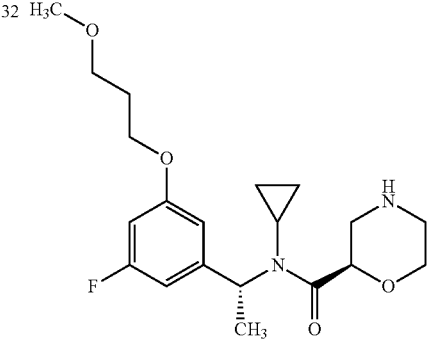 | | 380.4571 | A | 381 [M + H]+ | O |
| 33 | 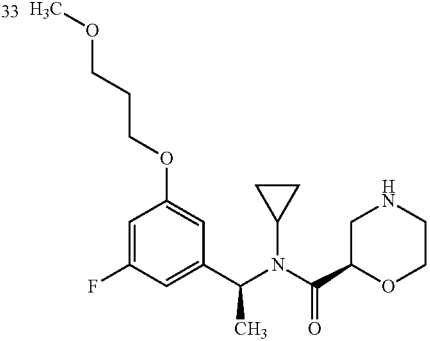 | | 380.4571 | A | 381 [M + H]+ | O |
TABLE 8
| | | | | | | |
|---|---|---|---|---|---|---|
| 34 | 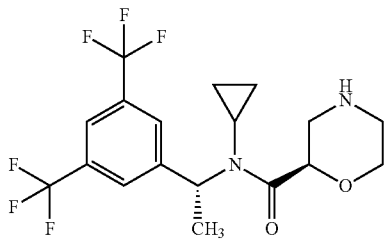 [SMILES: C[C@H](c1cc(C(F)(F)F)cc(C(F)(F)F)c1)N(C(=O)[C@H]1CNCCO1)C1CC1] | HCl | 446.817 | B | 411 [M + H]+ | P |

TABLE 8-continued
| # | Structure | | MW | | MS | | |
|---|---|---|---|---|---|---|---|
| 35 | 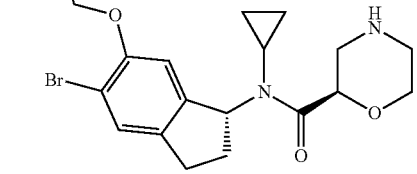 | | 453.38 | A | 453/455 | [M + H]+ | O |
| 36 | 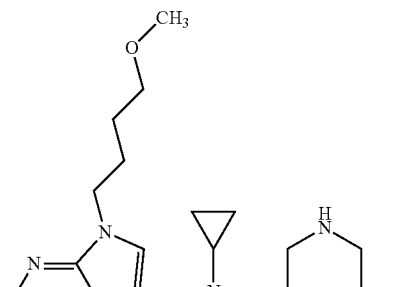 | | 414.5466 | A | 415 | | O |
| 37 | 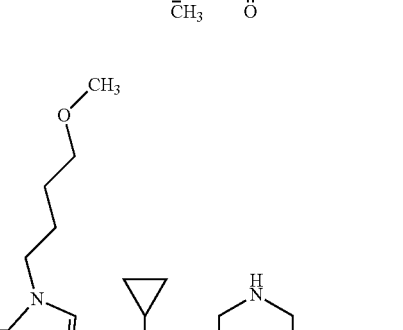 | | 418.5099 | A | 419 | [M + H]+ | O |
TABLE 9
| # | Structure | | MW | | MS | | |
|---|---|---|---|---|---|---|---|
| 38 |  | | 418.5099 | A | 419 | [M + H]+ | O |

TABLE 9-continued
| | | | | | | |
|---|---|---|---|---|---|---|
| 39 | 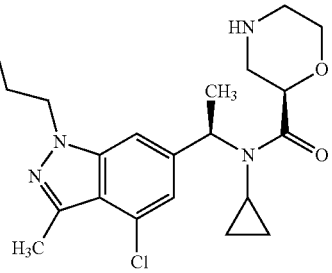 | 434.9649 | B | 435/437 | [M + H]+ | O |
| 40 | 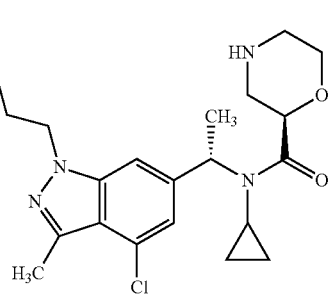 | 434.9649 | B | 435/437 | [M + H]+ | O |
| 41 | 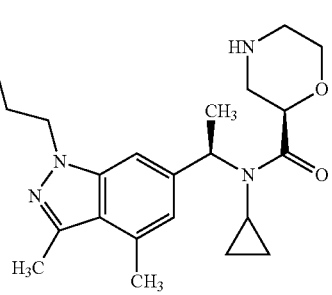 | 414.5466 | B | 415 | [M + H]+ | O |
TABLE 10
| | | | | | | |
|---|---|---|---|---|---|---|
| 42 | 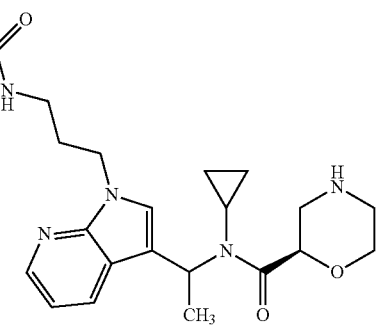 | 429.5179 | A | 430 | [M + H]+ | O |
| 43 | 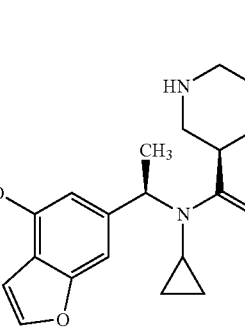 | 402.488 | A | 403 | [M + H]+ | O |

TABLE 10-continued

| # | Structure | MW | | Mass | Ion | |
|---|---|---|---|---|---|---|
| 44 | (4-(3-methoxypropoxy)benzofuran with N-cyclopropyl-N-[(1S)-ethyl]-morpholine-2-carboxamide) | 402.488 | A | 403 | [M + H]+ | O |
| 45 | (3,5-bis(3-methoxypropoxy)phenyl with N-cyclopropyl-(1S)-ethyl morpholine-2-carboxamide) | 450.5722 | A | 451 | [M + H]+ | O |

TABLE 11

| # | Structure | MW | | Mass | Ion | |
|---|---|---|---|---|---|---|
| 46 | (3,5-bis(3-methoxypropoxy)phenyl with N-cyclopropyl-(1R)-ethyl morpholine-2-carboxamide) | 450.5722 | A | 451 | [M + H]+ | O |
| 47 | (4-chloro-3,5-dimethoxyphenyl with N-cyclopropyl-(1S)-ethyl morpholine-2-carboxamide) | 368.8585 | A | 369/371 | [M + H]+ | O |
| 48 | (4-chloro-3,5-dimethoxyphenyl with N-cyclopropyl-(1R)-ethyl morpholine-2-carboxamide) | 368.8585 | A | 369/371 | [M + H]+ | O |
| 49 | (3-chloro-4,5-dimethoxyphenyl with N-cyclopropyl-(1S)-ethyl morpholine-2-carboxamide) | 368.8585 | A | 369/371 | [M + H]+ | O |

TABLE 12
| | | | | | |
|---|---|---|---|---|---|
| 50 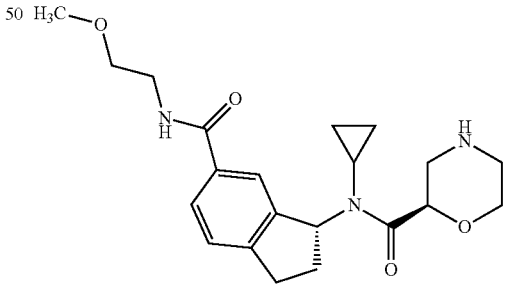 | 387.4771 | A | 388 | [M + H]+ | P |
| 51 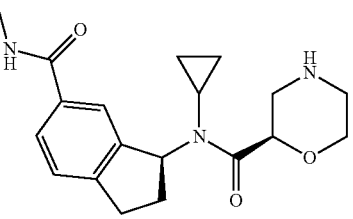 | 387.4771 | A | 388 | [M + H]+ | P |
| 52 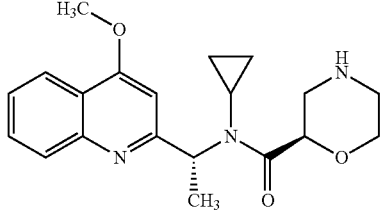 [SMILES: COc1cc([C@@H](C)N(C(=O)[C@H]2CNCCO2)C2CC2)nc2ccccc12] | 355.4355 | B | 356 | [M + H]+ | P |
| 53 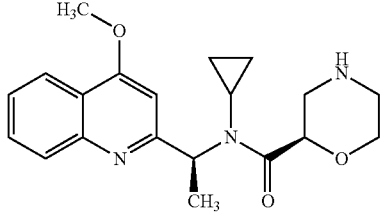 [SMILES: COc1cc([C@H](C)N(C(=O)[C@H]2CNCCO2)C2CC2)nc2ccccc12] | 355.4355 | B | 356 | [M + H]+ | O |
TABLE 13
| | | | | | | |
|---|---|---|---|---|---|---|
| 54 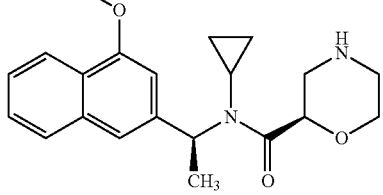 | HCl | 390.9084 | B | 355 | [M + H]+ | P |

TABLE 13-continued
| | | | | | | |
|---|---|---|---|---|---|---|
| 55 | 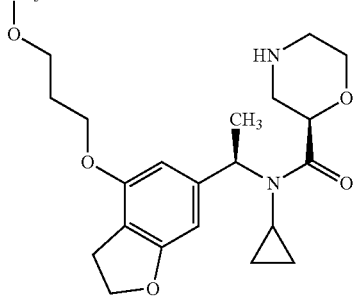 | 404.5038 | A | 405 | [M + H]+ | O |
| 56 | 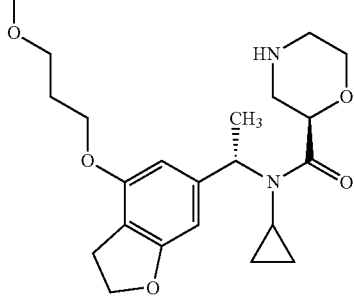 | 404.5038 | A | 405 | [M + H]+ | O |
| 57 | 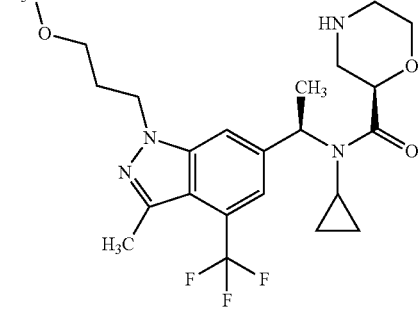 | 468.5169 | A | 469 | [M + H]+ | O |
TABLE 14
| | | | | | | |
|---|---|---|---|---|---|---|
| 58 | 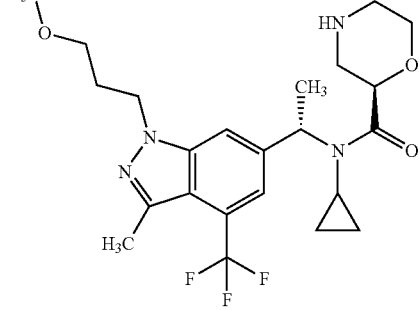 | 468.5169 | A | 469 | [M + H]+ | O |

TABLE 14-continued
| # | Structure | Mass | A | M+H | Note |
|---|---|---|---|---|---|
| 59 | 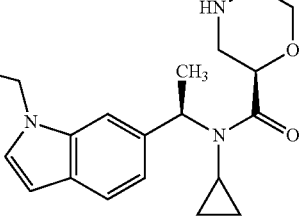 | 385.5049 | A | 386 | O |
| 60 | 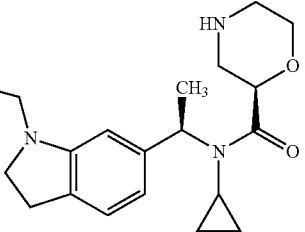 | 387.5207 | A | 388 [M + H]+ | O |
| 61 | 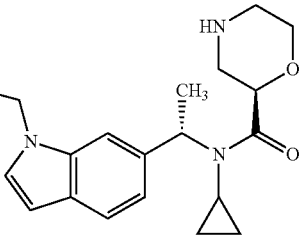 | 385.5049 | A | 386 | O |
TABLE 15
| # | Structure | Mass | A | M+H | Note |
|---|---|---|---|---|---|
| 62 | 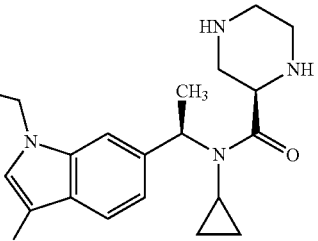 | 418.9659 | A | 419/421 [M + H]+ | O |
| 63 | 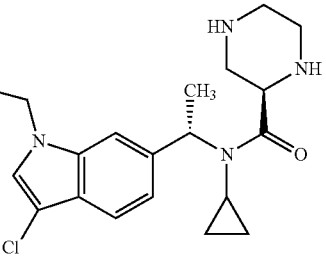 | 418.9659 | A | 419/421 [M + H]+ | O |

TABLE 15-continued
| 64 | 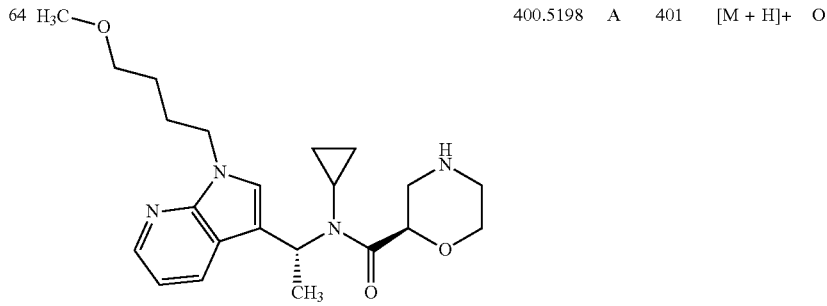 | | 400.5198 | A | 401 | [M + H]+ | O |
| 65 | 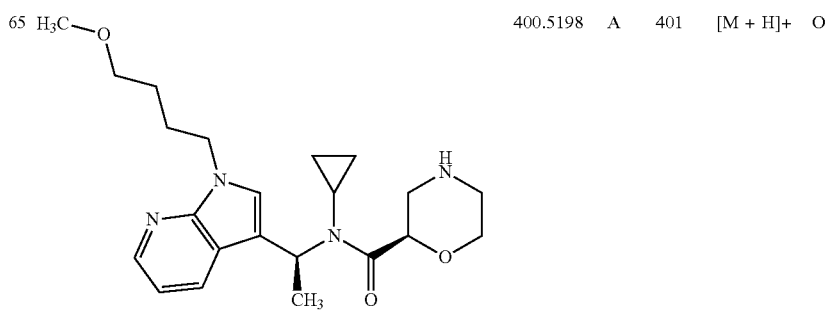 | | 400.5198 | A | 401 | [M + H]+ | O |
TABLE 16
| 66 | 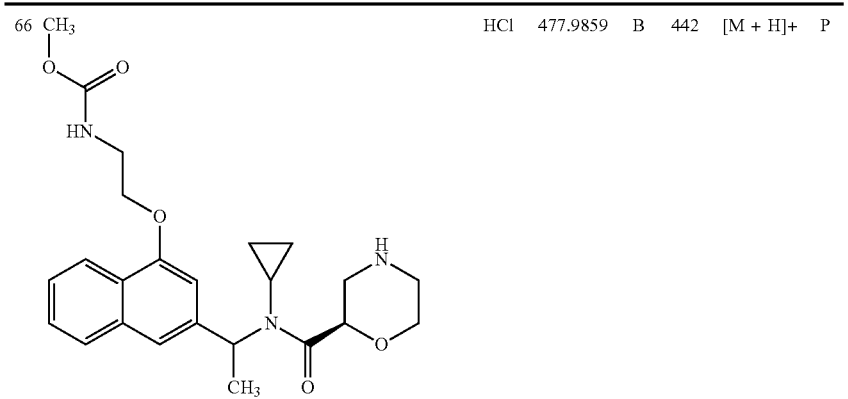 | HCl | 477.9859 | B | 442 | [M + H]+ | P |
| 67 | 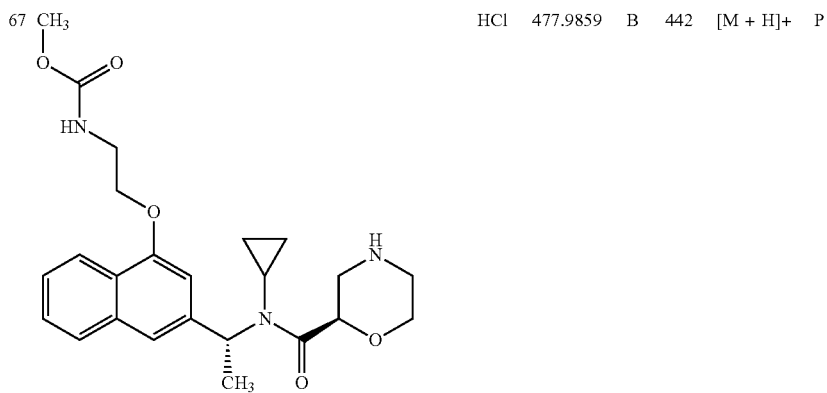 | HCl | 477.9859 | B | 442 | [M + H]+ | P |

TABLE 16-continued
| | | | | | | |
|---|---|---|---|---|---|---|
| 68 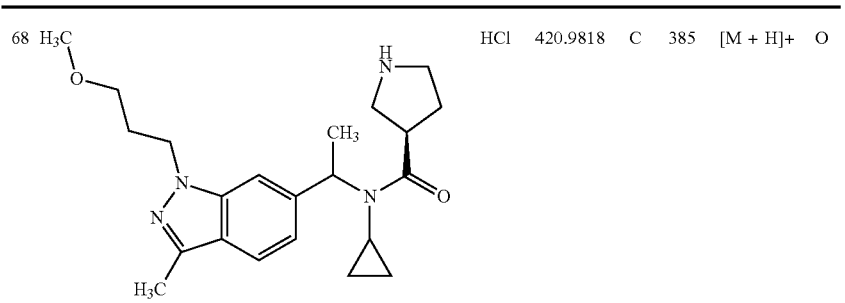 | HCl | 420.9818 | C | 385 | [M + H]+ | O |
| 69 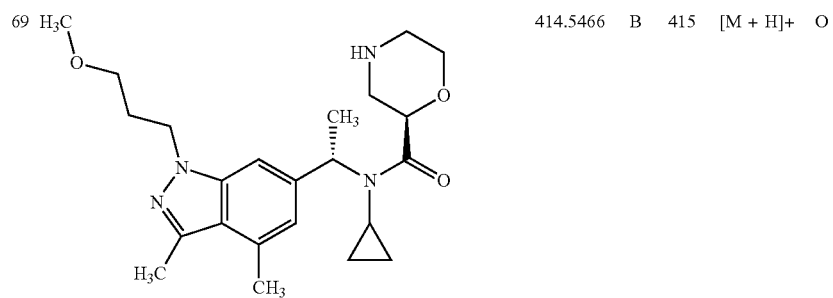 | | 414.5466 | B | 415 | [M + H]+ | O |
TABLE 17
| | | | | | | |
|---|---|---|---|---|---|---|
| 70 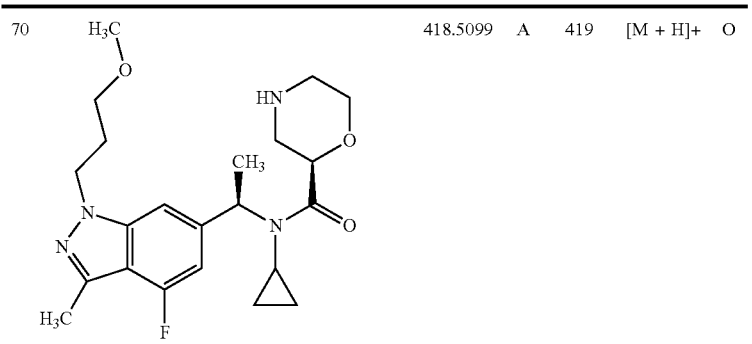 | | 418.5099 | A | 419 | [M + H]+ | O |
| 71 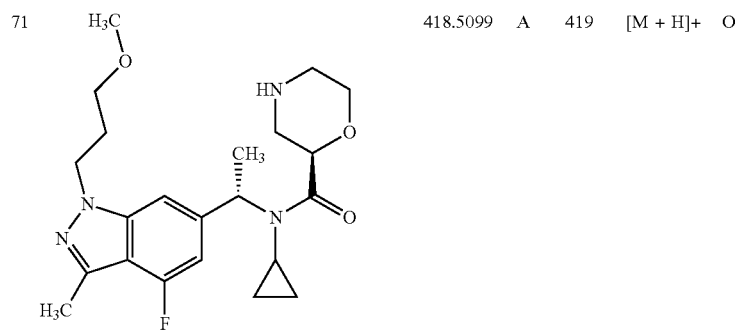 | | 418.5099 | A | 419 | [M + H]+ | O |

TABLE 17-continued
| 72 | 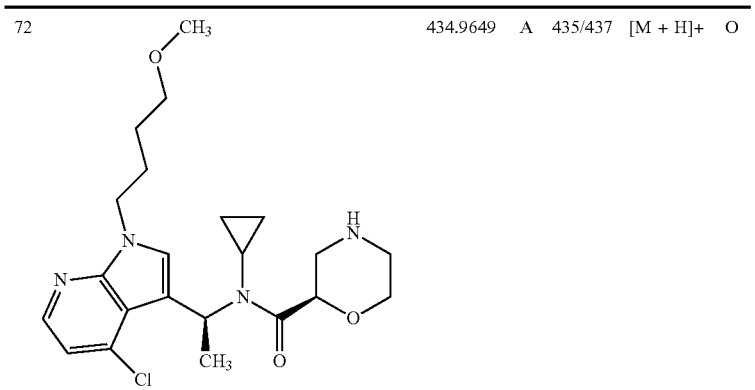 | 434.9649 | A | 435/437 | [M + H]+ | O |
| 73 | 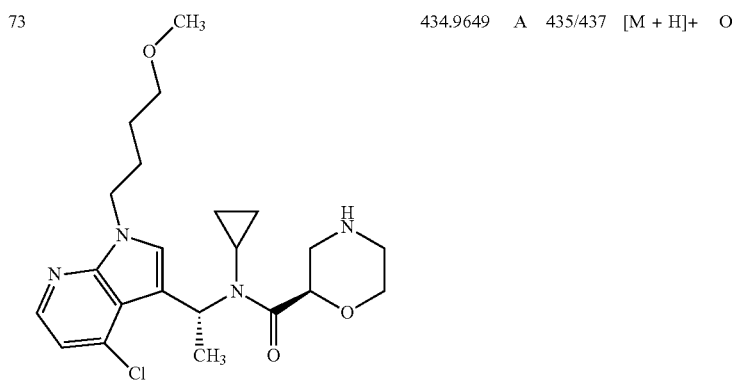 | 434.9649 | A | 435/437 | [M + H]+ | O |
TABLE 18
| 74 | 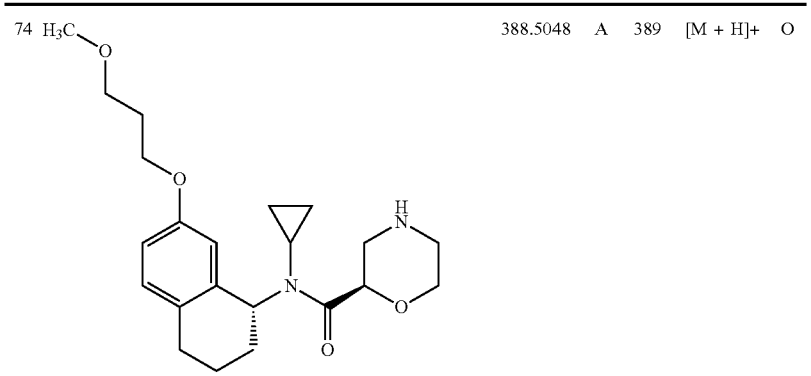 | 388.5048 | A | 389 | [M + H]+ | O |
| 75 | 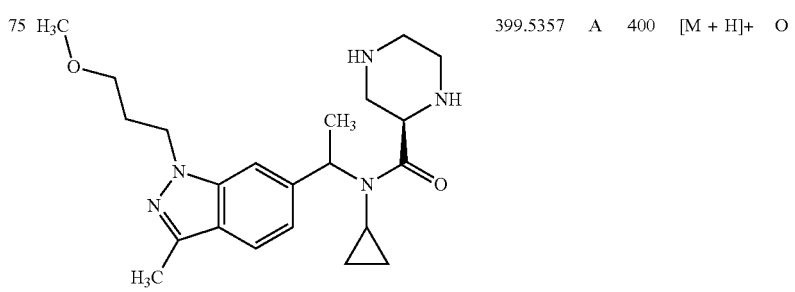 | 399.5357 | A | 400 | [M + H]+ | O |

TABLE 18-continued
| | | | | | | | |
|---|---|---|---|---|---|---|---|
| 76 | 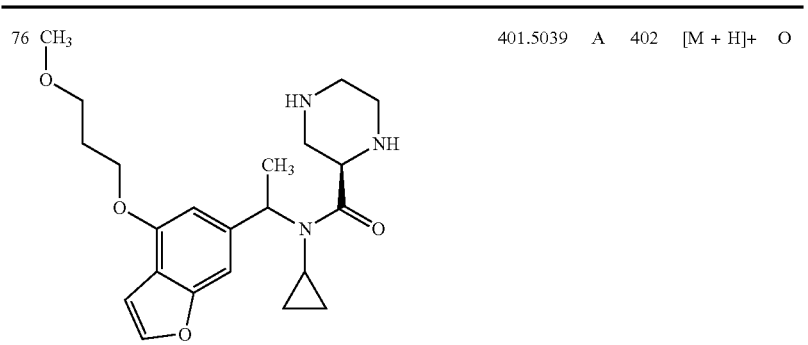 | 401.5039 | A | 402 | [M + H]+ | O |
| 77 | 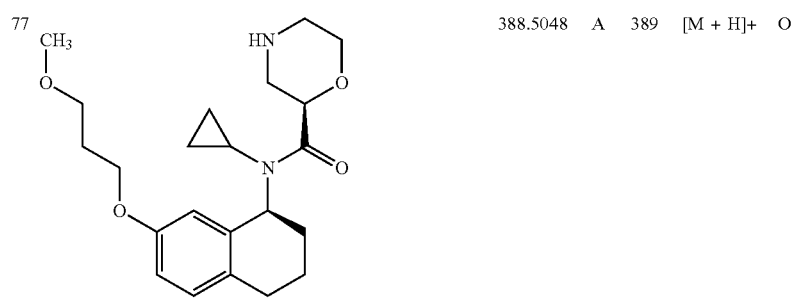 | 388.5048 | A | 389 | [M + H]+ | O |
TABLE 19
| | | | | | | | |
|---|---|---|---|---|---|---|---|
| 78 | 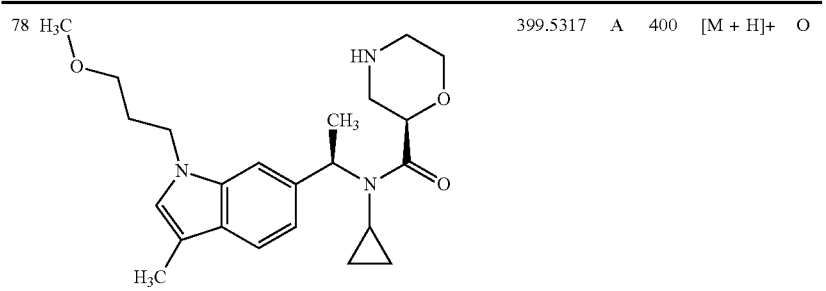 | 399.5317 | A | 400 | [M + H]+ | O |
| 79 | 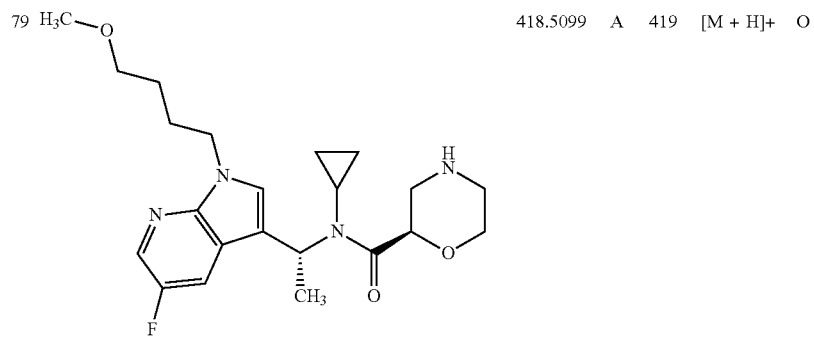 | 418.5099 | A | 419 | [M + H]+ | O |

TABLE 19-continued
| | | | | | | |
|---|---|---|---|---|---|---|
| 80 | 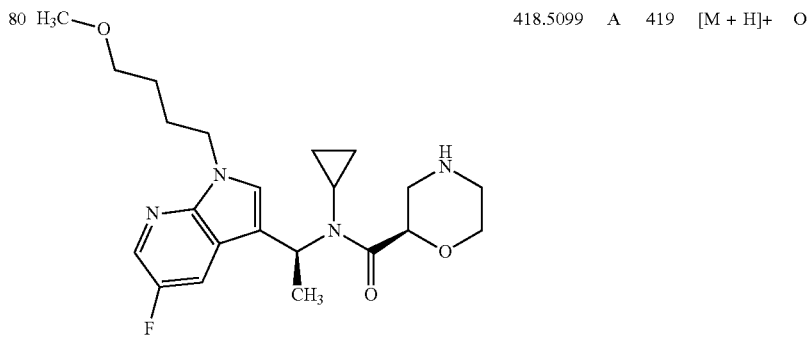 | 418.5099 | A | 419 | [M + H]+ | O |
| 81 | 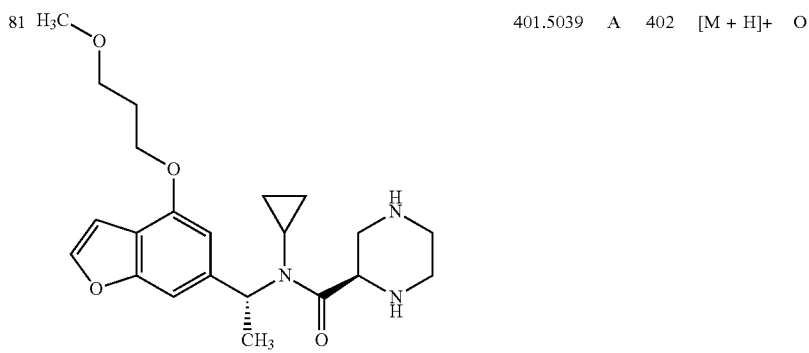 | 401.5039 | A | 402 | [M + H]+ | O |
TABLE 20
| | | | | | | |
|---|---|---|---|---|---|---|
| 82 | 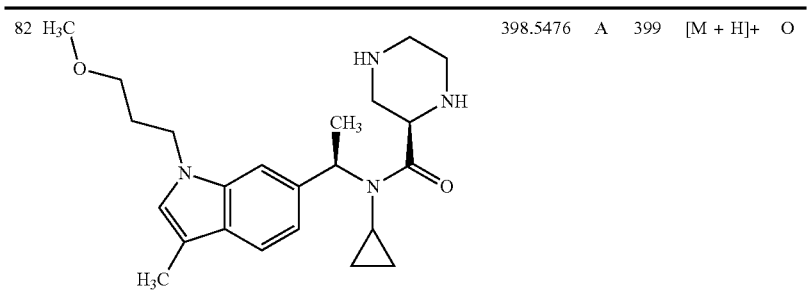 | 398.5476 | A | 399 | [M + H]+ | O |
| 83 | 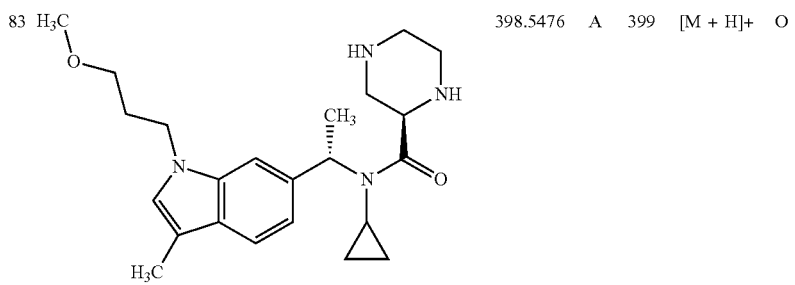 | 398.5476 | A | 399 | [M + H]+ | O |

TABLE 20-continued
| 84 | 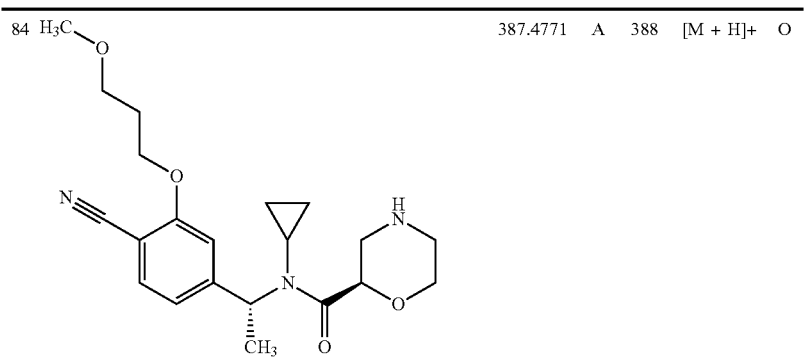 | 387.4771 | A | 388 | [M + H]+ | O |
| 85 | 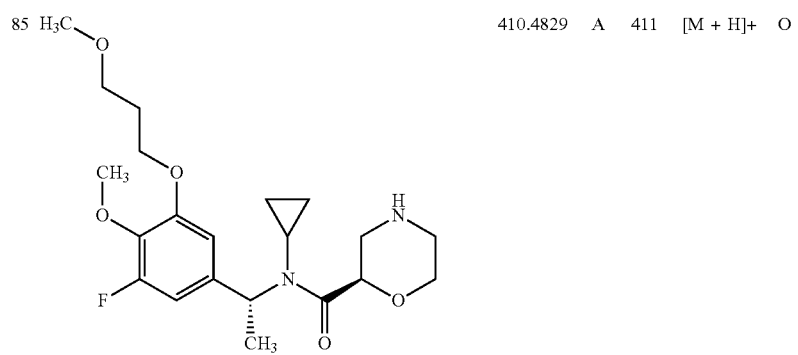 | 410.4829 | A | 411 | [M + H]+ | O |
TABLE 21
| 86 | 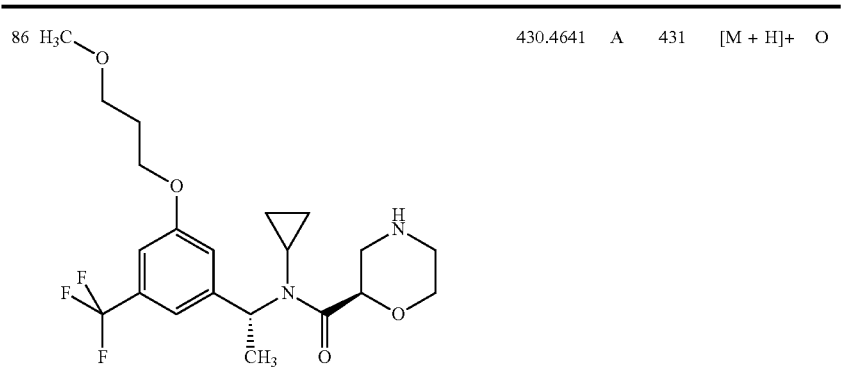 | 430.4641 | A | 431 | [M + H]+ | O |
| 87 | 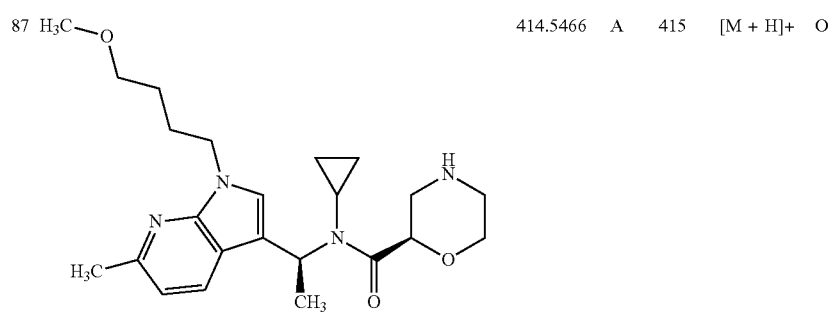 | 414.5466 | A | 415 | [M + H]+ | O |

TABLE 21-continued

| # | Structure | Mass | | m/z | | |
|---|---|---|---|---|---|---|
| 88 | H3C-O-(CH2)3-O-[Br, phenyl fused tetrahydronaphthalene]-N(cyclopropyl)-C(=O)-[morpholine-2-yl, NH] | 467.4009 | A | 467/469 | [M + H]+ | O |

TABLE 22

| # | Structure | Mass | | m/z | | |
|---|---|---|---|---|---|---|
| 89 | CH3-O-(CH2)3-O-[phenyl with OCH3 and Br]-CH(CH3)-N(cyclopropyl)-C(=O)-[morpholine-2-yl, HN] | 471.3889 | C | 471/473 | [M + H]+ | O |
| 90 | CH3-O-(CH2)3-O-[phenyl with OCH3 and Br]-CH(CH3)-N(cyclopropyl)-C(=O)-[morpholine-2-yl, HN] | 471.3889 | C | 471/473 | [M + H]+ | O |
| 91 | H3C-O-(CH2)3-N-[indazole with CH3 and Cl]-CH(CH3)-N(cyclopropyl)-C(=O)-[piperazine-2-yl, HN, NH] | 433.9808 | A | 434/436 | [M + H]+ | O |

TABLE 22-continued
| 92 | 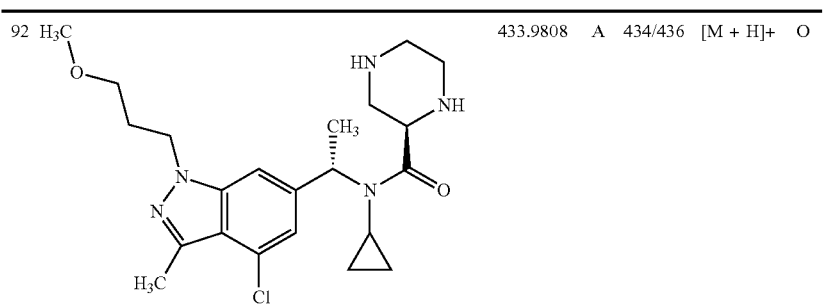 | 433.9808 | A | 434/436 | [M + H]+ | O |
| 93 | 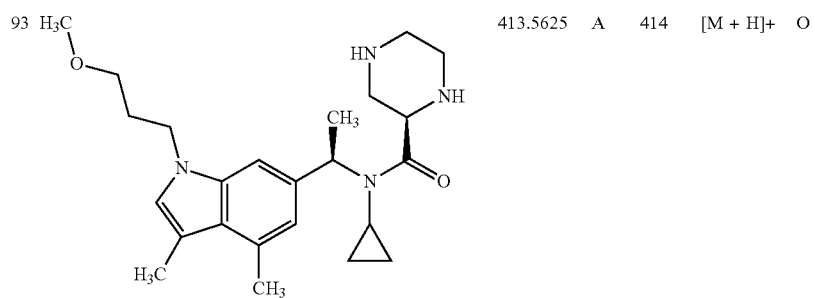 | 413.5625 | A | 414 | [M + H]+ | O |
TABLE 23
| 94 | 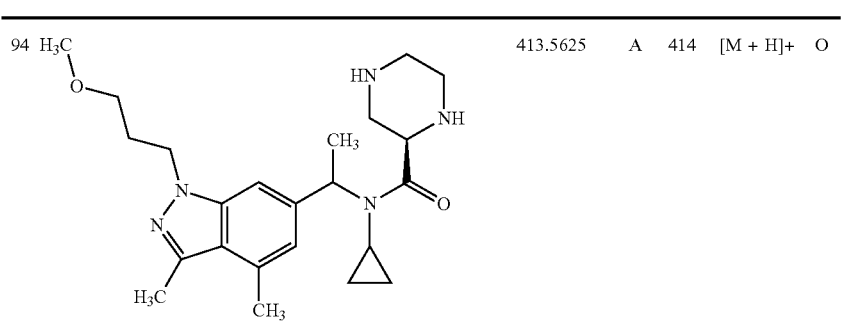 | 413.5625 | A | 414 | [M + H]+ | O |
| 95 | 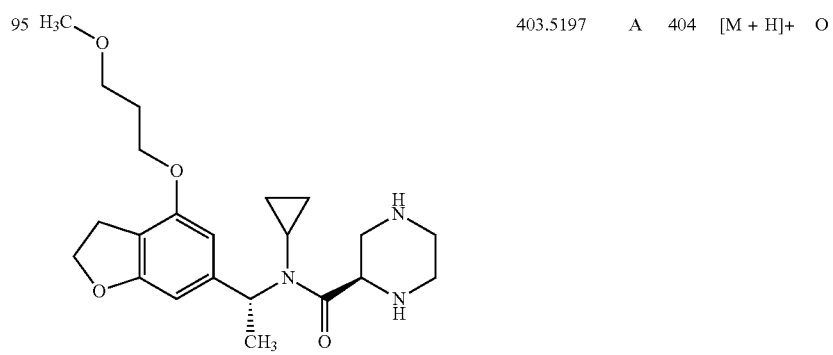 | 403.5197 | A | 404 | [M + H]+ | O |

TABLE 23-continued

| | Structure | MW | Method | MS | |
|---|---|---|---|---|---|
| 96 | (structure) | 403.51971 | A | 404 [M + H]+ | O |
| 97 | (structure) | 400.5198 | C | 401 [M + H]+ | O |

TABLE 24

| | Structure | MW | Method | MS | |
|---|---|---|---|---|---|
| 98 | (structure) | 400.5198 | C | 401 [M + H]+ | O |
| 99 | (structure) | 386.493 | C | 387 [M + H]+ | O |
| 100 | (structure) | 386.493 | C | 387 [M + H]+ | O |

TABLE 24-continued
| | | | | | | |
|---|---|---|---|---|---|---|
| 101 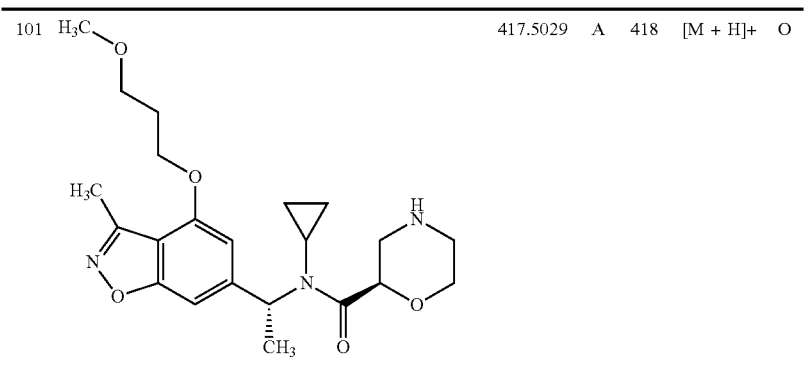 | 417.5029 | A | 418 | [M + H]+ | O |
TABLE 25
| | | | | | | |
|---|---|---|---|---|---|---|
| 102 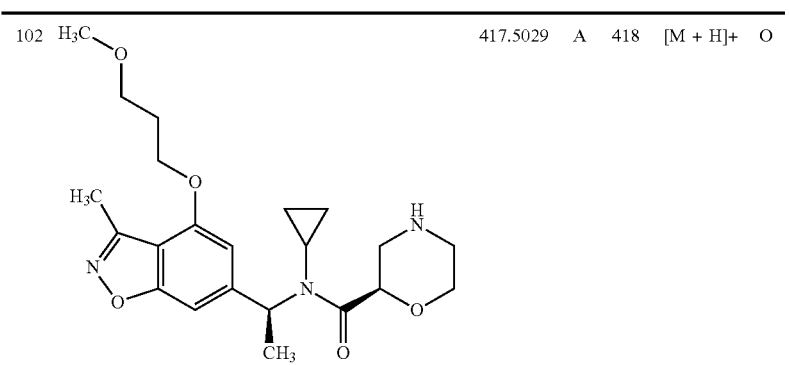 | 417.5029 | A | 418 | [M + H]+ | O |
| 103 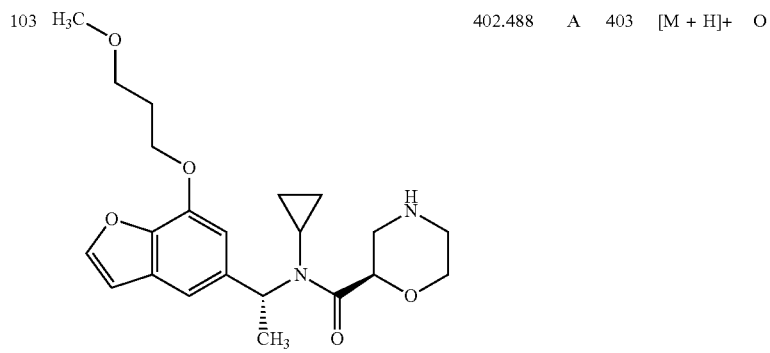 | 402.488 | A | 403 | [M + H]+ | O |
| 104 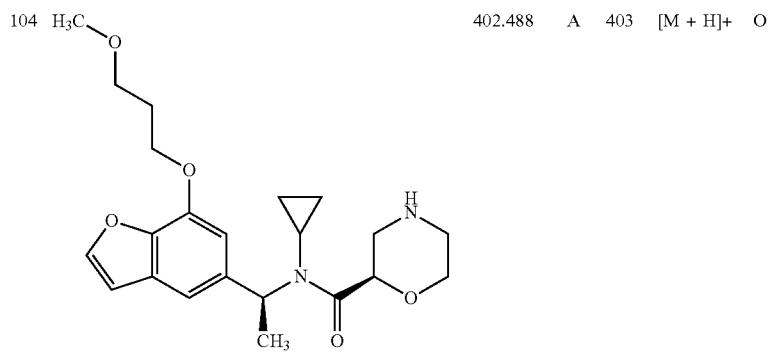 | 402.488 | A | 403 | [M + H]+ | O |

TABLE 25-continued

| | | | | | | |
|---|---|---|---|---|---|---|
| 105 [structure] | 404.5038 | A | 405 | [M + H]+ | O | |

TABLE 26

| | | | | | | |
|---|---|---|---|---|---|---|
| 106 [structure] | 404.5038 | A | 405 | [M + H]+ | O | |
| 107 [structure] | 416.5188 | A | 417 | [M + H]+ | O | |
| 108 [structure] | 416.5188 | A | 417 | [M + H]+ | O | |

TABLE 26-continued

| 109 | [structure: 1-methyl-7-(3-methoxypropoxy)indazole with N-cyclopropyl-morpholine-2-carboxamide, CH3 stereocenter] | | 416.5188 | A | 417 | [M + H]+ | O |
|---|---|---|---|---|---|---|---|

TABLE 27

| 110 | [structure: 1-methyl-7-(3-methoxypropoxy)indazole with N-cyclopropyl-morpholine-2-carboxamide, CH3 stereocenter opposite] | | 416.5188 | A | 417 | [M + H]+ | O |
|---|---|---|---|---|---|---|---|
| 111 | [structure: quinazolin-4(3H)-one with N-cyclopropyl-morpholine-2-carboxamide] | HCl | 378.8578 | B | 343 | [M + H]+ | P |
| 112 | [structure: quinazolin-4(3H)-one with N-cyclopropyl-morpholine-2-carboxamide, opposite stereo] | HCl | 378.8578 | B | 343 | [M + H]+ | P |
| 113 | [structure: 8-methoxy-tetrahydronaphthalen-2-yl N-cyclopropyl-morpholine-2-carboxamide] | | 330.4254 | A | 331 | [M + H]+ | P |

TABLE 28

| # | Structure | Mass | | # | Ion | |
|---|---|---|---|---|---|---|
| 114 | 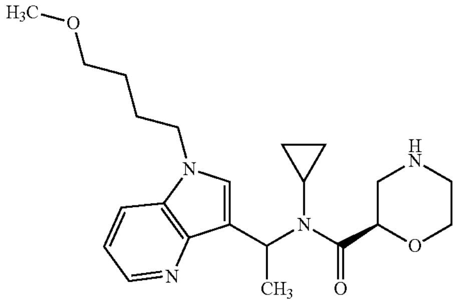 [SMILES: COCCCCn1cc([C@@H](C)N(C(=O)[C@H]2CNCCO2)C2CC2)c2cccnc21] | 400.5198 | A | 401 | [M + H]+ | O |
| 115 | 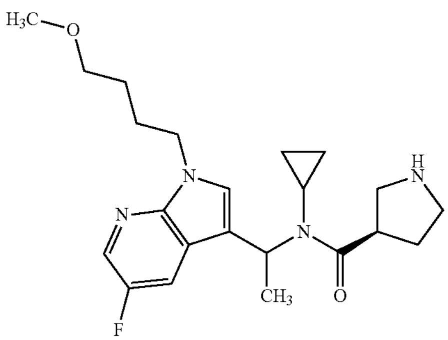 [SMILES: COCCCCn1cc(C(C)N(C(=O)[C@@H]2CCNC2)C2CC2)c2cc(F)cnc21] | 402.5109 | A | 403 | [M + H]+ | O |
| 116 | 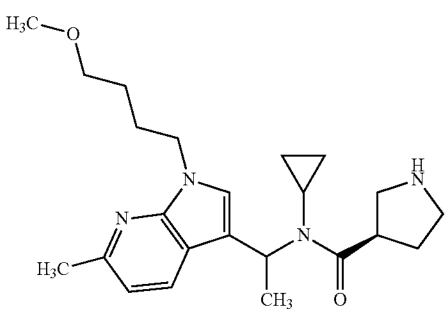 [SMILES: COCCCCn1cc(C(C)N(C(=O)[C@@H]2CCNC2)C2CC2)c2ccc(C)nc21] | 398.5476 | A | 399 | [M + H]+ | O |
| 117 | 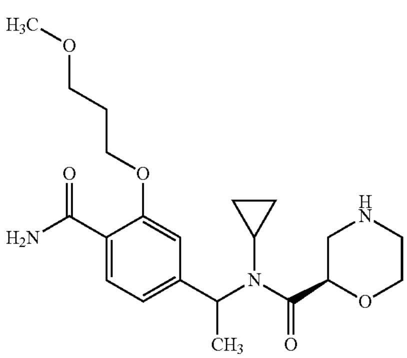 [SMILES: COCCCOc1cc(C(C)N(C(=O)[C@H]2CNCCO2)C2CC2)ccc1C(N)=O] | 405.4919 | C | 406 | [M + H]+ | O |

TABLE 29
| 118 | 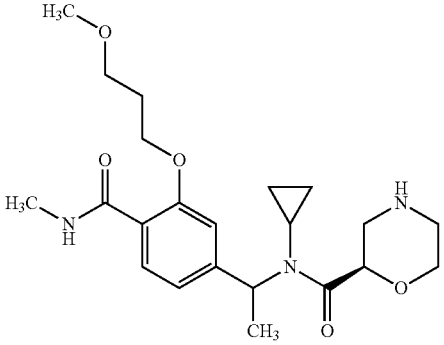 [SMILES: CNC(=O)c1ccc(C(C)N(C(=O)[C@H]2CNCCO2)C2CC2)cc1OCCCOC] | | 419.5187 | C | 420 | [M + H]+ | O |
|---|---|---|---|---|---|---|---|
| 119 | 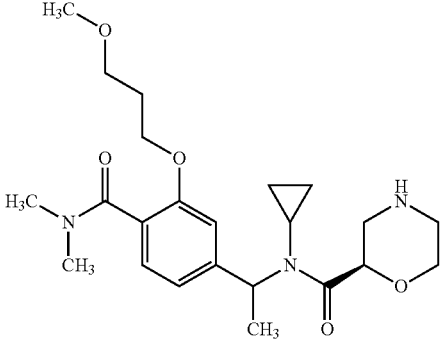 [SMILES: COCCCOc1cc(C(C)N(C(=O)[C@H]2CNCCO2)C2CC2)ccc1C(=O)N(C)C] | | 433.5455 | C | 434 | [M + H]+ | O |
| 120 | 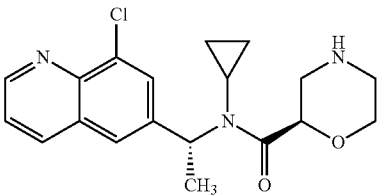 [SMILES: C[C@H](c1cc(Cl)c2ncccc2c1)N(C(=O)[C@H]1CNCCO1)C1CC1] | 2*HCl | 432.7768 | B | 360/362 | [M + H]+ | P |
| 121 | 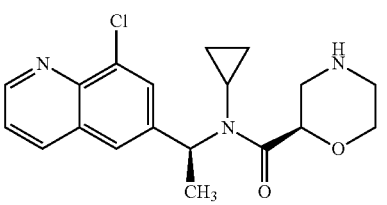 [SMILES: C[C@@H](c1cc(Cl)c2ncccc2c1)N(C(=O)[C@H]1CNCCO1)C1CC1] | 2*HCl | 432.7768 | B | 360/362 | [M + H]+ | P |
TABLE 30
| 122 | 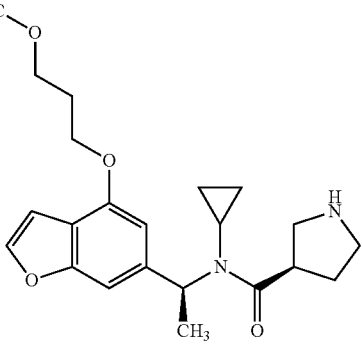 | 386.489 | A | 387 | [M + H]+ | O |
|---|---|---|---|---|---|---|

TABLE 30-continued
| | | | | | | |
|---|---|---|---|---|---|---|
| 123 | 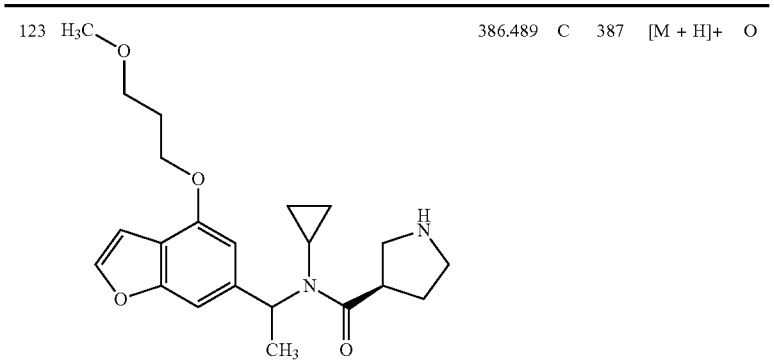 | 386.489 | C | 387 | [M + H]+ | O |
| 124 | 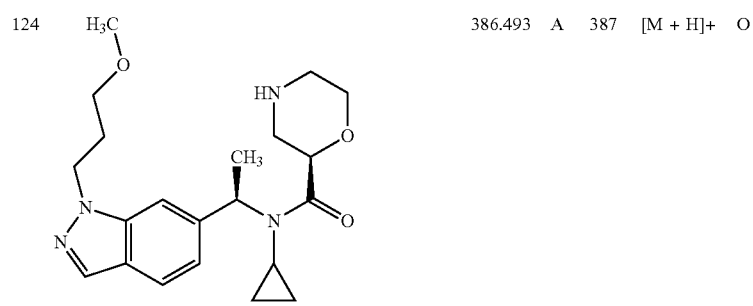 | 386.493 | A | 387 | [M + H]+ | O |
| 125 | 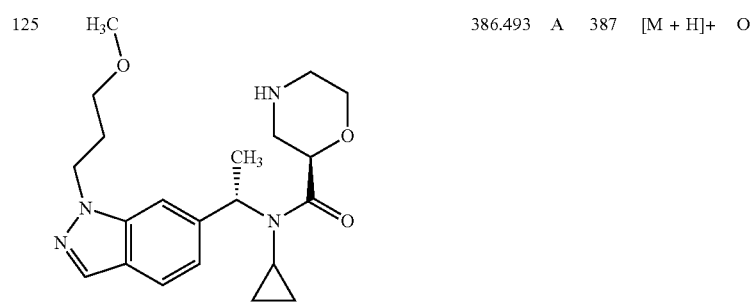 | 386.493 | A | 387 | [M + H]+ | O |
TABLE 31
| | | | | | | |
|---|---|---|---|---|---|---|
| 126 | 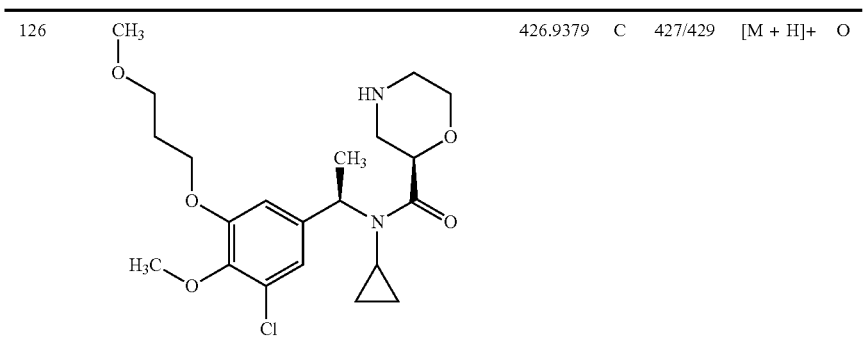 | 426.9379 | C | 427/429 | [M + H]+ | O |

TABLE 31-continued

| # | Structure | MW | C | MS | Ion | O |
|---|---|---|---|---|---|---|
| 127 | (3-methoxypropoxy, 4-methoxy, 5-chloro phenyl)-CH(CH3)-N(cyclopropyl)-C(O)-morpholine(NH) | 426.9379 | C | 427/429 | [M + H]+ | O |
| 128 | 1-(4-methoxybutyl)-pyrazolo[3,4-b]pyridin-3-yl-CH(CH3)-N(cyclopropyl)-C(O)-morpholine(NH) | 401.5079 | C | 402 | [M + H]+ | O |
| 129 | 1-(4-methoxybutyl)-pyrazolo[3,4-b]pyridin-3-yl-C*H(CH3)-N(cyclopropyl)-C(O)-morpholine(NH) | 401.5079 | C | 402 | [M + H]+ | O |

TABLE 32

| # | Structure | MW | C | MS | Ion | O |
|---|---|---|---|---|---|---|
| 130 | 1-(4-methoxybutyl)-indazol-3-yl-CH(CH3)-N(cyclopropyl)-C(O)-pyrrolidin-3-yl | 384.5208 | C | 385 | [M + H]+ | O |
| 131 | 1-(4-methoxybutyl)-indazol-3-yl-CH(CH3)-N(cyclopropyl)-C(O)-pyrrolidin-3-yl | 384.5208 | C | 385 | [M + H]+ | O |

TABLE 32-continued
| 132 | 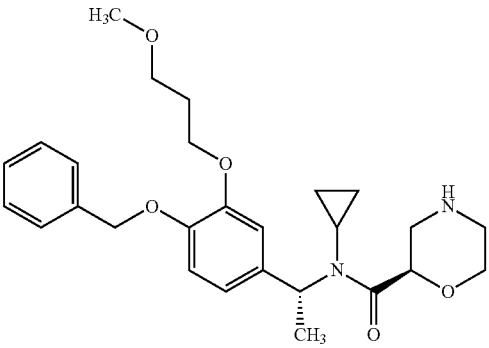 [SMILES: COCCCOc1cc([C@@H](C)N(C(=O)[C@H]2CNCCO2)C2CC2)ccc1OCc1ccccc1] | 468.5904 | A | 469 | [M + H]+ | O |
| 133 | 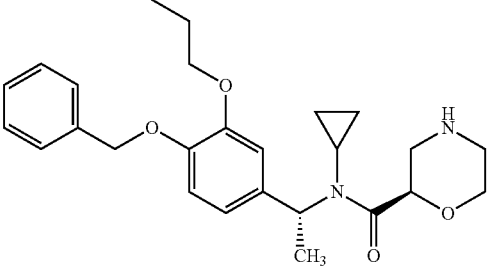 | 495.6203 | A | 496 | [M + H]+ | O |
TABLE 33
| 134 | 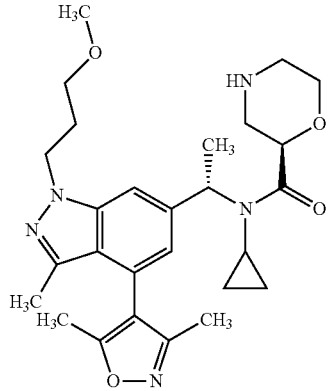 [SMILES: COCCCn1nc(C)c2c(-c3c(C)noc3C)cc([C@H](C)N(C(=O)[C@H]3CNCCO3)C3CC3)cc21] | 495.6203 | A | 496 | [M + H]+ | O |
| 135 | 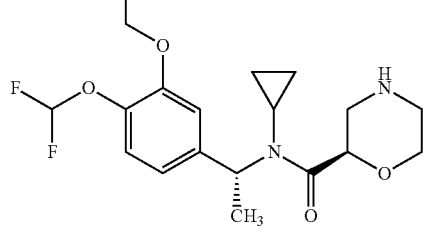 | 428.473 | C | 429 | [M + H]+ | O |

TABLE 33-continued

| # | Structure | Mass | | MS | | |
|---|---|---|---|---|---|---|
| 136 | (1-(3-methoxypropyl)-1H-pyrrolo[3,2-c]pyridin-6-yl)ethyl-N-cyclopropyl-morpholine-2-carboxamide | 386.493 | A | 387 | [M + H]+ | O |
| 137 | (1-(3-methoxypropyl)-3-chloro-1H-pyrrolo[3,2-c]pyridin-6-yl)ethyl-N-cyclopropyl-morpholine-2-carboxamide | 420.9381 | A | 421/423 | [M + H]+ | O |

TABLE 34

| # | Structure | Mass | | MS | | |
|---|---|---|---|---|---|---|
| 138 | (1-(3-methoxypropyl)-3-chloro-1H-pyrrolo[3,2-c]pyridin-6-yl)ethyl-N-cyclopropyl-morpholine-2-carboxamide | 420.9381 | A | 421/423 | [M + H]+ | O |
| 139 | 3-(4-methoxybutyl)-4-methoxyphenyl ethyl-N-cyclopropyl-morpholine-2-carboxamide | 390.5206 | A | 391 | [M + H]+ | O |
| 140 | (1-(3-methoxypropyl)-3-methyl-1H-pyrrolo[3,2-c]pyridin-6-yl)ethyl-N-cyclopropyl-morpholine-2-carboxamide | 400.5198 | A | 401 | [M + H]+ | O |

TABLE 34-continued
| 141 |  | 404.4831 | A | 405 | [M + H]+ | O |
TABLE 35
| 142 |  | 404.4831 | A | 405 | [M + H]+ | O |
| 143 |  | 399.5357 | A | 400 | [M + H]+ | O |
| 144 |  | 414.503 | C | 415 | [M + H]+ | O |

TABLE 35-continued
| | | | | | | |
|---|---|---|---|---|---|---|
| 145 |  | 414.503 | C | 415 | [M + H]+ | O |
TABLE 36
| | | | | | | |
|---|---|---|---|---|---|---|
| 146 |  | 386.493 | A | 387 | [M + H]+ | O |
| 147 |  | 416.5188 | C | 417 | [M + H]+ | O |
| 148 |  | 416.5188 | C | 417 | [M + H]+ | O |

TABLE 36-continued
| 149 | 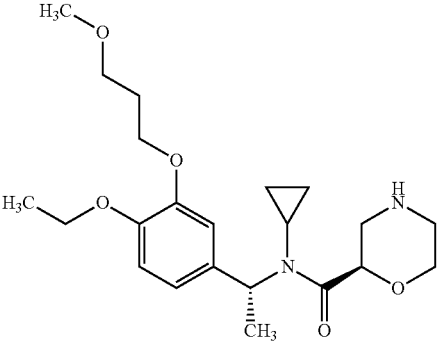 [SMILES: CCOc1ccc([C@@H](C)N(C(=O)[C@H]2CNCCO2)C2CC2)cc1OCCCOC] | 406.5196 | A | 407 | [M + H]+ | O |
TABLE 37
| 150 | 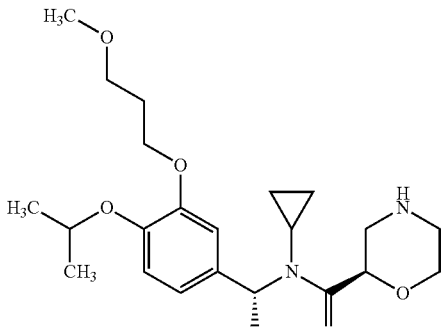 | 420.5464 | A | 421 | [M + H]+ | O |
| 151 | 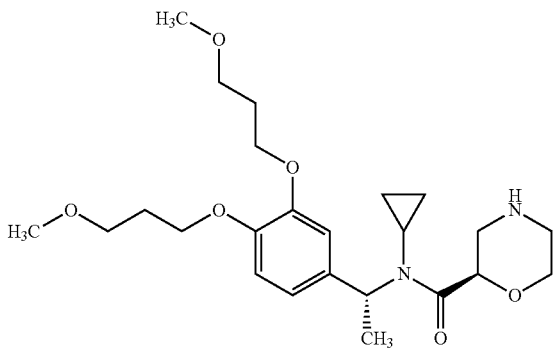 [SMILES: COCCCOc1ccc([C@@H](C)N(C(=O)[C@H]2CNCCO2)C2CC2)cc1OCCCOC] | 450.5722 | A | 451 | [M + H]+ | O |
| 152 | 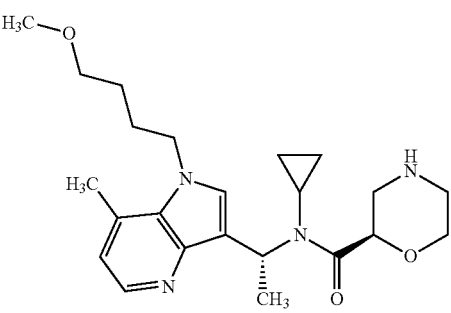 [SMILES: COCCCCn1cc([C@@H](C)N(C(=O)[C@H]2CNCCO2)C2CC2)c2nccc(C)c21] | 414.5466 | A | 415 | [M + H]+ | O |

TABLE 37-continued
| 153 |  | 414.5466 | A | 415 | [M + H]+ | O |
TABLE 38
| 154 | 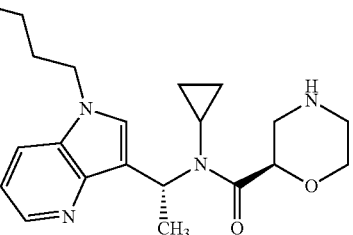 | 400.5145 | A | 401 | [M + H]+ | O |
| 155 | 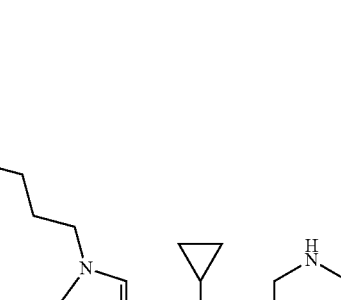 | 400.5145 | A | 401 | [M + H]+ | O |
| 156 | 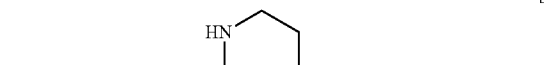 | 429.5126 | C | 430 | [M + H]+ | O |

TABLE 38-continued

| 157 | [structure: methyl carbamate-NH-propyl-indazole(6-F)-CH(CH3)-N(cyclopropyl)-C(O)-morpholine(NH)] | 447.5031 | C | 448 | [M + H]+ | O |

TABLE 39

| 158 | [structure: methyl carbamate-NH-propyl-indazole(6-F)-CH(CH3)-N(cyclopropyl)-C(O)-morpholine(NH)] | 447.5031 | C | 448 | [M + H]+ | O |
| 159 | [structure: H3C-O-propyl-pyrrolopyridine(3-CH3)-CH(CH3)-N(cyclopropyl)-C(O)-morpholine(NH)] | 400.5198 | A | 401 | [M + H]+ | O |
| 160 | [structure: H3C-O-propyl-pyrrolopyridine(3-CH3)-CH(CH3)-N(cyclopropyl)-C(O)-morpholine(NH)] | 400.5198 | A | 401 | [M + H]+ | O |

Ex. No.: Example Number
a: Salt
b: Method
C: MS Results APCI d: Ion species
e: Form
O: Oil
P: Powder

Example 161 tert-Butyl (2R)-2-[(cyclopropyl{1-[4-(3-methoxy-propoxy)-1-benzofuran-6-yl]ethyl}amino)-carbonyl]morpholine-4-carboxylate [Ex(161-1)]

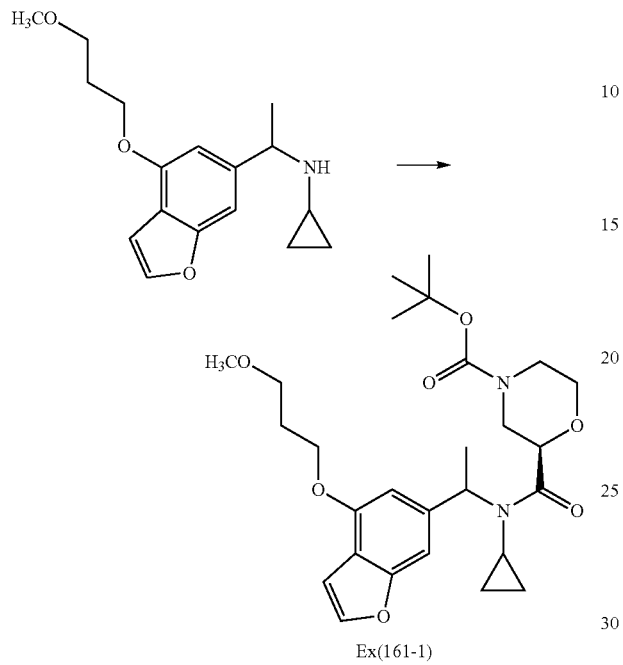

Ex(161-1)

To a solution of N-{1-[4-(3-methoxypropoxy)-1-benzofuran-6-yl]ethyl}-cyclopropanamine (200 mg) and (2R)-4-(tert-butoxycarbonyl)morpholine-2-carboxylic acid (240 mg) in N,N-dimethylformamide (7 mL) were added 1-ethyl-3-(3-dimethylaminopropyl)carbodiimide hydrochloride (212 mg) and 1-hydroxybenzotriazole (140 mg) under ice-cooling, and then stirred at room temperature for 18 hours. To the reaction mixture was added aqueous saturated sodium hydrogen carbonate solution, and the mixture was extracted with ethyl acetate. The organic layer was sequentially washed with water, 10% aqueous citric acid solution and saturated saline, and then concentrated under reduced pressure to give tert-butyl (2R)-2-[(cyclopropyl {1-[4-(3-methoxypropoxy)-1-benzofuran-6-yl]ethyl}amino)carbonyl]morpholine-4-carboxylate [Ex(161-1)] (306 mg) as a yellow oil.

APCI-MS m/z: 503 [M+H]$^+$.

Example 162 tert-Butyl (2R)-2-[(cyclopropyl{1-[1-(3-methoxy-propyl)-3-methyl-1H-indazol-6-yl]ethyl}amino)-carbonyl]morpholine-4-carboxylate [Ex(162-1), Ex(162-2)]

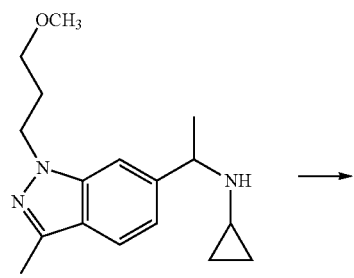

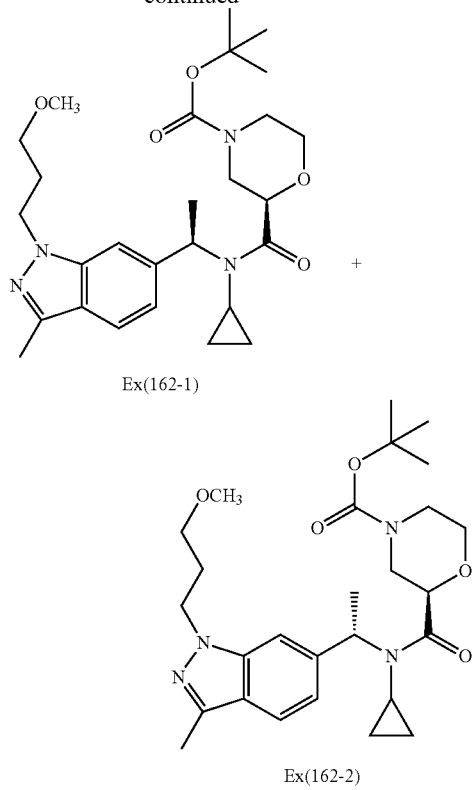

Ex(162-1)

Ex(162-2)

To a solution of N-{1-[1-(3-methoxypropyl)-3-methyl-1H-indazol-6-yl]ethyl}-cyclopropanamine (2.63 g) and (2R)-4-(tert-butoxycarbonyl)morpholine-2-carboxylic acid (2.32 g) in N,N-dimethylformamide (25 mL) were added 1-hydroxybenzotriazole (1.36 g) and 1-ethyl-3-(3-dimethylaminopropyl)carbodiimide hydrochloride (2.11 g) under ice-cooling, and then the mixture was stirred at room temperature for 3 hours. To the reaction mixture was added ethyl acetate, and the mixture was washed with saturated saline, dried over magnesium sulfate, and then concentrated under reduced pressure. The resulting residue was purified by silica gel column chromatography (eluent: n-hexane/ethyl acetate/methanol=30/3/1→9/3/1) to give tert-butyl (2R)-2-[(cyclopropyl {(1R)-1-[1-(3-methoxypropyl)-3-methyl-1H-indazol-6-yl]ethyl}amino)carbonyl]morpholine-4-carboxylate [Ex(162-1)] (1.71 g) and tert-butyl (2R)-2-[(cyclopropyl {(1S)-1-[1-(3-methoxypropyl)-3-methyl-1H-indazol-6-yl]ethyl}amino)carbonyl]morpholine-4-carboxylate [Ex(162-2)] (468 mg) as a colorless oil.

APCI-MS m/z: 435 [M+H]$^+$.

Example 163 tert-Butyl (2R)-2-({cyclopropyl[1-(2-naphthyl)ethyl]amino}carbonyl)morpholine-4-carboxylate [Ex(163-1)]

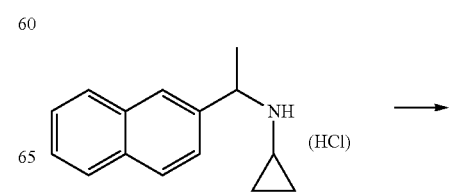

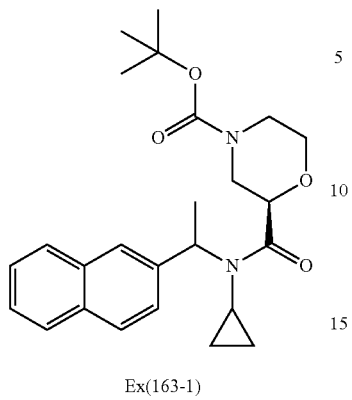

Ex(163-1)

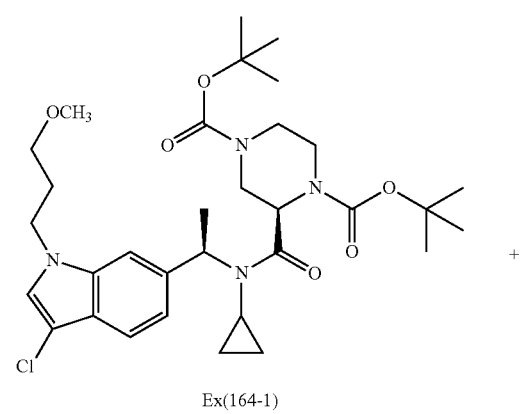

Ex(164-1)

To a solution of N-[1-(2-naphthyl)ethyl]cyclopropylamine hydrochloride (149 mg), (2R)-4-(tert-butoxycarbonyl) morpholine-2-carboxylic acid (208 mg) and 1-hydroxybenzotriazole (122 mg) in N,N-dimethylformamide (6 mL) was added diisopropylethylamine (0.125 µL), and the thereto was added 1-ethyl-3-(3-dimethylaminopropyl)carbodiimide hydrochloride (207 mg) under ice-cooling. The mixture was stirred at room temperature for 19 hours, and then to the reaction solution was added 1-normal aqueous sodium hydrogen carbonate solution, and the mixture was extracted with ethyl acetate. The organic layer was sequentially washed with water twice, saturated saline, dried over sodium sulfate, and then concentrated under reduced pressure. The residue was triturated with n-hexane-diethyl ether (5:1) to give tert-butyl (2R)-2-(cyclopropyl[1-(2-naphthyl)ethyl] amino carbonyl)morpholine-4-carboxylate [Ex(163-1)] (153 mg) as a colorless powder.

APCI-MS m/z: 425 [M+H]$^+$.

Example 164

Di-tert-butyl (2R)-2-{[{1-[3-chloro-1-(3-methoxypropyl)-1H-indol-6-yl]ethyl}(cyclopropyl)-amino] carbonyl}piperazine-1,4-dicarboxylate [Ex(164-1), Ex(164-2)]

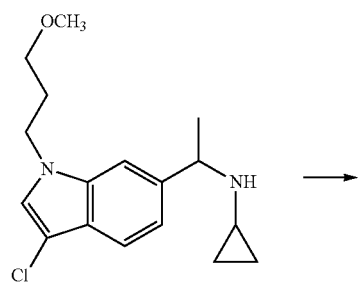

→

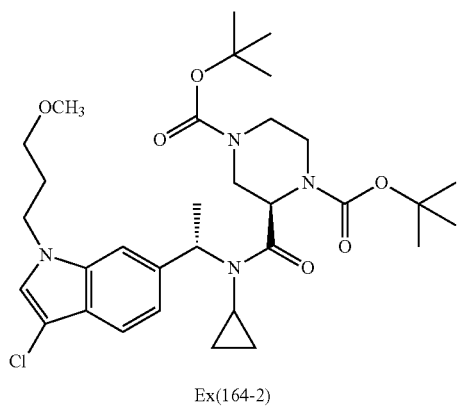

Ex(164-2)

To a solution of N-{1-[3-chloro-1-(3-methoxypropyl)-1H-indol-6-yl]ethyl}-cyclopropanamine (60 mg) and piperazinecarboxylic acid (77.5 mg) in dichloromethane (2 mL) were added diisopropylethylamine (0.085 mL) and diphenyl phosphorochloridate (0.037 mL) under ice-cooling, and the mixture was stirred at room temperature for 20 hours. To the reaction solution was added 0.5% aqueous hydrochloric acid solution under ice-cooling, and the mixture was extracted with ethyl acetate. The organic layer was washed with saturated saline, dried over magnesium sulfate, and then concentrated under reduced pressure. The resulting residue was purified by silica gel column chromatography (eluent: n-hexane/ethyl acetate=99/1→2/1) to give di-tert-butyl (2R)-2-{[{(1R)-1-[3-chloro-1-(3-methoxypropyl)-1H-indol-6-yl]ethyl}(cyclopropyl)amino]carbonyl}piperazine-1, 4-dicarboxylate [Ex(164-1)] (47.5 mg) and di-tert-butyl (2R)-2-{[{(1S)-1-[3-chloro-1-(3-methoxypropyl)-1H-indol-6-yl]ethyl}-(cyclopropyl)amino]carbonyl}piperazine-1,4-dicarboxylate [Ex(164-2)] (26.8 mg) as a colorless oil.

APCI-MS m/z: 636/638 [M+H]$^+$.

Example 165

Di-tert-butyl (2R)-2-[(cyclopropyl{1-[1-(3-methoxypropyl)-3,4-dimethyl-1H-indazol-6-yl]-ethyl}amino]carbonyl}piperazine-1,4-dicarboxylate [Ex(165-1), EX(165-2)]

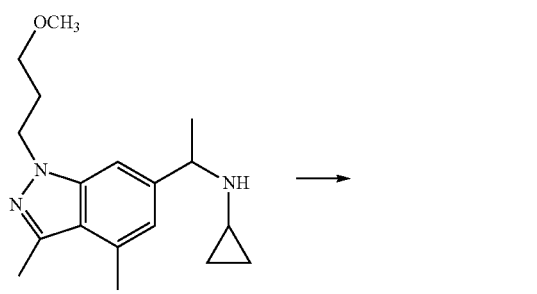

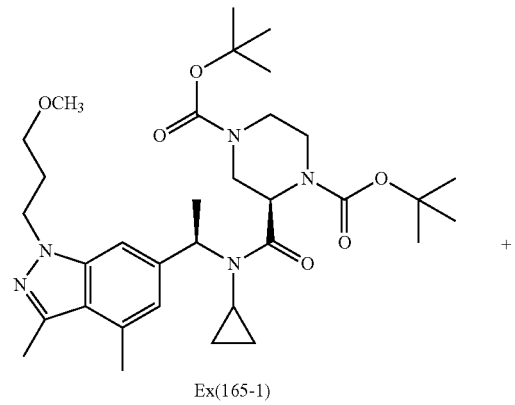

Ex(165-1)

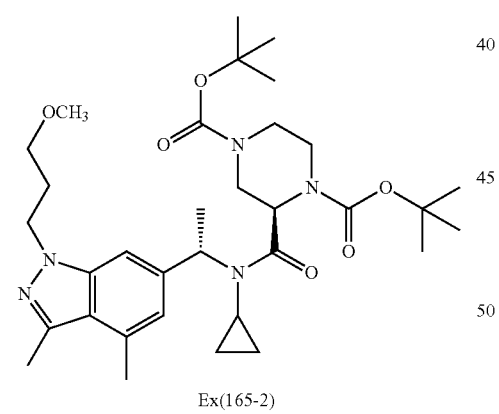

Ex(165-2)

To a solution of N-{1-[1-(3-methoxypropyl)-3,4-dimethyl-1H-indazol-6-yl]ethyl}cyclopropanamine (137 mg) and piperazinecarboxylic acid (180 mg) in dichloromethane (2.5 mL) were added diisopropylethylamine (0.20 mL) and bis(2-oxo-3-oxazolidinyl)phosphinic chloride (150 mg) under ice-cooling, and the mixture was stirred at room temperature for 15 hours. To the reaction solution was added water under ice-cooling, and the mixture was extracted with ethyl acetate. The organic layer was washed with saturated saline, dried over magnesium sulfate, and then concentrated under reduced pressure. The resulting residue was purified by silica gel column chromatography (eluent: n-hexane/ethyl acetate=2/1→4/1) to give di-tert-butyl (2R)-2-[(cyclopropyl{(1R)-1-[1-(3-methoxypropyl)-3,4-dimethyl-1H-indazol-6-yl]ethyl}amino]carbonyl}piperazine-1,4-dicarboxylate [Ex(165-1)] (45.6 mg) and di-tert-butyl (2R)-2-[(cyclopropyl{(1S)-1-[1-(3-methoxypropyl)-3,4-dimethyl-1H-indazol-6-yl]ethyl}-amino]carbonyl}piperazine-1,4-dicarboxylate [Ex(165-2)] (53.8 mg) as a colorless oil.

APCI-MS m/z: 614 [M+H]$^+$.

Example 166 tert-Butyl tert-butyl 2-[(cyclopropyl {1-[7-(3-methoxypropoxy)-2,3-dihydro-1-benzofuran-5-yl]-ethyl}amino)carbonyl]morpholine-4-carboxylate [Ex(166-1)]

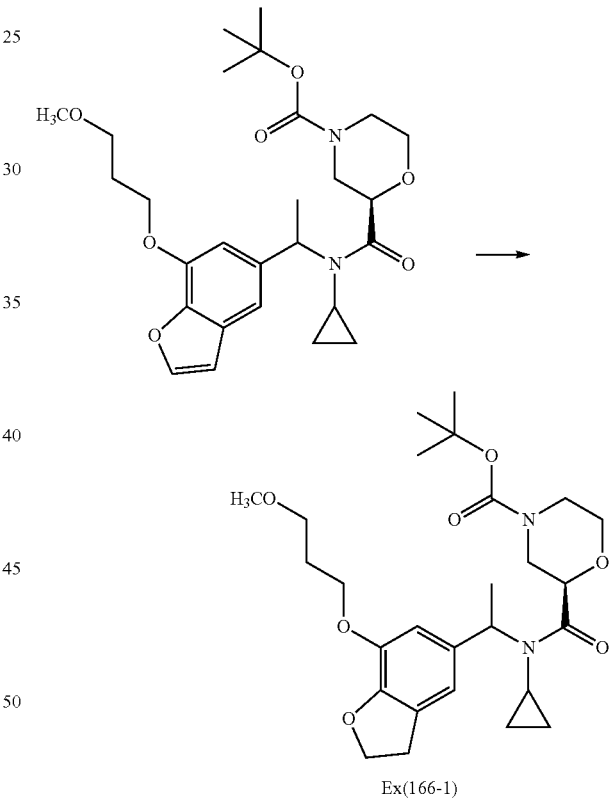

Ex(166-1)

To a solution of tert-butyl (2R)-2-[(cyclopropyl {1-[7-(3-methoxypropoxy)-1-benzofuran-5-yl]ethyl}amino)carbonyl]morpholine-4-carboxylate (200 mg) in ethanol (5.0 mL) was added 20% palladium hydroxide on carbon (100 mg), and the mixture was stirred under hydrogen for 5 hours. An insoluble was filtered, and then concentration under reduced pressure gave tert-butyl tert-butyl 2-[(cyclopropyl {1-[7-(3-methoxypropoxy)-2,3-dihydro-1-benzofuran-5-yl]ethyl}amino)carbonyl]morpholine-4-carboxylate [Ex(166-1)] (193 mg) as a colorless oil.

APCI-MS m/z: 505 [M+H]$^+$.

Example 167 tert-Butyl (2R)-2-[[(1R)-5-bromo-6-(3-methoxypropoxy)-2,3-dihydro-1H-inden-1-yl]-(cyclopropyl)amino)carbonyl]morpholine-4-carboxylate [Ex(167-1)]

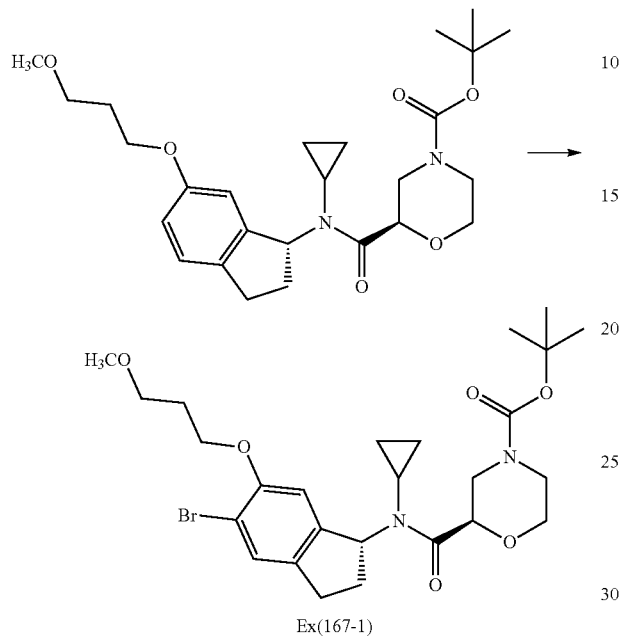

Ex(167-1)

To a suspension of N-bromosuccinimide (23.4 mg) in dichloromethane (0.5 mL) was added dropwise a solution of tert-butyl (2R)-2-({cyclopropyl[(1R)-6-(3-methoxypropoxy)-2,3-dihydro-1H-inden-1-yl]amino)carbonyl]morpholine-4-carboxylate (62.4 mg) in dichloromethane (1.5 mL) under ice-cooling, and the mixture was stirred for 5 hours. The reaction solution was concentrated under reduced pressure, and the resulting residue was dissolved in ethyl acetate, and then sequentially washed with 1-normal aqueous sodium hydrogen carbonate solution, saturated saline, dried over sodium sulfate, and then concentrated under reduced pressure to give a crude product of tert-butyl (2R)-2-{[[(1R)-5-bromo-6-(3-methoxypropoxy)-2,3-dihydro-1H-inden-1-yl](cyclopropyl)amino)carbonyl]morpholine-4-carboxylate [Ex(167-1)] (74 mg) as a yellow oil.
APCI-MS m/z: 553/555 [M+H]⁺.

Example 168 tert-Butyl (2R)-2-[(cyclopropyl{(1R)-1-[4-(3-methoxypropyl)quinazolin-2-yl]ethyl}amino)-carbonyl]morpholin-4-carboxylate [Ex(168-1)]

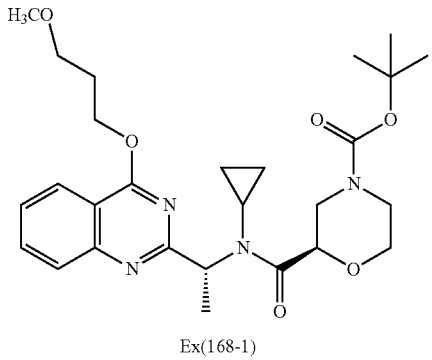

Ex(168-1)

To a solution of tert-butyl (2R)-2-({cyclopropyl[(1R)-1-(4-oxo-3,4-dihydroquinazolin-2-yl)ethyl]amino}carbonyl)morpholin-4-carboxylate (88 mg), 3-methoxy-1-propanol (36 mg) and triphenylphosphine (105 mg) in tetrahydrofuran (4 mL) was added dropwise diisopropyl azodicarboxylate (84 μL) under ice-cooling, and the mixture was stirred at room temperature for 19 hours. The reaction solution was concentrated, and the resulting residue was purified by silica gel column chromatography (eluent: n-hexane/ethyl acetate=2/1→1/2) to give tert-butyl (2R)-2-[(cyclopropyl{(1R)-1-[4-(3-methoxypropyl)quinazolin-2-yl]ethyl}amino)carbonyl]morpholin-4-carboxylate [Ex(168-1)] (38 mg) as a colorless oil.
APCI-MS m/z: 515 [M+H]⁺.

Example 169 tert-Butyl (2R)-2-[(cyclopropyl{(1R)-1-[4-ethoxy-3-(3-methoxypropoxy)phenyl]ethyl}amino)-carbonyl]morpholin-4-carboxylate [Ex(169-2)]

(1)

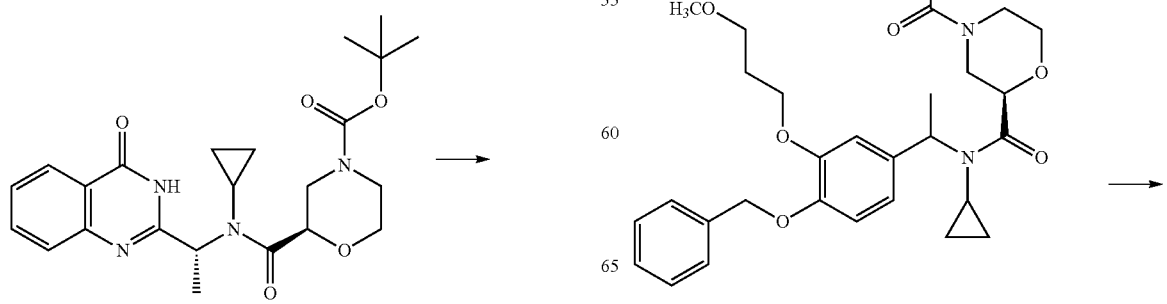

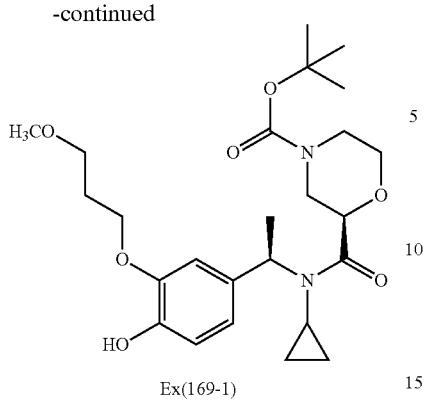

Ex(169-1)

concentrated under reduced pressure. The resulting residue was purified by NH-silica gel column chromatography (eluent: n-hexane/ethyl acetate=10/1→2/1) to give tert-butyl (2R)-2-[(cyclopropyl{(1R)-1-[4-ethoxy-3-(3-methoxypropoxy)phenyl]ethyl}amino)carbonyl]morpholin-4-carboxylate [Ex(169-2)] (60 mg) as a colorless oil.

APCI-MS m/z: 507 [M+H]$^+$.

Example 170

Methyl {3-[3-(1-{cyclopropyl[(2R)-morpholin-2-ylcarbonyl]amino}ethyl)-1H-indazol-1-yl]-propyl}carbamate [Ex(170-2)]

To a solution of tert-butyl (2R)-2-{[{1-[4-(benzyloxy)-3-(3-methoxypropoxy)phenyl]-ethyl}(cyclopropyl)amino]carbonyl}morpholin-4-carboxylate (1.45 g) in methanol (12 mL) was added 10% palladium on carbon (200 mg), and the mixture was stirred under hydrogen for 2 hours. An insoluble was filtered, and then concentrated under reduced pressure. The resulting residue was purified by silica gel column chromatography (eluent: n-hexane/ethyl acetate=2/1→1/2) to give tert-butyl (2R)-2-[(cyclopropyl{(1R)-1-[4-hydroxy-3-(3-methoxypropoxy)phenyl]ethyl}amino)carbonyl]morpholin-4-carboxylate [Ex(169-1)] (913 mg) as a colorless oil.

(2) Titled Compound [Ex(169-2)]

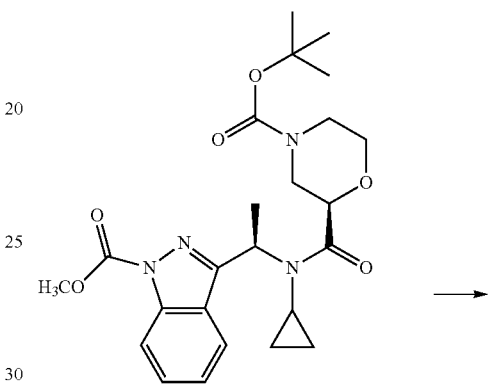

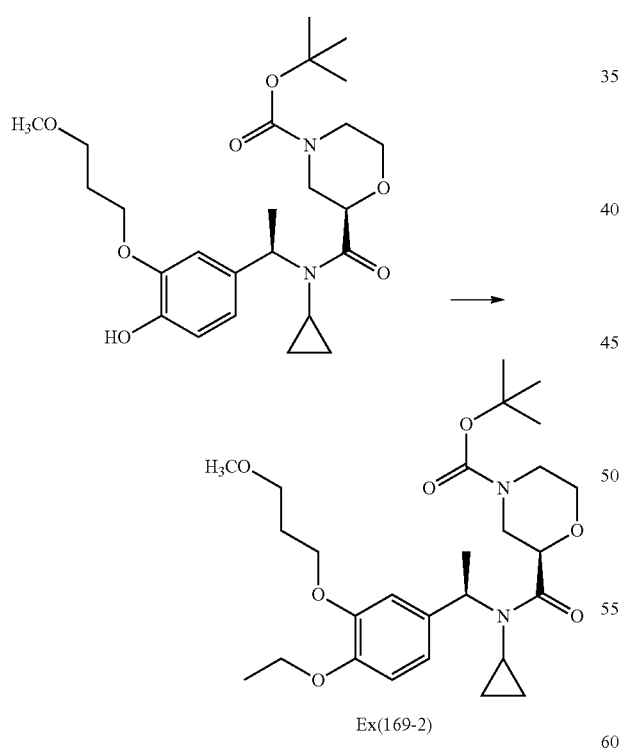

Ex(169-2)

To a solution of the compound obtained in the above (1) (100 mg) in acetonitrile (1.0 mL) were added potassium carbonate (34.7 mg) and iodoethane (35.8 mg), and the mixture was heated to reflux for 20 hours. The reaction solution was cooled to room temperature, and then diluted with ethyl acetate. An insoluble was filtered, and then

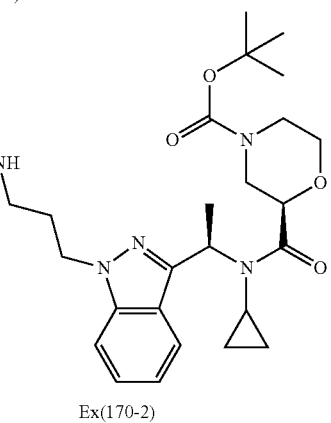

Ex(170-2)

(1) To a solution of methyl 3-{1-[{[(2R)-4-(tert-butoxycarbonyl)morpholin-2-yl]carbonyl}-(cyclopropyl)amino]ethyl}-1H-indazole-1-carboxylate (695 mg) in methanol (10 mL) was added potassium carbonate (407 mg), and the mixture was stirred at room temperature for 30 minutes. The reaction solution was concentrated, and then thereto was added ethyl acetate, and the mixture was washed with aqueous saturated sodium chloride solution. The organic layer was dried over magnesium sulfate, and then concentrated under reduced pressure to give tert-butyl (2R)-2-({cyclopropyl[1-(1-{3-[(methoxycarbonyl)amino]propyl}-1H-indazol-3-yl)-ethyl]amino}carbonyl)morpholine-4-carboxylate [Ex(170-1)] (577 mg) as a colorless powder.

APCI-MS m/z: 415 [M+H]$^+$.

(2) To a solution of the compound obtained in (1) (90 mg) and methyl (3-bromopropyl)carbamate (64 mg) in N,N-dimethylformamide (2 mL) was added potassium carbonate (60 mg), and the mixture was stirred at room temperature for 18 hours. To the reaction solution was added ethyl acetate, and the mixture was washed with aqueous saturated sodium chloride solution, dried over magnesium sulfate, and then concentrated under reduced pressure. The resulting residue was purified by silica gel column chromatography (eluent: n-hexane/ethyl acetate=1/20→1/1) to give methyl {3-[3-(1-{cyclopropyl[(2R)-morpholin-2-ylcarbonyl]amino}ethyl)-1H-indazol-1-yl]propyl}carbamate [Ex(170-2)] (74 mg) as a yellow oil.

Examples 171 to 267

The following N-protected nitrogen-containing saturated heterocyclic compounds were prepared in the similar manner to the above Examples 161 to 169. Each symbol of Methods A to C refers to each method according to the following method of Examples.

Method A: Examples 161 to 163
Method B: Example 164
Method C: Example 165
Method D: Example 166
Method E: Example 167
Method F: Example 168
Method G: Example 169

TABLE 40

| EX. No. | Structure | a | b | c | d | e |
|---|---|---|---|---|---|---|
| 171 | 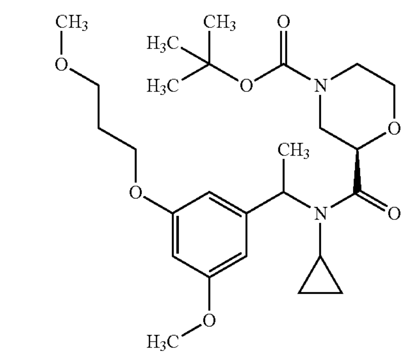 [SMILES: COCCCOc1cc(OC)cc(C(C)N(C(=O)[C@H]2CN(C(=O)OC(C)(C)C)CCO2)C2CC2)c1] | 492.609 | O | 493 | [M + H]+ | A |
| 172 | 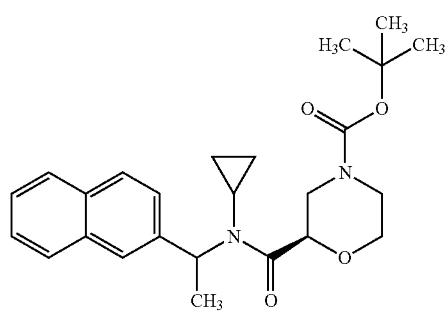 [SMILES: CC(c1ccc2ccccc2c1)N(C(=O)[C@H]1CN(C(=O)OC(C)(C)C)CCO1)C1CC1] | 424.5378 | P | 425 | [M + H]+ | A |
| 173 | 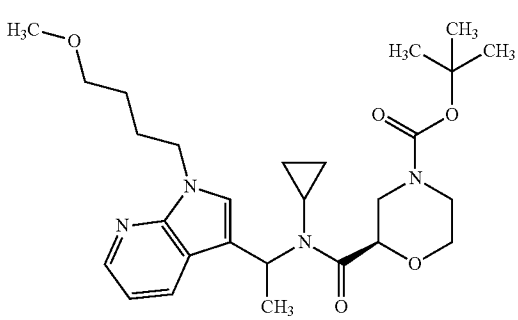 [SMILES: COCCCCn1cc(C(C)N(C(=O)[C@H]2CN(C(=O)OC(C)(C)C)CCO2)C2CC2)c2cccnc21] | 500.636 | O | 501 | [M + H]+ | A |

TABLE 40-continued

| EX. No. | Structure | a | b | c | d | e |
|---|---|---|---|---|---|---|
| 174 | 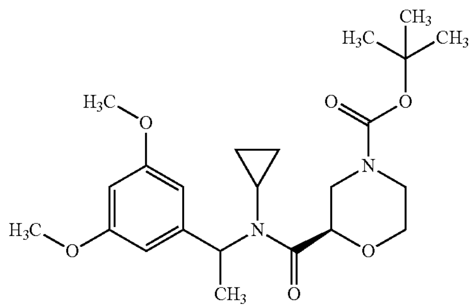 [SMILES: COc1cc(OC)cc(C(C)N(C(=O)[C@H]2CN(C(=O)OC(C)(C)C)CCO2)C2CC2)c1] | 434.5296 | O | 435 | [M + H]+ | A |

TABLE 41

| | | a | b | c | d | e |
|---|---|---|---|---|---|---|
| 175 | | 448.5564 | O | 449 | [M + H]+ | A |
| 176 | | 434.5296 | O | 435 | [M + H]+ | A |
| 177 | | 500.636 | O | 501 | [M + H]+ | A |

TABLE 41-continued
| 178 | 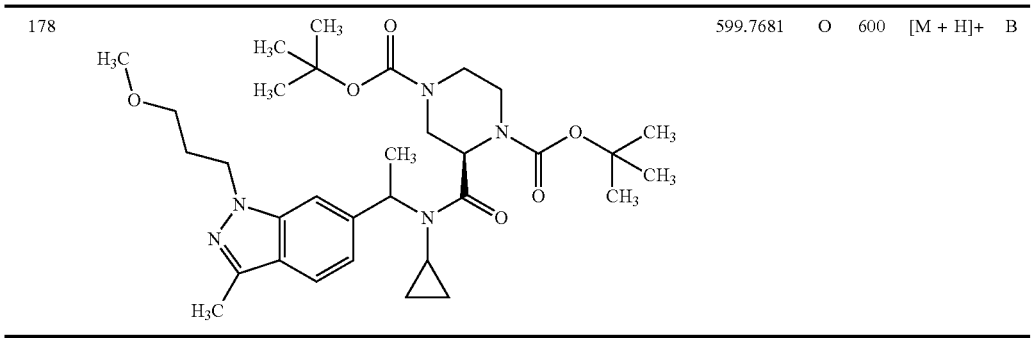 | 599.7681 | O | 600 | [M + H]+ | B |
TABLE 42
| 179 | 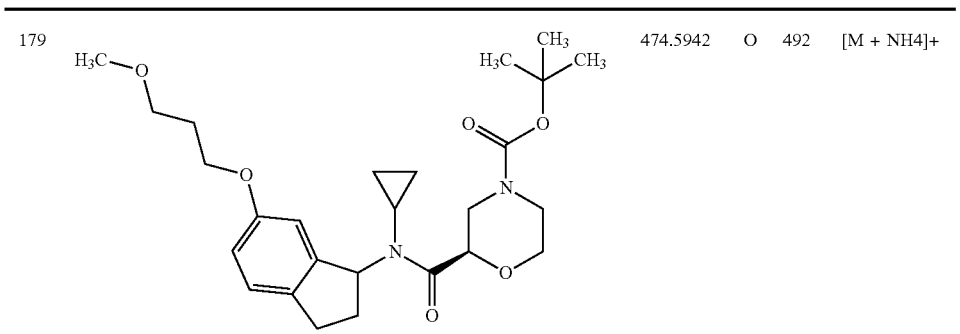 | 474.5942 | O | 492 | [M + NH4]+ |
| 180 | 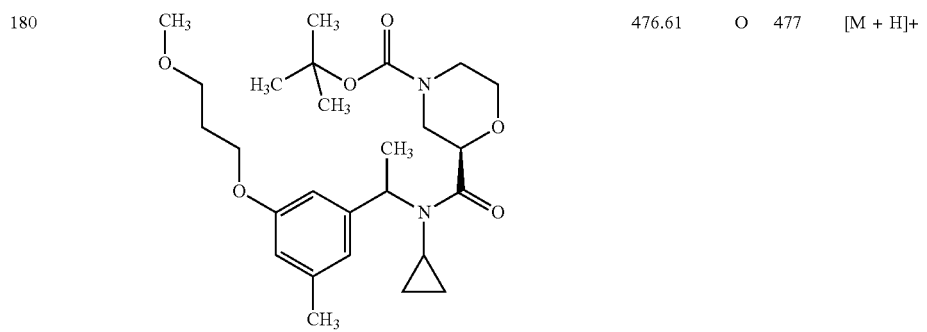 | 476.61 | O | 477 | [M + H]+ |
| 181 | 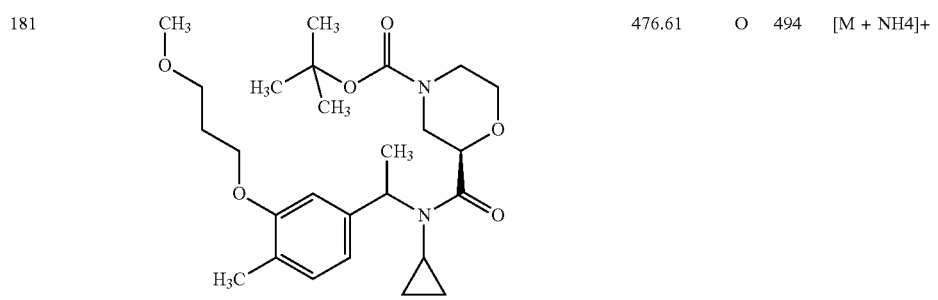 | 476.61 | O | 494 | [M + NH4]+ |

TABLE 42-continued
| 182 | 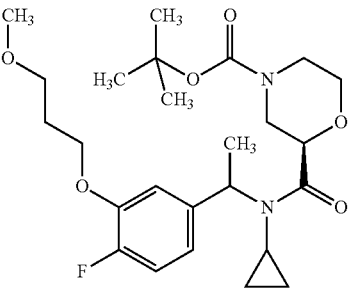 [SMILES: COCCCOc1cc(C(C)N(C(=O)[C@H]2CN(C(=O)OC(C)(C)C)CCO2)C2CC2)ccc1F] | 480.5733 | O | 498 | [M + NH4]+ | |
TABLE 43
| 183 | 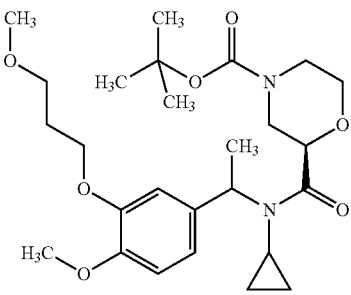 [SMILES: COCCCOc1cc(C(C)N(C(=O)[C@H]2CN(C(=O)OC(C)(C)C)CCO2)C2CC2)ccc1OC] | 492.609 | O | 510 | [M + NH4]+ | A |
| 184 | 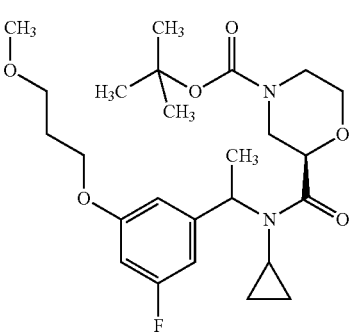 [SMILES: COCCCOc1cc(F)cc(C(C)N(C(=O)[C@H]2CN(C(=O)OC(C)(C)C)CCO2)C2CC2)c1] | 480.5733 | O | 481 | [M + H]+ | A |
| 185 | 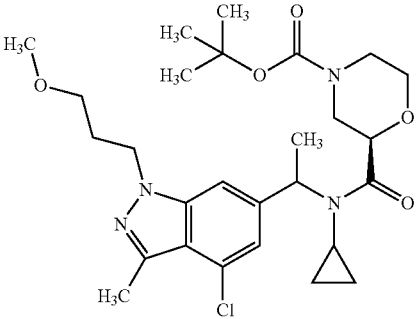 [SMILES: COCCCn1nc(C)c2c(Cl)cc(C(C)N(C(=O)[C@H]3CN(C(=O)OC(C)(C)C)CCO3)C3CC3)cc21] | 535.0811 | O | 535/537 | [M + H]+ | A |

TABLE 43-continued
| 186 | 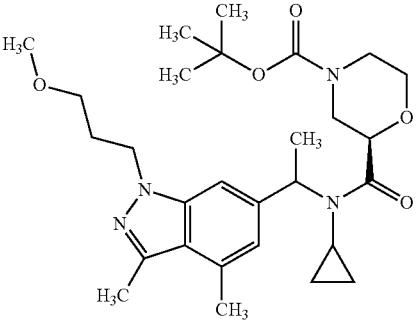 [SMILES: COCCCn1nc(C)c2c(C)cc(C(C)N(C(=O)[C@H]3CN(C(=O)OC(C)(C)C)CCO3)C3CC3)cc21] | 514.6628 | O | 515 | [M + H]+ | A |
TABLE 44
| 187 | | 518.6261 | O | 519 | [M + H]+ | A |
| 188 | | 514.6628 | O | 515 | [M + H]+ | A |
| 189 | | 502.6042 | O | 503 | [M + H]+ | A |

TABLE 44-continued
| 190 | 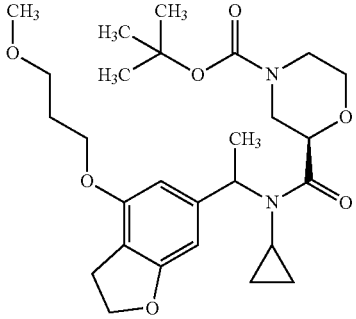 [SMILES: COCCCOc1cc(C(C)N(C(=O)[C@H]2CN(C(=O)OC(C)(C)C)CCO2)C2CC2)cc2c1CCO2] | 504.62 | O | 505 | [M + H]+ | D |
TABLE 45
| 191 | 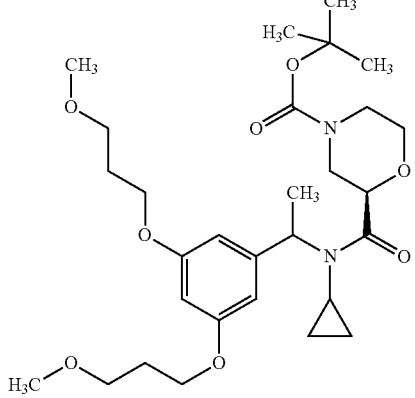 | 550.6884 | O | 568 | [M + NH4]+ | A |
| 192 | 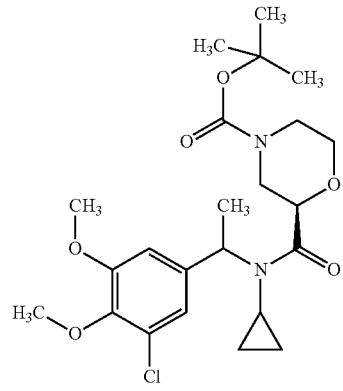 [SMILES: COc1cc(C(C)N(C(=O)[C@H]2CN(C(=O)OC(C)(C)C)CCO2)C2CC2)cc(Cl)c1OC] | 468.9747 | O | 469/471 | [M + H]+ | A |
| 193 | 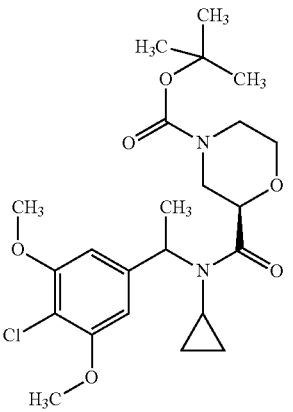 [SMILES: COc1cc(C(C)N(C(=O)[C@H]2CN(C(=O)OC(C)(C)C)CCO2)C2CC2)cc(OC)c1Cl] | 468.9747 | P | 469/471 | [M + H]+ | A |

TABLE 45-continued
| | | | | | | |
|---|---|---|---|---|---|---|
| 194 | 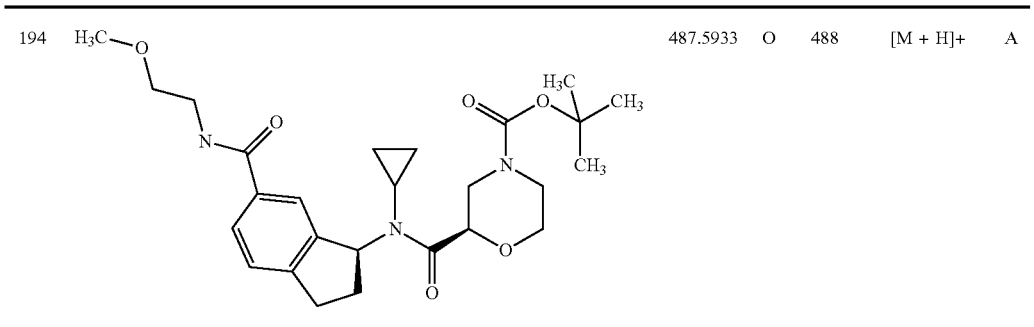 | 487.5933 | O | 488 | [M + H]+ | A |
TABLE 46
| | | | | | | |
|---|---|---|---|---|---|---|
| 195 | 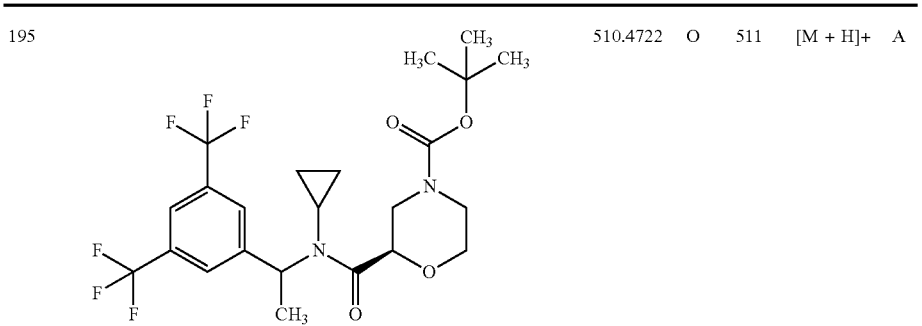 | 510.4722 | O | 511 | [M + H]+ | A |
| 196 | 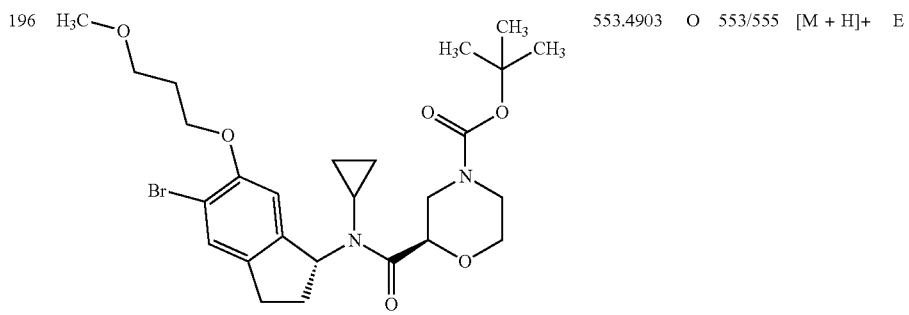 | 553.4903 | O | 553/555 | [M + H]+ | E |
| 197 | 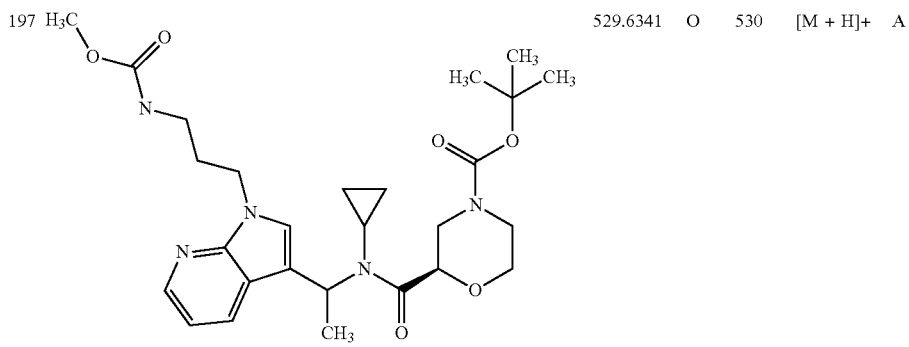 | 529.6341 | O | 530 | [M + H]+ | A |

TABLE 46-continued
| 198 | 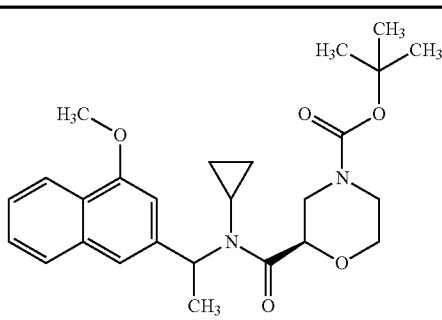 | | 454.5636 | O | 455 | [M + H]+ | A |
TABLE 47
| 199 | 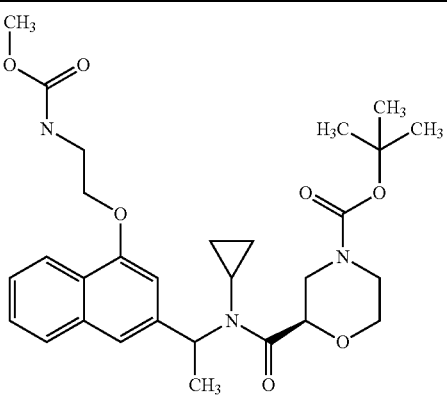 | | 541.6411 | P | 542 | [M + H]+ | A |
| 200 | 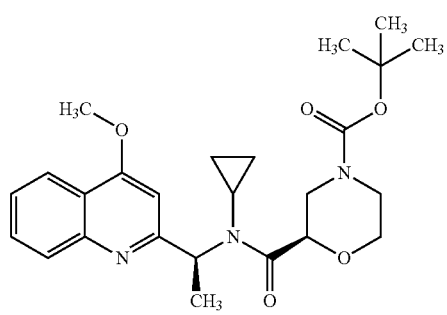 | Chiral | 455.5517 | P | 456 | [M + H]+ | A |
| 201 | 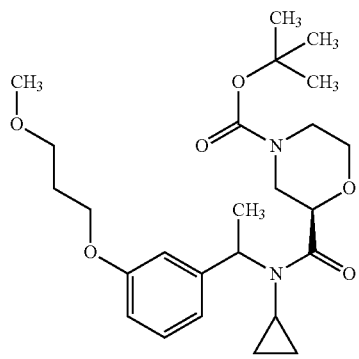 [SMILES: COCCCOc1cccc(C(C)N(C(=O)[C@H]2CN(C(=O)OC(C)(C)C)CCO2)C2CC2)c1] | | 462.5832 | O | 463 | [M + H]+ | A |

TABLE 47-continued
| | | | | | | |
|---|---|---|---|---|---|---|
| 202 | 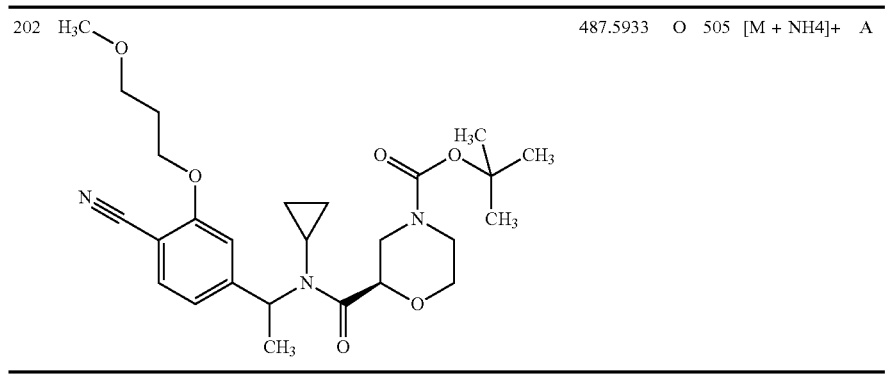 | 487.5933 | O | 505 | [M + NH4]+ | A |
TABLE 48
| | | | | | | |
|---|---|---|---|---|---|---|
| 203 | 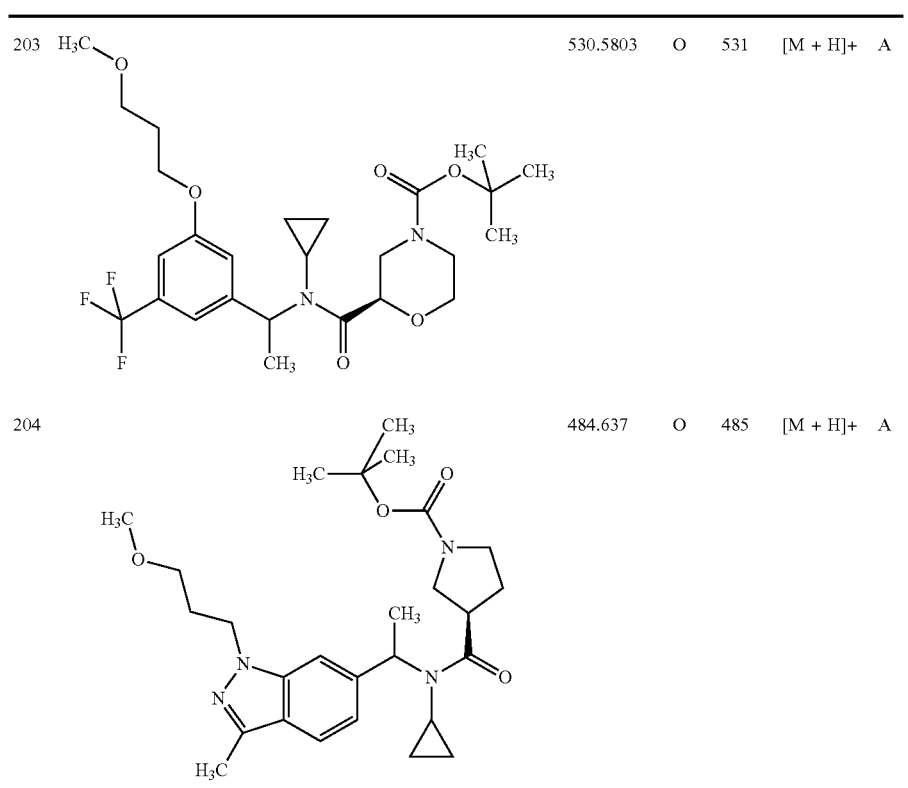 | 530.5803 | O | 531 | [M + H]+ | A |
| 204 | | 484.637 | O | 485 | [M + H]+ | A |
| 205 | 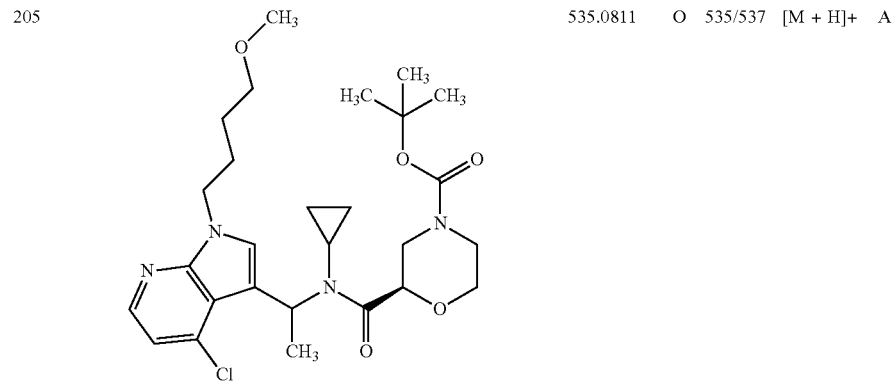 | 535.0811 | O | 535/537 | [M + H]+ | A |

TABLE 48-continued
| 206 | 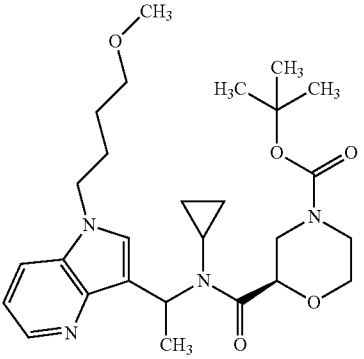 [SMILES: COCCCCn1cc(C(C)N(C(=O)[C@H]2CN(C(=O)OC(C)(C)C)CCO2)C2CC2)c2ncccc21] | 500.636 | O | 501 | [M + H]+ | A |
TABLE 49
| 207 | 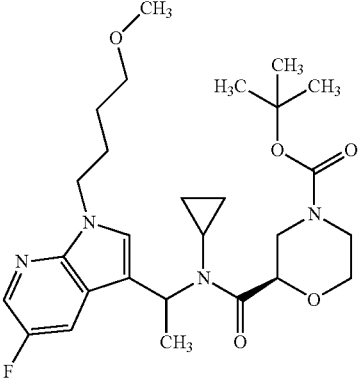 [SMILES: COCCCCn1cc(C(C)N(C(=O)[C@H]2CN(C(=O)OC(C)(C)C)CCO2)C2CC2)c2cc(F)cnc21] | 518.6261 | O | 519 | [M + H]+ | A |
| 208 | 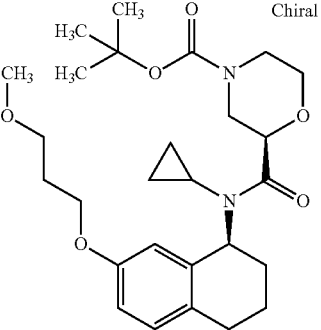 [SMILES: COCCCOc1ccc2c(c1)[C@@H](N(C(=O)[C@H]1CN(C(=O)OC(C)(C)C)CCO1)C1CC1)CCC2] Chiral | 488.621 | O | 489 | [M + H]+ | A |
| 209 | 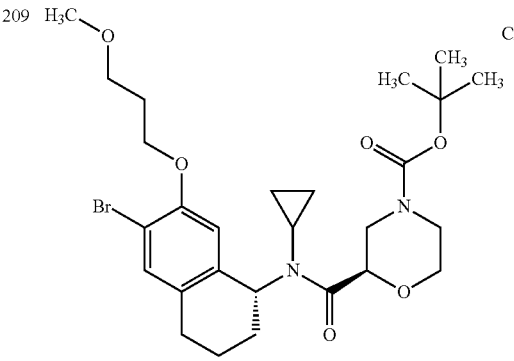 Chiral | 567.5171 | O | 567/569 | [M + H]+ | E |

TABLE 49-continued
| 210 |  | 510.5991 | O | 511 | [M + H]+ | A |
TABLE 50
| 211 | 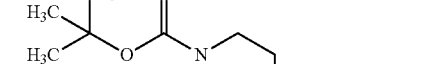 | 571.5051 | O | 571/573 | [M + H]+ | A |
| 212 | | 499.6479 | O | 500 | [M + H]+ | A |
| 213 | | 598.78 | O | 616 | [M + NH4]+ | B |

TABLE 50-continued
| 214 | 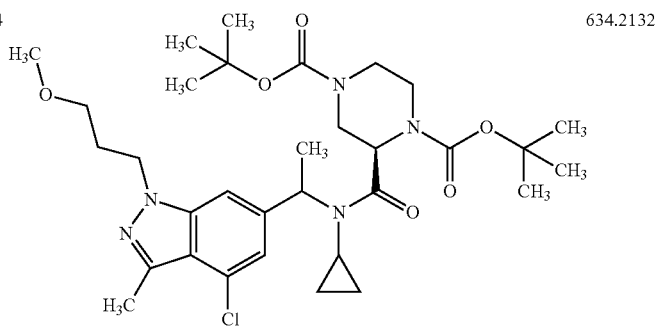 | | 634.2132 | O | 634/636 | [M + H]+ | C |
TABLE 51
| 215 | 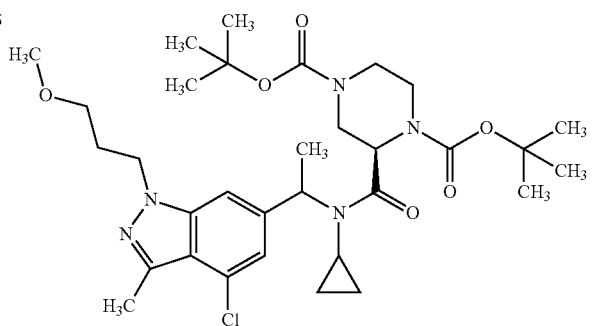 | | 613.7949 | O | 614 | [M + H]+ | C |
| 216 | 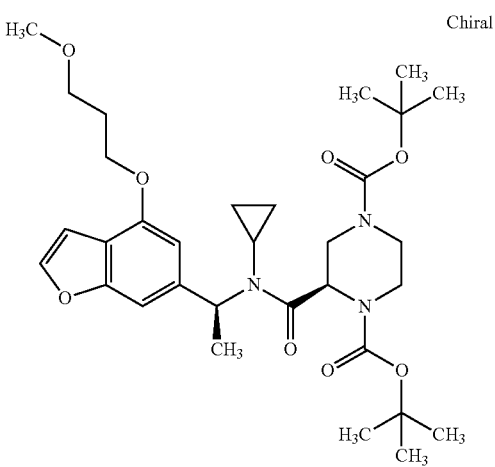 [SMILES: COCCCOc1cc([C@H](C)N(C(=O)[C@H]2CN(C(=O)OC(C)(C)C)CCN2C(=O)OC(C)(C)C)C2CC2)cc2occc12] | Chiral | 601.7363 | O | 602 | [M + H]+ | B |

TABLE 51-continued
| 217 | 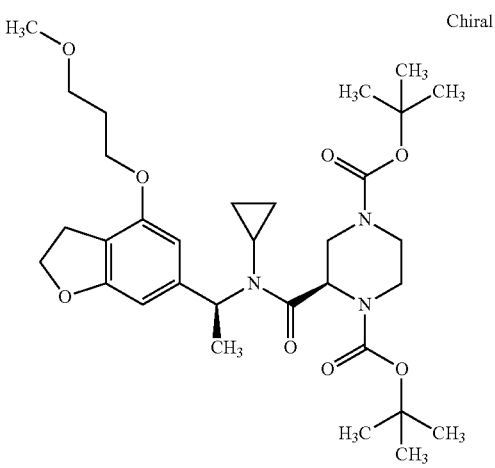 [SMILES: COCCCOc1cc([C@H](C)N(C(=O)[C@H]2CN(C(=O)OC(C)(C)C)CCN2C(=O)OC(C)(C)C)C2CC2)cc2c1CCO2] | Chiral | 603.7521 | O | 604 | [M + H]+ | D |
| 218 | 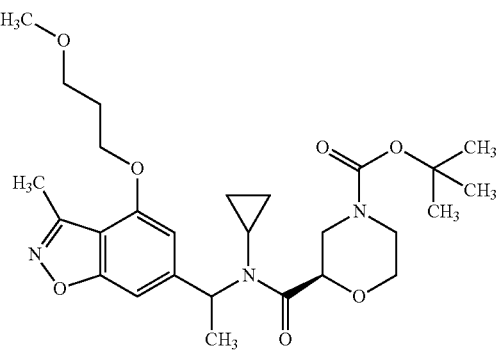 [SMILES: COCCCOc1cc(C(C)N(C(=O)[C@H]2CN(C(=O)OC(C)(C)C)CCO2)C2CC2)cc2onc(C)c12] | | 517.6191 | O | 518 | [M + H]+ | A |
TABLE 52
| 219 | 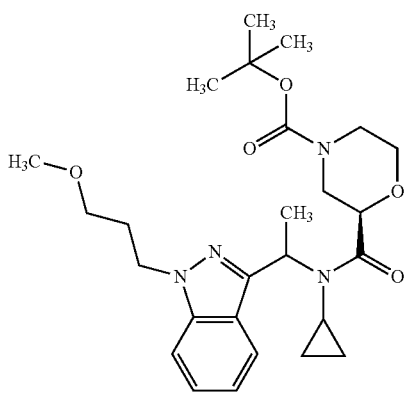 [SMILES: COCCCn1nc(C(C)N(C(=O)[C@H]2CN(C(=O)OC(C)(C)C)CCO2)C2CC2)c2ccccc21] | | 486.6092 | O | 487 | [M + H]+ | A |

TABLE 52-continued
| | | | | | | |
|---|---|---|---|---|---|---|
| 220 | 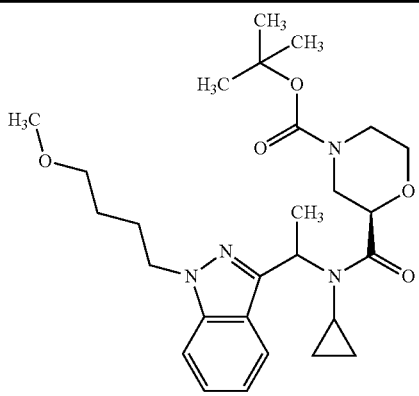 | 500.636 | O | 501 | [M + H]+ | A |
| 221 | 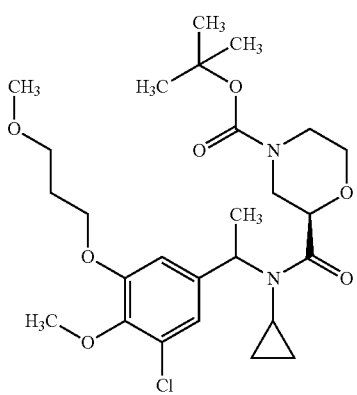 [SMILES: COCCCOc1cc(C(C)N(C(=O)[C@H]2CN(C(=O)OC(C)(C)C)CCO2)C2CC2)cc(Cl)c1OC] | 527.0541 | O | 527/529 | [M + H]+ | A |
| 222 | 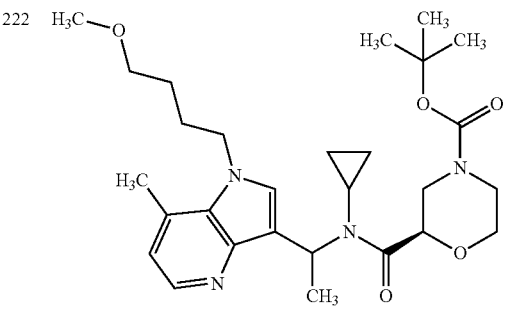 | 514.6628 | O | 515 | [M + H]+ | A |
TABLE 53
| | | | | | | |
|---|---|---|---|---|---|---|
| 223 | 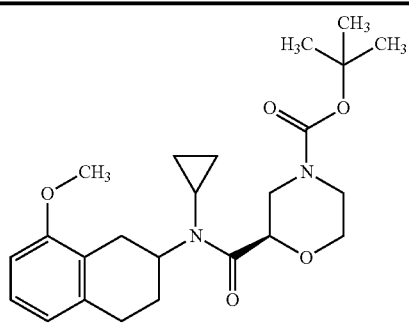 | 430.5416 | O | 431 | [M + H]+ | A |

TABLE 53-continued
| 224 | 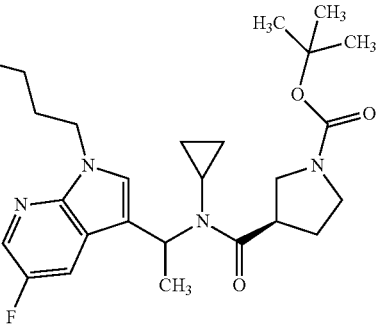 | 502.6271 | O | 503 | [M + H]+ | A |
| 225 | 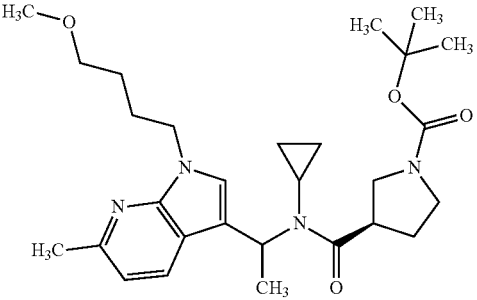 [SMILES: COCCCCn1cc(C(C)N(C(=O)[C@@H]2CCN(C(=O)OC(C)(C)C)C2)C2CC2)c2ccc(C)nc21] | 498.6638 | O | 499 | [M + H]+ | A |
| 226 | 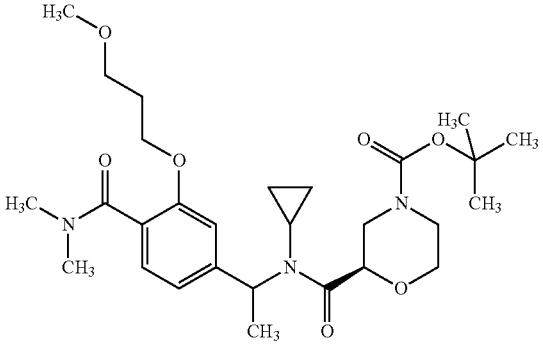 [SMILES: COCCCOc1cc(C(C)N(C(=O)[C@H]2CN(C(=O)OC(C)(C)C)CCO2)C2CC2)ccc1C(=O)N(C)C] | 533.6617 | O | 534 | [M + H]+ | A |
TABLE 54
| 227 | 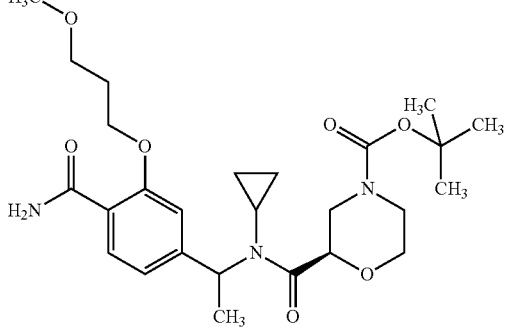 | 505.6081 | O | 506 | [M + H]+ | A |

TABLE 54-continued

| No. | Structure | MW | O | MS | Act |
|---|---|---|---|---|---|
| 228 | (structure) | 519.6349 | O | 520 [M + H]+ | A |
| 229 | (structure) | 502.6042 | O | 503 [M + H]+ | A |
| 230 | (structure) | 504.62 | O | 505 [M + H]+ | D |

TABLE 55

| No. | Structure | | MW | O | MS | Act |
|---|---|---|---|---|---|---|
| 231 | (structure) | Chiral | 484.637 | O | 485 [M + H]+ | A |

TABLE 55-continued
| | | | | | | | |
|---|---|---|---|---|---|---|---|
| 232 | 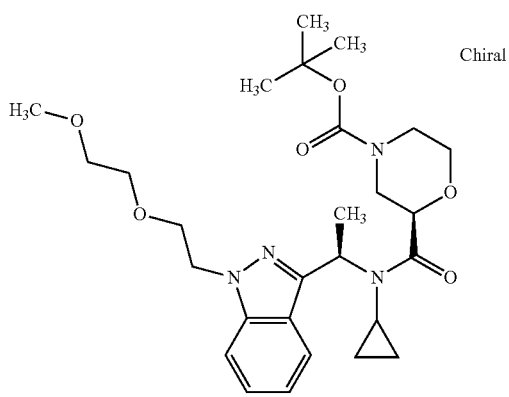 [SMILES: COCCOCCn1nc([C@@H](C)N(C(=O)[C@H]2CN(C(=O)OC(C)(C)C)CCO2)C2CC2)c2ccccc21] | | 516.635 | O | 517 | [M + H]+ | A |
| | | Chiral | | | | | |
| 233 | 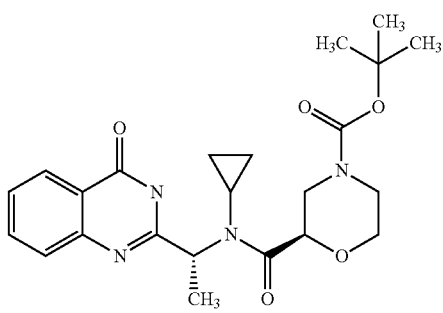 [SMILES: C[C@H](c1nc2ccccc2c(=O)[nH]1)N(C(=O)[C@H]1CN(C(=O)OC(C)(C)C)CCO1)C1CC1] | | 442.513 | P | 443 | [M + H]+ | A |
| 234 | 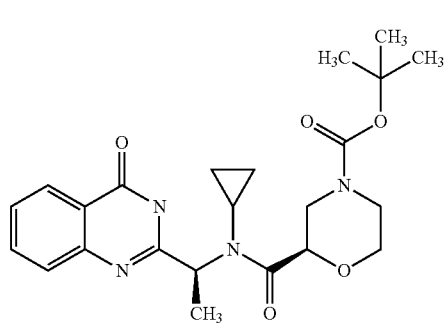 | Chiral | 442.513 | P | 443 | [M + H]+ | A |
TABLE 56
| | | | | | | |
|---|---|---|---|---|---|---|
| 235 | 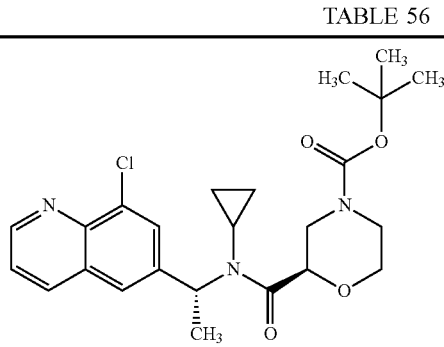 | 459.971 | P | 460/462 | [M + H]+ | A |

TABLE 56-continued
| | | | | | | |
|---|---|---|---|---|---|---|
| 236 | 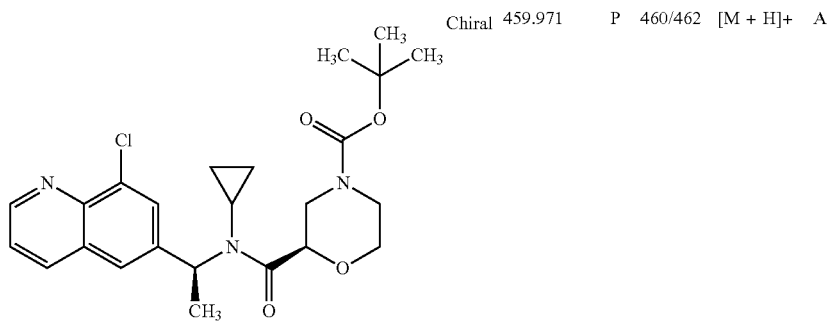 | Chiral | 459.971 | P | 460/462 | [M + H]+ | A |
| 237 | 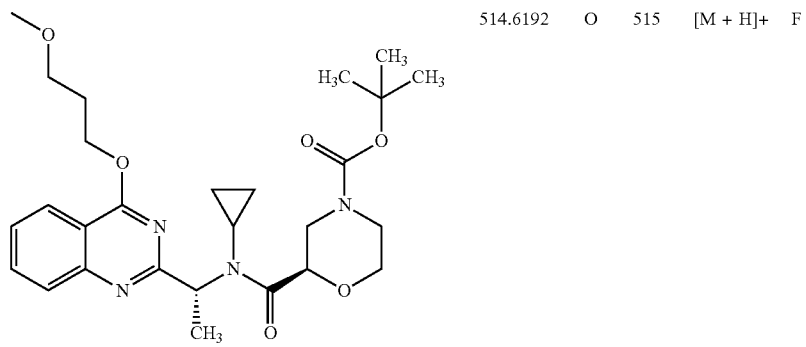 | | 514.6192 | O | 515 | [M + H]+ | F |
| 238 | 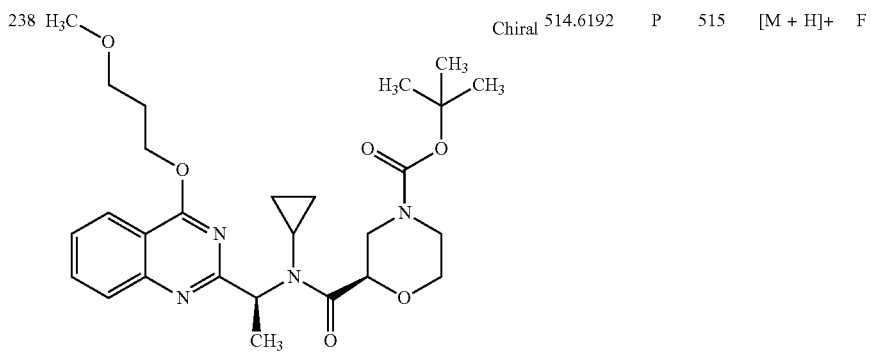 | Chiral | 514.6192 | P | 515 | [M + H]+ | F |
TABLE 57
| 239 | 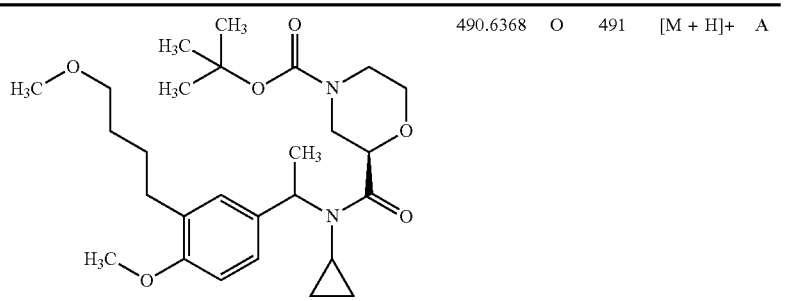 | | 490.6368 | O | 491 | [M + H]+ | A |

TABLE 57-continued
| 240 | 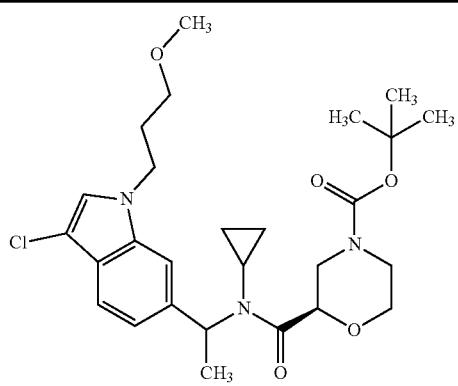 | 520.0662 | O | 520/522 | [M + H]+ | A |
| --- | --- | --- | --- | --- | --- | --- |
| 241 | 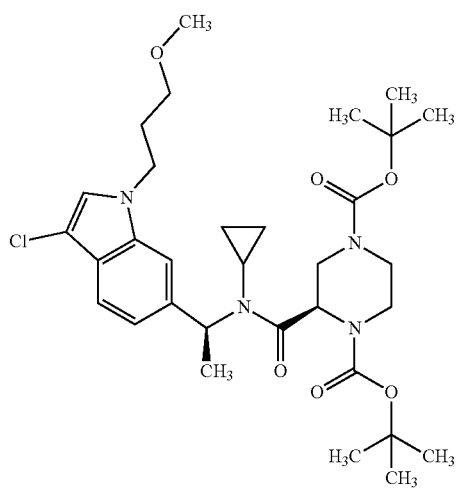 [SMILES: COCCCn1cc(Cl)c2ccc([C@H](C)N(C(=O)[C@H]3CN(C(=O)OC(C)(C)C)CCN3C(=O)OC(C)(C)C)C3CC3)cc21] | 619.1983 | O | 636/638 | [M + H]+ | B |
| 242 | 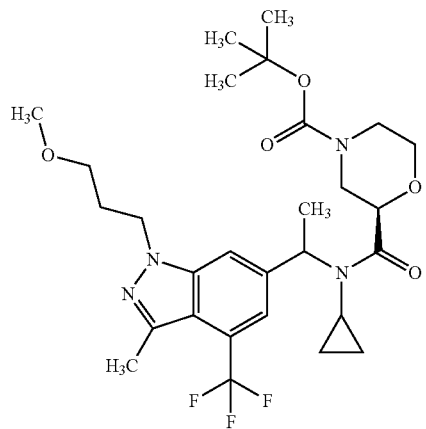 [SMILES: COCCCn1nc(C)c2c(C(F)(F)F)cc(C(C)N(C(=O)[C@H]3CN(C(=O)OC(C)(C)C)CCO3)C3CC3)cc21] | 568.6331 | O | 569 | [M + H]+ | A |

TABLE 58
| | | | | | | | |
|---|---|---|---|---|---|---|---|
| 243 | 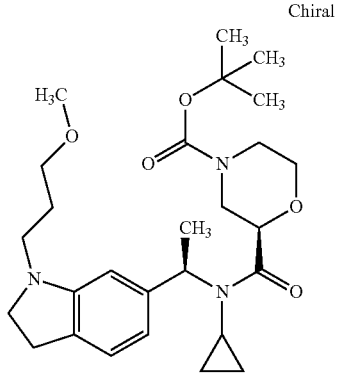 [SMILES: COCCCN1CCc2ccc([C@@H](C)N(C(=O)[C@H]3CN(C(=O)OC(C)(C)C)CCO3)C3CC3)cc21] | Chiral | 487.6369 | O | 488 | [M + H]+ | A |
| 244 | 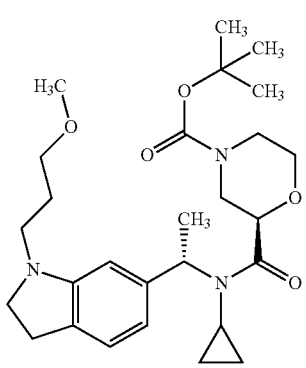 [SMILES: COCCCN1CCc2ccc([C@H](C)N(C(=O)[C@H]3CN(C(=O)OC(C)(C)C)CCO3)C3CC3)cc21] | | 487.6369 | O | 488 | [M + H]+ | A |
| 245 | 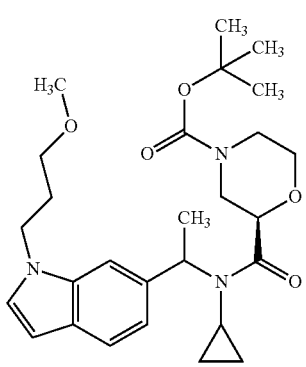 [SMILES: COCCCn1ccc2ccc(C(C)N(C(=O)[C@H]3CN(C(=O)OC(C)(C)C)CCO3)C3CC3)cc21] | | 485.6211 | O | 486 | [M + H]+ | A |
| 246 | 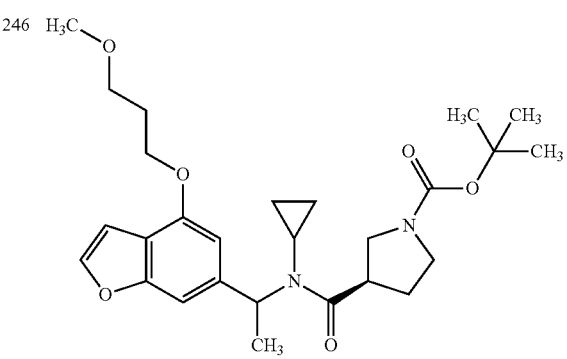 | | 486.6052 | O | 504 | [M + NH4]+ | A |

TABLE 59
| | | | | | | |
|---|---|---|---|---|---|---|
| 247 | 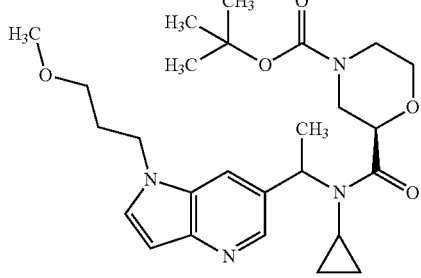 | 486.6092 | O | 487 | [M + H]+ | A |
| 248 | 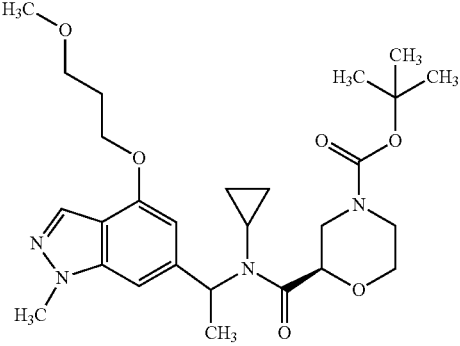 [SMILES: COCCCOc1cc(C(C)N(C(=O)[C@H]2CN(C(=O)OC(C)(C)C)CCO2)C2CC2)cc2c1cnn2C] | 516.635 | O | 517 | [M + H]+ | A |
| 249 | 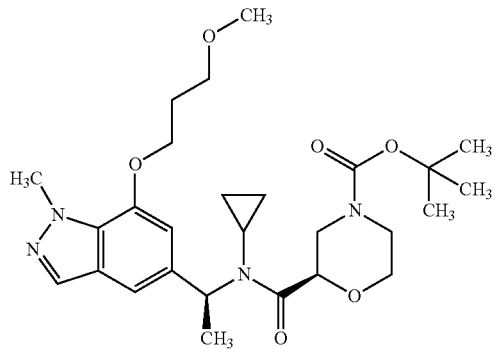 [SMILES: COCCCOc1cc([C@H](C)N(C(=O)[C@H]2CN(C(=O)OC(C)(C)C)CCO2)C2CC2)cc2cnn(C)c12] | 516.635 | O | 517 | [M + H]+ | A |
| 250 | 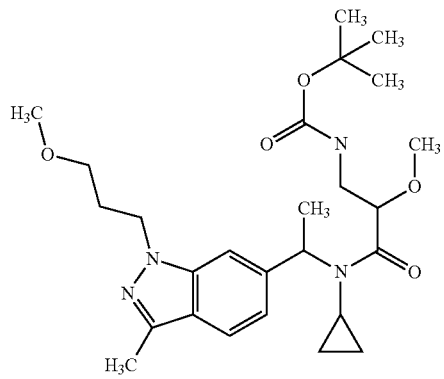 [SMILES: COCCCn1nc(C)c2ccc(C(C)N(C(=O)C(CNC(=O)OC(C)(C)C)OC)C3CC3)cc21] | 488.625 | O | 489 | [M + H]+ | A |

TABLE 60
| | | | | | | |
|---|---|---|---|---|---|---|
| 251 | 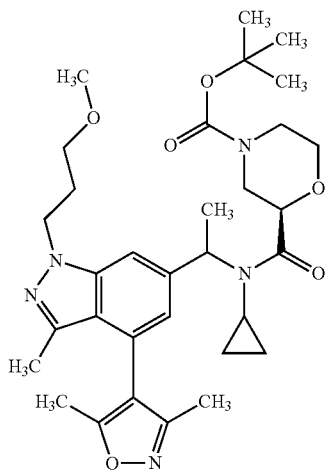 [SMILES: COCCCn1nc(C)c2c(-c3c(C)noc3C)cc(C(C)N(C(=O)[C@H]3CN(C(=O)OC(C)(C)C)CCO3)C3CC3)cc21] | 595.7365 | O | 596 | [M + H]+ | A |
| 252 | 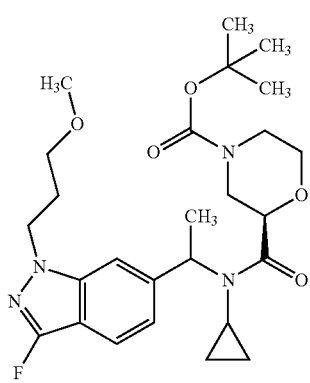 [SMILES: COCCCn1nc(F)c2ccc(C(C)N(C(=O)[C@H]3CN(C(=O)OC(C)(C)C)CCO3)C3CC3)cc21] | 504.5993 | O | 505 | [M + H]+ | A |
| 253 | 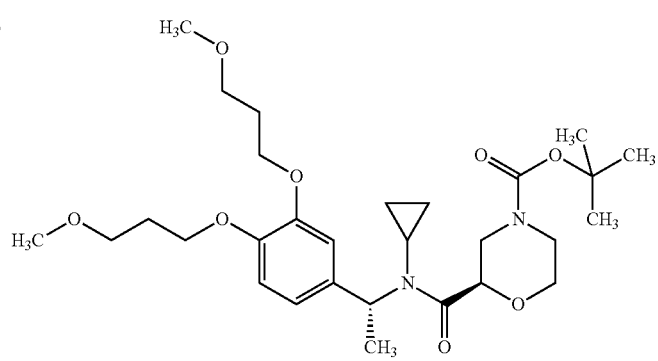 [SMILES: COCCCOc1ccc([C@@H](C)N(C(=O)[C@H]2CN(C(=O)OC(C)(C)C)CCO2)C2CC2)cc1OCCCOC] | 550.6884 | O | 568 | [M + NH4]+ | G |
| 254 | 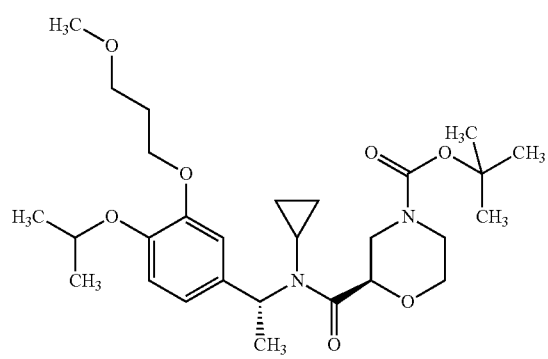 [SMILES: COCCCOc1cc([C@@H](C)N(C(=O)[C@H]2CN(C(=O)OC(C)(C)C)CCO2)C2CC2)ccc1OC(C)C] | 520.6626 | O | 521 | [M + H]+ | G |

TABLE 61
| 255 | 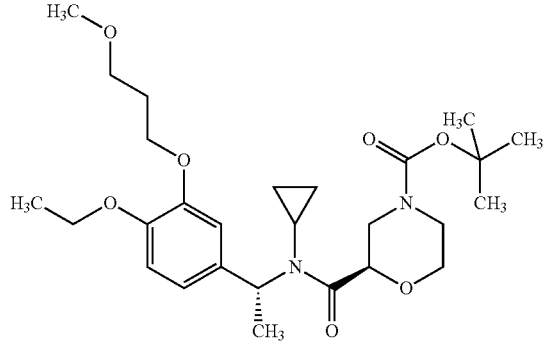 | 506.6358 | O | 507 | [M + H]+ | G |
| 256 | 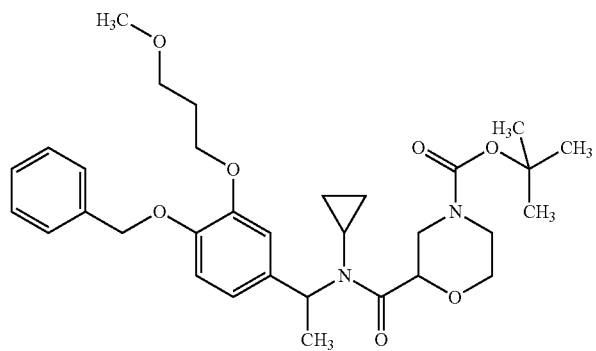 [SMILES: COCCCOc1cc(C(C)N(C(=O)C2CN(C(=O)OC(C)(C)C)CCO2)C2CC2)ccc1OCc1ccccc1] | 568.7066 | O | 569 | [M + H]+ | A |
| 257 | 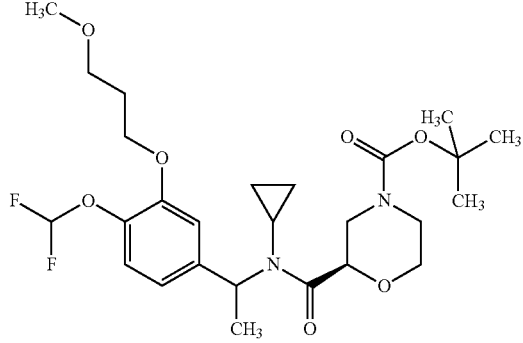 [SMILES: COCCCOc1cc(C(C)N(C(=O)[C@H]2CN(C(=O)OC(C)(C)C)CCO2)C2CC2)ccc1OC(F)F] | 528.5892 | O | 529 | [M + H]+ | A |
| 258 | 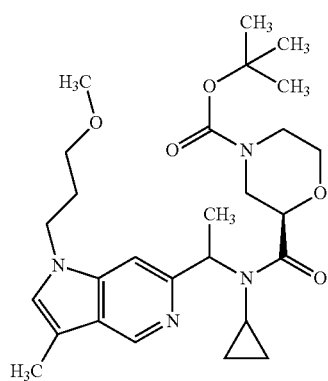 [SMILES: COCCCn1cc(C)c2cnc(C(C)N(C(=O)[C@H]3CN(C(=O)OC(C)(C)C)CCO3)C3CC3)cc21] | 500.636 | O | 501 | [M + H]+ | A |

TABLE 62
| 259 | 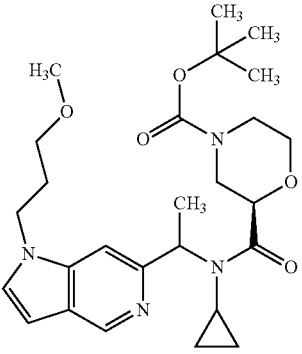 [SMILES: COCCCn1ccc2cnc(C(C)N(C(=O)[C@H]3CN(C(=O)OC(C)(C)C)CCO3)C3CC3)cc21] | 486.6092 | O | 487 | [M + H]+ | A |
| 260 | 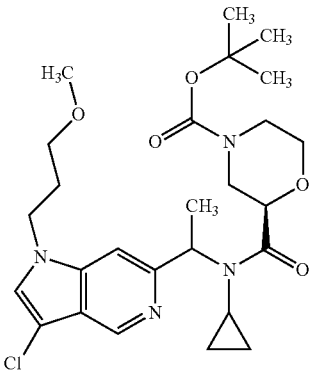 [SMILES: COCCCn1cc(Cl)c2cnc(C(C)N(C(=O)[C@H]3CN(C(=O)OC(C)(C)C)CCO3)C3CC3)cc21] | 521.0543 | O | 521/523 | [M + H]+ | A |
| 261 | 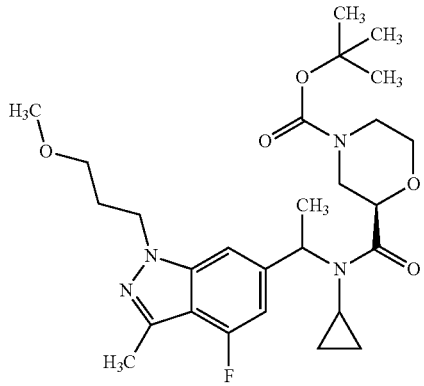 [SMILES: COCCCn1nc(C)c2c(F)cc(C(C)N(C(=O)[C@H]3CN(C(=O)OC(C)(C)C)CCO3)C3CC3)cc21] | 518.6261 | O | 519 | [M + H]+ | A |
| 262 | 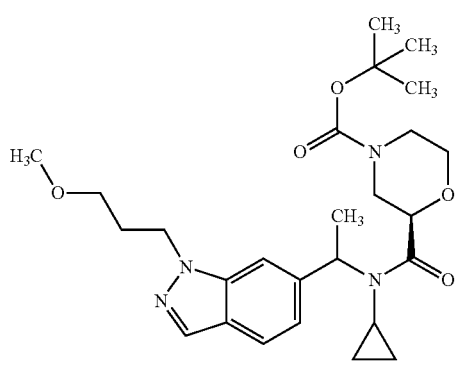 [SMILES: COCCCn1ncc2ccc(C(C)N(C(=O)[C@H]3CN(C(=O)OC(C)(C)C)CCO3)C3CC3)cc21] | 486.6092 | O | 487 | [M + H]+ | A |

TABLE 63
263 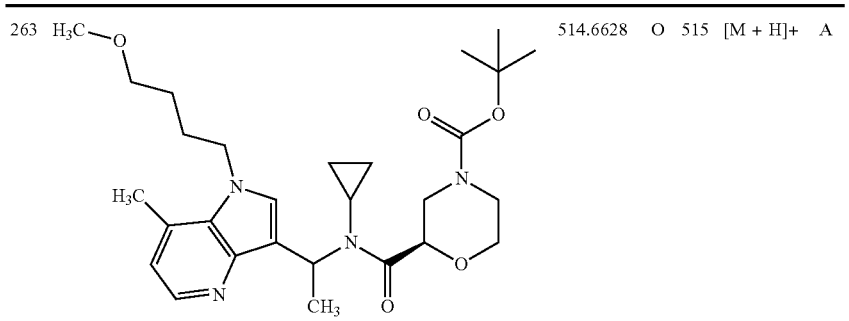 514.6628 O 515 [M + H]+ A
264 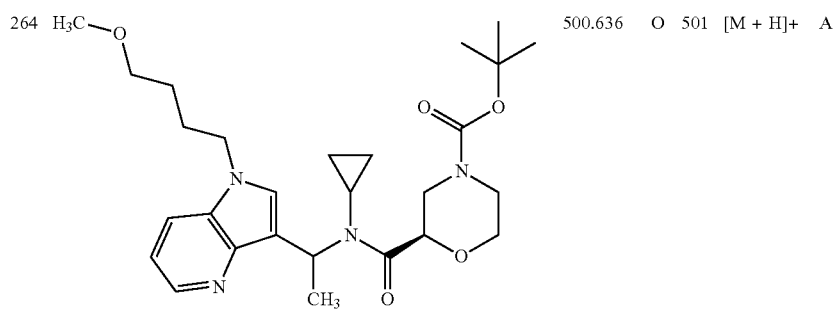 500.636 O 501 [M + H]+ A
265 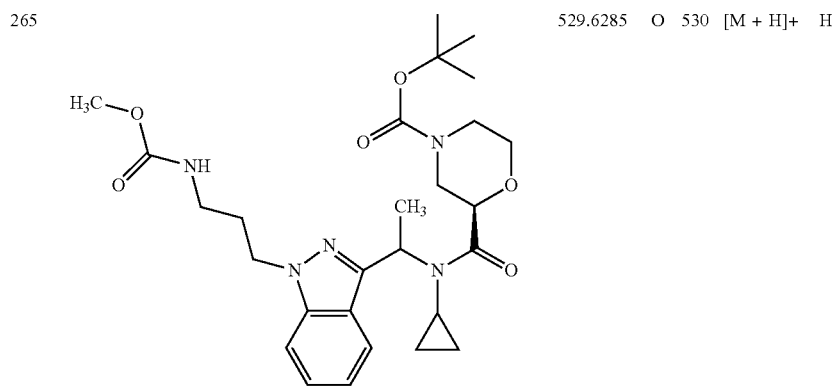 529.6285 O 530 [M + H]+ H
266 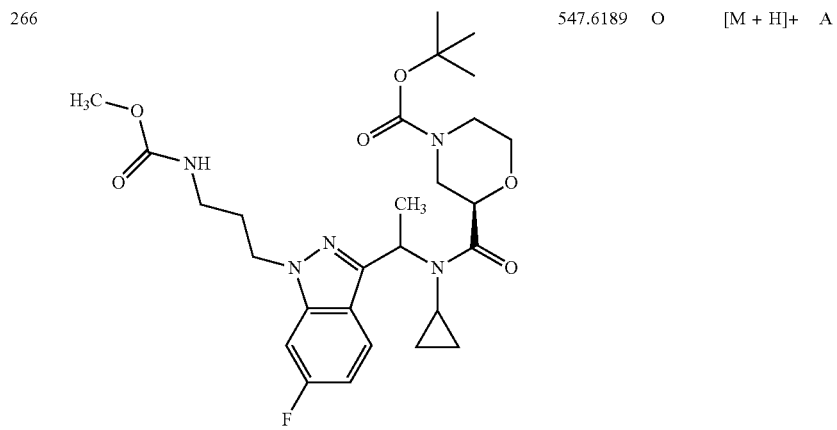 547.6189 O    [M + H]+ A

TABLE 64

| | | | | | | |
|---|---|---|---|---|---|---|
| 267 | 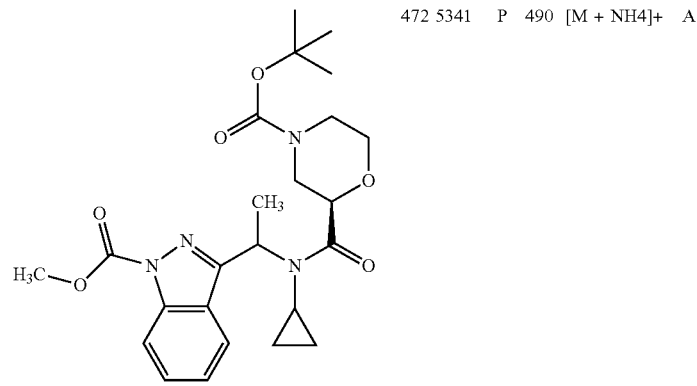 | 472.5341 | P | 490 | [M + NH4]+ | A |

Ex. No.: Example Number
a: Molecular weight
b: Properties
c: MS Results APCI
d: Ion species
e: Method
O: Oil
P: Powder Examples 268 to 287

The following nitrogen-containing saturated heterocyclic compounds, etc. were prepared in the similar manner to the above Examples 1 to 5. Each symbol of Methods A to C refers to each method according to the following method of Examples.
Method A: Examples 1, 2
Method B: Examples 3, 4
Method C: Example 5A

TABLE 65

| EX. No. | Structure | a MW | b | c | d | e |
|---|---|---|---|---|---|---|
| 268 | 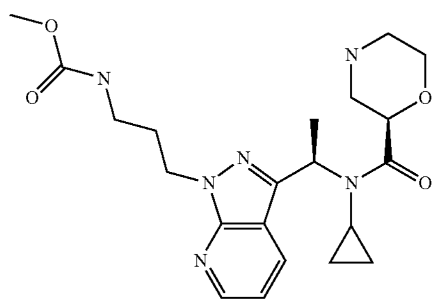 [SMILES: COC(=O)NCCCn1nc([C@@H](C)N(C(=O)[C@H]2CNCCO2)C2CC2)c2cccnc21] | 430.5007 | C | 431 | [M + H]+ | O |
| 269 | 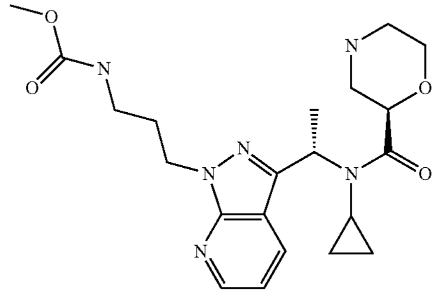 [SMILES: COC(=O)NCCCn1nc([C@H](C)N(C(=O)[C@H]2CNCCO2)C2CC2)c2cccnc21] | 430.5007 | C | 431 | [M + H]+ | O |

TABLE 65-continued

| EX. No. | Structure | a | MW | b | c | d | e |
|---|---|---|---|---|---|---|---|
| 270 | 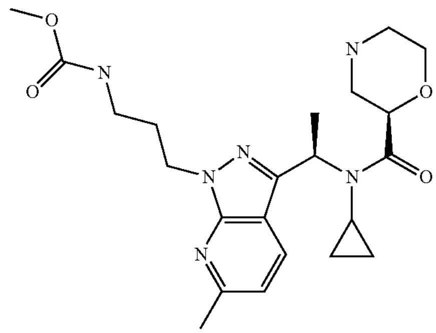 [SMILES: COC(=O)NCCCn1nc([C@@H](C)N(C(=O)[C@H]2CNCCO2)C2CC2)c2ccc(C)nc21] | | 444.5273 | C | 445 | [M + H]⁺ | O |
| 271 | 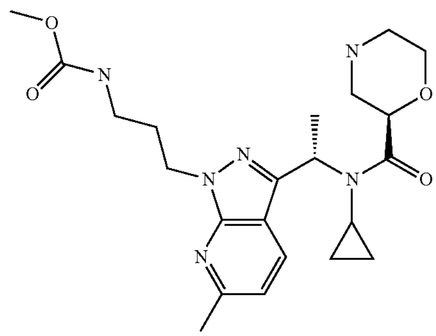 [SMILES: COC(=O)NCCCn1nc([C@H](C)N(C(=O)[C@H]2CNCCO2)C2CC2)c2ccc(C)nc21] | | 444.5273 | C | 445 | [M + H]⁺ | O |
| 272 | 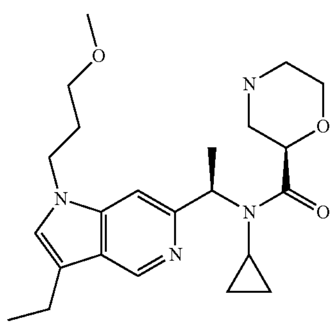 [SMILES: CCc1cn(CCCOC)c2cc([C@@H](C)N(C(=O)[C@H]3CNCCO3)C3CC3)ncc12] | | 414.5411 | C | 415 | [M + H]⁺ | O |
| 273 | 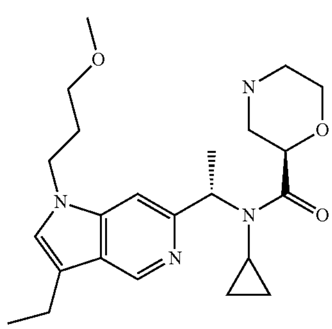 [SMILES: CCc1cn(CCCOC)c2cc([C@H](C)N(C(=O)[C@H]3CNCCO3)C3CC3)ncc12] | | 414.5411 | C | 415 | [M + H]⁺ | O |

Ex. No.: Example Number
a: Salt
b: Method
c: MS Results APCI
d: Ion species
e: Form
O: Oil TABLE 66
| EX. No. | Structure | a | MW | b | c | d | e |
|---|---|---|---|---|---|---|---|
| 274 | 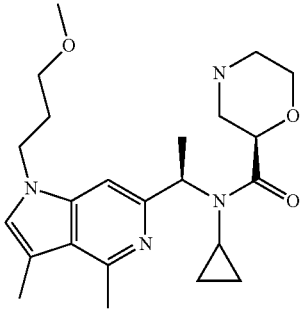 [SMILES: COCCCn1cc(C)c2c(C)nc([C@@H](C)N(C(=O)[C@H]3CNCCO3)C3CC3)cc21] | | 414.5411 | A | 415 | [M + H]⁺ | O |
| 275 | 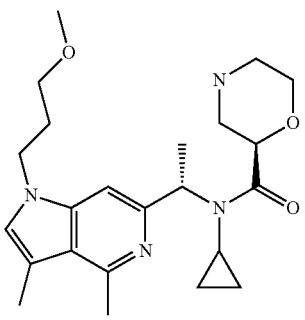 [SMILES: COCCCn1cc(C)c2c(C)nc([C@H](C)N(C(=O)[C@H]3CNCCO3)C3CC3)cc21] | | 414.5411 | A | 415 | [M + H]⁺ | O |
| 276 | 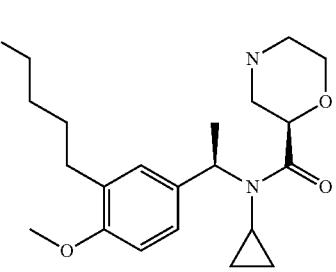 | | 390.5164 | A | 391 | [M + H]⁺ | O |
| 277 | 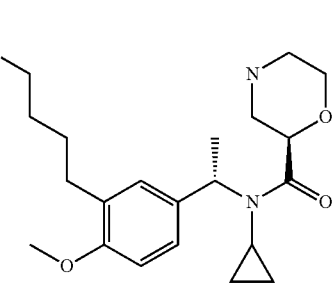 | | 390.5164 | A | 391 | [M + H]⁺ | O |
| 278 | 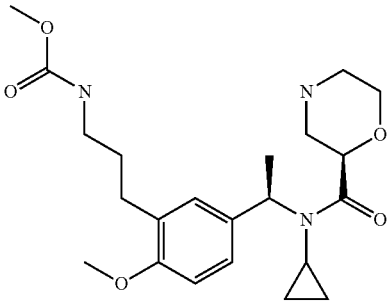 [SMILES: COC(=O)NCCCc1cc([C@@H](C)N(C(=O)[C@H]2CNCCO2)C2CC2)ccc1OC] | | 419.5145 | A | 420 | [M + H]⁺ | O |

TABLE 66-continued

| EX. No. | Structure | a | MW | b | c | d | e |
|---|---|---|---|---|---|---|---|
| 279 | 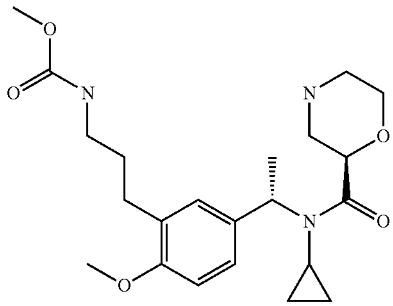 [SMILES: COC(=O)NCCCc1cc([C@H](C)N(C(=O)[C@H]2CNCCO2)C2CC2)ccc1OC] | | 419.5145 | A | 420 | [M + H]⁺ | O |

Ex. No.: Example Number
a: Salt
b: Method
c: MS Results APCI
d: Ion species
e: Form
O: Oil

TABLE 67

| EX. No. | Structure | a | MW | b | c | d | e |
|---|---|---|---|---|---|---|---|
| 280 | 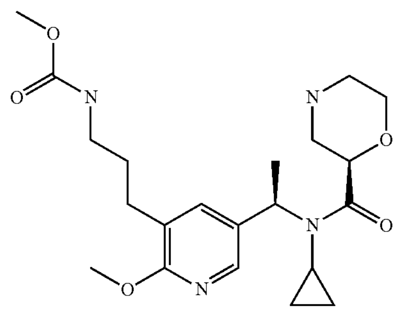 [SMILES: COC(=O)NCCCc1cc([C@@H](C)N(C(=O)[C@H]2CNCCO2)C2CC2)cnc1OC] | | 420.5026 | C | 421 | [M + H]⁺ | O |
| 281 | 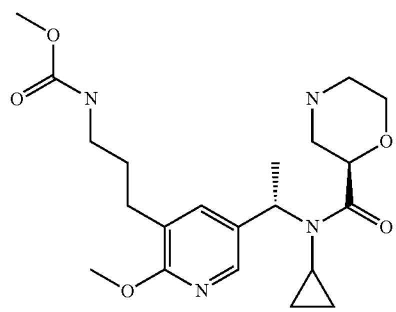 [SMILES: COC(=O)NCCCc1cc([C@H](C)N(C(=O)[C@H]2CNCCO2)C2CC2)cnc1OC] | | 420.5026 | C | 421 | [M + H]⁺ | O |
| 282 | 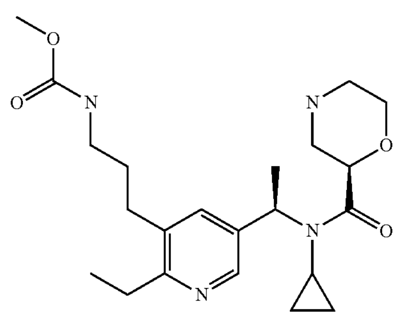 [SMILES: CCc1ncc([C@@H](C)N(C(=O)[C@H]2CNCCO2)C2CC2)cc1CCCNC(=O)OC] | | 418.5298 | C | 419 | [M + H]⁺ | O |

TABLE 67-continued

| EX. No. | Structure | a | MW | b | c | d | e |
|---|---|---|---|---|---|---|---|
| 283 | 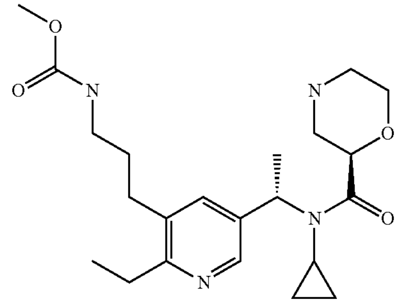 [SMILES: CCc1ncc([C@H](C)N(C(=O)[C@H]2CNCCO2)C2CC2)cc1CCCNC(=O)OC] | | 418.5298 | C | 419 | [M + H]+ | O |
| 284 | 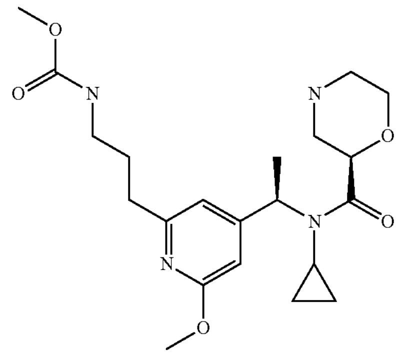 [SMILES: COC(=O)NCCCc1cc([C@@H](C)N(C(=O)[C@H]2CNCCO2)C2CC2)cc(OC)n1] | | 420.5026 | C | 421 | [M + H]+ | O |
| 285 | 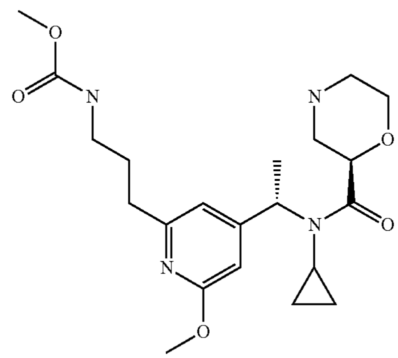 [SMILES: COC(=O)NCCCc1cc([C@H](C)N(C(=O)[C@H]2CNCCO2)C2CC2)cc(OC)n1] | | 420.5026 | C | 421 | [M + H]+ | O |

Ex. No.: Example Number
a: Salt
b: Method
c: MS Results APCI
d: Ion species
e: Form
O: Oil

TABLE 68

| EX. No. | Structure | a | MW | b | c | d | e |
|---|---|---|---|---|---|---|---|
| 286 | 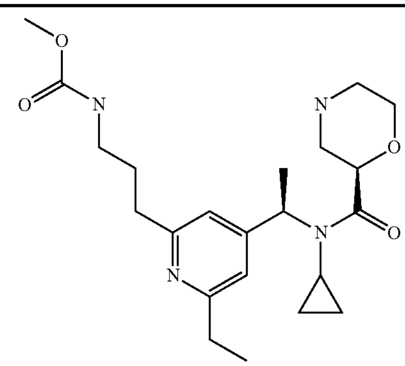 | | 418.5298 | C | 419 | [M + H]+ | O |

TABLE 68-continued
| EX. No. | Structure | a | MW | b | c | d | e |
|---|---|---|---|---|---|---|---|
| 287 | 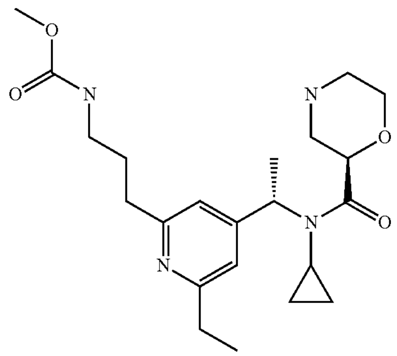 [SMILES: CCc1cc([C@H](C)N(C(=O)[C@H]2CNCCO2)C2CC2)cc(CCCNC(=O)OC)n1] | | 418.5298 | C | 419 | [M + H]⁺ | O |
Ex. No.: Example Number
a: Salt
b: Method
c: MS Results APCI
d: Ion species
e: Form
O: Oil
Examples 288 to 294
The following N-protected nitrogen-containing saturated heterocyclic compounds were prepared in the similar manner to the above Examples 161 to 163 (Method A).
TABLE 69
| EX. No. | Structure | a | b | c | d | e |
|---|---|---|---|---|---|---|
| 288 | 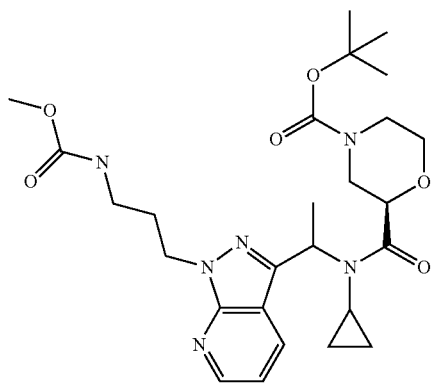 [SMILES: COC(=O)NCCCn1nc(C(C)N(C(=O)[C@H]2CN(C(=O)OC(C)(C)C)CCO2)C2CC2)c2cccnc21] | 530.6165 | O | 531 | [M + H]⁺ | A |
| 289 | 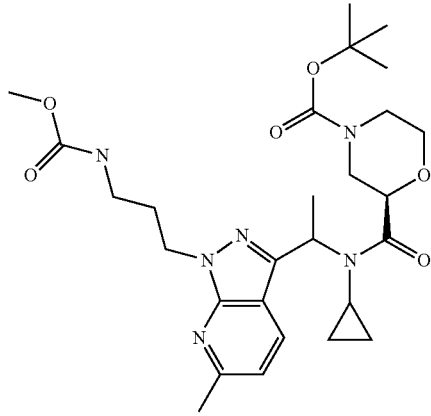 [SMILES: COC(=O)NCCCn1nc(C(C)N(C(=O)[C@H]2CN(C(=O)OC(C)(C)C)CCO2)C2CC2)c2ccc(C)nc21] | 544.6431 | O | 545 | [M + H]⁺ | A |

TABLE 69-continued

| EX. No. | Structure | a | b | c | d | e |
|---|---|---|---|---|---|---|
| 290 | 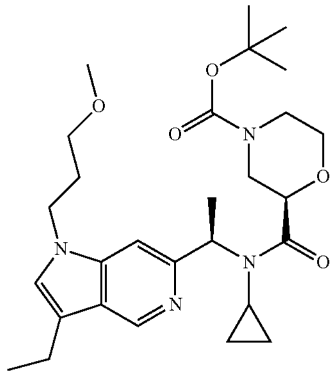 [SMILES: CCc1cn(CCCOC)c2cc([C@@H](C)N(C(=O)[C@H]3CN(C(=O)OC(C)(C)C)CCO3)C3CC3)ncc12] | 514.6569 | O | 515 | [M + H]⁺ | A |
| 291 | 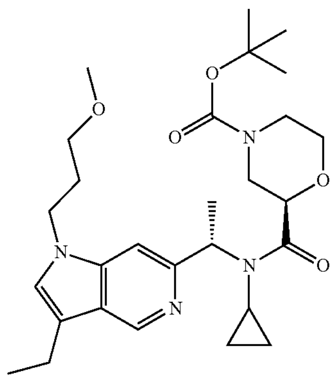 [SMILES: CCc1cn(CCCOC)c2cc([C@H](C)N(C(=O)[C@H]3CN(C(=O)OC(C)(C)C)CCO3)C3CC3)ncc12] | 514.6569 | O | 515 | [M + H]⁺ | A |
| 292 | 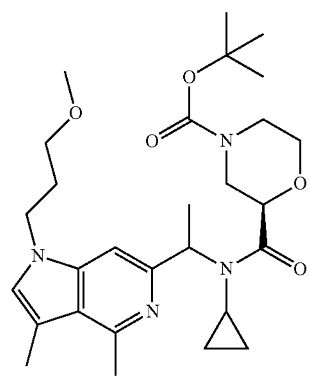 [SMILES: COCCCn1cc(C)c2c(C)nc(C(C)N(C(=O)[C@H]3CN(C(=O)OC(C)(C)C)CCO3)C3CC3)cc21] | 514.6569 | O | 515 | [M + H]⁺ | A |
| 293 | 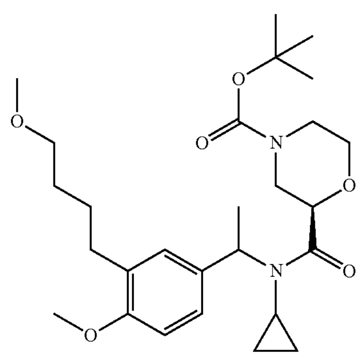 [SMILES: COCCCCc1cc(C(C)N(C(=O)[C@H]2CN(C(=O)OC(C)(C)C)CCO2)C2CC2)ccc1OC] | 490.6322 | O | 491 | [M + H]⁺ | A |

Ex. No.: Example Number
a: Molecular weight
b: Properties
C: MS Results APCI
d: Ion species
e: Method
O: Oil TABLE 70
| EX. No. | Structure | a | b | c | d | e |
|---|---|---|---|---|---|---|
| 294 | 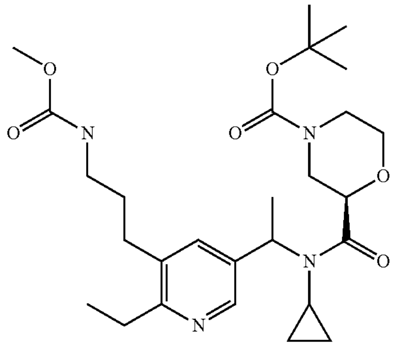 [SMILES: CCc1ncc(C(C)N(C(=O)[C@H]2CN(C(=O)OC(C)(C)C)CCO2)C2CC2)cc1CCCNC(=O)OC] | 518.6456 | O | 519 | [M + H]+ | A |
Ex. No.: Example Number
a: Molecular weight
b: Properties
C: MS Results APCI
d: Ion species
e: Method
O: Oil
Example 295
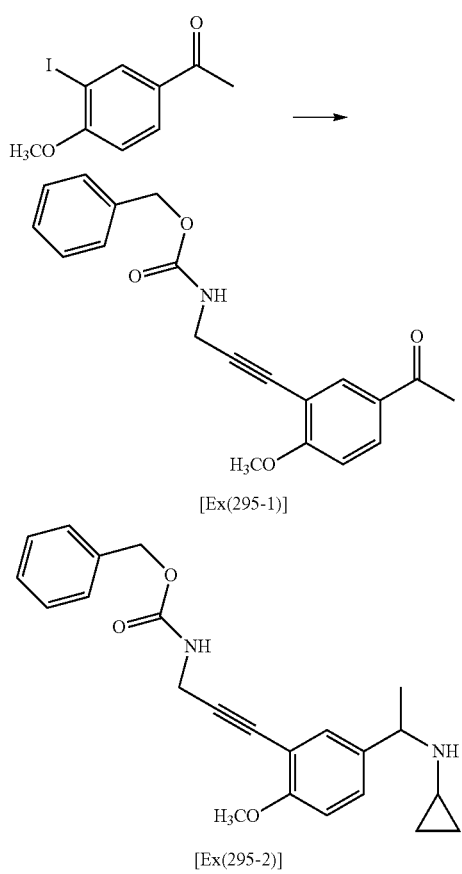
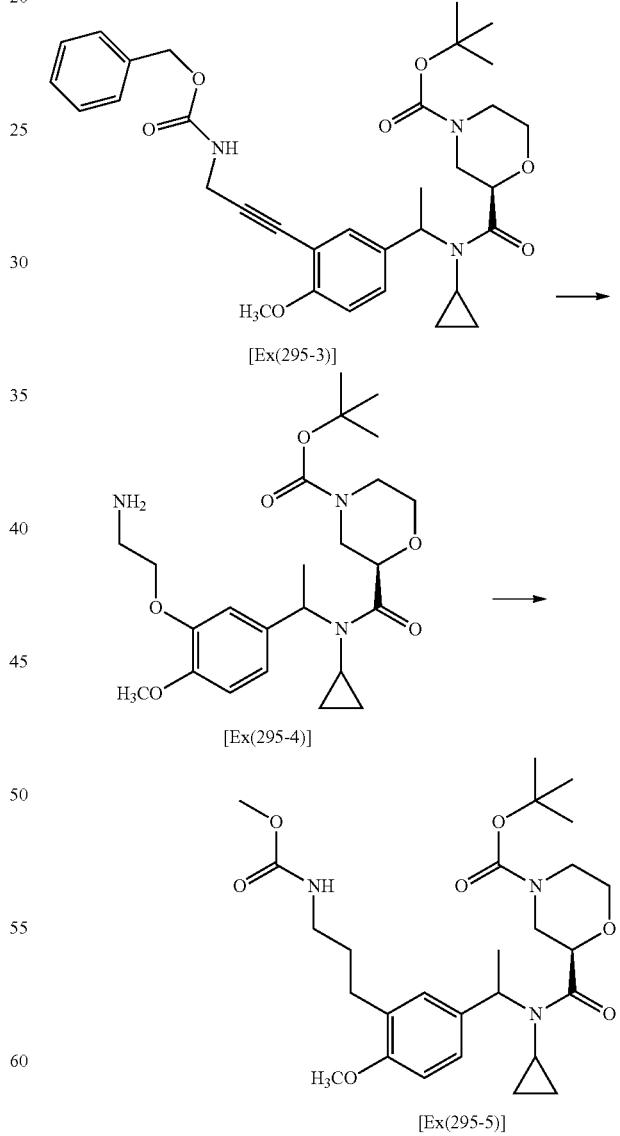
1) To a solution of 1-(3-iodo-4-methoxyphenyl)ethanone (10 g) in diethylamine (181 mL) were added benzyl prop-2-yn-1-ylcarbamate (8.2 g), dichlorobis(triphenylphosphine)palladium (II) (2.54 g) and copper (I) iodide (689 mg), and the mixture was stirred at 50° C. for 2 hours. The reaction solution was cooled, and then thereto was added water, and the mixture was extracted with chloroform. The organic layer was sequentially washed with 2-normal hydrochloric acid, water, and then dried over magnesium sulfate, and concentrated under reduced pressure. The resulting residue was purified by silica gel column chromatography (eluent: chloroform→chloroform/ethyl acetate=1/1) to give benzyl [3-(5-acetyl-2-methoxyphenyl)prop-2-yn-1-yl]carbamate [Ex(295-1)] (5.3 g) as a red solid.

APCI-MS m/z: 355[M+NH$_4$]$^+$.

2) Benzyl[3-(5-acetyl-2-methoxyphenyl)prop-2-yn-1-yl]carbamate and cyclopropylamine were treated in the similar manner to Reference Example 6(6) to give benzyl (3-{5-[1-(cyclopropylamino)ethyl]-2-methoxyphenyl}prop-2-yn-1-yl)carbamate [Ex(295-2)] as a yellow oil.

APCI-MS m/z: 379 [M+H]$^+$.

3) Benzyl (3-{5-[1-(cyclopropylamino)ethyl]-2-methoxyphenyl}prop-2-yn-1-yl)carbamate and (2R)-4-(tert-butoxycarbonyl)morpholine-2-carboxylic acid were treated in the similar manner to Example 162 to give tert-butyl (2R)-2-{[{1-[3-(3-[(benzyloxy)carbonyl]amino prop-1-yn-1-yl)-4-methoxyphenyl]ethyl}(cyclopropyl)amino] carbonyl}morpholine-4-carboxylate [Ex(295-3)] as a colorless solid.

APCI-MS m/z: 609[M+NH$_4$]$^+$.

4) To a solution of tert-butyl (2R)-2-{[{1-[3-(3-{[(benzyloxy)carbonyl]amino}prop-1-yn-1-yl)-4-methoxyphenyl]ethyl}(cyclopropyl)amino]carbonyl}morpholin-4-carboxylate (2.82 g) in methanol (25 mL) was added 10% palladium on carbon (282 mg), and the mixture was stirred under hydrogen for 7 hours. An insoluble was filtered off, and then the filtrate was concentrated under reduced pressure, and the resulting residue was purified by NH-silica gel column chromatography (eluent: chloroform→chloroform/methanol=33/1) to give tert-butyl (2R)-2-[1-[3-(3-aminopropyl)-4-methoxyphenyl]ethyl (cyclopropyl)amino]carbonyl morpholin-4-carboxylate [Ex(295-4)] (1.49 g) as a colorless oil.

APCI-MS m/z: 462 [M+H]$^+$.

5) tert-Butyl (2R)-2-{[{1-[3-(3-aminopropyl)-4-methoxyphenyl]ethyl}(cyclopropyl)amino]-carbonyl}morpholin-4-carboxylater and methyl chloroformate were treated in the similar manner to Reference Example 28(5) to give tert-butyl (2R)-2-({cyclopropyl[1-(4-methoxy-3-{3-[(methoxycarbonyl)amino]propyl}phenyl)ethyl]amino}carbonyl)morpholin-4-carboxylate [Ex(295-5)] as a colorless oil.

APCI-MS m/z: 504 [M+H]$^+$.

Example 296

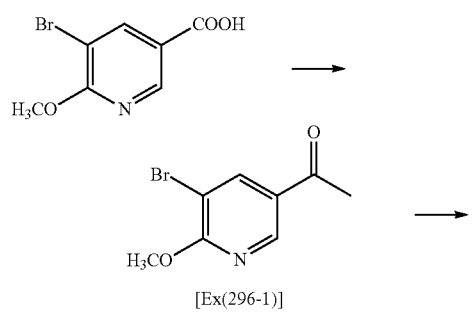

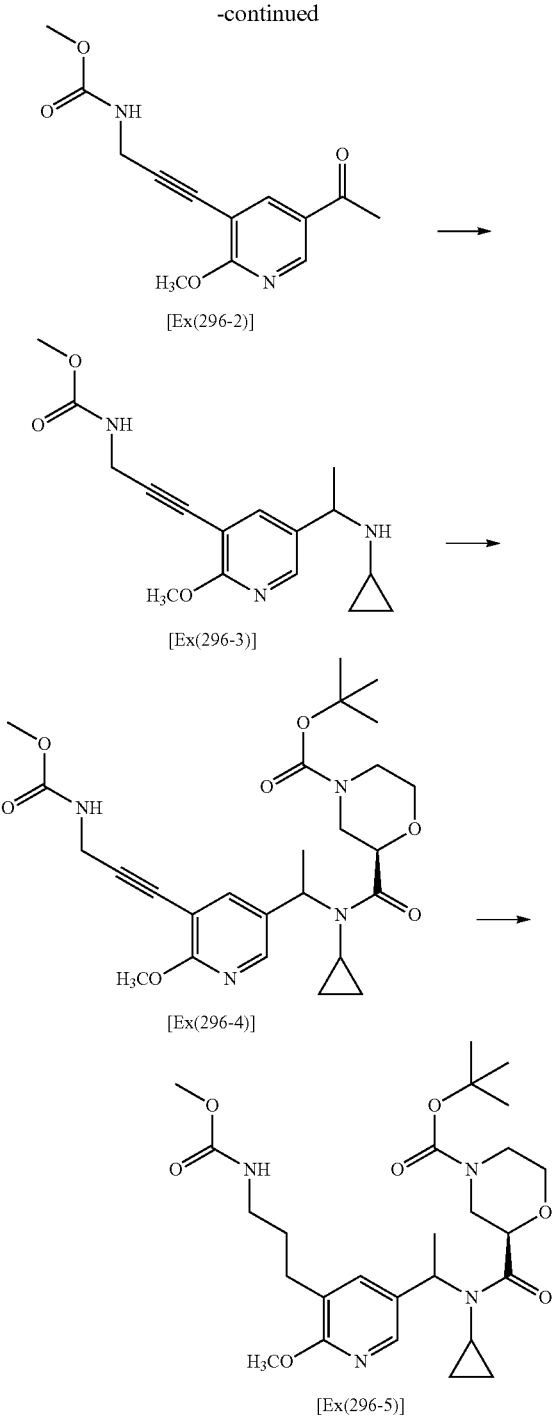

1) 5-Bromo-6-methoxynicotinic acid and N,O-dimethylhydroxylamine hydrochloride were treated in the similar manner to Reference Example 7(5), and then the resulting compound and methylmagnesium bromide were treated in the similar manner to Reference Example 7(6) to give 1-(5-bromo-6-methoxypyridin-3-yl)ethanone [Ex(296-1)] as a colorless powder.

APCI-MS m/z: 230/232 [M+H]$^+$.

2) Bis(benzonitrile)dichloropalladium (II) (12 mg) and copper (I) iodide (3.8 mg) were added to 1,4-dioxane (1 mL) under argon, and then thereto were added a solution of 10% tri-t-butylphosphine in hexane (179 μL), diisopropylamine (168 μL), 1-(5-bromo-6-methoxypyridin-3-yl)ethanone (230 mg) and a solution of methyl prop-2-yn-1-ylcarbamate (149 mg) in 1,4-dioxane (1 mL). The mixture was stirred at room temperature for 5 hours. The reaction solution was concentrated under reduced pressure, and the resulting residue was purified by silica gel column chromatography (eluent: n-hexane/ethyl acetate=3/1→1/3) to give methyl [3-(5-acetyl-2-methoxypyridin-3-yl)prop-2-yn-1-yl]carbamate [Ex(296-2)] (188 mg) as a pale yellow powder.

APCI-MS m/z: 263 [M+H]$^+$.

3) Methyl[3-(5-acetyl-2-methoxypyridin-3-yl)prop-2-yn-1-yl]carbamate and cyclopropylamine were treated in the similar manner to Reference Example 6(6) to give methyl (3-{5-[1-(cyclopropylamino)ethyl]-2-methoxypyridin-3-yl}prop-2-yn-1-yl)carbamate [Ex(296-3)] as a colorless oil.

APCI-MS m/z: 304 [M+H]$^+$.

4) Methyl (3-{5-[1-(cyclopropylamino)ethyl]-2-methoxypyridin-3-yl}prop-2-yn-1-yl)carbamate and (2R)-4-(tert-butoxycarbonyl)morpholine-2-carboxylic acid were treated in the similar manner to Example 162 to give tert-butyl (2R)-2-({cyclopropyl[1-(6-methoxy-5-{3-[(methoxycarbonyl)amino]prop-1-yn-1-yl}pyridin-3-yl)ethyl]amino}carbonyl)morpholine-4-carboxylate [Ex(296-4)] as a colorless oil.

APCI-MS m/z: 517 [M+H]$^+$.

5) To a solution of tert-butyl (2R)-2-({cyclopropyl[1-(6-methoxy-5-{3-[(methoxycarbonyl)-amino]prop-1-yn-1-yl}pyridin-3-yl)ethyl]amino}carbonyl)morpholin-4-carboxylate (150 mg) in ethyl acetate (2.5 mL)-tetrahydrofuran (2.5 mL) was added 10% palladium on carbon (30 mg), and the mixture was stirred under hydrogen for 45 minutes. An insoluble was filtered off, and then the filtrate was concentrated under reduced pressure, and the resulting residue was purified by NH-silica gel column chromatography (eluent: ethyl acetate) to give tert-butyl (2R)-2-({cyclopropyl[1-(6-methoxy-5-{3-[(methoxycarbonyl)amino]propyl}pyridin-3-yl)ethyl]amino}carbonyl)morpholine-4-carboxylate [Ex(296-5)] (159 mg) as a colorless oil.

APCI-MS m/z: 521 [M+H]$^+$.

Example 297

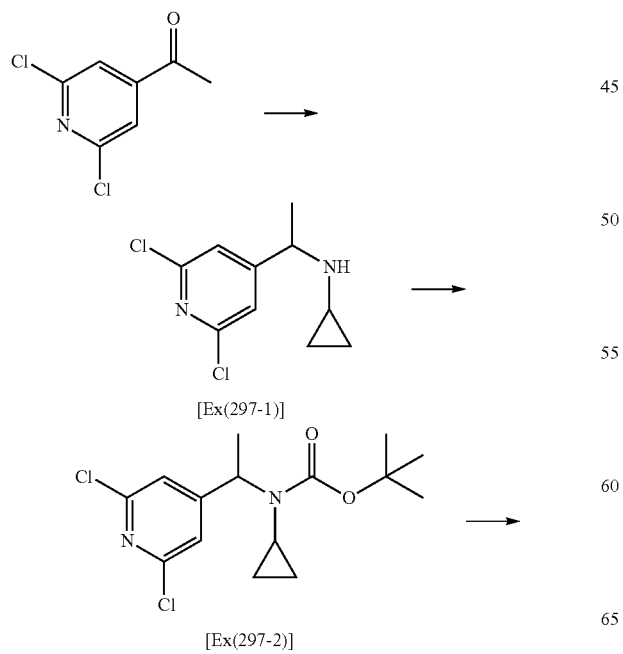

[Ex(297-1)]

[Ex(297-2)]

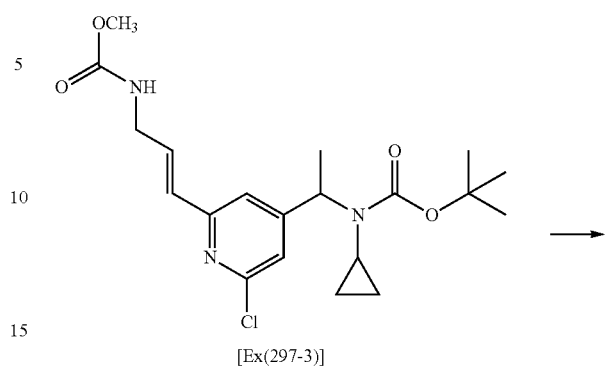

[Ex(297-3)]

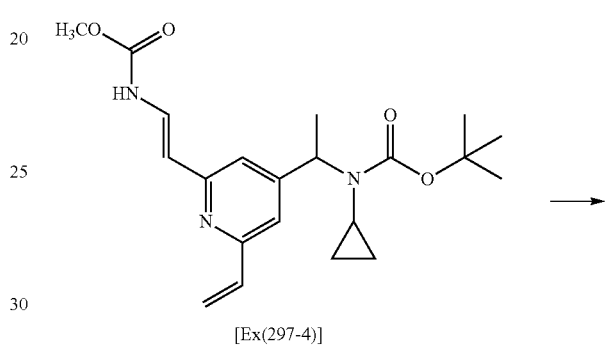

[Ex(297-4)]

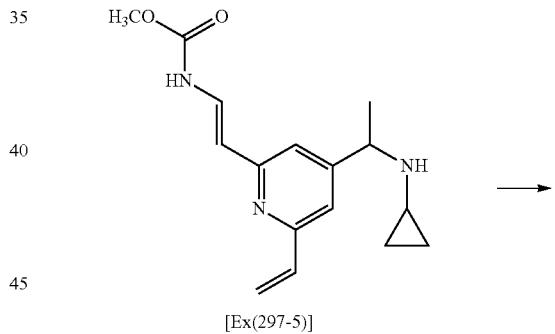

[Ex(297-5)]

[Ex(297-6)]

-continued

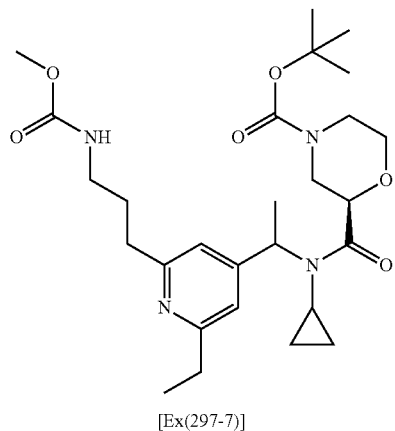

[Ex(297-7)]

1) 1-(2,6-Dichloropyridin-4-yl)ethanone and cyclopropylamine were treated in the similar manner to Reference Example 6(6) to give N-[1-(2,6-dichloropyridin-4-yl)ethyl]-cyclopropylamine [Ex(297-1)] as a pale yellow oil.

APCI-MS m/z: 231/233 [M+H]+.

2) To a solution of N-[1-(2,6-dichloropyridin-4-yl)ethyl]cyclopropylamine (430 mg) in tetrahydrofuran (5 mL) were added di-tert-butyl dicarbonate (487 mg) and triethylamine (518 μL), and the mixture was heated to reflux for 24 hours. The reaction solution was cooled, and then thereto was added water, and the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=10/1→4/1) to give tert-butyl cyclopropyl[1-(2,6-dichloropyridin-4-yl)ethyl]carbamate [Ex(297-2)] (420 mg) as a pale yellow oil.

APCI-MS m/z: 331/333 [M+H]+.

3) To a solution of tert-butyl cyclopropyl[1-(2,6-dichloropyridin-4-yl)ethyl]carbamate (155 mg) in dimethoxyethane (4 mL) were added methyl [(2E)-3-(4,4,5,5-tetramethyl-1,3,2-dioxaboran-2-yl)prop-2-en-1-yl]carbamate (113 mg), 2M potassium carbonate (257 μL) and tetrakis(triphenylphosphine)palladium (0) (27 mg), and the mixture was heated to reflux for 3 hours. The reaction solution was cooled, and then thereto was added water, and the mixture was extracted with ethyl acetate. The organic layer was washed with saturated saline, dried over magnesium sulfate, and then concentrated under reduced pressure. The resulting residue was purified by silica gel column chromatography (eluent: n-hexane/ethyl acetate=3/1→ethyl acetate) to give methyl [(2E)-3-(4-{1-[(tert-butoxycarbonyl)(cyclopropyl)amino]ethyl}-6-chloropyridin-2-yl)prop-2-en-1-yl]carbamate [Ex(297-3)] (98 mg) as a pale yellow oil.

APCI-MS m/z: 410/412 [M+H]+.

4) Methyl [(2E)-3-(4-{1-[(tert-butoxycarbonyl)(cyclopropyl)amino]ethyl}-6-chloropyridin-2-yl)-prop-2-en-1-yl]carbamate and vinyl boronic acid pinacol ester were treated in the similar manner to Reference Example 113(6) to give methyl [(E)-2-(4-{1-[(tert-butoxycarbonyl)(cyclopropyl)amino]ethyl}-6-vinylpyridin-2-yl)vinyl]carbamate [Ex(297-4)] as a yellow oil.

APCI-MS m/z: 402 [M+H]+.

5) Methyl [(E)-2-(4-{1-[(tert-butoxycarbonyl)(cyclopropyl)amino]ethyl}-6-vinylpyridin-2-yl)vinyl]carbamate and trifluoroacetic acid were treated in the similar manner to Reference Example 113(8) to give methyl ((E)-2-{4-[1-(cyclopropylamino)ethyl]-6-vinylpyridin-2-yl}vinyl)carbamate [Ex(297-5)] as a pale yellow oil.

APCI-MS m/z: 302 [M+H]+.

6) Methyl ((E)-2-{4-[1-(cyclopropylamino)ethyl]-6-vinylpyridin-2-yl}vinyl)carbamate and (2R)-4-(tert-butoxycarbonyl)morpholin-2-carboxylic acid were treated in the similar manner to Example 162 to give tert-butyl (2R)-2-({cyclopropyl[1-(2-{(1E)-3-[(methoxycarbonyl)amino]prop-1-en-1-yl}-6-vinylpyridin-4-yl)ethyl]amino}carbonyl)morpholin-4-carboxylate [Ex(297-6)] as a yellow oil. APCI-MS m/z: 515 [M+H]+.

7) tert-Butyl (2R)-2-({cyclopropyl[1-(2-{(1E)-3-[(methoxycarbonyl)amino]prop-1-en-1-yl}-6-vinylpyridin-4-yl)ethyl]amino}carbonyl)morpholine-4-carboxylate was reduced in the similar manner to Example 296(5) to give tert-butyl (2R)-2-({cyclopropyl[1-(2-ethyl-6-{3-[(methoxycarbonyl)amino]propyl}pyridin-4-yl)ethyl]amino}carbonyl)morpholin-4-carboxylate [Ex(297-7)] as a colorless oil.

APCI-MS m/z: 519 [M+H]+.

Example 298

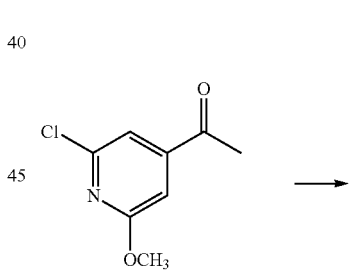

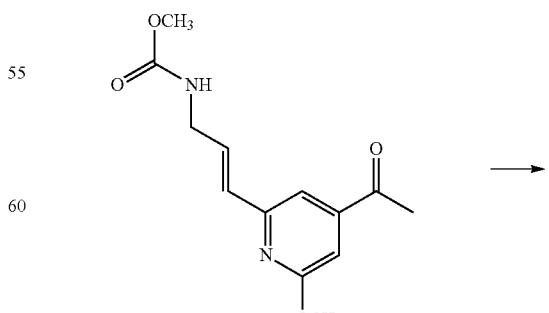

[Ex(298-1)]

183
-continued

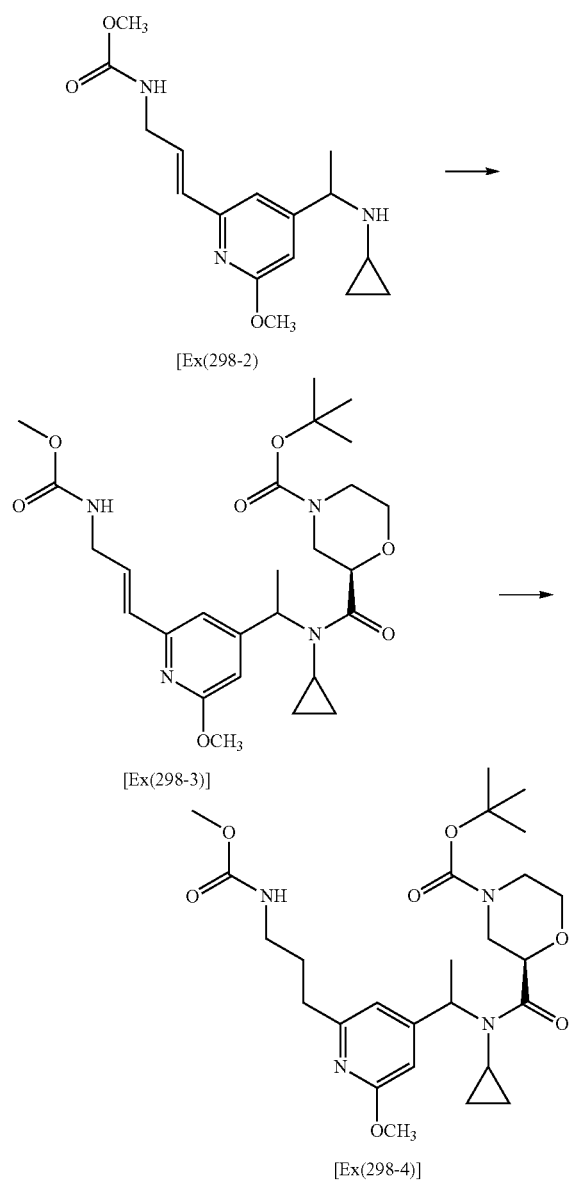

[Ex(298-2)]

[Ex(298-3)]

[Ex(298-4)]

184

1) 1-(2-Chloro-6-methoxypyridin-4-yl)ethanone and methyl [(2E)-3-(4,4,5,5-tetramethyl-1,3,2-dioxaboran-2-yl)prop-2-en-1-yl]carbamate were treated in the similar manner to Example 297(3) to give methyl [(2E)-3-(4-acetyl-6-methoxypyridin-2-yl)prop-2-en-1-yl]carbamate [Ex(298-1)] as a colorless powder.

APCI-MS m/z: 265 [M+H]$^+$.

2) Methyl [(2E)-3-(4-acetyl-6-methoxypyridin-2-yl)prop-2-en-1-yl]carbamate and cyclopropylamine were treated in the similar manner to Reference Example 6(6) to give methyl ((2E)-3-{4-[1-(cyclopropylamino)ethyl]-6-methoxypyridin-2-yl}prop-2-en-1-yl)carbamate [Ex(298-2)] as a colorless oil.

APCI-MS m/z: 306 [M+H]$^+$.

3) Methyl ((2E)-3-{4-[1-(cyclopropylamino)ethyl]-6-methoxypyridin-2-yl}prop-2-en-1-yl)carbamate and (2R)-4-(tert-butoxycarbonyl)morpholine-2-carboxylic acid were treated in the similar manner to Example 162 to give tert-butyl (2R)-2-({cyclopropyl[1-(2-methoxy-6-{(1E)-3-[(methoxycarbonyl)amino]prop-1-en-1-yl}pyridin-4-yl)ethyl]amino}carbonyl)morpholine-4-carboxylate [Ex(298-3)] as a colorless oil.

APCI-MS m/z: 519 [M+H]$^+$.

4) tert-Butyl (2R)-2-({cyclopropyl[1-(2-methoxy-6-{(1E)-3-[(methoxycarbonyl)amino]-prop-1-en-1-yl}pyridin-4-yl)ethyl]amino}carbonyl)morpholin-4-carboxylate was reduced in the similar manner to Example 296(5) to give tert-butyl (2R)-2-({cyclopropyl[1-(2-methoxy-6-{3-[(methoxycarbonyl)amino]propyl}pyridin-4-yl)ethyl]amino}carbonyl)morpholin-4-carboxylate [Ex(298-4)] as a colorless oil.

APCI-MS m/z: 521 [M+H]$^+$.

Examples 299 to 308 were synthesized according to a combination of the methods described herein and conventional methods.

TABLE 71

| EX. No. | Structural formula | a | b | c |
|---|---|---|---|---|
| 299 | | 2HCl | 465 | [M + H]$^+$ |

TABLE 71-continued

| EX. No. | Structural formula | a | b | c |
|---|---|---|---|---|
| 300 | | 2HCl | 465 | [M + H]+ |
| 301 | | 2HCl | 463 | [M + H]+ |
| 302 | | 2HCl | 463 | [M + H]+ |
| 303 | | 2HCl | 449 | [M + H]+ |

Ex. No.: Example Number
a: Salt
b: Mass spectrometric value
c: Ion species

TABLE 72

| EX. No. | Structural formula | a | b | c |
|---|---|---|---|---|
| 304 | | 2HCl | 449 | [M + H]+ |
| 305 | | 2HCl | 483 | [M + H]+ |
| 306 | | 2HCl | 483 | [M + H]+ |
| 307 | | 2HCl | 483 | [M + H]+ |

TABLE 72-continued

| EX. No. | Structural formula | a | b | c |
|---|---|---|---|---|
| 308 | (structure shown) | 2HCl | 483 | [M + H]⁺ |

Ex. No.: Example Number
a: Salt
b: Mass spectrometric value
c: Ion species

Reference Example 1

N-[1-(2-Naphthyl)ethyl]cyclopropylamine hydrochloride [REx(1-2)]

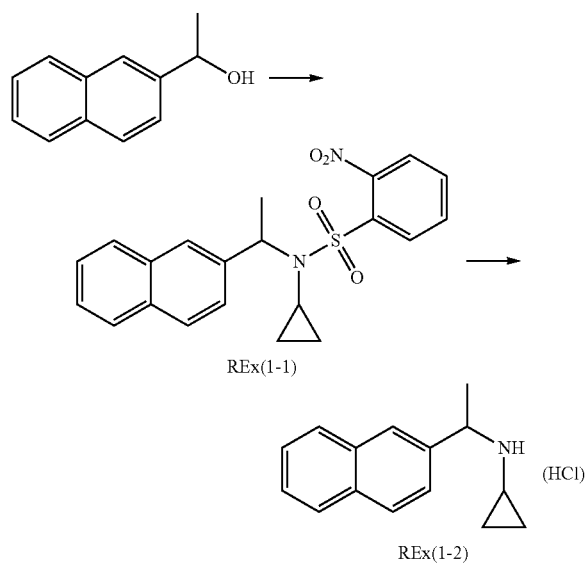

(1) N-Cyclopropyl-N-[1-(2-naphthyl)ethyl]-2-nitrobenzenesulfonamide [REx(1-1)]:

To a solution of 1-(2-naphthyl)ethanol (344 mg), N-cyclopropyl-2-nitrobenzenesulfonamide (581 mg) and triphenylphosphine (787 mg) in tetrahydrofuran (10 mL) was added dropwise diisopropyl azodicarboxylate (590 μL) under ice-cooling, and the mixture was stirred at room temperature for 3 hours. The reaction solution was concentrated, and the resulting residue was purified by silica gel column chromatography (eluent: n-hexane/ethyl acetate=4/1→41/1), and then triturated with diethyl ether-n-hexane (1:1) to give N-cyclopropyl-N-[1-(2-naphthyl)ethyl]-2-nitrobenzenesulfonamide [REx(1-1)] (499 mg) as a colorless powder.

APCI-MS m/z: 397 [M+H]⁺.

(2) N-[1-(2-Naphthyl)ethyl]cyclopropylamine hydrochloride [REx(1-2)]:

To a solution of the compound obtained in (1) (480 mg) and 4-bromothiophenol (250 mg) in N,N-dimethylformamide (12 mL) was added potassium carbonate (304 mg), and the mixture was stirred at room temperature for 17 hours. To the reaction solution was added water, and the mixture was extracted with ethyl acetate. The organic layer was sequentially washed with water twice and saturated saline, dried over sodium sulfate, and then concentrated under reduced pressure. The resulting residue was dissolved in ethyl acetate (5 mL), and then thereto was added 4-normal hydrogen chloride-ethyl acetate (1 mL). The precipitated solid was filtered to give N-[1-(2-naphthyl)ethyl]cyclopropylamine hydrochloride [REx(1-2)] (211 mg) as a colorless powder.

APCI-MS m/z: 212 [M+H]⁺.

Reference Example 2

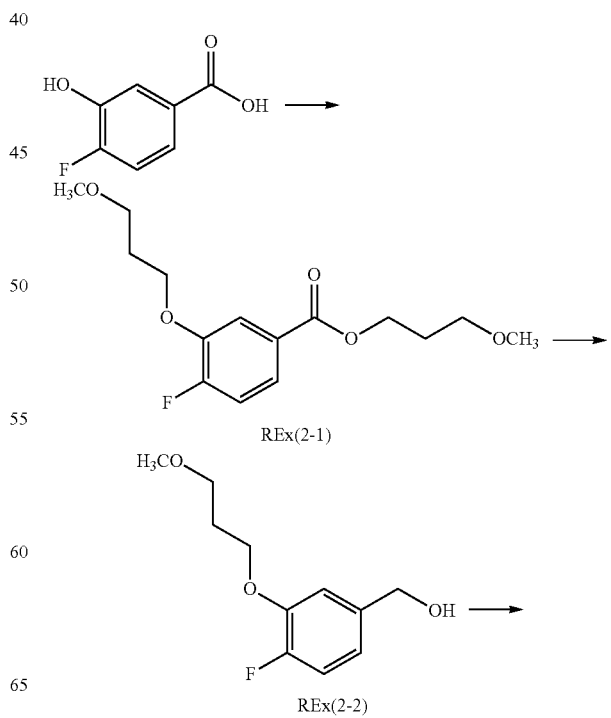

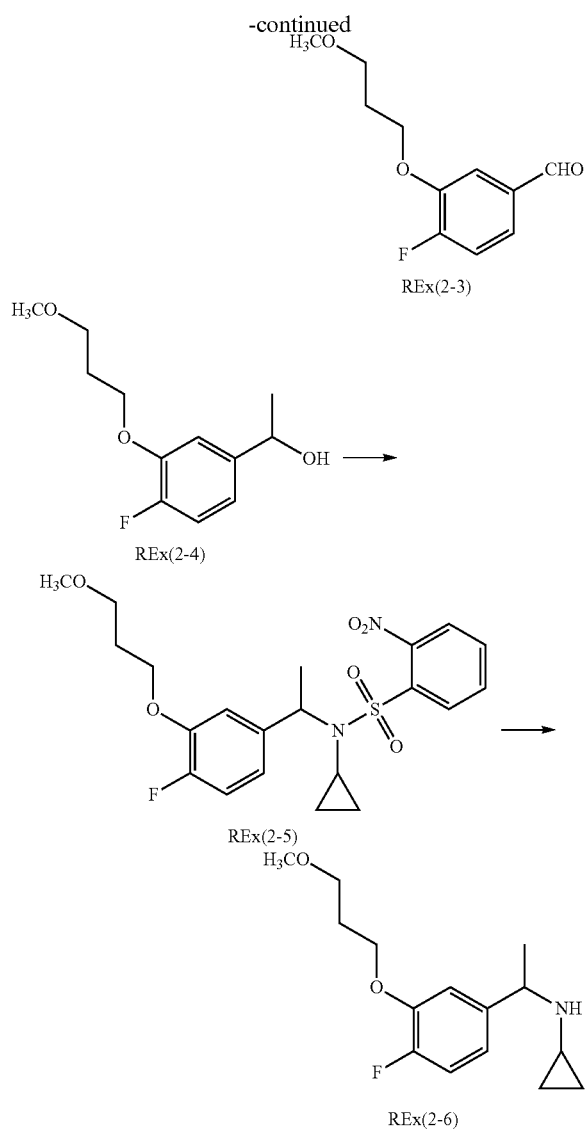

(1) 3-Methoxypropyl 4-fluoro-3-(3-methoxypropoxy)benzoate [REx(2-1)]:

To a solution of 4-fluoro-3-hydroxybenzoic acid (2.0 g) in acetonitrile (100 mL)-N,N-dimethylformamide (50 mL)-water (2.0 mL) were added potassium carbonate (5.31 g) and 1-bromo-3-methoxypropane (4.32 g), and the mixture was heated to reflux at 90° C. for 18 hours. To the reaction mixture was added water under ice-cooling, and then the mixture was extracted with ethyl acetate. The organic layer was washed with saturated saline, dried over magnesium sulfate, and then concentrated under reduced pressure. The resulting residue was purified by silica gel column chromatography (eluent: n-hexane/ethyl acetate=4/1→1/2 to give 3-methoxypropyl 4-fluoro-3-(3-methoxypropoxy)benzoate [REx(2-1)] (2.72 g) as a colorless oil.

APCI-MS m/z: 301 [M+H]$^+$.

(2) [Fluoro-3-(3-methoxypropoxy)phenyl]methanol [REx(2-2)]:

To a suspension of lithium aluminum hydride (344 mg) in tetrahydrofuran (20 mL) was added dropwise a solution of the compound obtained in the above (1) (2.72 g) in tetrahydrofuran (8 mL) under ice-cooling, and then the mixture was stirred under the cooling for 1 hour. Under the cooling, to the reaction mixture were sequentially and slowly added water and 2-normal aqueous sodium hydroxide solution (1 mL), and then the mixture was stirred at room temperature for 1 hour. An insoluble was filtered off through Celite, and the filtrate was washed with aqueous saturated sodium hydrogen carbonate solution, and then dried over magnesium sulfate. The resultant was concentrated under reduced pressure, and the resulting residue was purified by silica gel column chromatography (eluent: n-hexane/ethyl acetate=2/1→1/2) to give [fluoro-3-(3-methoxypropoxy)phenyl]methanol [REx(2-2)] (1.78 g) as a colorless oil.

APCI-MS m/z: 232[M+NH$_4$]$^+$.

(3) 4-Fluoro-3-(3-methoxypropoxy)benzaldehyde [REx(2-3)]:

To a solution of the compound obtained in the above (2) (1.65 g) in dichloromethane (43 mL) was added 85% activated manganese dioxide (7.88 g), and the mixture was stirred at room temperature for 1 hour, and then the mixture was heated to reflux for 2 hours. An insoluble was filtered off through Celite, and then the filtrate was concentrated under reduced pressure to give 4-fluoro-3-(3-methoxypropoxy)benzaldehyde [REx(2-3)] (1.59 g) as a colorless oil.

APCI-MS m/z: 213 [M+H]$^+$.

(4) 1-[4-Fluoro-3-(3-methoxypropoxy)phenyl]ethanol [REx(2-4)]:

To a solution of the compound obtained in the above (3) (1.55 g) in tetrahydrofuran (30 mL) was added dropwise a solution of methylmagnesium bromide in 3M diethyl ether (2.68 mL) under ice-cooling, and the mixture was stirred at the same temperature for 10 minutes. Under ice-cooling, thereto was added aqueous ammonium chloride solution, and the mixture was extracted with ethyl acetate. The organic layer was sequentially washed with water and saturated saline, and then dried over magnesium sulfate and concentrated under reduced pressure to give 1-[4-fluoro-3-(3-methoxypropoxy)phenyl]ethanol [REx(2-4)] (1.43 g) as a yellow oil.

APCI-MS m/z: 246 [M+NH$_4$]$^+$.

(5) Then, an amine compound [REx(2-6)] may be obtained in the similar manner to Reference Example 1.

Reference Example 3

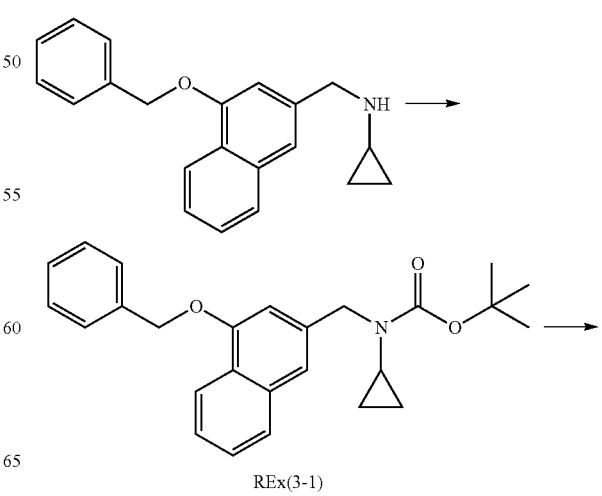

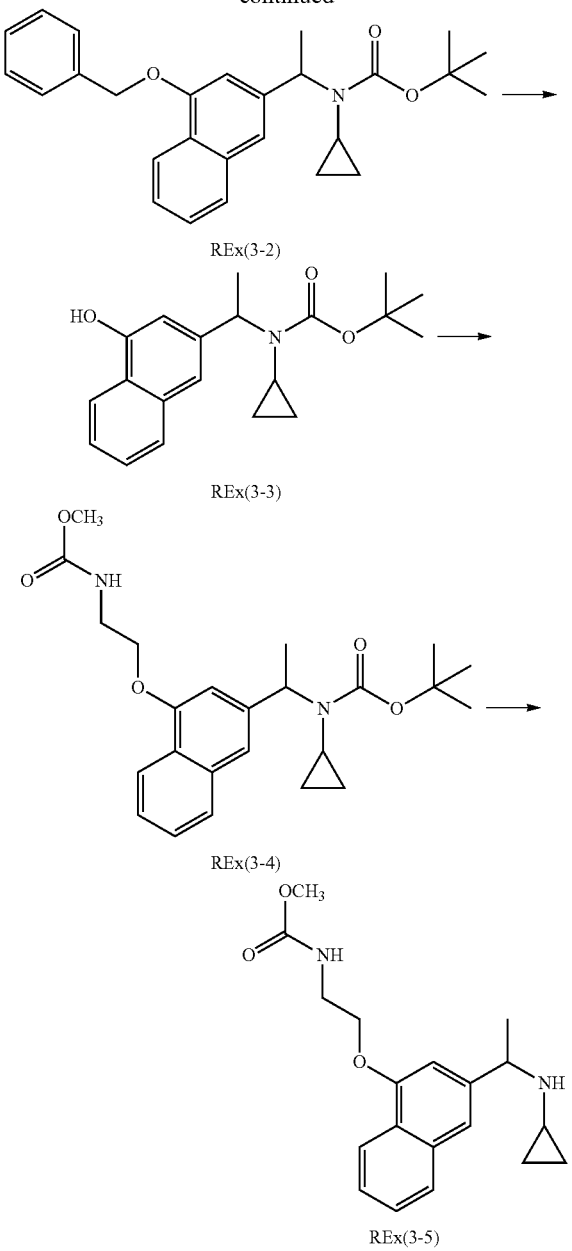

(1) tert-Butyl {[4-(benzyloxy)-2-naphthyl]methyl}cyclopropylcarbamate [REx(3-1)]:

To a solution of N-{[4-(benzyloxy)-2-naphthyl]methyl}cyclopropylamine (12.3 g) in dichloromethane (150 mL) were added triethylamine (5.93 mL) and di-t-butyl dicarbonate (9.29 g) under ice-cooling, and the mixture was stirred at room temperature for 3 hours. To the reaction solution was added saturated aqueous ammonium chloride solution under ice-cooling, and the mixture was extracted with chloroform. The organic layer was washed with water and saturated saline, dried over sodium sulfate, and then concentrated under reduced pressure. The resulting residue was purified by silica gel column chromatography (eluent: n-hexane/ethyl acetate=19/1→9/1) to give tert-butyl {[4-(benzyloxy)-2-naphthyl]methyl}cyclopropylcarbamate [REx(3-1)] (15.8 g) as a colorless powder.

APCI-MS m/z: 404 [M+H]$^+$.

(2) tert-Butyl {1-[4-(benzyloxy)-2-naphthyl]ethyl} cyclopropylcarbamate [REx(3-2)]:

To a solution of the compound obtained in the above (1) (807 mg) and tetramethylethylenediamine (0.39 μL) in tetrahydrofuran (10 mL) were added dropwise a solution of 1.55M n-butyllithium in hexane (1.55 mL) at −78° C. under argon over 5 minutes. The mixture was stirred at the same temperature for 1 hour, and then thereto was added iodomethane (0.187 μL) at −78° C. The mixture was stirred at the same temperature for 30 minutes, and then stirred under ice-cooling for 2 hours. To the reaction solution was added saturated aqueous ammonium chloride solution under ice-cooling, and then the mixture was extracted with ethyl acetate. The organic layer was washed with water twice and saturated saline, dried over sodium sulfate, and then concentrated under reduced pressure. The resulting residue was purified by silica gel column chromatography (eluent: n-hexane/ethyl acetate=20/1→6/1) to give tert-butyl {1-[4-(benzyloxy)-2-naphthyl]ethyl}cyclopropylcarbamate [REx(3-2)] (611 mg) as a colorless oil.

APCI-MS m/z: 418 [M+H]$^+$.

(3) tert-Butyl[1-(4-hydroxy2-naphthyl)ethyl]carbamate [REx(3-3)]:

To a solution of the compound obtained in the above (2) (126 mg) in methanol (3 mL) was added 10% palladium on carbon (13 mg), and the mixture was stirred under hydrogen for 3 hours. The reaction solution was diluted with ethyl acetate, and a catalyst was filtered, and then the resultant was concentrated under reduced pressure. The resulting residue was triturated with isopropyl ether/n-hexane (1:1) to give tert-butyl cyclopropyl[1-(4-hydroxy2-naphthyl)ethyl]carbamate [REx(3-3)] (50 mg) as a colorless powder.

ESI-MS m/z: 326[M−H]$^-$.

(4) Methyl {2-[(3-{1-[(tert-butoxycarbonyl)(cyclopropyl)amino]ethyl}-1-naphthyl)oxy]ethyl}carbamate [REx(3-4)]:

To a solution of the compound obtained in the above (3) (243 mg) and methyl (2-bromoethyl)carbamate (203 mg) in acetonitrile (10 mL) was added potassium carbonate (205 mg), and the mixture was stirred at 80° C. for 7 hours. After cooling, to the reaction solution was added water, and the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=4/1→1/1) to give methyl {2-[(3-{1-[(tert-butoxycarbonyl)(cyclopropyl)amino]ethyl}-1-naphthyl)oxy]ethyl}carbamate [REx(3-4)] (161 mg) as a pale yellow oil.

APCI-MS m/z: 429 [M+H]$^+$.

(5) Methyl[2-({3-[1-(cyclopropylamino)ethyl]-1-naphthyl}oxy)ethyl]carbamate [REx(3-5)]:

To a solution of the compound obtained in the above (4) (156 mg) in chloroform (2 mL) was added 4-normal hydrogen chloride-dioxane solution (2 mL) under ice-cooling, and the mixture was stirred at room temperature for 1 hour. The mixture was concentrated under reduced pressure, and to the resulting residue was added aqueous saturated sodium hydrogen carbonate solution, and the mixture was extracted with chloroform. The organic layer was dried over sodium sulfate, and then concentrated under reduced pressure. The resulting residue was purified by silica gel column chromatography (eluent: ethyl acetate→ethyl acetate/methanol=10/1) to give methyl [2-({3-[1-(cyclopropylamino)ethyl]-1-naphthyl}oxy)ethyl]carbamate [REx(3-5)] (76 mg) as a pale yellow oil.

APCI-MS m/z: 329 [M+H]$^+$.

Reference Example 4

[1-(4-Methoxy-2-naphthyl)ethyl]cyclopropylamine [REx(4-1)]

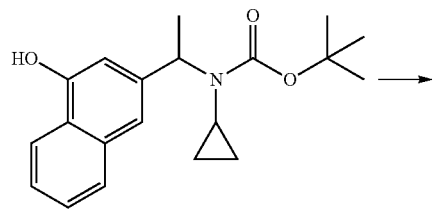

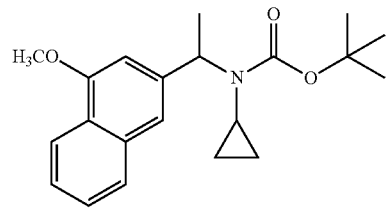

REx(4-1)

To a mixture of tert-butyl cyclopropyl[1-(4-hydroxy2-naphthyl)ethyl]carbamate (43 mg) and potassium carbonate (27 mg) was added N,N-dimethylformamide (2.0 mL), and then thereto added methyl iodide (0.016 mL), and the mixture was stirred at room temperature for 4 hours. After cooling, to the reaction solution was added water, and the mixture was extracted with ethyl acetate. The organic layer was sequentially washed with water twice and saturated saline, dried over sodium sulfate, and then concentrated under reduced pressure. The resulting residue was purified by silica gel column chromatography (eluent: n-hexane/ethyl acetate=10/1→4/1) to give tert-butyl cyclopropyl[1-(4-methoxy-2-naphthyl)ethyl]carbamate [REx(4-1)] (33 mg) as a colorless oil.

APCI-MS m/z: 342 [M+H]$^+$.

Then, deprotection of Boc group according to any one of methods of Examples 1 to 5 may give the desired amine compound.

Reference Example 5

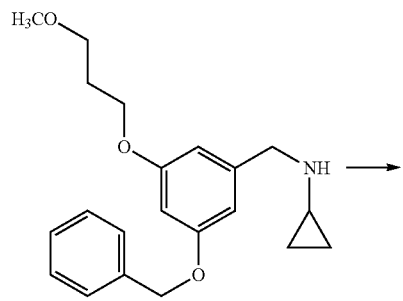

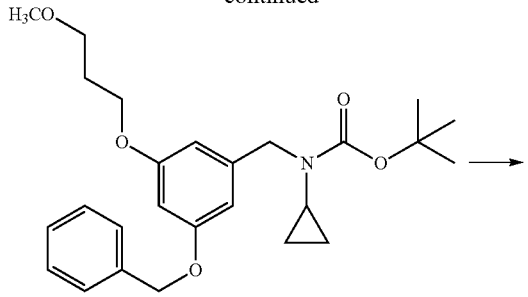

REx(5-1)

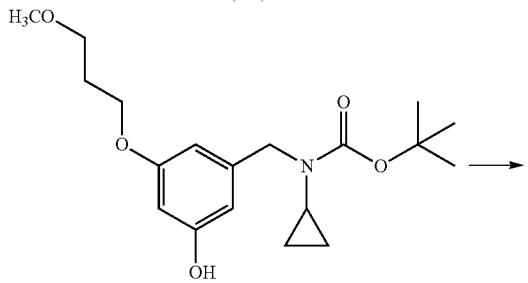

REx(5-2)

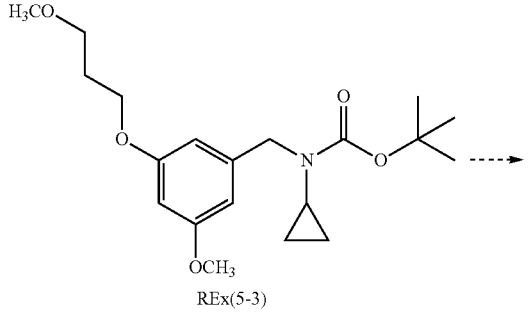

REx(5-3)

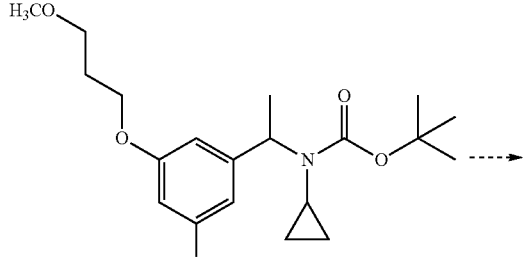

REx(5-4)

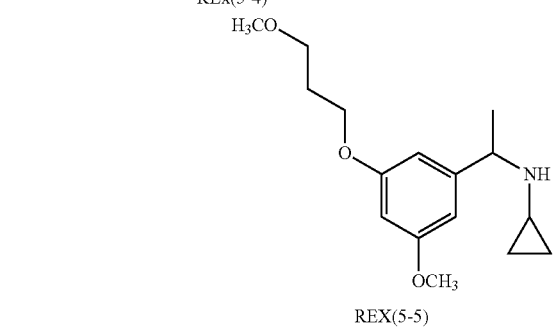

REX(5-5)

(1) tert-Butyl[3-(benzyloxy)-5-(3-methoxypropoxy)benzyl]cyclopropylcarbamate [REx(5-1)]:

To a solution of N-[3-(benzyloxy)-5-(3-methoxypropoxy)benzyl]cyclopropylamine (15.4 g) in dichloromethane (190 mL) were added triethylamine (6.60 mL) and di-t-butyl dicarbonate (10.3 g) under ice-cooling, and the mixture was stirred at room temperature for 4 hours. To the reaction solution was added saturated aqueous ammonium chloride solution under ice-cooling, and the mixture was extracted with chloroform. The organic layer was washed with water and saturated saline, dried over sodium sulfate, and then concentrated under reduced pressure. The resulting residue was purified by silica gel column chromatography (eluent: n-hexane/ethyl acetate=14/1) to give tert-butyl [3-(benzyloxy)-5-(3-methoxypropoxy)benzyl]cyclopropylcarbamate [REx(5-1)] (20.0 g) as a colorless oil.

APCI-MS m/z: 459[M+NH4]$^+$.

(2) tert-Butyl cyclopropyl[3-hydroxy5-(3-methoxypropoxy)benzyl]carbamate [REx(5-2)]:

To a solution of the compound obtained in the above (1) (14.0 g) in ethanol (210 mL) was added 20% palladium hydroxide on carbon (2.80 g), and the mixture was stirred under hydrogen for 30 minutes. An insoluble was filtered, and then concentrated under reduced pressure. The resulting residue was purified by silica gel column chromatography (eluent: n-hexane/ethyl acetate=4/1→2/1) to give tert-butyl cyclopropyl[3-hydroxy5-(3-methoxypropoxy)benzyl]carbamate [REx(5-2)] (11.0 g) as a colorless oil.

APCI-MS m/z: 352 [M+H]$^+$.

(3) tert-Butyl cyclopropyl[3-methoxy-5-(3-methoxypropoxy)benzyl]carbamate [REx(5-3)]:

To a solution of the compound obtained in the above (2) (3.51 g) in N,N-dimethylformamide (50 mL) was added potassium carbonate (2.07 g), and then thereto was added iodomethane (0.75 mL) under ice-cooling, and the mixture was stirred at room temperature for 23 hours. To the reaction solution was added water, and the mixture was extracted with ethyl acetate. The organic layer was sequentially washed with water twice and saturated saline, dried over sodium sulfate, and then concentrated under reduced pressure.

The resulting residue was purified by silica gel column chromatography (eluent: n-hexane/ethyl acetate=3/1) to give tert-butyl cyclopropyl[3-methoxy-5-(3-methoxypropoxy)benzyl]carbamate [REx(5-3)] (3.65 g) as a colorless oil.

APCI-MS m/z: 366 [M+H]$^+$.

(4) Methylation according to the method of Reference Example 3(2), then deprotecting Boc group according to any one of methods of Examples 1 to 5 give the desired amine compound [REx(5-5)].

Reference Example 6

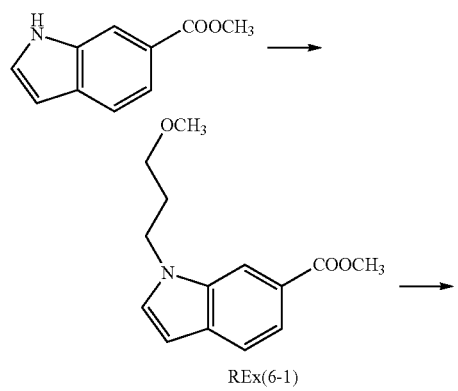

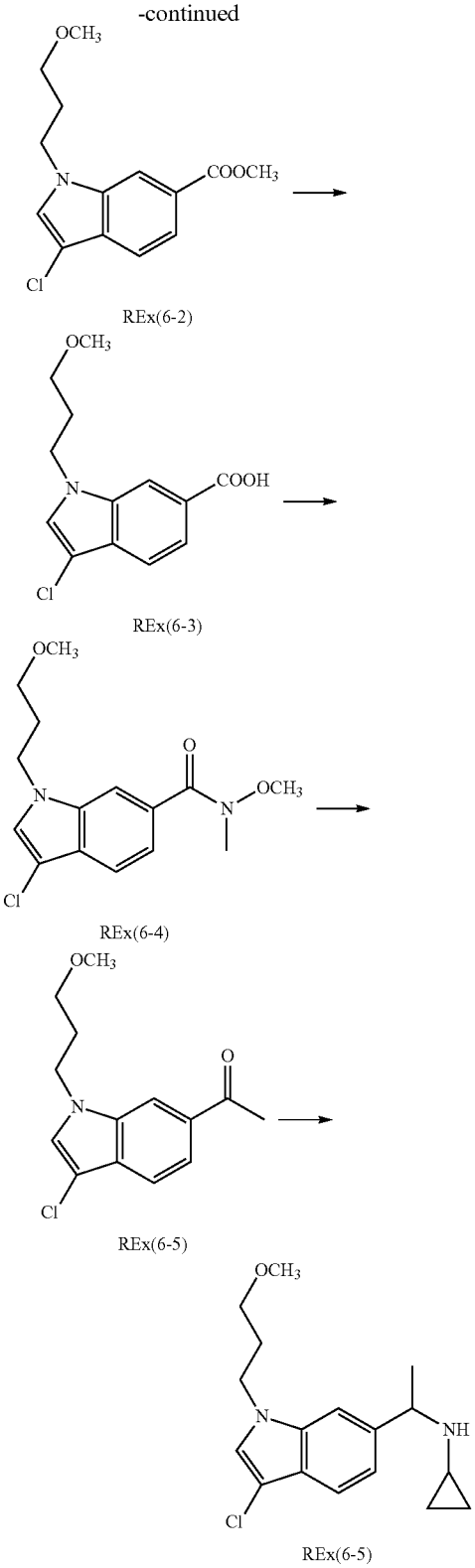

(1) Methyl 1-(3-methoxypropyl)-1H-indole-6-carboxylate [REx(6-1)]:

To a solution of methyl 1H-indole-6-carboxylate (5.0 g) in N,N-dimethylformamide (40 mL) was added drop by drop 60% oil-based sodium hydride (1.37 g) under ice-cooling, and then the mixture was stirred at room temperature for 15 minutes. Then, thereto was added dropwise a solution of 1-bromo-3-methoxypropane (5.24 g) in N,N-dimethylformamide (10 mL) under ice-cooling, and then thereto was added potassium iodide (948 mg), and the mixture was stirred at room temperature for 3 hours. To the reaction mixture was sequentially added ethyl acetate and water under ice-cooling, and the organic layer was separated. The organic layer was washed with water twice and saturated saline, dried over sodium sulfate, and then concentrated under reduced pressure. The resulting residue was purified by silica gel column chromatography (eluent: n-hexane/ethyl acetate=9/1→4/1) to give methyl 1-(3-methoxypropyl)-1H-indole-6-carboxylate [REx(6-1)] (5.8 g) as a colorless oil.

APCI-MS m/z: 248 [M+H]+.

(2) Methyl 3-chloro-1-(3-methoxypropyl)-1H-indole-6-carboxylate [REx(6-2)]:

To a solution of the compound obtained in the above (1) (2.78 g) in dichloromethane (35 mL) was added N-chlorosuccinimide (1.65 g) under ice-cooling, and the mixture was stirred at room temperature for 18 hours. To the reaction mixture was added water, and the mixture was extracted with chloroform. The organic layer was washed with saturated saline, dried over sodium sulfate, and then concentrated under reduced pressure. The resulting residue was purified by silica gel column chromatography (eluent: n-hexane→n-hexane/ethyl acetate=2/1) to give methyl 3-chloro-1-(3-methoxypropyl)-1H-indole-6-carboxylate [REx(6-2)] (3.10 g) as a yellow oil.

APCI-MS m/z: 282/284 [M+H]+.

(3) 3-Chloro-1-(3-methoxypropyl)-1H-indole-6-carboxylic acid [REx(6-3)]:

To a solution of the compound obtained in the above (2) (1.20 g) in ethanol (10 mL) was added 2-normal aqueous sodium hydroxide solution (4.26 mL) under ice-cooling, and the mixture was stirred at room temperature for 20 hours. The reaction mixture was concentrated, and then the mixture was acidified by adding 2-normal hydrochloric acid under ice-cooling, and then thereto was added water, and the mixture was extracted with ethyl acetate. The organic layer was washed with saturated saline, and then concentrated under reduced pressure to give 3-chloro-1-(3-methoxypropyl)-1H-indole-6-carboxylic acid [REx(6-3)] (1.14 g) as a colorless powder.

ESI-MS m/z: 266/268[M−H]−.

(4) 3-Chloro-N-methoxy-1-(3-methoxypropyl)-N-methyl-1H-indole-6-carboxamide [REx(6-4)]:

To a solution of the compound obtained in the above (3) (1.14 g), N,O-dimethylhydroxyamine hydrochloride (831 mg), 1-ethyl-3-(3-dimethylaminopropyl)-carbodiimide hydrochloride (1.25 g) and 1-hydroxybenzotriazole (863 mg) in chloroform (12 mL) was added diisopropylethylamine (1.85 mL) under ice-cooling, and then the mixture was stirred at room temperature for 24 hours. To the reaction mixture was added aqueous saturated sodium hydrogen carbonate solution under ice-cooling, and the mixture was extracted with chloroform. The organic layer was sequentially washed with water and saturated saline, dried over magnesium sulfate, and then concentrated under reduced pressure. The resulting residue was purified by silica gel column chromatography (eluent: n-hexane/ethyl acetate=1/1→1/3) to give 3-chloro-N-methoxy-1-(3-methoxypropyl)-N-methyl-1H-indole-6-carboxamide [REx(6-4)] (1.20 g) as a pale yellow oil.

APCI-MS m/z: 311/313 [M+H]+.

(5) 1-[3-Chloro-1-(3-methoxypropyl)-1H-indol-6-yl]ethanone [REx(6-5)]:

To a solution of the compound obtained in the above (4) (1.20 g) in tetrahydrofuran (15 mL) was added dropwise a 3M solution of methylmagnesium bromide in diethyl ether (2.56 mL) under ice-cooling, and the mixture was stirred at the same temperature for 1 hour. To the reaction solution was added 1-normal hydrochloric acid under ice-cooling, and the mixture was extracted with ethyl acetate. The organic layer was washed with saturated saline, and then dried over magnesium sulfate and concentrated under reduced pressure. The resulting residue was purified by silica gel column chromatography (eluent: n-hexane/ethyl acetate=4/1→1/1) to give 1-[3-chloro-1-(3-methoxypropyl)-1H-indol-6-yl]ethanone [REx(6-5)] (945 mg) as a pale yellow oil.

APCI-MS m/z: 266/268 [M+H]+.

(6) N-{1-[3-Chloro-1-(3-methoxypropyl)-1H-indol-6-yl]ethyl}cyclopropanamine [REx(6-6)]:

To a solution of the compound obtained in the above (5) (155 mg) and cyclopropylamine (99.9 mg) in dichloroethane (3.0 mL) were added magnesium sulfate (351 mg), sodium triacetoxyborohydride (371 mg) and acetic acid (105 mg), and then the mixture was stirred at room temperature for 17 hours. To the reaction mixture was added aqueous saturated sodium hydrogen carbonate solution under ice-cooling, and the mixture was extracted with chloroform. The organic layer was washed with saturated saline, dried over magnesium sulfate, and then concentrated under reduced pressure. The resulting residue was purified by silica gel column chromatography (eluent: ethyl acetate→ethyl acetate/methanol=20/1) to give N-{1-[3-chloro-1-(3-methoxypropyl)-1H-indol-6-yl]ethyl}cyclopropanamine [REx(6-6)] (111 mg) as a pale yellow oil.

APCI-MS m/z: 307/309 [M+H]+.

Reference Example 7

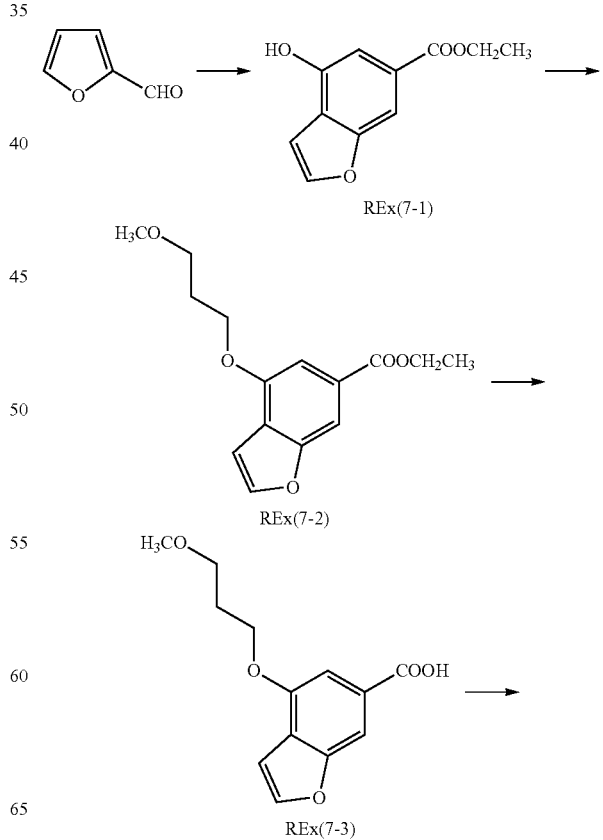

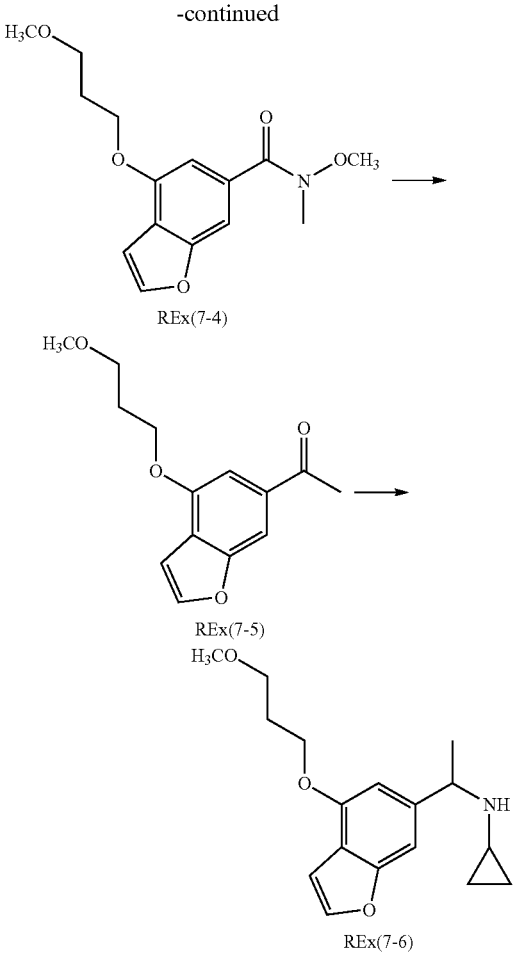

REx(7-4)

REx(7-5)

REx(7-6)

(1) Ethyl 4-(acetyloxy)benzofuran-6-carboxylate:

To a suspension of 60% oil-based sodium hydride (6.50 g) in tetrahydrofuran (400 mL) was added dropwise a solution of 4-tert-butyl 1-ethyl 2-(diethoxyphosphoryl)succinate (55.0 g) in tetrahydrofuran (100 mL) under ice-cooling over 30 minutes, and then the mixture was stirred under the cooling for 1 hour. Then, thereto was added a solution of 2-furaldehyde (12.8 mL) in tetrahydrofuran (40 mL) under ice-cooling over 15 minutes, and the mixture was stirred at room temperature for 1 hour. Ice water was poured into the reaction mixture under ice-cooling, and the mixture was extracted with ethyl acetate. The organic layer was sequentially washed with water and saturated saline, dried over sodium sulfate, and then concentrated under reduced pressure to give 4-tert-butyl 1-ethyl (2E)-2-(2-furylmethylene)succinate (47.0 g) as a brown oil crude. Then, the oil (47.0 g) was stirred in trifluoroacetic acid (100 mL) at room temperature for 1 hour, and then concentrated under reduced pressure. The resulting residue was treated azeotropically with toluene several times to give (3E)-3-(ethoxycarbonyl)-4-(2-furyl)-but-3-enoic acid (39.2 g) as a brown oil crude. Then, the oil (39.2 g) was dissolved in acetic anhydride (100 mL), and thereto was added potassium acetate (19.8 g), and then the mixture was heated to reflux for 45 minutes. The reaction mixture was let stand to be cooled, and then thereto was added water (100 mL), and then the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=5/1) to give ethyl 4-(acetyloxy)benzofuran-6-carboxylate (24.7 g) as a pale orange solid. APCI-MS m/z: 266[M+NH$_4$]$^+$.

(2) Ethyl 4-hydroxy-1-benzofuran-6-carboxylate [REx(7-1)]:

To a solution of the compound obtained in the above (1) (24.7 g) in ethanol (150 mL) was added potassium carbonate (42.0 g), and the mixture was heated to reflux for 30 minutes. The reaction mixture was ice-cooled, and then acidified by 10% hydrochloric acid, and then extracted with ethyl acetate. The organic layer was washed with saturated saline, dried over sodium sulfate, and then concentrated under reduced pressure. The resulting residue was triturated with n-hexane-dichloromethane (5:1) to give ethyl 4-hydroxy-1-benzofuran-6-carboxylate [REx(7-1)] (19.6 g) as a pale yellow powder.

APCI-MS m/z: 207 [M+H]$^+$.

(3) Ethyl 4-(3-methoxypropoxy)-1-benzofuran-6-carboxylate [REx(7-2)]:

To a solution of the compound obtained in the above (2) (5.0 g) in acetonitrile (50 mL) were added potassium carbonate (5.0 g) and 1-bromo-3-methoxypropane (4.54 g), and the mixture was heated to reflux for 1.5 hours. To the reaction mixture was added water under ice-cooling, and then the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=5/1→2/1) to give ethyl 4-(3-methoxypropoxy)-1-benzofuran-6-carboxylate [REx(7-2)] (6.61 g) as a colorless oil.

APCI-MS m/z: 279 [M+H]$^+$.

(4) 4-(3-Methoxypropoxy)-1-benzofuran-6-carboxylic acid [REx(7-3)]:

To a solution of the compound obtained in the above (3) (2.64 g) in ethanol (20 mL) was added 2-normal aqueous sodium hydroxide solution (9.5 mL), and the mixture was stirred at room temperature for 3 hours. Then, thereto was added 2-normal hydrochloric acid under ice-cooling, and the mixture was extracted with ethyl acetate. The organic layer was washed with saturated saline, dried over magnesium sulfate, and then concentrated under reduced pressure to give 4-(3-methoxypropoxy)-1-benzofuran-6-carboxylic acid [REx(7-3)] (2.40 g) as a colorless powder.

APCI-MS m/z: 265 [M+H+MeOH—H$_2$O]$^+$.

(5) N-Methoxy-4-(3-methoxypropoxy)-N-methyl-1-benzofuran-6-carboxamide [REx(7-4)]:

To a solution of the compound obtained in the above (4) (2.39 g), N,O-dimethylhydroxyamine.hydrochloride (1.86 g), 1-ethyl-3-(3-dimethylaminopropyl)carbodiimide hydrochloride (2.74 g) and 1-hydroxybenzotriazole (1.93 g) in chloroform (30 mL) was added diisopropylethylamine (4.2 mL) under ice-cooling, and the mixture was stirred at room temperature for 4 hours. Under ice-cooling, to the reaction mixture was added aqueous saturated sodium hydrogen carbonate solution, and the mixture was extracted with chloroform. The organic layer was sequentially washed with water and saturated saline, dried over magnesium sulfate, and then concentrated under reduced pressure. The resulting residue was purified by silica gel column chromatography (eluent: n-hexane/ethyl acetate=1/1→1/3) to give N-methoxy-4-(3-methoxypropoxy)-N-methyl-1-benzofuran-6-carboxamide [REx(7-4)] (2.67 g) as a pale yellow oil.

APCI-MS m/z: 294 [M+H]$^+$.

(6) 1-[4-((3-Methoxypropoxy)-1-benzofuran-6-yl]ethanone [REx(7-5)]:

To a solution of the compound obtained in the above (5) (2.67 g) in tetrahydrofuran (30 mL) was added dropwise a 3M solution of methylmagnesium bromide in diethyl ether (6.1 mL) under ice-cooling, and the mixture was stirred at the same temperature for 15 minutes. Under ice-cooling, 10% hydrochloric acid was poured into the mixture, and then the mixture was extracted with ethyl acetate. The organic layer was washed with saturated saline, and then dried over magnesium sulfate and concentrated under reduced pressure. The resulting residue was purified by silica gel column chromatography (eluent: n-hexane/ethyl acetate=4/1→1/1) to give 1-[4-((3-methoxypropoxy)-1-benzofuran-6-yl]ethanone [REx(7-5)] (2.15 g) as a colorless powder.

APCI-MS m/z: 249 [M+1-1]$^+$.

(7) N-{1-[4-(3-Methoxypropoxy)-1-benzofuran-6-yl]ethyl}cyclopropanamine [REx(7-6)]:

To a solution of the compound obtained in the above (6) (2.15 g) and cyclopropylamine (2.10 mL) in dichloroethane (150 mL) were added sodium triacetoxyborohydride (5.50 g), acetic acid (1.48 mL) and magnesium sulfate (5.20 g), and then the mixture was stirred at room temperature for 23 hours. Thereto was added aqueous saturated sodium hydrogen carbonate solution under ice-cooling, and the mixture was extracted with chloroform. The organic layer was washed with saturated saline, dried over magnesium sulfate, and then concentrated under reduced pressure. The resulting residue was purified by silica gel column chromatography (eluent: chloroform/methanol=20/1→13/1) to give N-{1-[4-(3-methoxypropoxy)-1-benzofuran-6-yl]ethyl}cyclopropanamine [REx(7-6)] (2.47 g) as a pale yellow oil.

APCI-MS m/z: 290 [M+H]$^+$.

Reference Example 8

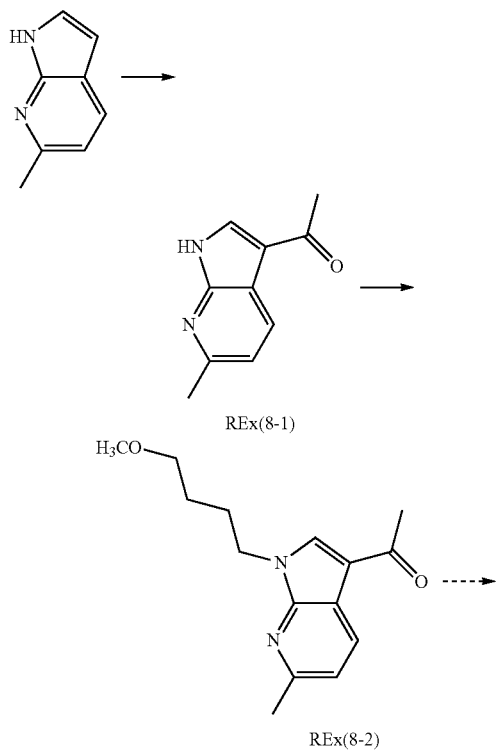

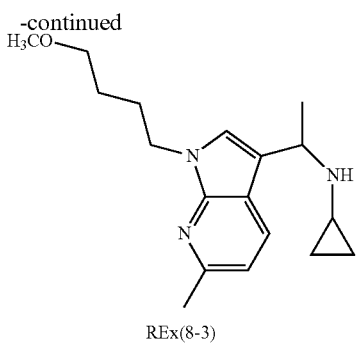

(1) 1-(6-Methyl-1H-pyrrolo[2,3-b]pyridin-3-yl)ethanone [REx(8-1)]:

To a solution of 6-methyl-1H-pyrrolo[2,3-b]pyridine (500 mg) in dichloroethane (6 mL) were added aluminum chloride (1.09 g) and acetyl chloride (0.40 mL), and then the mixture was stirred at room temperature for 1.5 hours. The reaction solution was poured into aqueous saturated sodium hydrogen carbonate solution, and extracted with chloroform. The organic layer was washed with saturated saline, dried over magnesium sulfate, and then concentrated under reduced pressure. The resulting residue was triturated with isopropyl ether to give 1-(6-methyl-1H-pyrrolo[2,3-b]pyridin-3-yl)ethanone [REx(8-1)] (481 mg) as a yellow powder.

APCI-MS m/z: 175 [M+H]$^+$.

(2) 1-[1-(4-Methoxybutyl)-6-methyl-1H-pyrrolo[2,3-b]pyridin-3-yl]ethanone [REx(8-2)]:

To a solution of the compound obtained in the above (1) (280 mg) in N,N-dimethylformamide (6 mL) was added 60% oil-based sodium hydride (83.6 mg), and then the mixture was stirred at room temperature for 30 minutes. Thereto was added dropwise a solution of 4-methoxybutyl 4-methylbenzenesulfonate in N,N-dimethylformamide (1 mL), and then thereto was added potassium iodide (267 mg), and the mixture was stirred at 50° C. for 1 hour. The reaction mixture was poured into water, and extracted with ethyl acetate. The organic layer was washed with water twice and saturated saline, dried over magnesium sulfate, and then concentrated under reduced pressure. The resulting residue was purified by silica gel column chromatography (eluent: n-hexane/ethyl acetate=2/1→1/9) to give 1-[1-(4-methoxybutyl)-6-methyl-1H-pyrrolo[2,3-b]pyridin-3-yl]ethanone [REx(8-2)] (366 mg) as a yellow oil.

APCI-MS m/z: 261 [M+H]$^+$.

(3) An amine compound [REx(8-3)] is obtained in the similar manner to Reference Example 7(7).

Reference Example 9

1-[1-(3-Methoxypropyl)-3-methyl-1H-indol-6-yl]ethanone [REx(9-1)]

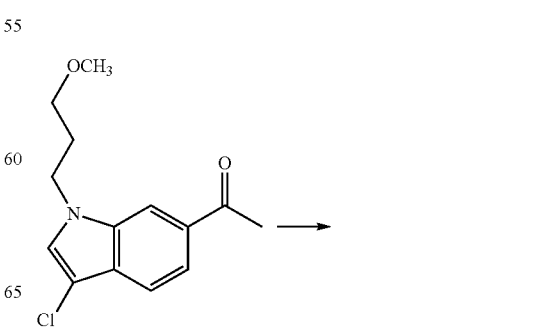

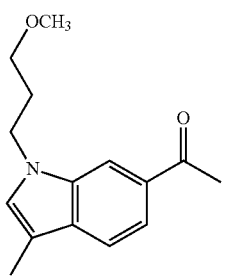

REx(9-1)

To a solution of 1-[3-chloro-1-(3-methoxypropyl)-1H-indol-6-yl]ethanone (843 mg) in 1,4-dioxane (15 mL) were added potassium phosphate (1.35 g), trimethylboroxine (883 mg), tris(dibenzylideneacetone)dipalladium (290 mg) and 2-dicyclohexylphosphino-2',4',6'-triisopropyl-1,1'-biphenyl (X-Phos) (605 mg) under argon, and the mixture was heated to stir at 110° C. for 4 hours. Thereto was added water under ice-cooling, and the mixture was extracted with ethyl acetate. The organic layer was washed with saturated saline, dried over magnesium sulfate, and then concentrated under reduced pressure. The resulting residue was purified by silica gel column chromatography (eluent: n-hexane/ethyl acetate=3/1→3/2) to give 1-[1-(3-methoxypropyl)-3-methyl-1H-indol-6-yl]ethanone [REx(9-1)] (663 mg) as a yellow oil.

APCI-MS m/z: 246 [M+H]$^+$.

Reference Example 10

Methyl 1-(3-methoxypropyl)indoline-6-carboxylate [REx(10-1)]

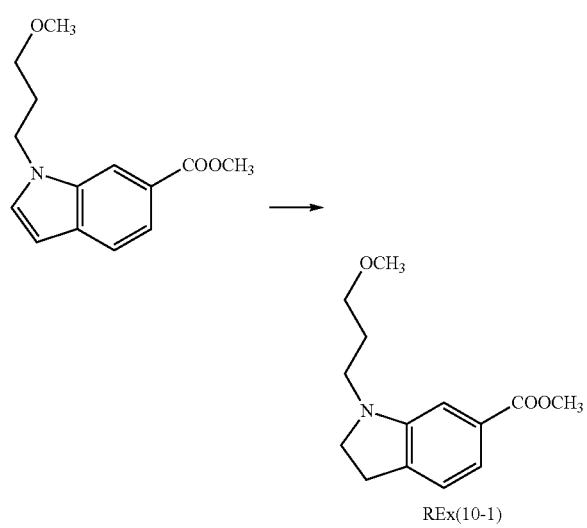

REx(10-1)

To a mixture of methyl 1-(3-methoxypropyl)-1H-indole-6-carboxylate (1.5 g) and sodium cyanohydroborate (1.61 g) was added acetic acid (15 mL) under ice-cooling, and the mixture was stirred at room temperature for 3 hours. To the reaction solution was added aqueous saturated sodium hydrogen carbonate solution under ice-cooling, and the mixture was neutralized by adding sodium hydrogen carbonate, and then extracted with ethyl acetate. The organic layer was washed with saturated saline, dried over sodium sulfate, and then concentrated under reduced pressure. The resulting residue was purified by silica gel column chromatography (eluent: n-hexane→n-hexane/ethyl acetate=2/1) to give methyl 1-(3-methoxypropyl)indoline-6-carboxylate [REx(10-1)] (1.20) as a pale yellow oil.

APCI-MS m/z: 250 [M+H]$^+$.

Reference Example 11

6-(3-Methoxypropoxy)indan-1-one [REx(11-1)]

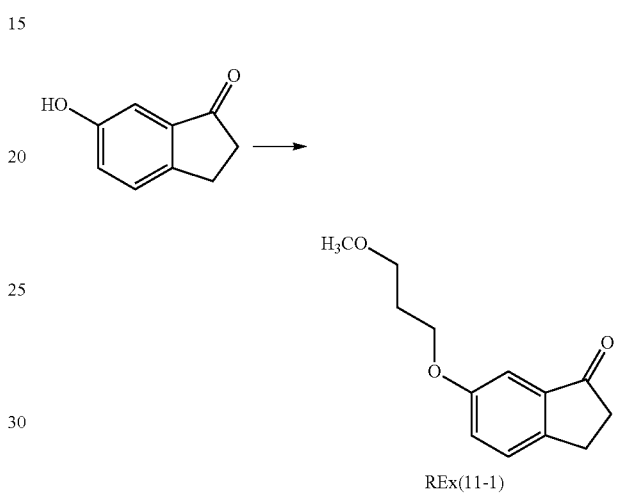

REx(11-1)

To a solution of 6-hydroxyindan-1-one (1.48 g) in acetonitrile (30 mL) were added 4-methoxybutyl 4-methylbenzenesulfonate (2.93 g), potassium iodide (166 mg) and potassium carbonate (2.07 g), and the mixture was heated to stir at 80° C. for 5 hours. To the reaction mixture was added water under ice-cooling, and then the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=7/3), and then triturated with n-hexane/isopropyl ether (2:1) to give 6-(3-methoxypropoxy)indan-1-one [REx(11-1)] (1.1 g) as a colorless powder.

APCI-MS m/z: 221 [M+H]$^+$.

Reference Example 12

7-(3-Methoxypropoxy)-3,4-dihydronaphthalen-1 (2H)-one [REx(12-1)]

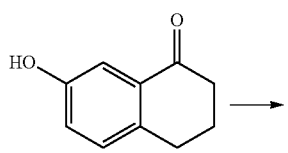

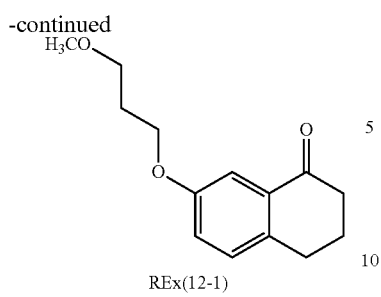

REx(12-1)

To a solution of 7-hydroxy-1-tetralone (4.05 g) in acetonitrile (75 mL) were added 1-bromo-3-methoxypropane (4.59 g), potassium iodide (415 mg) and potassium carbonate (5.18 g), and the mixture was heated to stir at 80° C. for 23 hours. To the reaction mixture was added water under ice-cooling, and then the mixture was extracted with ethyl acetate. The organic layer was washed with saturated saline, dried over sodium sulfate, and then concentrated under reduced pressure. The resulting residue was triturated with n-hexane to give 7-(3-methoxypropoxy)-3,4-dihydronaphthalen-1(2H)-one [REx(12-1)] (4.80 g) as a colorless powder.

APCI-MS m/z: 235 [M+H]$^+$.

Reference Example 13

N-(2-Methoxyethyl)-3-oxoindan-5-carboxamide [REx(13-1)]

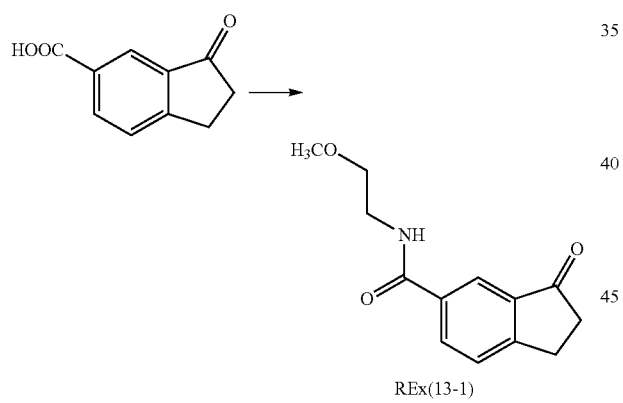

REx(13-1)

To a suspension of 1-indanone-6-carboxylic acid (1.76 g) in N,N-dimethylformamide (50 mL) was added carbonyldiimidazole (3.24 g), and the mixture was stirred at room temperature for 1 hour. Thereto was added a solution of 2-methoxyethylamine (3.76 g) in dichloromethane (50 mL) under ice-cooling, and the mixture was stirred at room temperature for 4 hours. The reaction solution was concentrated under reduced pressure, and then dissolved in chloroform. The organic layer was washed with aqueous saturated sodium hydrogen carbonate solution, dried over sodium sulfate, and then concentrated under reduced pressure. The resulting residue was dissolved in tetrahydrofuran (20 mL), and then thereto was added 1-normal hydrochloric acid (20 mL), and the mixture was stirred at room temperature for 12 hours. To the reaction solution was added water, and the mixture was extracted with ethyl acetate. The organic layer was washed with saturated saline, dried over sodium sulfate, and then concentrated under reduced pressure. The resulting residue was triturated with isopropyl ether-ethyl acetate (2:1) to give N-(2-methoxyethyl)-3-oxoindan-5-carboxamide [REx(13-1)] (1.87 g) as a brown powder.

APCI-MS m/z: 234 [M+H]$^+$.

Reference Example 14

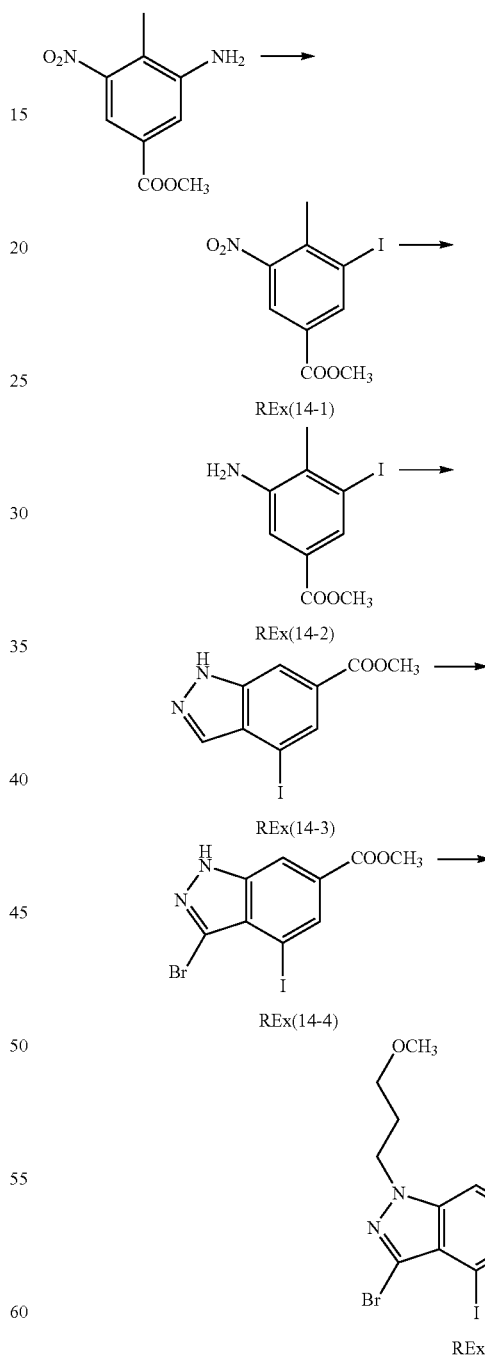

(1) Methyl 3-iodo-4-methyl-5-nitrobenzoate [REx(14-1)]:

To a suspension of methyl 3-amino-4-methyl-5-nitrobenzoate (36.0 g) in 6-normal hydrochloric acid (276 mL) was added dropwise a solution of sodium nitrite (13.0 g) in water (35 mL) under ice-salt-cooling over 20 minutes, and the mixture was stirred under ice-cooling for 1 hour. Then, thereto was added dropwise a solution of potassium iodide (34.1 g) in water (280 mL) under ice-cooling over 20 minutes, and the mixture was stirred at room temperature for 2 hours. To the reaction solution was added water under ice-cooling, and the mixture was extracted with chloroform. The organic layer was sequentially washed with aqueous saturated sodium thiosulfate solution and saturated saline, dried over sodium sulfate, and then concentrated under reduced pressure. The resulting residue was purified by silica gel column chromatography (eluent: n-hexane/ethyl acetate=50/1) to give methyl 3-iodo-4-methyl-5-nitrobenzoate [REx(14-1)] (40.5 g) as a yellow powder.

(2) Methyl 3-amino-5-iodo-4-methylbenzoate [REx(14-2)]:

To a solution of the compound obtained in the above (1) (40.5 g) in ethyl acetate (500 mL) was added tin (II) chloride dihydrate (142 g), and the mixture was heated to stir at 60° C. for 1 hour. Aqueous sodium hydrogen carbonate solution was poured into the reaction mixture under ice-cooling, and then an insoluble was filtered through Celite. The organic layer was separated, and then washed with saturated saline, dried over sodium sulfate, and then concentrated under reduced pressure to give methyl 3-amino-5-iodo-4-methylbenzoate [REx(14-2)] (35.3 g) as a pale yellow powder.

APCI-MS m/z: 292 [M+H]$^+$.

(3) Methyl 4-iodo-1H-indazole-6-carboxylate [REx(14-3)]:

To a suspension of the compound obtained in the above (2) (35.3 g) in water (615 mL) were added concentrated hydrochloric acid (102 mL) and ammonium tetrafluoroborate (16.5 g), and the mixture was cooled to −3° C. Under the cooling, thereto was added dropwise a solution of sodium nitrite (9.20 g) in water (34 mL) over 20 minutes. The mixture was stirred at −3° C. for 1 hour, and then the precipitated crystal was filtered, sequentially washed with water (100 mL) and diethyl ether (100 mL), and then dried under reduced pressure. The resulting solid was suspended in chloroform (420 mL), and then thereto were added potassium acetate (13.1 g) and 18-crown-6 (801 mg), and the mixture was stirred at room temperature for 15 hours. To the reaction mixture was added water under ice-cooling, and then the mixture was extracted with chloroform. The organic layer was washed with saturated saline, dried over sodium sulfate, and then concentrated under reduced pressure. The resulting residue was triturated with chloroform to give methyl 4-iodo-1H-indazole-6-carboxylate [REx(14-3)] (18.9 g) as a pale orange powder.

APCI-MS m/z: 303 [M+H]$^+$.

(4) Methyl 3-bromo-4-iodo-1H-indazole-6-carboxylate [REx(14-4)]:

The compound obtained in the above (3) (24.5 g) was dissolved in acetic acid (720 mL), and after blocking out light, bromine (8.30 mL) was added dropwise to the mixture at room temperature. After stirring at room temperature for 40 hours, bromine (4.15 mL) was added thereto, and the mixture was stirred for additional 24 hours at room temperature. Then, thereto were added acetic acid (100 mL) and bromine (4.15 mL), and the mixture was stirred at room temperature for 6 hours. The reaction mixture was poured into ice water, and then thereto was added sodium thiosulfate, and the mixture was stirred at room temperature for 20 minutes, and then the precipitated solid was filtered. The solid was washed with water, and then dissolved in ethyl acetate and washed with saturated saline. The organic layer was dried over sodium sulfate, and then concentrated under reduced pressure. The resulting residue was triturated with isopropyl ether to give methyl 3-bromo-4-iodo-1H-indazole-6-carboxylate [REx(14-4)] (27.3 g) as a pale yellow powder.

APCI-MS m/z: 381/383 [M+H]$^+$.

(5) Methyl 3-bromo-4-iodo-1-(3-methoxypropyl)-1H-indazole-6-carboxylate [REx(14-5)]:

To a solution of the compound obtained in the above (4) (22.3 g) in N,N-dimethylformamide (200 mL) was added 60% oil-based sodium hydride (2.81 g) under ice-cooling, and the mixture was stirred at room temperature for 15 minutes. To the mixture was added a solution of 1-bromo-3-methoxypropane (10.8 g) in N,N-dimethylformamide (40 mL) under ice-cooling, and the mixture was stirred at room temperature for 18 hours. 10% Hydrochloric acid was poured into the reaction solution under ice-cooling, and then the mixture was extracted with ethyl acetate. The organic layer was sequentially washed with water and saturated saline, dried over sodium sulfate, and then concentrated under reduced pressure. The resulting residue was purified by silica gel column chromatography (eluent: n-hexane/ethyl acetate=9/1) to give methyl 3-bromo-4-iodo-1-(3-methoxypropyl)-1H-indazole-6-carboxylate [REx(14-5)] (23.5 g) as a pale orange powder.

APCI-MS m/z: 453/455 [M+H]$^+$.

Reference Example 15

1-[4-Chloro-1-(3-methoxypropyl)-3-methyl-1H-indazol-6-yl]ethanone [REx(15-1)]

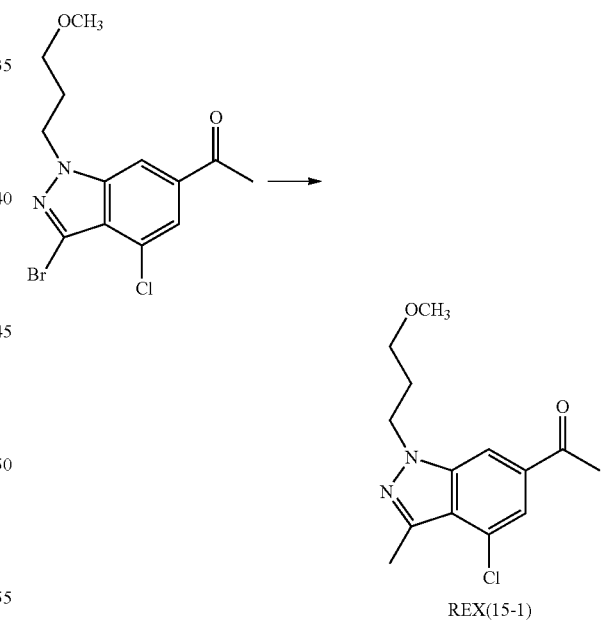

REX(15-1)

To a solution of 1-[3-bromo-4-chloro-1-(3-methoxypropyl)-1H-indazol-6-yl]ethanone (1.0 g) in 1,4-dioxane (20 mL) were added potassium carbonate (1.2 g), trimethylboroxine (0.41 mL) and 1,1'-bis(diphenylphosphino)ferrocene dichloropalladium (II) (212 mg) under argon, and the mixture was heated to stir at 80° C. for 24 hours. Then, thereto was added water under ice-cooling, and the mixture was extracted with ethyl acetate. The organic layer was washed with saturated saline, dried over magnesium sulfate, and then concentrated under reduced pressure. The resulting residue was purified by NH-silica gel column chromatography (eluent: n-hexane/ethyl acetate=4/1→3/2) to give 1-[4-chloro-1-(3-methoxypropyl)-3-methyl-1H-indazol-6-yl]ethanone [REx(15-1)] (392 mg) as a pale yellow oil.

APCI-MS m/z: 281/283 [M+H]$^+$.

Reference Example 16

1-[1-(3-Methoxypropyl)-3,4-dimethyl-1H-indazol-6-yl]ethanone [REx(16-1)]

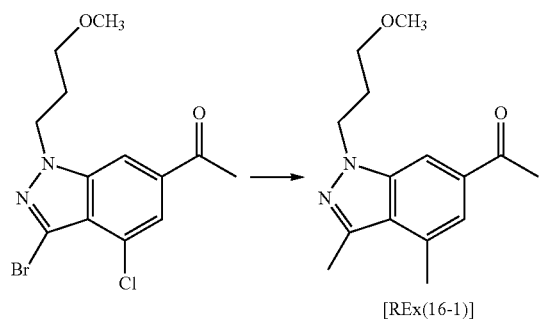 [SMILES: COCCCn1nc(Br)c2c(Cl)cc(C(C)=O)cc21 ; COCCCn1nc(C)c2c(C)cc(C(C)=O)cc21]

[REx(16-1)]

To a solution of 1-[3-bromo-4-chloro-1-(3-methoxypropyl)-1H-indazol-6-yl]ethanone (1.0 g) in 1,4-dioxane (7.5 mL) were added potassium carbonate (1.2 g), trimethylboroxine (1.0 mL) and 1,1'-bis(diphenylphosphino)ferrocene dichloropalladium (II) (212 mg) under argon, and the mixture was heated to stir at 110° C. for 24 hours. Then, thereto was added water under ice-cooling, and the mixture was extracted with ethyl acetate. The organic layer was washed with saturated saline, dried over magnesium sulfate, and then concentrated under reduced pressure. The resulting residue was purified by NH-silica gel column chromatography (eluent: n-hexane/ethyl acetate=3/1→1/1) to give 1-[1-(3-methoxypropyl)-3,4-dimethyl-1H-indazol-6-yl]ethanone [REx(16-1)] (689 mg) as an orange oil.

APCI-MS m/z: 261 [M+H]$^+$.

Reference Example 17

1-[3-Bromo-1-(3-methoxypropyl)-4-(trifluoromethyl)-1H-indazol-6-yl]ethanone [REx(17-1)]

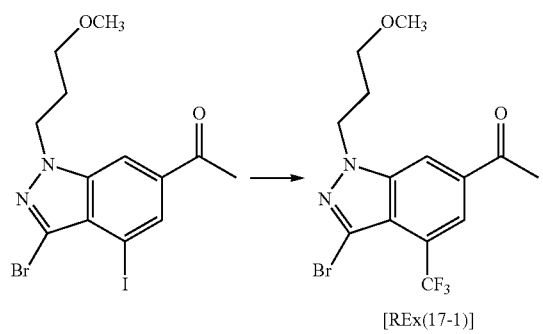 [SMILES: COCCCn1nc(Br)c2c(I)cc(C(C)=O)cc21 ; COCCCn1nc(Br)c2c(C(F)(F)F)cc(C(C)=O)cc21]

[REx(17-1)]

A mixture of 1-[3-bromo-4-iodo-1-(3-methoxypropyl)-1H-indazol-6-yl]ethanone (500 mg), methyl fluorosulfonyldifluoroacetate (1.36 g), hexamethylphosphorylamide (1.27 g) and copper (I) iodide (337 mg) was heated to stir in N,N-dimethylformamide (7.0 mL) under argon at 75° C. for 15 hours. Water and ethyl acetate were poured into the reaction mixture under ice-cooling, and then an insoluble was filtered through Celite. The organic layer was separated, and then sequentially washed with water and saturated saline, dried over sodium sulfate, and then concentrated under reduced pressure. The resulting residue was purified by silica gel column chromatography (eluent: n-hexane→n-hexane/ethyl acetate=1/1) to give 1-[3-bromo-1-(3-methoxypropyl)-4-(trifluoromethyl)-1H-indazol-6-yl]ethanone [REx(17-1)] (87 mg) as a yellow oil.

APCI-MS m/z: 379/381 [M+H]$^+$.

Reference Example 18

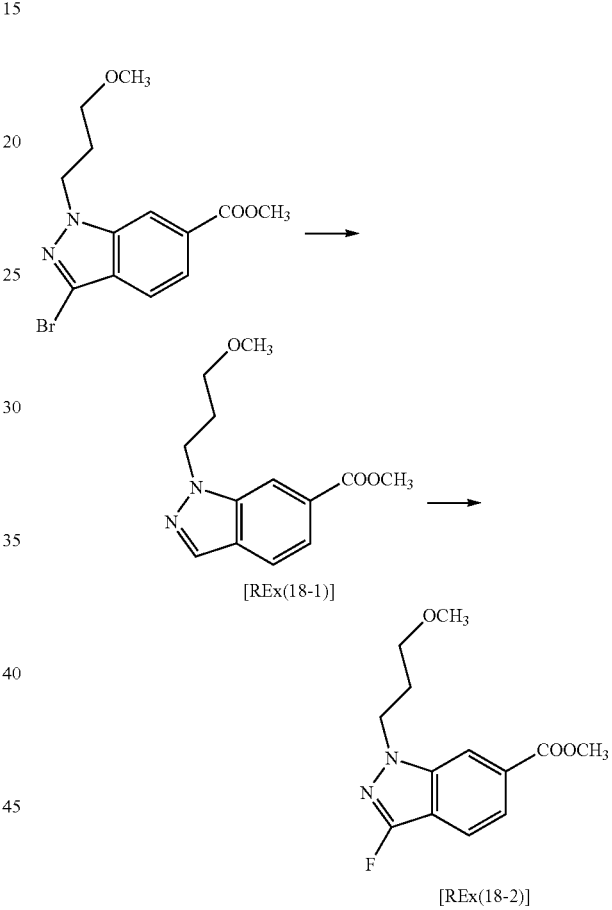

[REx(18-1)]

[REx(18-2)]

(1) Methyl 1-(3-methoxypropyl)-1H-indazole-6-carboxylate [REx(18-1)]:

To a solution of methyl 3-bromo-1-(3-methoxypropyl)-1H-indazole-6-carboxylate (3.0 g) and diisopropylethylamine (2.4 mL) in methanol (60 mL) was added 10% palladium on carbon catalyst (600 mg), and the mixture was stirred under hydrogen for 1 hour. An insoluble was filtered, and then the filtrate was concentrated under reduced pressure. The residue was dissolved in chloroform, sequentially washed with 10% hydrochloric acid water and saturated saline, and then concentrated under reduced pressure to give methyl 1-(3-methoxypropyl)-1H-indazole-6-carboxylate [REx(18-1)] (2.40 g) as a pale yellow oil.

(2) Methyl 3-fluoro-1-(3-methoxypropyl)-1H-indazole-6-carboxylate [REx(18-2)]:

To a solution of the compound obtained in the above (1) (2.20 g) in acetonitrile (30 mL) was added Selectfluor (Registered trademark) (3.45 g), and the mixture was stirred at 80° C. for 15 hours. Then, thereto was added aqueous sodium hydrogen carbonate solution under ice-cooling, and the mixture was extracted with ethyl acetate. The organic layer was washed with saturated saline, dried over sodium sulfate, and then concentrated under reduced pressure. The resulting residue was purified by silica gel column chromatography (eluent: n-hexane→n-hexane/ethyl acetate=5/1) to give methyl 3-fluoro-1-(3-methoxypropyl)-1H-indazole-6-carboxylate [REx(18-2)] (1.01 g) as a colorless oil.

APCI-MS m/z: 267 [M+H]$^+$.

Reference Example 19

1-[3-Fluoro-5-(3-methoxypropoxy)phenyl]ethanone [REx(19-2)]

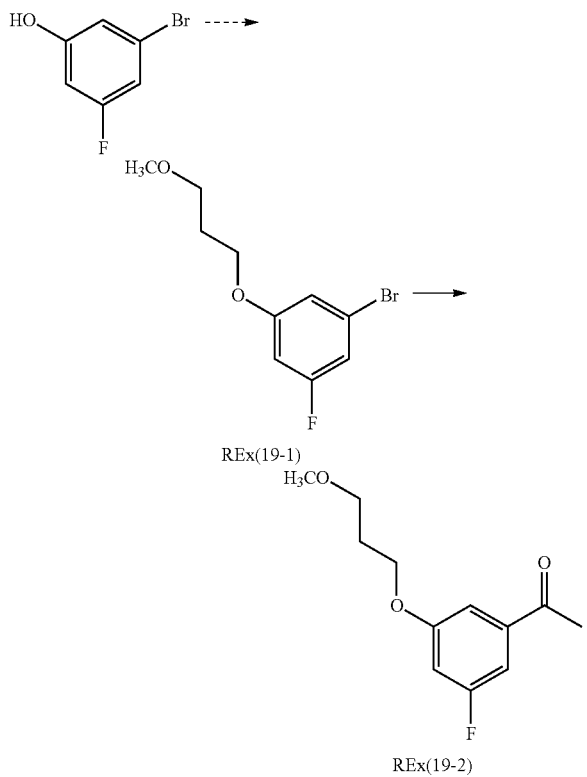

1-Bromo-3-fluoro-5-(3-methoxypropoxy)benzene (4.0 g) was added to water (30.4 mL), and then thereto were added ethylene glycol monovinyl ether (6.8 mL), potassium carbonate (2.52 g), 1,3-bis(diphenylphosphino)propane (125 mg) and palladium acetate (34 mg), and the mixture was heated to stir at 90° C. for 22 hours. After cooling, thereto was added concentrated hydrochloric acid (7.2 mL), and the mixture was stirred at room temperature for 20 minutes. The reaction solution was extracted with ethyl acetate, washed with saturated saline, and then dried over magnesium sulfate. After concentrating under reduced pressure, the resulting residue was purified by silica gel column chromatography (eluent: n-hexane/ethyl acetate=20/1→2/1) to give 1-[3-fluoro-5-(3-methoxypropoxy)phenyl]ethanone [REx(19-2)] (1.03 g) as a yellow oil.

APCI-MS m/z: 227 [M+H]$^+$.

A starting material is prepared from 1-bromo-3-fluorophenol, for example, in the similar manner to Reference Example 11 or 12.

Reference Example 20

1-[3-Hydroxy-5-(3-methoxypropoxy)phenyl]ethanone [REx(20-1)]

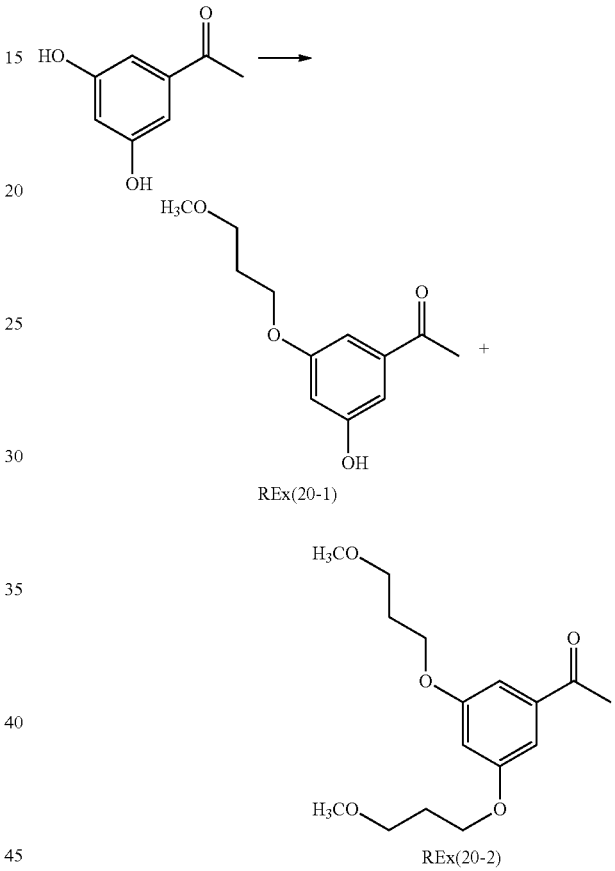

To a solution of 1-(3,5-dihydroxyphenyl)ethanone (10 g) in N,N-dimethylformamide (164 mL)-water (5 mL) were added potassium carbonate (13.6 g) and 3-methoxypropyl 4-methylbenzene sulfonate (16.1 g), and the mixture was heated to stir at 80° C. for 2 hours. The reaction solution was concentrated under reduced pressure, and then thereto was added water, and then the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=3/1→1/1) to give 1-[3-hydroxy-5-(3-methoxypropoxy)phenyl]ethanone [REx(20-1)] (4.65 g) as a colorless powder and 1-[3,5-bis(3-methoxypropoxy)phenyl]ethanone [REx(20-2)] (4.98 g) as a colorless oil.

2: APCI-MS m/z: 225 [M+H]$^+$.

3: APCI-MS m/z: 297 [M+H]$^+$.

Reference Example 21

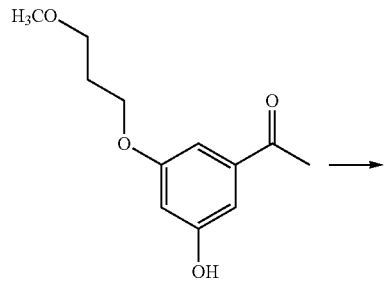

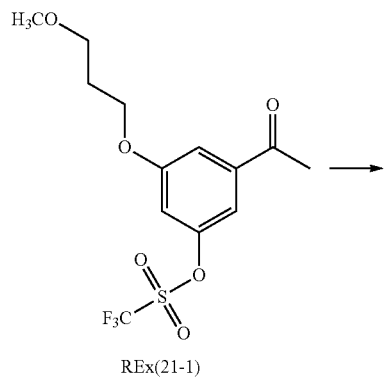

REx(21-1)

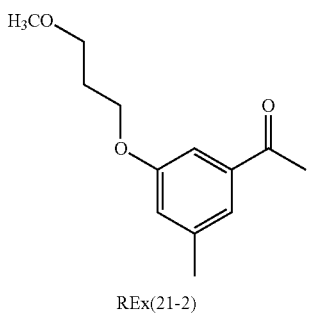

REx(21-2)

(1) 3-Acetyl-5-(3-methoxypropoxy)phenyltrifluoromethanesulfonate [REx(21-1)]:

To a solution of 1-[3-hydroxy-5-(3-methoxypropoxy)phenyl]ethanone (4.65 g) in chloroform (100 mL) was added pyridine (5.02 mL) under ice-cooling, and then thereto was added dropwise trifluoromethanesulfonic anhydride (3.67 mL) under the ice-cooling, and then the mixture was stirred at the same temperature for 20 minutes. Then, thereto was added 1-normal hydrochloric acid, and the mixture was extracted with chloroform, and then the organic layer was sequentially washed with water and saturated saline, dried over magnesium sulfate, and then concentrated under reduced pressure to give a crude product of 3-acetyl-5-(3-methoxypropoxy)phenyltrifluoromethanesulfonate [REx(21-1)] (8.22 g) as a yellow oil.

APCI-MS m/z: 374[M+NH$_4$]$^+$.

(2) 1-[3-(3-Methoxypropoxy)-5-methylphenyl]ethanone [REx(21-2)]:

To a solution of the compound obtained in the (1) (8.22 g) in 1,4-dioxane (100 mL) were added potassium carbonate (8.6 g), trimethylboroxine (3.5 mL) and 1,1'-bis(diphenylphosphino)ferrocene dichloropalladium (II) (1.51 g), and the mixture was heated to stir at 110° C. for 2 hours. After cooling to room temperature, thereto was added water, and the mixture was extracted with ethyl acetate. The organic layer was washed with saturated saline, dried over magnesium sulfate, and then concentrated under reduced pressure. The resulting residue was purified by silica gel column chromatography (eluent: n-hexane→n-hexane/ethyl acetate=5/1) to give 1-[3-(3-methoxypropoxy)-5-methylphenyl]ethanone [REx(21-2)] (4.15 g) as a brown oil.

APCI-MS m/z: 223 [M+H]$^+$.

Reference Example 22

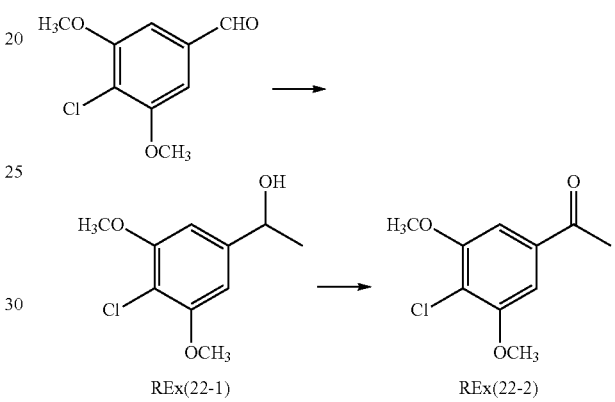

REx(22-1)   REx(22-2)

(1) 1-(4-Chloro-3,5-dimethoxyphenyl)ethanol [REx(22-1)]:

To a solution of 4-chloro-3,5-dimethoxybenzaldehyde (1.0 g) in tetrahydrofuran (20 mL) was added dropowise a 3M solution of methylmagnesium bromide in diethyl ether (1.83 mL) under ice-cooling, and the mixture was stirred at the same temperature for 1 hour. Then, thereto was added aqueous ammonium chloride solution under ice-cooling, and the mixture was extracted with ethyl acetate. The organic layer was sequentially washed with water and saturated saline, and then dried over magnesium sulfate and concentrated under reduced pressure to give a crude product of 1-(4-chloro-3,5-dimethoxyphenyl)ethanol [REx(22-1)] (1.23 g) as a colorless powder.

APCI-MS m/z: 200 [M+H—H$_2$O]$^+$.

(2) 1-(4-Chloro-3,5-dimethoxyphenyl)ethanone [REx(22-2)]:

To a solution of the compound obtained in the above (1) (1.23 g) in dichloromethane (28 mL) was added 85% activated manganese dioxide (5.81 g), and the mixture was stirred at 40° C. for 4 hours. The reaction solution was cooled to room temperature, and then thereto was added water-chloroform, and an insoluble was filtered off through Celite, and then the organic layer was separated. The organic layer was concentrated under reduced pressure, and the resulting residue was purified by silica gel column chromatography (eluent: n-hexane/ethyl acetate=10/1→1/1) to give 1-(4-chloro-3,5-dimethoxyphenyl)ethanone [REx(22-2)] (723 mg) as a colorless powder.

APCI-MS m/z: 215 [M+H]$^+$.

Reference Example 23

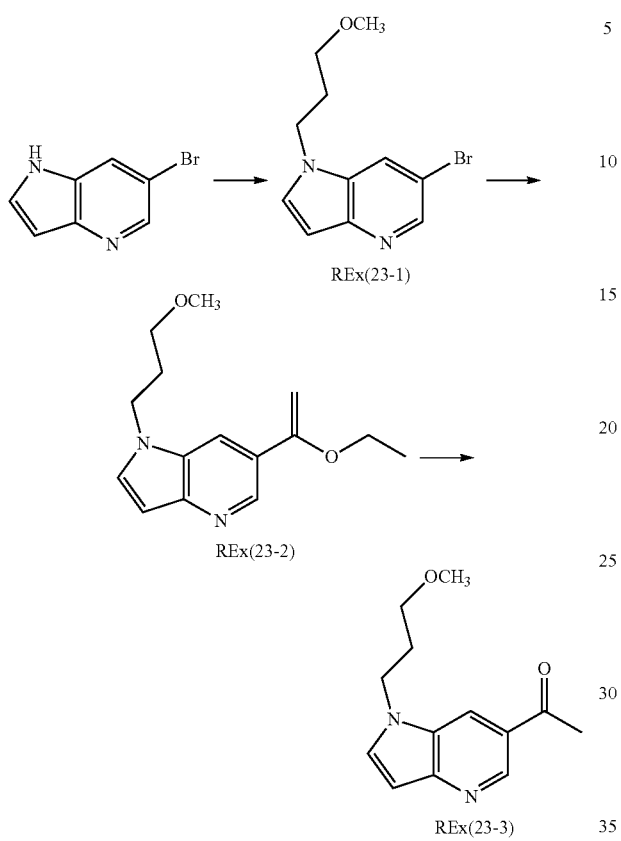

(1) 6-(1-Ethoxyvinyl)-1-(3-methoxypropyl)-1H-pyrrolo[3,2-b]pyridine [REx(23-2)]:

To a solution of 6-bromo-1-(3-methoxypropyl)-1H-pyrrolo[3,2-b]pyridine (1.5 g) in toluene (30 mL) were added tri-n-butyltin-1-ethoxyvinyl (5.65 mL) and dichlorobis-(triphenylphosphine)palladium (II) (782 mg), and the mixture was heated to stir at 110° C. for 30 minutes. The reaction solution was cooled to room temperature, and then thereto was added water-ethyl acetate, and an insoluble was filtered through Celite. The organic layer was separated, and then washed with saturated saline, dried over magnesium sulfate, and then concentrated under reduced pressure. The resulting residue was purified by NH-silica gel column chromatography (eluent: n-hexane/ethyl acetate=4/1→1/1) to give 6-(1-ethoxyvinyl)-1-(3-methoxypropyl)-1H-pyrrolo[3,2-b]pyridine [REx(23-2)] (1.69 g) as a yellow oil.

A starting compound [REx(23-1)] is obtained by 3-methoxypropylation at N of 6-bromo-1-1H-pyrrolo[3,2-b]pyridine.

APCI-MS m/z: 261 [M+H]$^+$.

(2) 1-[1-(3-Methoxypropyl)-1H-pyrrolo[3,2-b]pyridin-6-yl]ethanone [REx(23-3)]:

The compound obtained in the above (1) (1.69 g) was dissolved in chloroform (20 mL), and then thereto was added 4-normal hydrogen chloride/1,4-dioxane under ice-cooling, and the mixture was stirred at the same temperature for 2 hours. Then, thereto was added aqueous saturated sodium hydrogen carbonate solution under ice-cooling, and the mixture was extracted with chloroform. The organic layer was washed with saturated saline, dried over magnesium sulfate, and then concentrated under reduced pressure. The resulting residue was purified by NH-silica gel column chromatography (eluent: n-hexane/ethyl acetate=2/1→1/1) to give 1-[1-(3-methoxypropyl)-1H-pyrrolo[3,2-b]pyridin-6-yl]ethanone [REx(23-3)] (766 mg) as a yellow oil.

APCI-MS m/z: 233 [M+H]$^+$.

Reference Example 24

1-[4-Methoxy-3-(4-methoxybutyl)phenyl]ethanone [REx(24-1)]

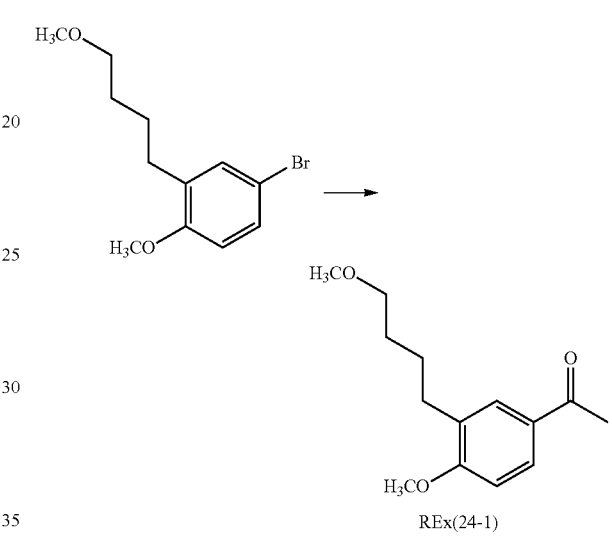

To a solution of 4-bromo-1-methoxy-2-(4-methoxybutyl)benzene (523 mg) in tetrahydrofuran (10 mL) were added lithium chloride (326 mg), tetrakis(triphenylphosphine)palladium (0) (381 mg) and tri-n-butyltin-1-ethoxyvinyl (1.11 mL), and the mixture was heated to stir at 80° C. for 20 hours. The reaction solution was cooled to room temperature, and then thereto was added aqueous potassium fluoride solution, and the mixture was stirred for 30 minutes. The mixture was extracted with diethyl ether, and then thereto was added 10% hydrochloric acid, and the mixture was stirred for 1 hour. The organic layer was separated, dried over magnesium sulfate, and then concentrated under reduced pressure. The resulting residue was purified by silica gel column chromatography (eluent: n-hexane/ethyl acetate=9/1→1/1) to give 1-[4-methoxy-3-(4-methoxybutyl)phenyl]ethanone [REx(24-1)] (195 mg) as a yellow oil.

APCI-MS m/z: 237 [M+H]$^+$.

Reference Example 25

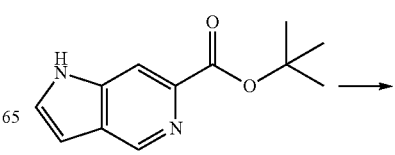

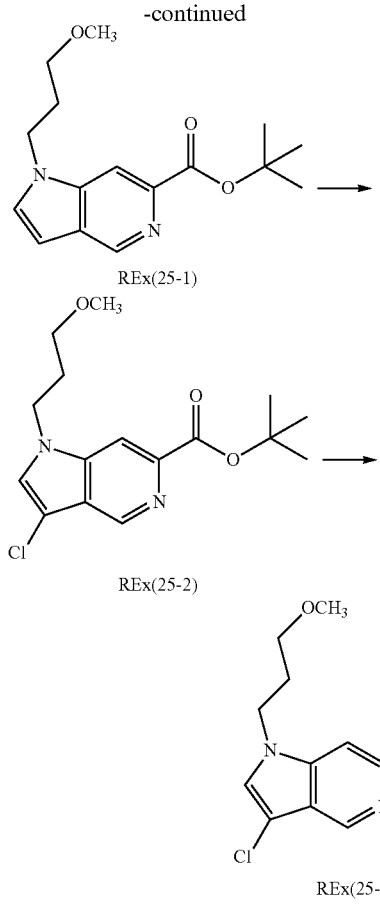

REx(25-1)

REx(25-2)

REx(25-3)

(1) tert-Butyl 1-(3-methoxypropyl)-1H-pyrrolo[3,2-c]pyridine-6-carboxylate [REx(25-1)]:

To a solution of tert-butyl 1H-pyrrolo[3,2-c]pyridine-6-carboxylate (2.0 g) in N,N-dimethylformamide (15 mL) was added drop by drop 60% oil-based sodium hydride (385 mg) under ice-cooling, and then the mixture was stirred at room temperature for 15 minutes. Then, thereto was added dropwise a solution of 1-bromo-3-methoxypropane (1.47 g) in N,N-dimethylformamide (5 mL) under ice-cooling, and then the mixture was stirred at room temperature for 18 hours. To the reaction mixture was added water under ice-cooling, and the mixture was extracted with ethyl acetate. The organic layer was sequentially washed with water and saturated saline, dried over sodium sulfate, and then concentrated under reduced pressure. The resulting residue was purified by silica gel column chromatography (eluent: n-hexane/ethyl acetate=1/1) to give tert-butyl 1-(3-methoxypropyl)-1H-pyrrolo[3,2-c]pyridine-6-carboxylate [REx(25-1)] (2.52 g) as a yellow oil.

APCI-MS m/z: 291 [M+H]$^+$.

(2) tert-Butyl 3-chloro-1-(3-methoxypropyl)-1H-pyrrolo[3,2-c]pyridine-6-carboxylate [REx(25-2)]:

To a solution of the compound obtained in the above (1) (2.52 g) in dichloromethane (50 mL) was added N-chlorosuccinimide (1.50 g) under ice-cooling, and the mixture was stirred at room temperature for 72 hours. To the reaction mixture was added water under ice-cooling, and the mixture was extracted with chloroform. The organic layer was washed with saturated saline, dried over sodium sulfate, and then concentrated under reduced pressure. The resulting residue was purified by NH-silica gel column chromatography (eluent: n-hexane/ethyl acetate=9/1) to give tert-butyl 3-chloro-1-(3-methoxypropyl)-1H-pyrrolo[3,2-c]pyridine-6-carboxylate [REx(25-2)] (2.45 g) as a colorless powder.

APCI-MS m/z: 325/327 [M+H]$^+$.

(3) 3-Chloro-1-(3-methoxypropyl)-1H-pyrrolo[3,2-c]pyridine-6-carboxylic acid. hydrochloride [REx(25-3)]:

The compound obtained in the above (2) (2.42 g) was added to trifluoroacetic acid (24 mL), and the mixture was stirred at room temperature for 2 hours. To the reaction solution was added 1-normal hydrochloric acid water (15 mL) under ice-cooling, and then the mixture was concentrated under reduced pressure. The resulting residue was triturated with isopropyl ether to give 3-chloro-1-(3-methoxypropyl)-1H-pyrrolo[3,2-c]pyridine-6-carboxylic acid hydrochloride [REx(25-3)] (2.20 g) as a brown powder.

ESI-MS m/z: 267/269[M−H]$^-$.

Reference Example 26

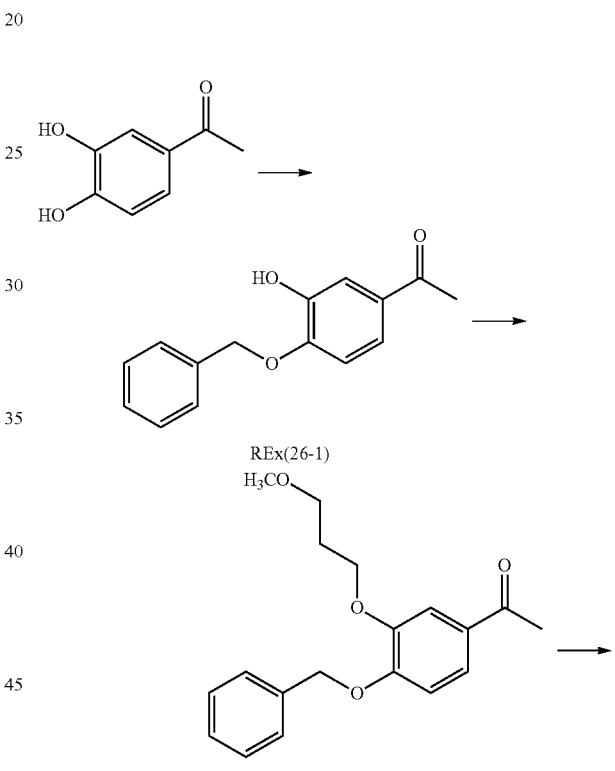

REx(26-1)

REx(26-2)

(1) 1-[4-(Benzyloxy)-3-hydroxyphenyl]ethanone [REx(26-1)]:

To a solution of 3',4'-dihydroxyacetophenone (25.4 g) in N,N-dimethylacetamide (420 mL) were added potassium carbonate (23.1 g) and benzyl bromide (19.9 mL) under ice-cooling, and the mixture was stirred at room temperature for 90 minutes. An insoluble was filtered, and then diluted with ethyl acetate. The organic layer was sequentially washed with water and saturated saline, dried over magnesium sulfate, and then concentrated under reduced pressure. The resulting residue was purified by silica gel column chromatography (eluent: n-hexane→n-hexane/ethyl acetate=20/1), and then triturated with ethyl acetate to give 1-[4-(benzyloxy)-3-hydroxyphenyl]ethanone [REx(26-1)] (11.0 g) as a colorless powder.

APCI-MS m/z: 243 [M+H]$^+$.

(2) 1-[4-(Benzyloxy)-3-(3-methoxypropyl)phenyl]ethanone [REx(26-2)]:

To a solution of the compound obtained in the above (1) (11.0 g) in acetonitrile (113 mL) were added potassium carbonate (9.37 g) and 3-methoxypropyl 4-methylbenzene sulfonate (13.2 g), and the mixture was heated to reflux for 20 hours. The reaction solution was cooled to room temperature, and then thereto was added water, and the mixture was extracted with ethyl acetate. The organic layer was dried over magnesium sulfate, and then concentrated under reduced pressure. The resulting residue was triturated with diisopropyl ether to give 1-[4-(benzyloxy)-3-(3-methoxypropyl)phenyl]ethanone [REx(26-2)] (8.75 g) as a colorless powder.

APCI-MS m/z: 315 [M+H]$^+$.

Reference Example 27

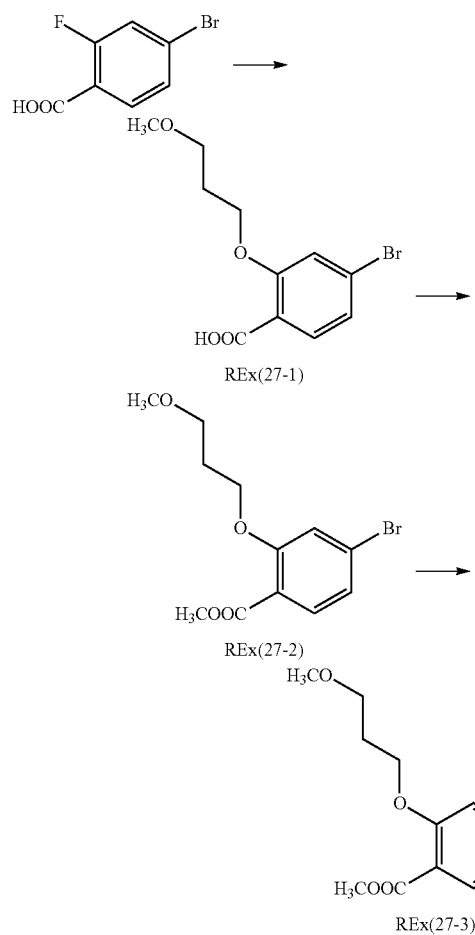

(1) 4-Bromo-2-(3-methoxypropoxy)benzoic acid [REx(27-1)]:

To a solution of 3-methoxy-1-propanol (5.02 g) in N,N-dimethylformamide (37 mL) was added 60% oil-based sodium hydride (2.05 g), and the mixture was stirred at room temperature for 30 minutes. Then, thereto was added dropwise a solution of 4-bromo-2-fluorobenzoic acid (300 mg) in N,N-dimethylformamide (60 mL), and the mixture was stirred at room temperature for 20 hours. To the reaction solution was added water and n-hexane, and then the mixed solution was acidified by concentrated hydrochloric acid. The resulting colorless powder was filtered to give 4-bromo-2-(3-methoxypropoxy)benzoic acid [REx(27-1)] (4.43 g).

ESI-MS m/z: 289[M−H]—.

(2) Methyl 4-bromo-2-(3-methoxypropoxy)benzoate [REx(27-2)]:

To a mixture of the compound obtained in the above (1) (4.42 g) and potassium carbonate (4.22 g) was added N,N-dimethylformamide (20 mL), and then thereto was added methyl iodide (1.43 mL), and the mixture was stirred at room temperature for 30 minutes. After cooling, to the reaction solution was added water, and the mixture was extracted with ethyl acetate. The organic layer was sequentially washed with water twice and saturated saline, dried over magnesium sulfate, and then concentrated under reduced pressure. The resulting residue was purified by silica gel column chromatography (eluent: n-hexane/ethyl acetate=20/1→3/1) to give methyl 4-bromo-2-(3-methoxypropoxy)benzoate [REx(27-2)] (4.01 g) as a colorless oil.

APCI-MS m/z: 343/305 [M+H]$^+$.

(3) Methyl 4-acetyl-2-(3-methoxypropoxy)benzoate [REx(27-3)]:

To a solution of the compound obtained in the above (2) (4.0 g) in toluene (44 mL) were added tri-n-butyltin-1-ethoxyvinyl (8.90 mL) and dichlorobis(triphenylphosphine) palladium (II) (1.85 g), and the mixture was heated to stir at 100° C. for 17 hours. The reaction solution was cooled to room temperature, and then thereto was added 4-normal hydrogen chloride-1,4-dioxane (24 mL), and the mixture was stirred at room temperature for 1 hour. To the reaction solution was added water, and the mixture was extracted with ethyl acetate. The organic layer was washed with saturated saline, and then thereto were added magnesium sulfate and NH-silica gel, and an insoluble was filtered. The filtrate was concentrated under reduced pressure. The resulting residue was purified by silica gel column chromatography (eluent: n-hexane/ethyl acetate=20/1) to give methyl 4-acetyl-2-(3-methoxypropoxy)benzoate [REx(27-3)] (1.02 g) as a yellow oil.

APCI-MS m/z: 267 [M+H]$^+$.

Reference Example 28

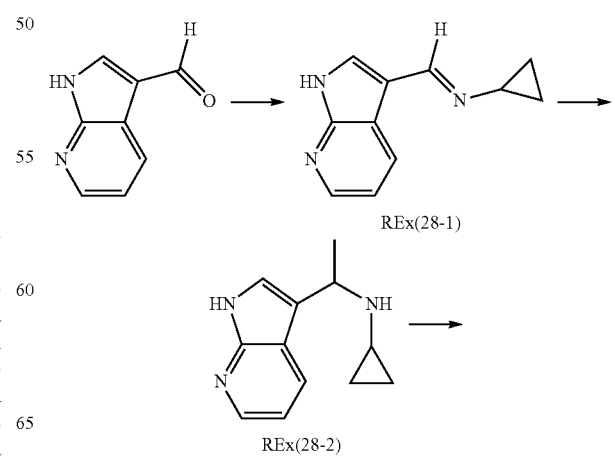

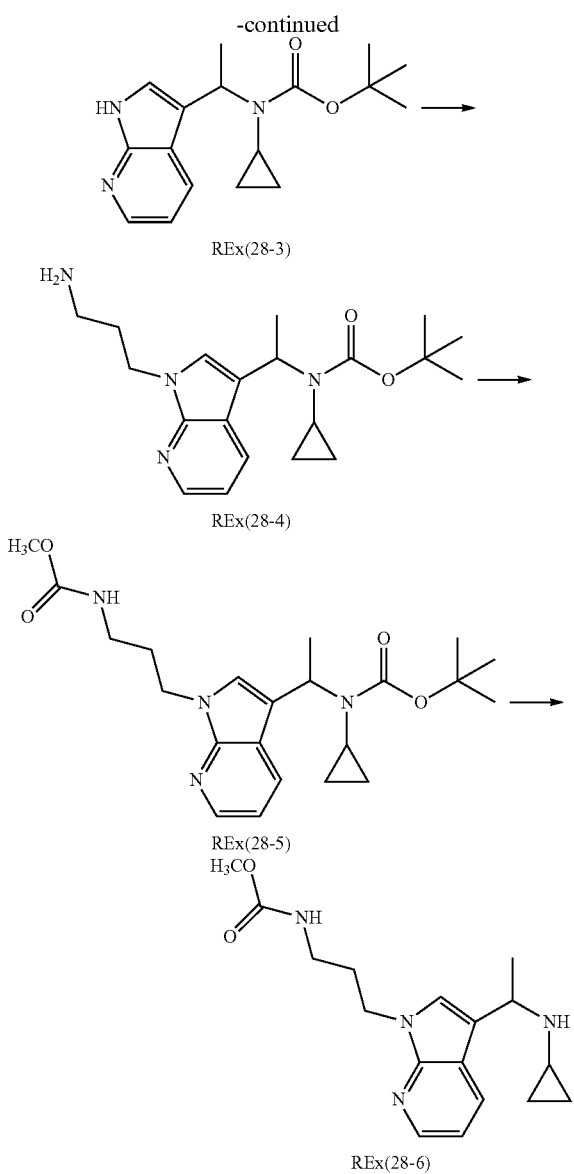

(1) N-[(1E)-1H-Pyrrolo[2,3-b]pyridin-3-ylmethylene]cyclopropylamine [REx(28-1)]:

To a suspension of 1H-pyrrolo[2,3-b]pyridin-3-carbaldehyde (1.46 g) in ethanol (30 mL) was added cyclopropylamine (1.41 mL), and the mixture was stirred at 50° C. for 19 hours. The reaction solution was concentrated under reduced pressure, and then treated azeotropically with toluene. The resulting residue was triturated with isopropyl ether/n-hexane (3:1) to give N-[(1E)-1H-pyrrolo[2,3-b]pyridin-3-ylmethylene]cyclopropylamine [REx(28-1)] (1.75 g) as a colorless powder.

APCI-MS m/z: 186 [M+H]$^+$.

(2) N-[1-(1H-Pyrrolo[2,3-b]pyridin-3-yl)ethyl]cyclopropylamine [REx(28-2)]:

To a suspension of the compound obtained in the above (1) (1.11 g) and 1-(trimethylsilyl)-1H-benzotriazole (2.20 mL) in toluene (50 mL) was added dropwise a 3M solution of methylmagnesium bromide in diethyl ether (10 mL) under ice-cooling over 10 minutes, and the mixture was stirred at 110° C. for 6 hours. The reaction solution was poured into ice-cooled ammonium chloride solution, and extracted with ethyl acetate. An insoluble was filtered, and then the organic layer was separated, and the aqueous layer was extracted with chloroform. The organic layers were collected, dried over sodium sulfate, and then concentrated under reduced pressure. The resulting residue was dissolved in ethyl acetate, and extracted with 10% aqueous citric acid solution. The aqueous layer was alkalified by aqueous potassium carbonate solution, and then extracted with chloroform. The organic layer was dried over sodium sulfate, and then concentrated under reduced pressure to give a crude product of N-[1-(1H-pyrrolo[2,3-b]pyridin-3-yl)ethyl]cyclopropylamine [REx(28-2)] (800 mg) as a yellow oil.

(3) tert-Butyl cyclopropyl[1-(1H-pyrrolo[2,3-b]pyridin-3-yl)ethyl]carbamate [REx(28-3)]:

To a solution of the compound obtained in the above (2) (800 mg) and potassium carbonate (1.10 g) in tetrahydrofuran (10 mL)-water (10 mL) was added a solution of di-t-butyl dicarbonate (786 mg) in tetrahydrofuran (1 mL), and the mixture was stirred at room temperature for 6 hours. To the reaction solution was added water, and the mixture was extracted with ethyl acetate. The organic layer was sequentially washed with water and saturated saline, dried over sodium sulfate, and then concentrated under reduced pressure. The resulting residue was dissolved in acetonitrile (20 mL), and then thereto were added sodium hydroxide (320 mg) and tetrabutylammonium hydrogen sulfate (68 mg), and the mixture was stirred at 50° C. for 30 minutes. The reaction solution was cooled, and then an insoluble was filtered, and the filtrate was concentrated under reduced pressure. The resulting residue was dissolved in ethyl acetate, and washed with water. The organic layer was dried over sodium sulfate, and then concentrated under reduced pressure. The resulting residue was purified by silica gel column chromatography (eluent: n-hexane/ethyl acetate=3/1→1/3) to give tert-butyl cyclopropyl[1-(1H-pyrrolo[2,3-b]pyridin-3-yl)ethyl]carbamate [REx(28-3)] (338 mg) as a pale yellow oil.

APCI-MS m/z: 302 [M+H]$^+$.

(4) tert-Butyl {1-[1-(3-aminopropyl)-1H-pyrrolo[2,3-b]pyridin-3-yl]ethyl}-cyclopropylcarbamate [REx(28-4)]:

To a solution of the compound obtained in the above (3) (301 mg) in acetonitrile (10 mL) were added sodium hydroxide (300 mg) and tetrabutylammonium hydrogen sulfate (17 mg), and the mixture was stirred at room temperature for 15 minutes. Then, thereto was added 3-chloropropylamine hydrochloride (650 mg), and the mixture was stirred at 70° C. for 4 hours. The reaction solution was cooled, and then an insoluble was filtered, and the filtrate was concentrated under reduced pressure. The resulting residue was dissolved in ethyl acetate, and sequentially washed with water and saturated saline. The organic layer was dried over sodium sulfate, and then concentrated under reduced pressure to give a crude product of tert-butyl {1-[1-(3-aminopropyl)-1H-pyrrolo[2,3-b]pyridin-3-yl]ethyl}cyclopropylcarbamate [REx(28-4)] (378 mg) as a yellow oil.

APCI-MS m/z: 359 [M+H]$^+$.

(5) Methyl [3-(3-{1-[(tert-butoxycarbonyl)(cyclopropyl)amino]ethyl}-1H-pyrrolo[2,3-b]pyridin-1-yl)propyl]carbamate [REx(28-5)]:

To a solution of the compound obtained in the above (4) (370 mg) in chloroform (10 mL) were added pyridine (0.25 mL) and methyl chloroformate (0.16 mL) under ice-cooling, and the mixture was stirred at room temperature for 2 hours. The reaction solution was concentrated, and then treated azeotropically with toluene. The resulting residue was dissolved in chloroform, and washed with 1-normal aqueous sodium hydrogen carbonate solution. The organic layer was dried over sodium sulfate, and then concentrated under reduced pressure. The resulting residue was purified by silica gel column chromatography (eluent: n-hexane/ethyl acetate=1/1→ethyl acetate) to give methyl [3-(3-{1-[(tert-butoxycarbonyl)-(cyclopropyl)amino]ethyl}-1H-pyrrolo[2,3-b]pyridin-1-yl)propyl]carbamate [REx(28-5)] (203 mg) as a colorless oil.

APCI-MS m/z: 417 [M+H]$^+$.

(6) Methyl (3-{3-[1-(cyclopropylamino)ethyl]-1H-pyrrolo[2,3-b]pyridin-1-yl}propyl)carbamate [REx(28-6)]:

To a solution of the compound obtained in the above (5) (187 mg) and 2,6-lutidine (0.157 mL) in dichloromethane (4 mL) was added trimethylsilyltriflate (0.180 µL) under ice-cooling, and the mixture was stirred at the same temperature for 1 hour. Then, thereto were added aqueous saturated sodium hydrogen carbonate solution and methanol (2 mL) under ice-cooling, and the mixture was extracted with chloroform. The organic layer was dried over magnesium sulfate, and then concentrated under reduced pressure. The resulting residue was purified by silica gel column chromatography (eluent: chloroform→chloroform/methanol=5/1→chloroform/methanol/ammonia water=50/10/1) to give methyl (3-{3-[1-(cyclopropylamino)ethyl]-1H-pyrrolo[2,3-b]pyridin-1-yl}propyl)carbamate [REx(28-6)] (89 mg) as a colorless oil.

Reference Example 29

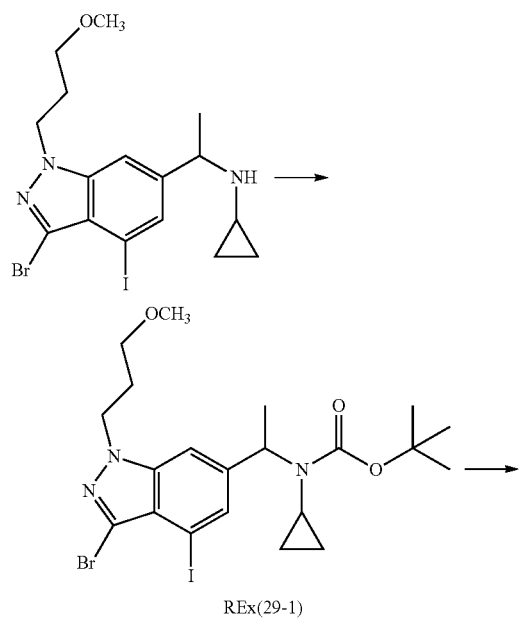

REx(29-1)

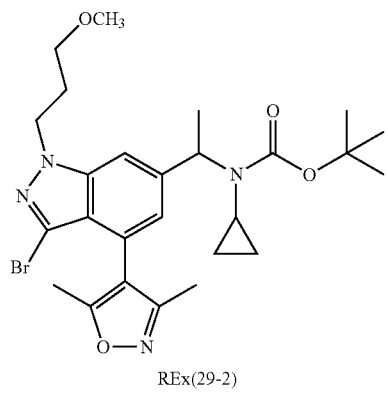

REx(29-2)

(1) tert-Butyl N-{1-[3-bromo-4-iodo-1-(3-methoxypropyl)-1H-indazol-6-yl]ethyl}-cyclopropylcarbamate [REx(29-1)]:

To a solution of N-{1-[3-bromo-4-iodo-1-(3-methoxypropyl)-1H-indazol-6-yl]ethyl}cyclopropanamine (10.2 g) in dichloromethane (200 mL) was added di-t-butyl dicarbonate (5.12 g) under ice-cooling, and the mixture was stirred at room temperature for 21 hours. Then, thereto was added dimethylaminopyridine (261 mg), and the mixture was stirred for additional 6 hours at room temperature. To the reaction solution was added water under ice-cooling, and the mixture was extracted with chloroform. The organic layer was washed with saturated saline, dried over sodium sulfate, and then concentrated under reduced pressure. The resulting residue was purified by silica gel column chromatography (eluent: n-hexane/ethyl acetate=9/1→4/1) to give tert-butyl N-{1-[3-bromo-4-iodo-1-(3-methoxypropyl)-1H-indazol-6-yl]ethyl}cyclopropylcarbamate [REx(29-1)] (7.62 g) as a yellow oil.

(2) tert-Butyl {1-[3-bromo-4-(3,5-dimethylisoxazol-4-yl)-1-(3-methoxypropyl)-1H-indazol-6-yl]ethyl}-cyclopropylcarbamate [REx(29-2)]:

To a solution of the compound obtained in the above (1) (300 mg) and 3,5-dimethylisoxazol-4-boronic acid (146 mg) in dimethoxyethane (5.0 mL) was added 2M aqueous sodium carbonate solution (2.6 mL) under argon, and then thereto was added tetrakis(triphenylphosphine)palladium (0) (30 mg), and the mixture was stirred at 105° C. for 22 hours. Then, thereto was added water under ice-cooling, and the mixture was extracted with ethyl acetate. The organic layer was washed with saturated saline, dried over sodium sulfate, and then concentrated under reduced pressure. The resulting residue was purified by silica gel column chromatography (eluent: n-hexane→n-hexane/ethyl acetate=3/2) to give tert-butyl {1-[3-bromo-4-(3,5-dimethylisoxazol-4-yl)-1-(3-methoxypropyl)-1H-indazol-6-yl]ethyl}-cyclopropylcarbamate [REx(29-2)] (154 mg) as a colorless oil.

APCI-MS m/z: 547/549 [M+H]$^+$.

Deprotection of Boc group is done according to the above method.

Reference Example 30 tert-Butyl cyclopropyl {1-[1-(3-methoxypropyl)-1H-indazol-6-yl]ethyl}carbamate [REx(30-1)]

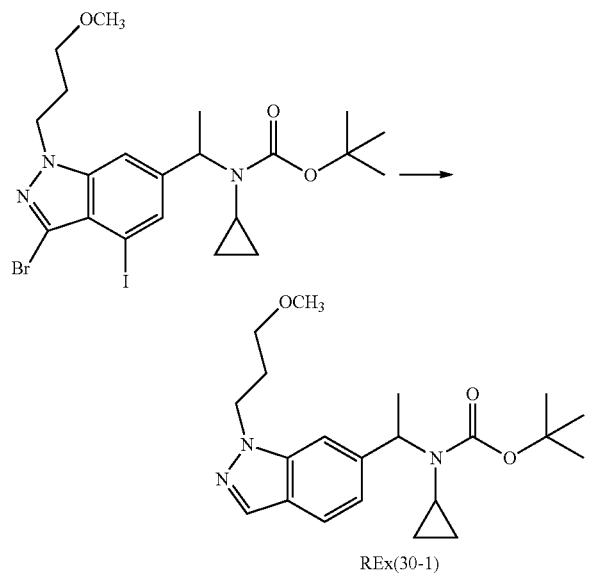

REx(30-1)

To a solution of tert-butyl N-{1-[3-bromo-4-iodo-1-(3-methoxypropyl)-1H-indazol-6-yl]ethyl}cyclopropylcarbamate (1.0 g) in 1,4-dioxane (20 mL) were added diisopropylethylamine (0.90 mL) and 10% palladium on carbon catalyst (200 mg), and the mixture was stirred under hydrogen for 42 hours. An insoluble was filtered, and then the filtrate was sequentially washed with aqueous saturated sodium hydrogen carbonate solution and saturated saline, dried over sodium sulfate, and then concentrated under reduced pressure. The resulting residue was purified by silica gel column chromatography (eluent: n-hexane/ethyl acetate=911-411) to give tert-butyl cyclopropyl {1-[1-(3-methoxypropyl)-1H-indazol-6-yl]ethyl}carbamate [REx(30-1)] (167 mg) as a colorless oil.

APCI-MS m/z: 374 [M+H]⁺.

Reference Example 31

N-{1-[3-(3-Methoxypropyl)-5-(trifluoromethyl)phenyl]ethyl}cyclopropanamine [REx(31-1)]

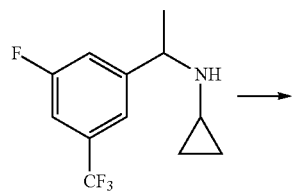

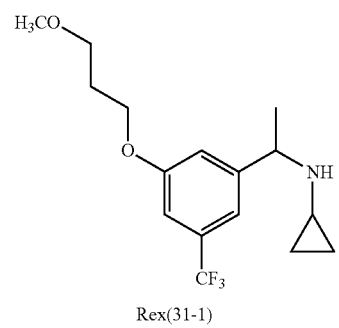

Rex(31-1)

To a solution of 3-methoxy-1-propanol (0.14 mL) in N,N-dimethylformamide (3.0 mL) was added 60% oil-based sodium hydride (97 mg), and the mixture was stirred at room temperature for 10 minutes. Then, thereto was added dropwise a solution of N-{1-[3-fluoro-5-(trifluoromethyl)phenyl]ethyl}cyclopropylamine (300 mg) in N,N-dimethylformamide (1.0 mL), and the mixture was heated to stir at 40° C. for 4 hours. After cooling to room temperature, thereto was added water, and the mixture was extracted with ethyl acetate. The organic layer was sequentially washed with water and saturated saline, dried over magnesium sulfate, and then concentrated under reduced pressure. The resulting residue was purified by silica gel column chromatography (eluent: n-hexane/ethyl acetate=10/1→2/3) to give N-{1-[3-(3-methoxypropyl)-5-(trifluoromethyl)phenyl]ethyl}cyclopropanamine [REx(31-1)] (227 mg) as a colorless oil.

APCI-MS m/z: 318 [M+H]⁺.

Reference Example 32

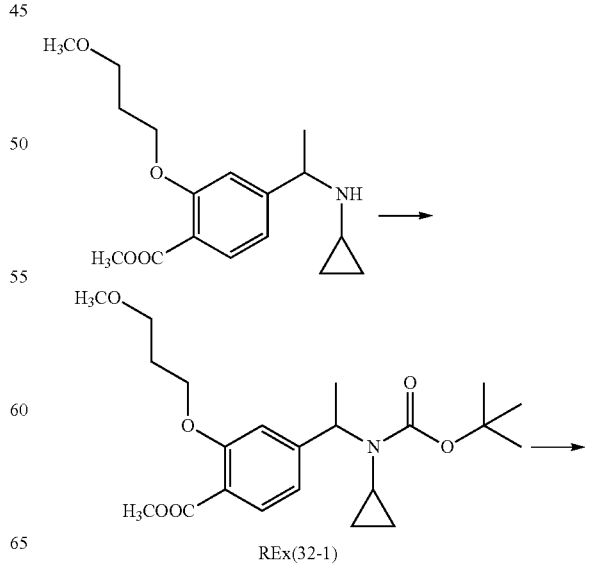

REx(32-1)

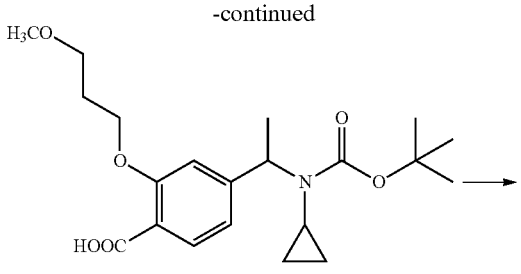

REx(32-2)

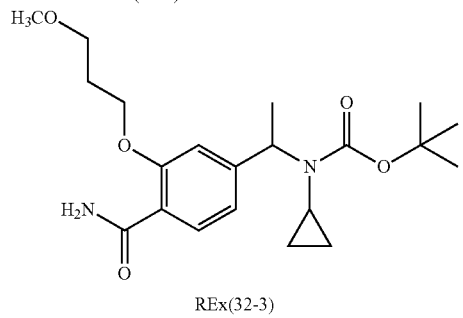

REx(32-3)

(1) Methyl 4-{1-[(tert-butoxycarbonyl)(cyclopropyl)amino]ethyl}-2-(3-methoxypropoxy)benzoate [REx(32-1)]:

To a solution of methyl 4-[1-(cyclopropylamino)ethyl]-2-(3-methoxypropoxy)benzoate (1.20 g) in chloroform (9.6 mL) were added di-t-butyl dicarbonate (2.00 g) and triethylamine (2.34 mL) under ice-cooling, and the mixture was stirred at room temperature for 20 hours. To the reaction solution was added water under ice-cooling, and the mixture was extracted with chloroform. The organic layer was dried over magnesium sulfate, and then concentrated under reduced pressure. The resulting residue was purified by silica gel column chromatography (eluent: n-hexane/ethyl acetate=10/1→2/1) to give methyl 4-{1-[(tert-butoxycarbonyl)-(cyclopropyl)amino]ethyl}-2-(3-methoxypropoxy)benzoate (7.62 g) as a colorless oil.

APCI-MS m/z: 408 [M+H]$^+$.

(2) 4-{1-[(tert-Butoxycarbonyl)(cyclopropyl)amino]ethyl}-2-(3-methoxypropoxy)benzoic acid [REx(32-2)]:

To a solution of the compound obtained in the above (1) (1.10 g) in methanol (13.5 mL) was added 2-normal aqueous sodium hydroxide solution (13.5 mL), and the mixture was stirred at room temperature for 2 hours. To the reaction solution was added chloroform, and then thereto was added 2-normal hydrochloric acid (13.5 mL) under ice-cooling. The organic layer was separated, and then washed with water, dried over magnesium sulfate, and then concentrated under reduced pressure. The resulting residue was purified by silica gel column chromatography (eluent: chloroform→chloroform/methanol=20/1) to give 4-{1-[(tert-butoxycarbonyl)(cyclopropyl)amino]ethyl}-2-(3-methoxypropoxy) benzoic acid (1.14 g) as a colorless oil.

ESI-MS m/z: 392[M−H]$^−$ (3) tert-butyl 1-[4-(aminocarbonyl)-3-(3-methoxypropoxy)phenyl]ethyl-cyclopropylcarbamate [REx(32-3)]:

To a solution of the compound obtained in the above (2) (250 mg) in N,N-dimethylformamide (3.2 mL) were added ammonium chloride (40.8 mg), diisopropylethylamine (0.133 mL), 1-ethyl-3-(3-dimethylaminopropyl)carbodiimide hydrochloride (146 mg) and 1-hydroxybenzotriazole (103 mg), and then the mixture was stirred at room temperature for 30 minutes. To the reaction mixture was added water, and the mixture was extracted with ethyl acetate. The organic layer was sequentially washed with water and saturated saline, and then concentrated under reduced pressure. The resulting residue was purified by silica gel column chromatography (eluent: n-hexane/ethyl acetate=3/2→1/6) to give tert-butyl {1-[4-(aminocarbonyl)-3-(3-methoxypropoxy)phenyl]ethyl}cyclopropylcarbamate (164 mg) as a colorless oil.

APCI-MS m/z: 393 [M+H]$^+$.

Similarly, deprotection of Boc group is done according to the above method.

Reference Example 33

2-[1-(Cyclopropylamino)ethyl]quinazolin-4(3H)-one [REx(33-1)]

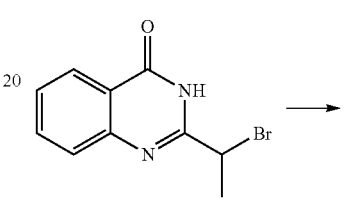

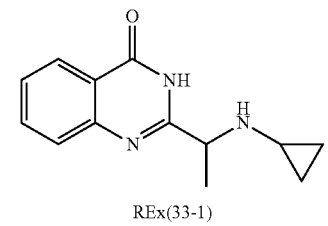

REx(33-1)

To a suspension of 2-(1-bromoethyl)quinazolin-4(3H)-one (2.53 g) in N,N-dimethylformamide (30 mL) was added cyclopropylamine (3.46 mL), and the mixture was diluted with N,N-dimethylformamide (20 mL) and water (1 mL), and then stirred for 18 hours. The reaction solution was concentrated under reduced pressure, and to the residue was added aqueous sodium hydrogen carbonate solution, and then the mixture was extracted with chloroform. The organic layer was dried over sodium sulfate, and then concentrated under reduced pressure. The resulting residue was triturated with diisopropyl ether/ethyl acetate (20:1) to give 2-[1-(cyclopropylamino)ethyl]quinazolin-4(3H)-one [REx(33-1)] (1.71 g) as a colorless powder.

APCI-MS m/z: 230 [M+H]$^+$.

Reference Examples 34 to 100

The following compounds of Reference Examples 34 to 100 were prepared according to the methods of the above Reference Examples. Each symbol of Methods A-1 to F refers to each method according to the following methods of Reference Examples.

Method A-1 Reference Example 1
Method A-2 Reference Example 2
Method B Reference Example 3
Method C-1 Reference Example 6
Method C-2 Reference Example 7
Method C-3 Reference Example 8
Method D Reference Example 28
Method E-1 Reference Example 29
Method E-2 Reference Example 30
Method E-3 Reference Example 31
Method E-4 Reference Example 32
Method F Reference Example 33

TABLE 73

| Ref. EX. No. | Structural formula | a | b | c | d | e | f |
|---|---|---|---|---|---|---|---|
| 34 | | HCl | 279.3746 | P | 280 | [M + H]+ | B |
| 35 | | HCl | 221.2955 | P | 222 | [M + H]+ | C-2 |
| 36 | | | 287.3999 | O | 288 | [M + H]+ | C-3 |
| 37 | | | 221.29551 | O | 222 | [M + H]+ | C-2 |

TABLE 74

| | | | | | | | |
|---|---|---|---|---|---|---|---|
| 38 | | | 235.322 | O | 236 | [M + H]+ | C-2 |
| 39 | | HCl | 211.3022 | P | 212 | [M + H]+ | A |

TABLE 74-continued
| | | | | | | | |
|---|---|---|---|---|---|---|---|
| 40 | 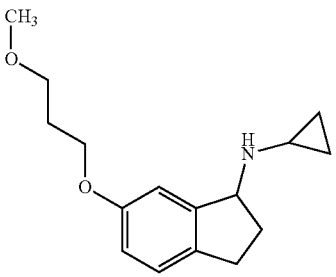 [SMILES: COCCCOc1ccc2c(c1)C(NC1CC1)CC2] | HCl | 261.3593 | P | 262 | [M + H]+ | C-2 |
| 41 | 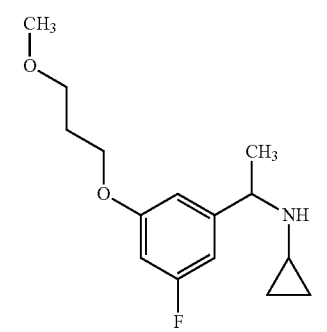 [SMILES: COCCCOc1cc(F)cc(C(C)NC2CC2)c1] | | 267.3391 | O | 268 | [M + H]+ | C-2 |
TABLE 75
| | | | | | | | |
|---|---|---|---|---|---|---|---|
| 42 | 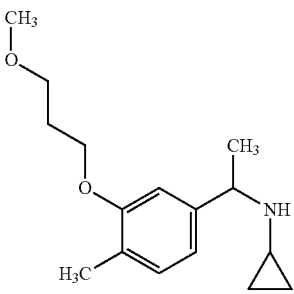 [SMILES: COCCCOc1cc(C(C)NC2CC2)ccc1C] | | 263.3752 | O | 264 | [M + H]+ | A-2 |
| 43 | 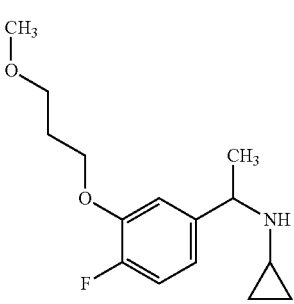 [SMILES: COCCCOc1cc(C(C)NC2CC2)ccc1F] | | 267.3391 | O | 268 | [M + H]+ | A-2 |
| 44 | 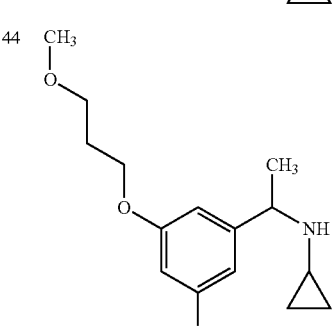 | | 263.3752 | O | 264 | [M + H]+ | C-2 |

TABLE 75-continued
| 45 | 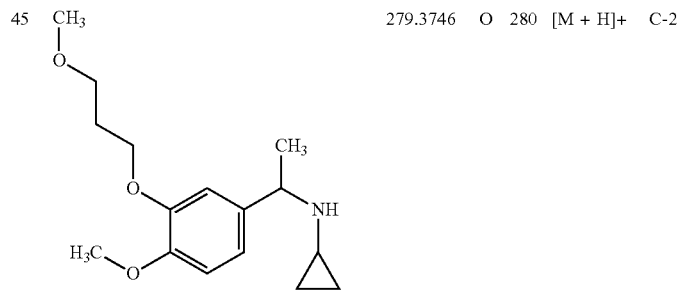 | 279.3746 | O | 280 | [M + H]+ | C-2 |
TABLE 76
| 46 | 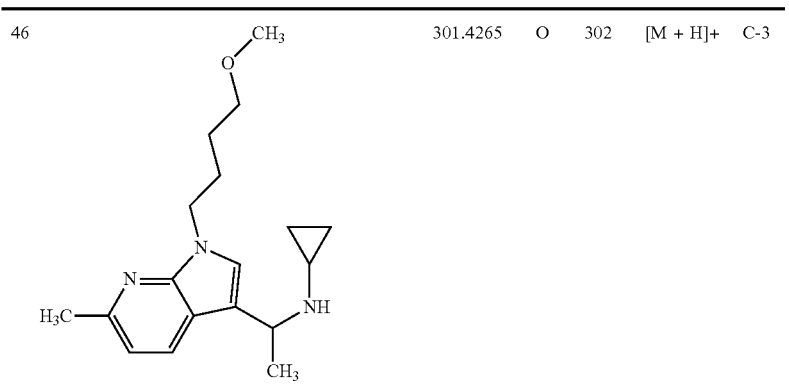 | 301.4265 | O | 302 | [M + H]+ | C-3 |
| 47 | 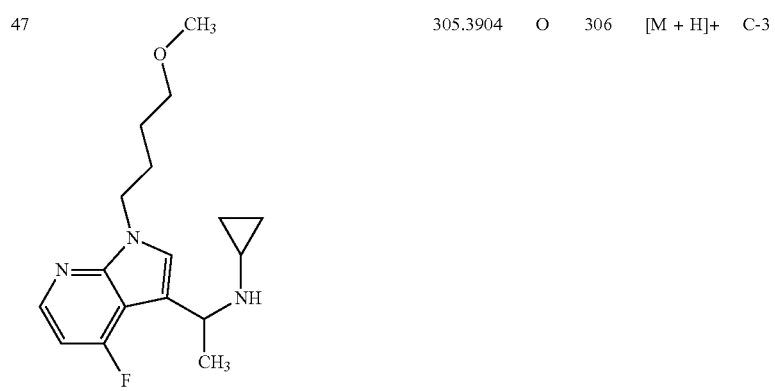 | 305.3904 | O | 306 | [M + H]+ | C-3 |
| 48 | 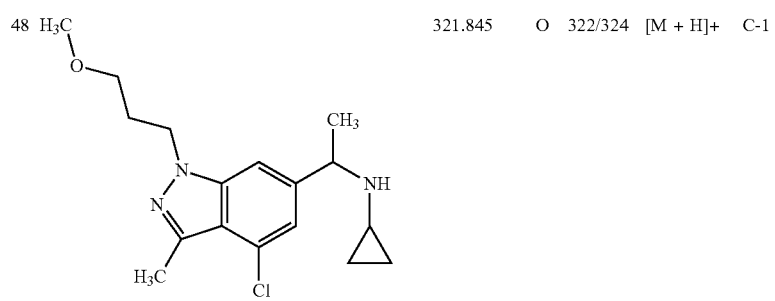 | 321.845 | O | 322/324 | [M + H]+ | C-1 |

TABLE 76-continued
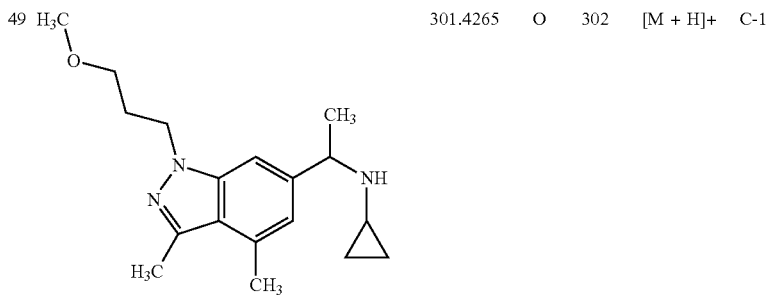
| 49 | | 301.4265 | O | 302 | [M + H]+ | C-1 |
TABLE 77
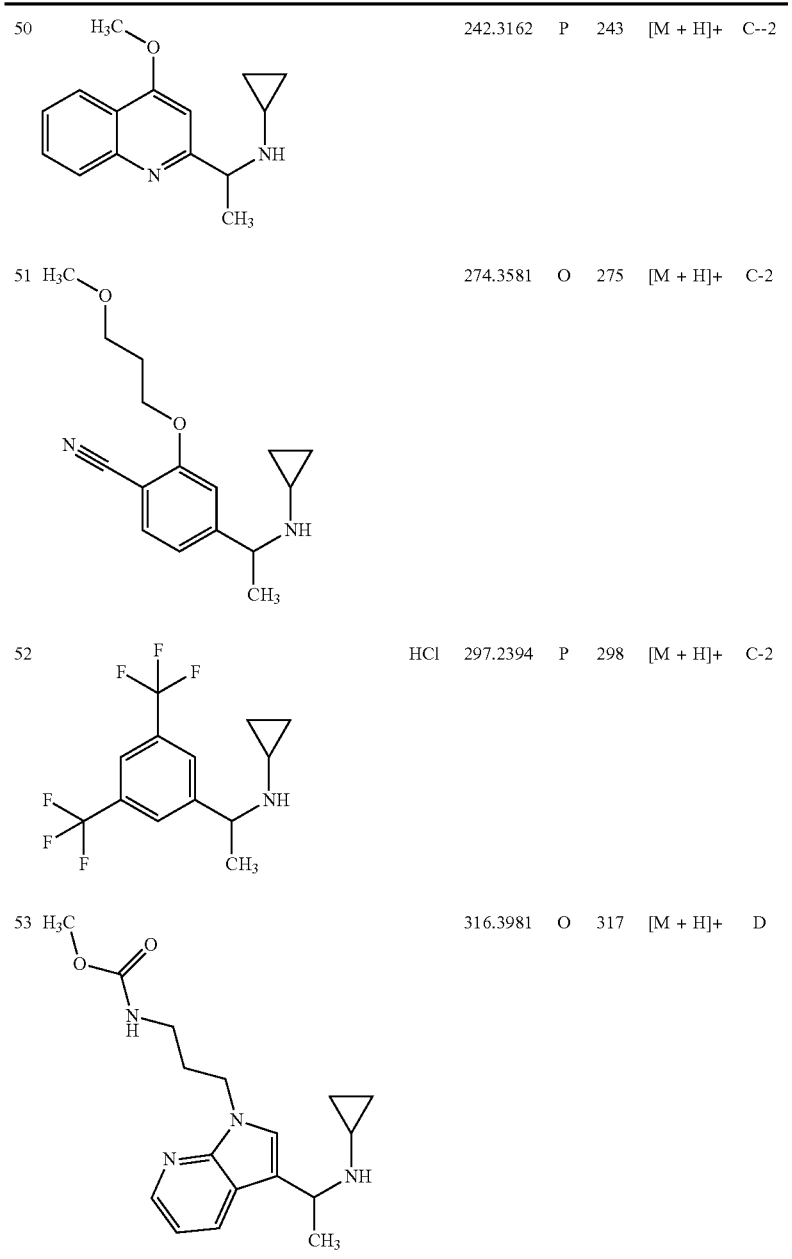
| 50 | | 242.3162 | P | 243 | [M + H]+ | C-2 |
| 51 | | 274.3581 | O | 275 | [M + H]+ | C-2 |
| 52 | HCl | 297.2394 | P | 298 | [M + H]+ | C-2 |
| 53 | | 316.3981 | O | 317 | [M + H]+ | D |

TABLE 78
| | | | | | | |
|---|---|---|---|---|---|---|
| 54 | 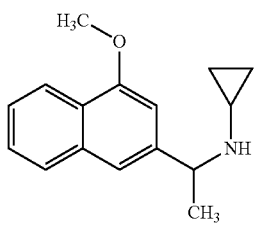 [SMILES: COc1cc(C(C)NC2CC2)cc2ccccc12] | 241.3282 | O | 242 | [M + H]+ | B |
| 55 | 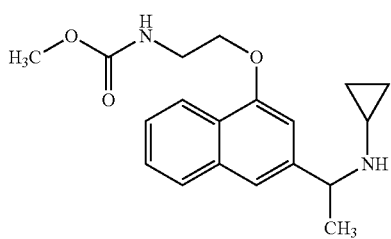 [SMILES: COC(=O)NCCOc1cc(C(C)NC2CC2)cc2ccccc12] | 328.4055 | O | 329 | [M + H]+ | B |
| 56 | 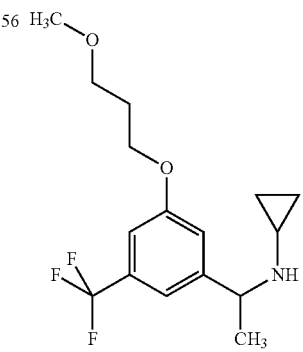 | 317.3466 | O | 318 | [M + H]+ | E-3 |
| 57 | 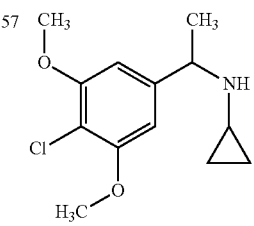 | 255.7405 | O | 256/258 | [M + H]+ | C-2 |
TABLE 79
| | | | | | | |
|---|---|---|---|---|---|---|
| 58 | 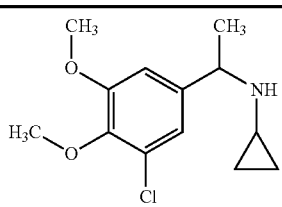 | 255.7405 | O | 256/258 | [M + H]+ | C-2 |

TABLE 79-continued

| 59 | (structure) | 337.4537 | O | 338 | [M + H]+ | C-2 |
| 60 | (structure) | 274.3581 | O | 275 | [M + H]+ | C-2 |
| 61 | (structure) | 274.4011 | O | 275 | [M + H]+ | C-1 |

TABLE 80

| 62 | (structure) | 275.3859 | O | 276 | [M + H]+ | C-2 |
| 63 | (structure) | 289.3694 | O | 290 | [M + H]+ | C-2 |

TABLE 80-continued
| 64 | 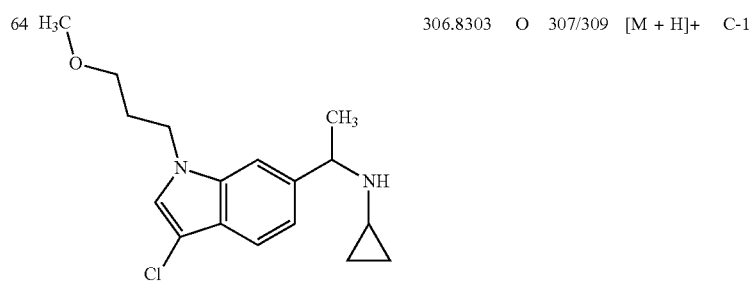 | 306.8303 | O | 307/309 | [M + H]+ | C-1 |
| 65 | 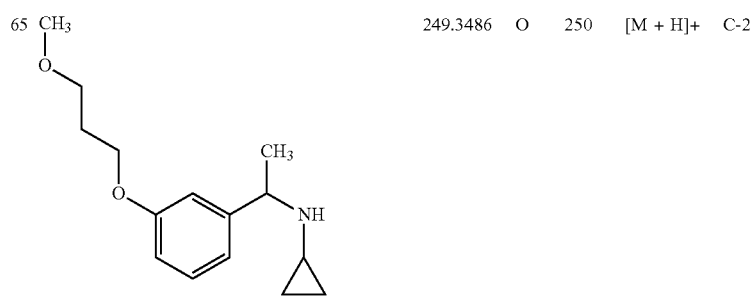 | 249.3486 | O | 250 | [M + H]+ | C-2 |
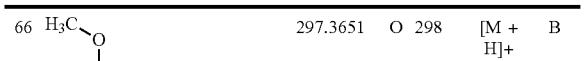
TABLE 81
| 66 | 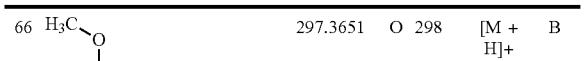 | 297.3651 | O | 298 | [M + H]+ | B |
| 67 | | 355.3979 | O | 356 | [M + H]+ | C-1 |
TABLE 81-continued
| 68 | 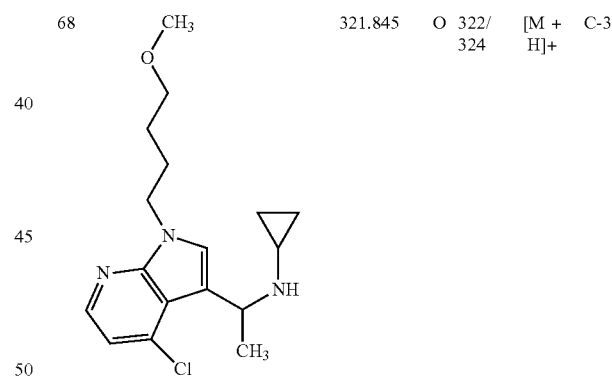 | 321.845 | O | 322/324 | [M + H]+ | C-3 |
| 69 | 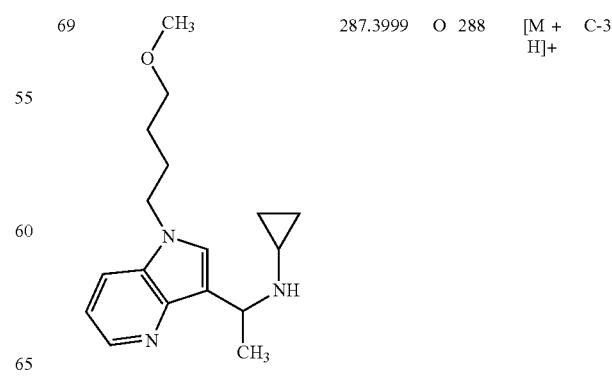 | 287.3999 | O | 288 | [M + H]+ | C-3 |

TABLE 82

| # | Structure | Mass | | M+ | Ion | Method |
|---|---|---|---|---|---|---|
| 70 | (7-azaindole with 5-F, N-(CH2)4-OCH3, 3-CH(CH3)NH-cyclopropyl) | 305.3904 | O | 306 | [M + H]+ | C-3 |
| 71 | (phenyl with OCH3, O(CH2)3OCH3, Br, CH(CH3)NH-cyclopropyl) | 358.2707 | O | 358/360 | [M + H]+ | C-2 |
| 72 | (indazole with N-(CH2)3-OCH3, 3-CH(CH3)NH-cyclopropyl) | 273.3733 | O | 274 | [M + H]+ | C-3 |
| 73 | (indazole with N-(CH2)4-OCH3, 3-CH(CH3)NH-cyclopropyl) | 287.3999 | O | 288 | [M + H]+ | C-3 |

TABLE 83

| # | Structure | Mass | | M+ | Ion | Method |
|---|---|---|---|---|---|---|
| 74 | (indole with 3-CH3, N-(CH2)3-OCH3, 6-CH(CH3)NH-cyclopropyl) | 286.4118 | O | 287 | [M + H]+ | C-1 |

TABLE 83-continued
| | | | | | | |
|---|---|---|---|---|---|---|
| 75 | 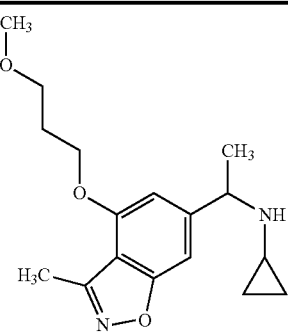 | 304.3841 | O | 305 | [M + H]+ | C-2 |
| 76 | 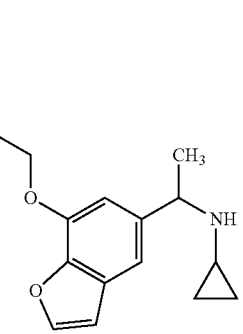 | 289.3694 | O | 290 | [M + H]+ | C-2 |
| 77 | 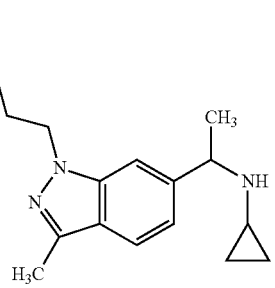 | 287.3999 | O | 288 | [M + H]+ | C-1 |
TABLE 84
| | | | | | | |
|---|---|---|---|---|---|---|
| 78 | 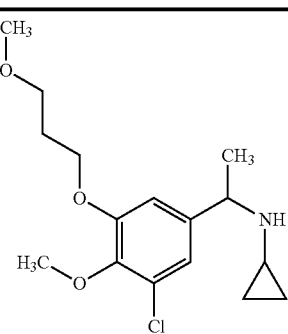 | 313.8197 | O | 314/316 | [M + H]+ | C-2 |
| 79 | 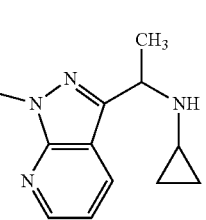 | 288.388 | O | 289 | [M + H]+ | C-3 |

TABLE 84-continued
| | | | | | | |
|---|---|---|---|---|---|---|
| 80 | 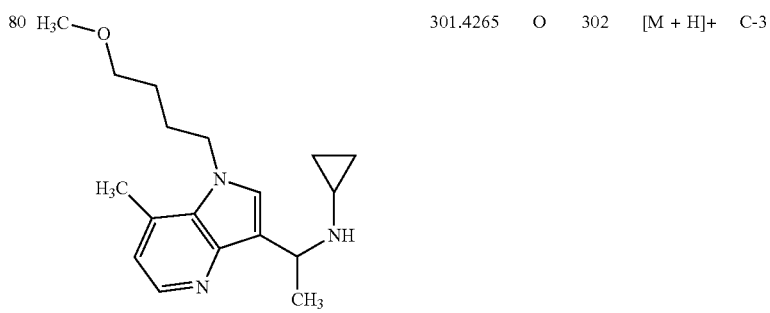 | 301.4265 | O | 302 | [M + H]+ | C-3 |
| 81 | 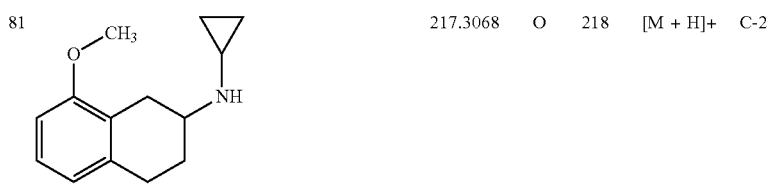 | 217.3068 | O | 218 | [M + H]+ | C-2 |
TABLE 85
| | | | | | | |
|---|---|---|---|---|---|---|
| 82 | 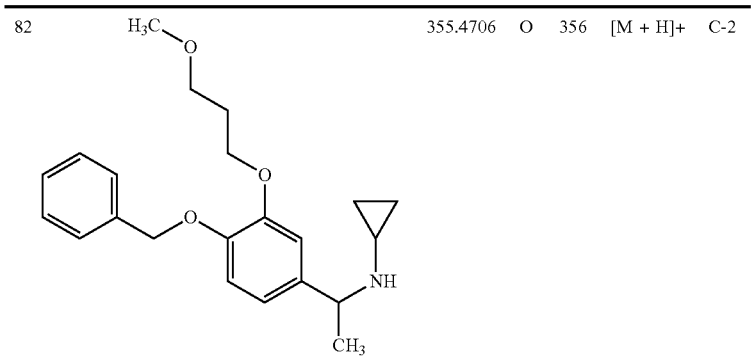 | 355.4706 | O | 356 | [M + H]+ | C-2 |
| 83 | 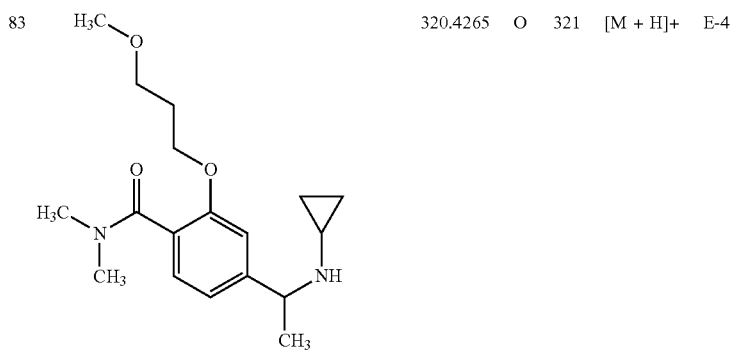 | 320.4265 | O | 321 | [M + H]+ | E-4 |
| 84 | 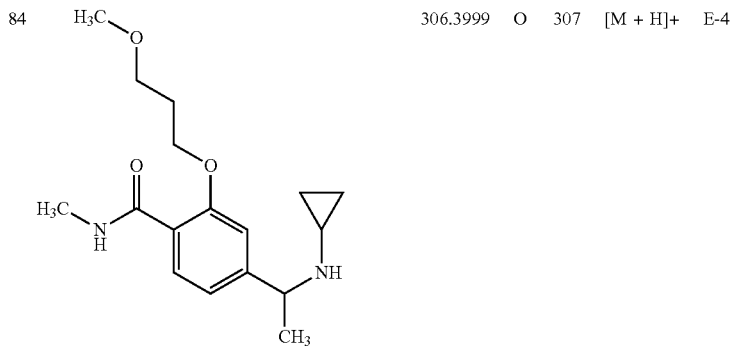 | 306.3999 | O | 307 | [M + H]+ | E-4 |

251 252
TABLE 85-continued
| | | | | |
|---|---|---|---|---|
| 85 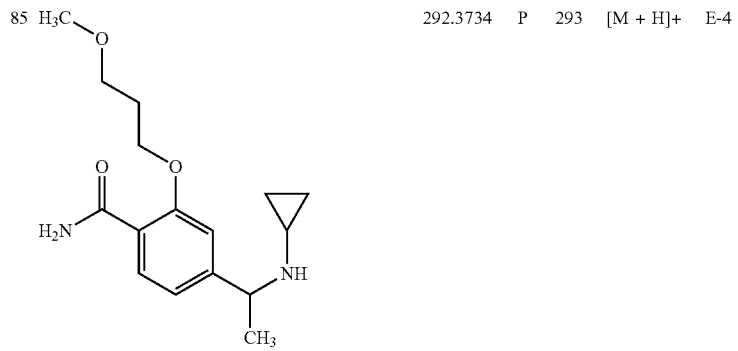 | 292.3734 | P | 293 [M + H]+ | E-4 |
TABLE 86
| | | | | |
|---|---|---|---|---|
| 86 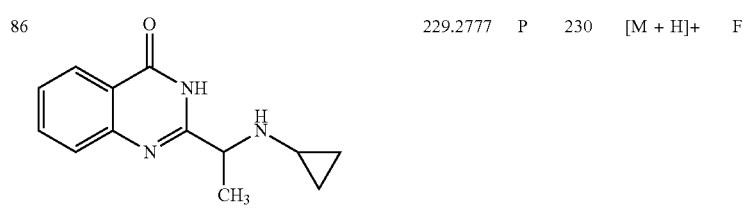 | 229.2777 | P | 230 [M + H]+ | F |
| 87 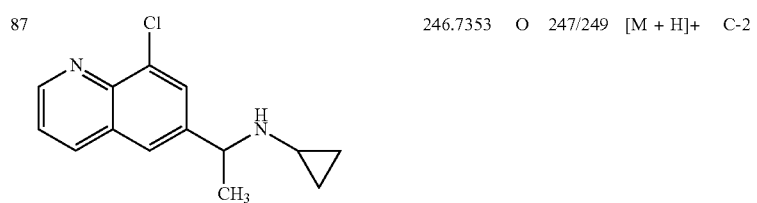 | 246.7353 | O | 247/249 [M + H]+ | C-2 |
| 88 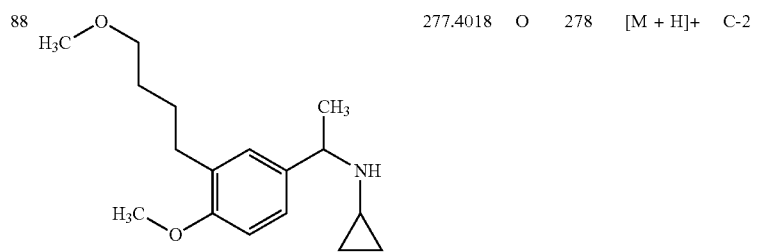 | 277.4018 | O | 278 [M + H]+ | C-2 |
| 89 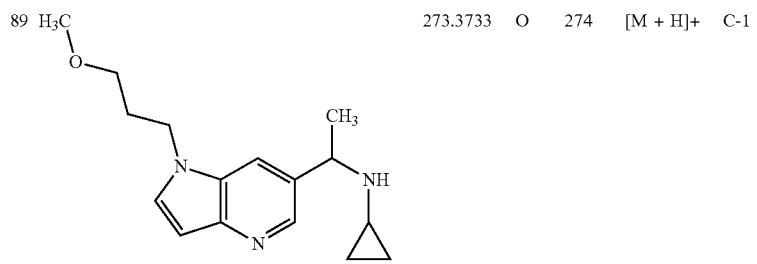 | 273.3733 | O | 274 [M + H]+ | C-1 |

TABLE 87
| 90 | 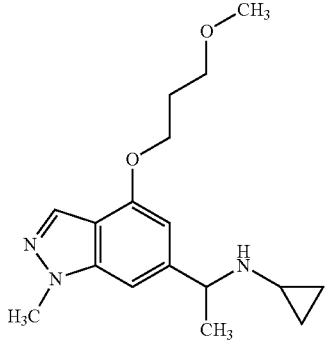 [SMILES: COCCCOc1cc(C(C)NC2CC2)cc2c1cnn2C] | 303.3993 | O | 304 | [M + H]+ | C-2 |
| 91 | 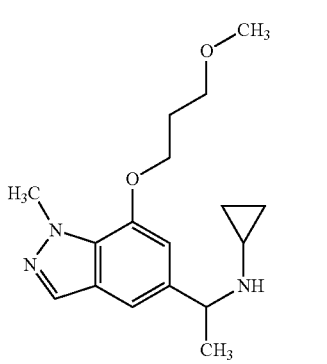 [SMILES: COCCCOc1cc(C(C)NC2CC2)cc2cnn(C)c12] | 303.3993 | O | 304 | [M + H]+ | C-2 |
| 92 | 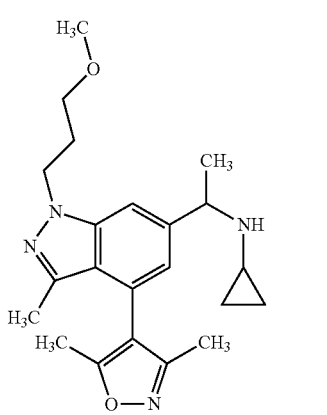 [SMILES: COCCCn1nc(C)c2c(-c3c(C)noc3C)cc(C(C)NC3CC3)cc21] | 382.4992 | O | 383 | [M + H]+ | E-1 |
| 93 | 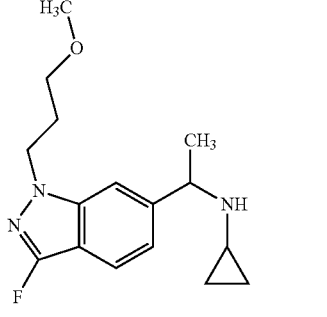 [SMILES: COCCCn1nc(F)c2ccc(C(C)NC3CC3)cc21] | 291.3638 | O | 292 | [M + H]+ | C-1 |

TABLE 88

| # | Structure | MW | | [M+H] | Ion | Method |
|---|---|---|---|---|---|---|
| 94 | (structure) | 315.3555 | O | 316 | [M + H]+ | C-2 |
| 95 | (structure) | 287.3999 | O | 288 | [M + H]+ | C-1 |
| 96 | (structure) | 307.8184 | O | 308/310 | [M + H]+ | C-1 |
| 97 | (structure) | 273.3733 | O | 274 | [M + H]+ | E-2 |

TABLE 89

| # | Structure | MW | | [M+H] | Ion | Method |
|---|---|---|---|---|---|---|
| 98 | (structure) | 305.3904 | O | 306 | [M + H]+ | C-1 |

TABLE 89-continued

| | | | | | | | |
|---|---|---|---|---|---|---|---|
| 99 | 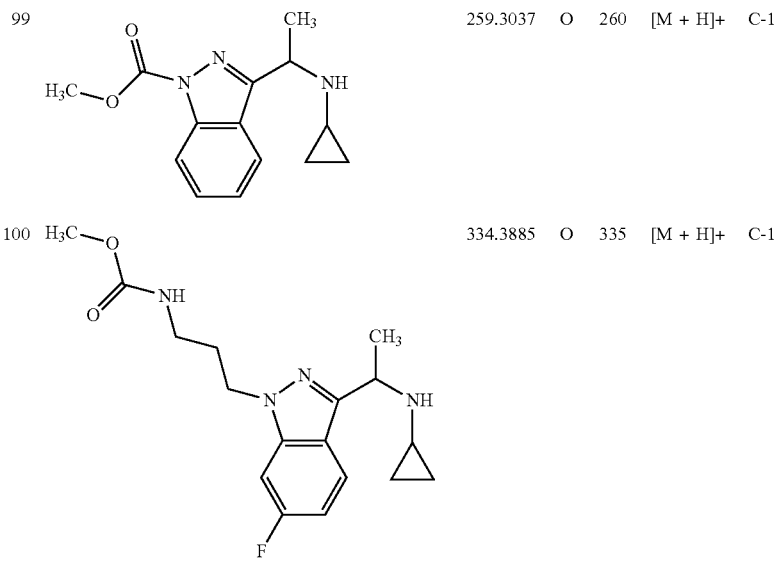 | | 259.3037 | O | 260 | [M + H]+ | C-1 |
| 100 | | | 334.3885 | O | 335 | [M + H]+ | C-1 |

Ref Ex. No.: Reference Example Number
a: Salt
b: Molecular weight
c: Properties
d: MS Results APCI
e: Ion species
f: Method
O: Oil
P: Powder

Reference Example 101

Methyl 3-acetyl-1H-indazole-1-carboxylate

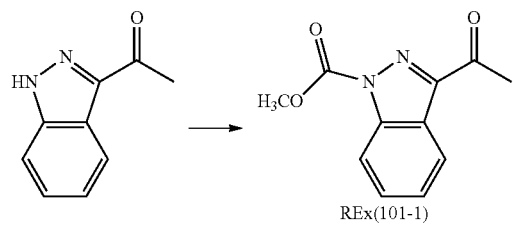 [SMILES: CC(=O)c1n[nH]c2ccccc12 ; COC(=O)n1nc(C(C)=O)c2ccccc21]

REx(101-1)

To a solution of 1-(1H-indazol-3-yl)ethanone (5.0 g) and triethylamine (6.53 mL) in chloroform (80 mL) was added dropwise a solution of methyl chlorocarbonate (3.24 g) in chloroform (20 mL) under ice-cooling over 1 hour, and the mixture was stirred at room temperature for 14 hours. The reaction solution was washed with aqueous saturated sodium chloride solution, dried over magnesium sulfate, and then concentrated under reduced pressure. The resulting residue was triturated with n-hexane to give methyl 3-acetyl-1H-indazole-1-carboxylate) [REx(101-1)] (6.67 g) as a colorless powder.

APCI-MS m/z: 219 [M+H]+.

Reference Example 102

Methyl[3-(3-acetyl-6-fluoro-1H-indazol-1-yl)propyl]carbamate [REx(102-2)]

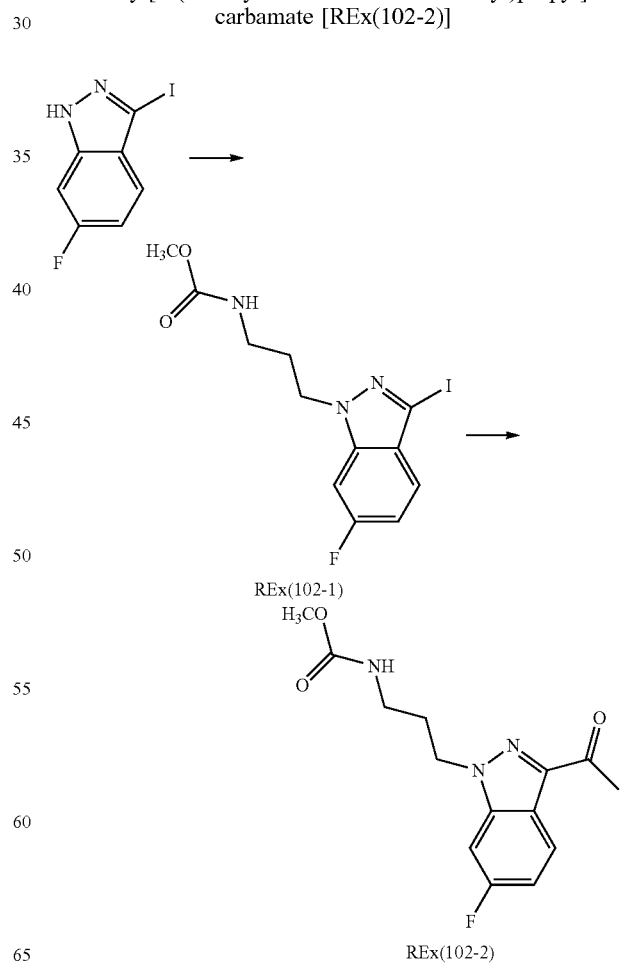

REx(102-1)

REx(102-2)

(1) To a solution of 6-fluoro-3-iodo-1H-indazole (1.5 g) and methyl (3-bromopropyl)carbamate (1.68 g) in N,N-dimethylformamide (5 mL) was added potassium carbonate (1.58 g), and the mixture was stirred at room temperature for 3 days. To the reaction solution was added ethyl acetate, and the mixture was washed with aqueous saturated sodium chloride solution, dried over magnesium sulfate, and then concentrated under reduced pressure. The resulting residue was purified by silica gel column chromatography (eluent: n-hexane/ethyl acetate=1/20→3/2) to give methyl [3-(6-fluoro-3-iodo-1H-indazol-1-yl)propyl]carbamate [REx(102-1)] (836 mg) as a red oil.

APCI-MS m/z: 378 [M+H]$^+$.

(2) To a solution of the compound obtained in (1) (830 mg) in 1,4-dioxane (10 mL) were added tri-n-butyltin-1-ethoxyvinyl (1.03 and dichlorobis(triphenylphosphine)palladium (II) (155 mg), and the mixture was heated to reflux for 17 hours. The reaction solution was cooled to room temperature, and then thereto was added a solution of potassium fluoride (250 mg) in water (3 mL), and the mixture was stirred at room temperature for 15 minutes. Then, thereto was added 1-normal hydrochloric acid (5 mL), and the mixture was stirred at room temperature for 1 hour, and then an insoluble was filtered. To the filtrate was added ethyl acetate, and the mixture was washed with aqueous saturated sodium chloride solution, dried over magnesium sulfate, and then concentrated under reduced pressure. The resulting residue was purified by silica gel column chromatography (eluent: n-hexane/ethyl acetate=20/1→4/1) to give methyl [3-(3-acetyl-6-fluoro-1H-indazol-1-yl)propyl]carbamate [REx(102-2)] (437 mg) as a red oil.

APCI-MS m/z: 294 [M+H]$^+$.

1) To 1-[1-(4-methoxybenzyl)-1H-pyrazolo[3,4-b]pyridin-3-yl]ethanone (3.14 g) was added trifluoroacetic acid (20 mL), and the mixture was heated to reflux for 2 days. The reaction solution was concentrated under reduced pressure. The resulting residue was diluted with ethyl acetate, and then sequentially washed with aqueous saturated sodium hydrogen carbonate solution and saturated saline, dried over magnesium sulfate, and then concentrated under reduced pressure. The resulting residue was purified by silica gel column chromatography (eluent: n-hexane/ethyl acetate=95/5-7/3) to give 1-(1H-pyrazolo[3,4-b]pyridin-3-yl)ethanone) [REx(103-1)] (1.73 g) as a pale yellow powder.

APCI-MS m/z: 162 [M+H]$^+$.

2) To a solution of 1-(1H-pyrazolo[3,4-b]pyridin-3-yl)ethanone (500 mg) and methyl (3-bromopropyl)carbamate (912 mg) in N,N-dimethylformamide (5 mL) was added potassium carbonate (864 mg), and the mixture was stirred at room temperature for 3 days. To the reaction solution was added ethyl acetate, and the mixture was washed with saturated saline, dried over magnesium sulfate, and then concentrated under reduced pressure. The resulting residue was purified by silica gel column chromatography (eluent: n-hexane/ethyl acetate=95/5→1/1) to give methyl [3-(3-acetyl-1H-pyrazolo[3,4-b]pyridin-1-yl)propyl]carbamate) [REx(103-2)] (308 mg) as a red oil.

APCI-MS m/z: 277 [M+H]$^+$.

Reference Example 104

Reference Example 103

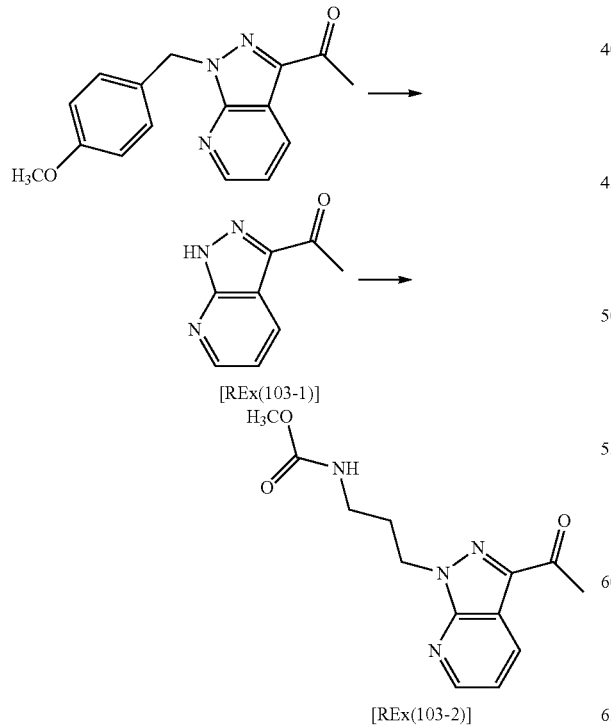

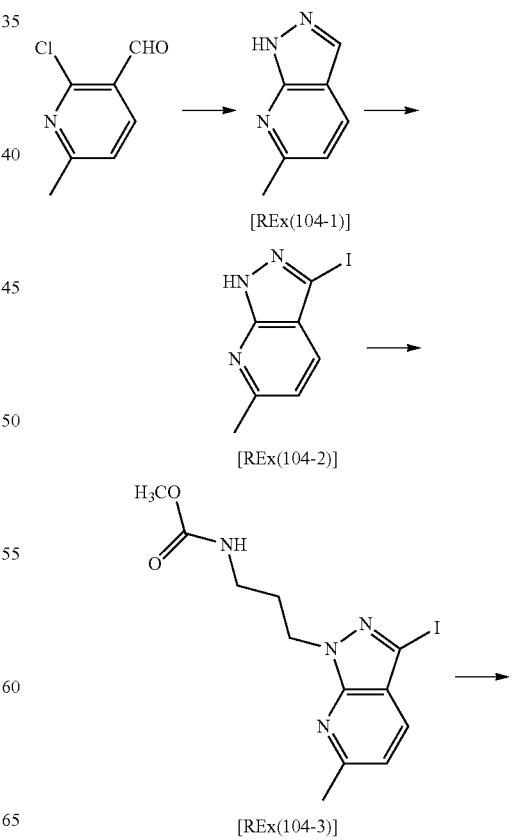

261
-continued

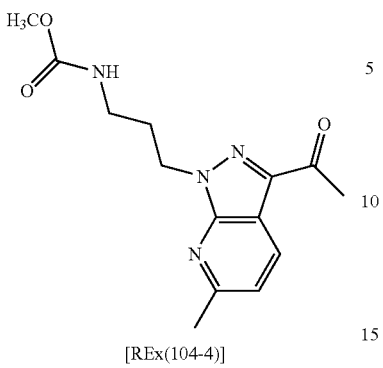

[REx(104-4)]

1) To a mixture of 2-chloro-6-methylnicotinaldehyde (5.0 g) and hydrazine monohydrate (6.24 mL) was added para-toluenesulfonic acid monohydrate (3.67 g), and the mixture was stirred at 130° C. for 18 hours. The reaction solution was cooled, and then thereto was added 10% aqueous citric acid solution, and the mixture was stirred at room temperature for 30 minutes. The reaction solution was extracted with ethyl acetate, and washed with saturated saline. The organic layer was dried over sodium sulfate, and then concentrated under reduced pressure to give 6-methyl-1H-pyrazolo[3,4-b]pyridine [REx(104-1)] (3.61 g) as a brown powder.

APCI-MS m/z: 134 [M+H]$^+$.

2) To a solution of 6-methyl-1H-pyrazolo[3,4-b]pyridine (4.44 g) and iodine (16.9 g) in N,N-dimethylformamide (100 mL) was added potassium hydroxide (7.48 g) under ice-cooling, and the mixture was stirred at room temperature for 4 hours. The reaction solution was poured into ice water, and the precipitate was filtered. The filtrate was extracted with ethyl acetate, washed with saturated saline, and then dried over sodium sulfate and concentrated under reduced pressure. The resulting residue was combined with the above-mentioned precipitate and purified by silica gel column chromatography (eluent: chloroform→chloroform/methanol=19/1) to give 3-iodo-6-methyl-1H-pyrazolo[3,4-b]pyridine [REx(104-2)] (6.48 g) as a brown powder.

APCI-MS m/z: 260 [M+H]$^+$.

3) 3-Iodo-6-methyl-1H-pyrazolo[3,4-b]pyridine and methyl (3-bromopropyl)carbamate were treated in the similar manner to Reference Example 102(1) to give methyl[3-(3-iodo-6-methyl-1H-pyrazolo[3,4-b]pyridin-1-yl)propyl]carbamate [REx(104-3)] as a colorless powder.

APCI-MS m/z: 375 [M+H]$^+$.

4) Methyl[3-(3-iodo-6-methyl-1H-pyrazolo[3,4-b]pyridin-1-yl)propyl]carbamate and tri-n-butyltin-ethoxyvinyl were treated in the similar manner to Reference Example 102(2) to give methyl [3-(3-acetyl-6-methyl-1H-pyrazolo[3,4-b]pyridin-1-yl)propyl]carbamate [REx(104-4)] as a colorless powder.

APCI-MS m/z: 291 [M+H]$^+$.

262
Reference Example 105

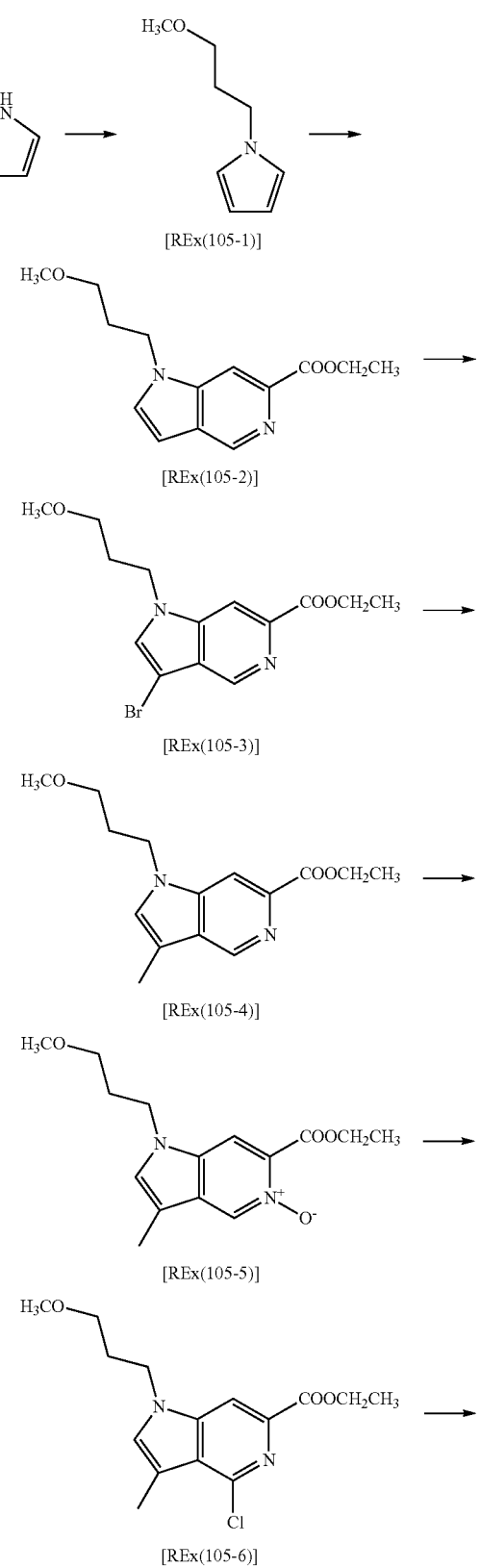

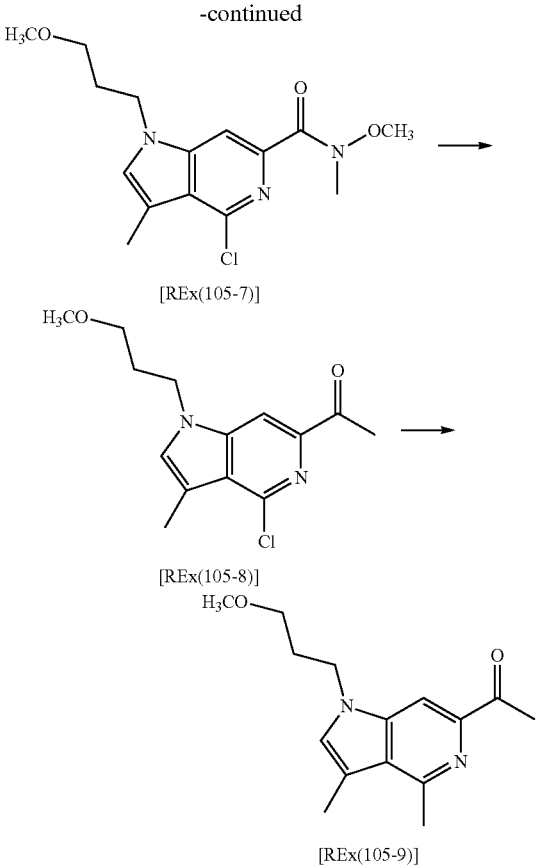

[REx(105-7)]

[REx(105-8)]

[REx(105-9)]

1) To a solution of 1H-pyrrole (5.0 g) in N,N-dimethylformamide (40 mL) was added drop by drop sodium hydride (3.58 g) under ice-cooling, and then the mixture was stirred at room temperature for 20 minutes. Then, thereto was added dropwise a solution of 1-bromo-3-methoxypropane (2.74 g) in N,N-dimethylformamide (2 mL) under ice-cooling, and the mixture was stirred at room temperature for 2 hours. To the reaction mixture was added water under ice-cooling, and then the mixture was extracted with diethyl ether. The organic layer was washed with saturated saline, dried over sodium sulfate, and then concentrated under reduced pressure. The resulting residue was purified by silica gel column chromatography (eluent: n-hexane/ethyl acetate=100/1→20/1) to give 1-(3-methoxypropyl)-1H-pyrrole [REx(105-1)] (9.07 g) as a colorless oil. 2) A solution of 1-(3-methoxypropyl)-1H-pyrrole (3.92 g), ethyl 3-dimethylamino-2-(dimethylaminomethyleneamino)acrylate (7.20 g) (ref. Liebigs Ann. Chem. 1980, 344-357) and trifluoroacetic acid (8.33 mL) in acetic acid (32 mL) was stirred at room temperature for 18 hours, and then heated to reflux for 3 hours. After cooling, the reaction solution was concentrated under reduced pressure. To the resulting residue was added aqueous saturated sodium hydrogen carbonate solution under ice-cooling, and the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=1/1→AcOEt) to give ethyl 1-(3-methoxypropyl)-1H-pyrrolo[3,2-c]pyridine-6-carboxylate [REx(105-2)] (4.79 g) as a brown oil.

APCI-MS m/z: 263 [M+H]$^+$.

3) To a solution of ethyl 1-(3-methoxypropyl)-1H-pyrrolo[3,2-c]pyridine-6-carboxylate (2.00 g) in dichloromethane (40 mL) was added N-bromosuccinimide (1.49 g) under ice-cooling, and the mixture was stirred at room temperature for 3 hours. To the reaction solution was added water, and the mixture was extracted with chloroform. The organic layer was washed with saturated saline, dried over sodium sulfate, and then concentrated under reduced pressure. The resulting residue was purified by NH-silica gel column chromatography (eluent: n-hexane/ethyl acetate=9/1→4/1) to give ethyl 3-bromo-1-(3-methoxypropyl)-1H-pyrrolo[3,2-c]pyridine-6-carboxylate [REx(105-3)] (2.12 g) as a yellow oil.

APCI-MS m/z: 341/343 [M+H]$^+$.

4) To a solution of ethyl 3-bromo-1-(3-methoxypropyl)-1H-pyrrolo[3,2-c]pyridine-6-carboxylate (1.70 g) in 1,4-dioxane (25 mL) were added trimethylboroxine (2.09 mL), cesium carbonate (4.87 g), 2-dicyclohexylphosphino-2',4',6'-triisopropyl-1,1'-biphenyl (X-Phos) (297 mg) and tris(dibenzylideneacetone)dipalladium (228 mg) under argon, and the mixture was stirred at 110° C. for 15 hours. The reaction solution was cooled, and then thereto was added water, and the mixture was extracted with ethyl acetate. The organic layer was washed with saturated saline, dried over sodium sulfate, and then concentrated under reduced pressure. The resulting residue was purified by silica gel column chromatography (eluent: n-hexane→ethyl acetate) to give ethyl 1-(3-methoxypropyl)-3-methyl-1H-pyrrolo[3,2-c]pyridine-6-carboxylate [REx(105-4)] (831 mg) as a yellow oil.

APCI-MS m/z: 277 [M+H]$^+$.

5) To a solution of ethyl 1-(3-methoxypropyl)-3-methyl-1H-pyrrolo[3,2-c]pyridine-6-carboxylate (100 mg) in chloroform (2 mL) was added meta-chloroperoxybenzoic acid (250 mg) under ice-cooling, and then the mixture was stirred at room temperature for 2 hours. The reaction solution was concentrated, and then the resulting residue was purified by NH-silica gel column chromatography (eluent: ethyl acetate→ethyl acetate/methanol=10/1) to give ethyl 1-(3-methoxypropyl)-3-methyl-1H-pyrrolo[3,2-c]pyridine-6-carboxylate 5-oxide [REx(105-5)] (41 mg) as a pale yellow oil.

APCI-MS m/z: 293 [M+H]$^+$.

6) A solution of ethyl 1-(3-methoxypropyl)-3-methyl-1H-pyrrolo[3,2-c]pyridine-6-carboxylate 5-oxide (40 mg) in phosphorus oxychloride (2 mL) was stirred at 100° C. for 1 hour. The reaction solution was concentrated, and the resulting residue was dissolved in ethyl acetate. It was sequentially washed with aqueous saturated sodium hydrogen carbonate solution and saturated saline, and dried over sodium sulfate, and then concentrated under reduced pressure. The resulting residue was purified by silica gel column chromatography (eluent: 4-chloro-1-(3-methoxypropyl)-3-methyl-1H-pyrrolo[3,2-c]pyridine-6-carboxylate [REx(105-6)] (23 mg) as a colorless powder.

APCI-MS m/z: 311/313[M+H]$^+$.

7) To a solution of ethyl 4-chloro-1-(3-methoxypropyl)-3-methyl-1H-pyrrolo[3,2-c]pyridine-6-carboxylate (290 mg) in ethanol (6 mL) was added 2-normal aqueous sodium hydroxide solution (0.95 mL) under ice-cooling, and the mixture was stirred at room temperature for 90 minutes. Then, thereto was added 2-normal hydrochloric acid (0.95 mL) under ice-cooling, and then the reaction solution was concentrated. To a solution of the residue in chloroform (6 mL) were added N,O-dimethylhydroxyamine hydrochloride (137 mg), 1-ethyl-3-(3-dimethylaminopropyl)carbodiimide hydrochloride (268 mg), 1-hydroxybenzotriazole (189 mg) and diisopropylethylamine (325 µL) under ice-cooling, and then the mixture was stirred at room temperature for 15 hours. To the reaction mixture was added aqueous saturated sodium hydrogen carbonate solution under ice-cooling, and the mixture was extracted with chloroform. The organic layer was sequentially washed with water and saturated saline, dried over sodium sulfate, and then concentrated under reduced pressure. The resulting residue was purified by silica gel column chromatography (eluent: n-hexane→ethyl acetate) to give 4-chloro-N-methoxy-1-(3-methoxypropyl)-N,3-dimethyl-1H-pyrrolo[3,2-c]pyridine-6-carboxamide [REx(105-7)] (277 mg) as a colorless oil.

APCI-MS m/z: 326/328 [M+H]⁺.

8) 4-Chloro-N-methoxy-1-(3-methoxypropyl)-N,3-dimethyl-1H-pyrrolo[3,2-c]pyridine-6-carboxamide and methylmagnesium bromide were treated in the similar manner to Reference Example 6(5) to give 1-[4-chloro-1-(3-methoxypropyl)-3-methyl-1H-pyrrolo[3,2-c]pyridin-6-yl]ethanone [REx(105-8)] as a colorless powder.

APCI-MS m/z: 281/283 [M+H]⁺.

9) To a solution of 1-[4-chloro-1-(3-methoxypropyl)-3-methyl-1H-pyrrolo[3,2-c]pyridin-6-yl]ethanone (50 mg) in 1,4-dioxane (2 mL) were added trimethylboroxine (50 μL), cesium carbonate (174 mg), 2-dicyclohexylphosphino-2',4',6'-triisopropyl-1,1'-biphenyl (X-Phos) (17 mg) and tris(dibenzylideneacetone)dipalladium (8 mg) under argon, and the mixture was stirred at 80° C. for 2 hours. The reaction solution was cooled, and then thereto was added water, and the mixture was extracted with ethyl acetate. The organic layer was washed with saturated saline, dried over sodium sulfate, and then concentrated under reduced pressure. The resulting residue was purified by silica gel column chromatography (eluent: n-hexane→n-hexane/ethyl acetate=1/1) to give 1-[1-(3-methoxypropyl)-3,4-dimethyl-1H-pyrrolo[3,2-c]pyridin-6-yl]ethanone [REx(105-9)] (105 mg) as a colorless oil.

APCI-MS m/z: 261 [M+H]⁺.

Reference Example 106

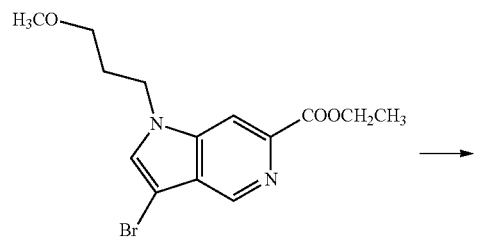

[REx(106-1)]

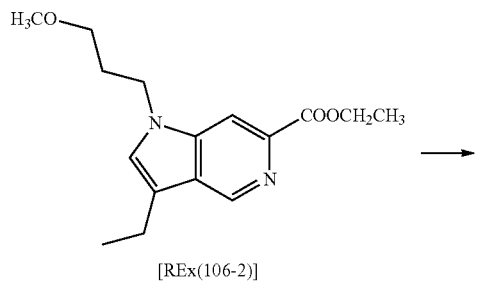

[REx(106-2)]

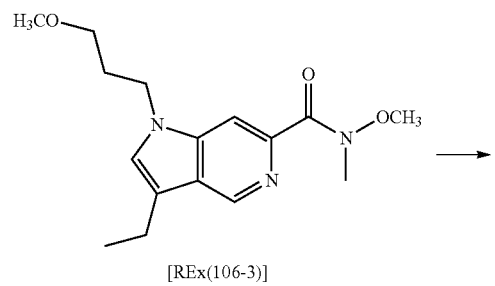

[REx(106-3)]

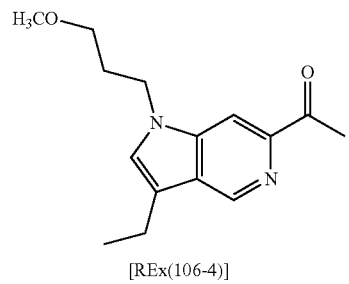

[REx(106-4)]

1) To a solution of ethyl 3-bromo-1-(3-methoxypropyl)-1H-pyrrolo[3,2-c]pyridine-6-carboxylate (200 mg) in 1,4-dioxane (2 mL) were added trivinylboroxine pyridine complex (141 mg), cesium 3-Ethyl-N-methoxy-1-(3-methoxypropyl)-N-methyl-1H-pyrrolo[3,2-c]pyridine-6-carboxamide and methylmagnesium bromide were treated in the similar manner to Reference Example 6(5) to give 1-[3-ethyl-1-(3-methoxypropyl)-1H-pyrrolo[3,2-c]pyridin-6-yl]ethanone [REx(106-4)] as a pale yellow oil.

APCI-MS m/z: 261 [M+H]⁺.

Reference Example 107

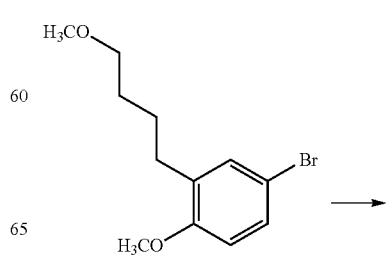

-continued

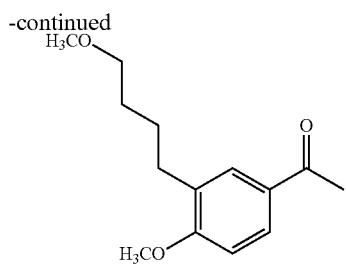

4-Bromo-1-methoxy-2-(4-methoxybutyl)benzene and tri-n-butyltin-1-ethoxyvinyl were treated in the similar manner to Reference Example 27(3) to give 1-[4-methoxy-3-(4-methoxybutyl)phenyl]ethanone as a yellow oil.

APCI-MS m/z: 237 [M+H]$^+$.

Reference Examples 108 to 112

Compounds of Reference Examples 103 to 107 were treated in the similar manner to Reference Example 6-(6) to give the following compounds.

TABLE 90

| Ref. EX. No. | Structural formula | a | b | c | d | e |
|---|---|---|---|---|---|---|
| 108 | | | 317.3861 | O | 318 | [M + H]$^+$ |
| 109 | | | 331.4127 | O | 332 | [M + H]$^+$ |
| 110 | | | 301.4265 | O | 302 | [M + H]$^+$ |
| 111 | | | 301.4265 | O | 302 | [M + H]$^+$ |

TABLE 90-continued
| Ref. EX. No. | Structural formula | a | b | c | d | e |
|---|---|---|---|---|---|---|
| 112 | 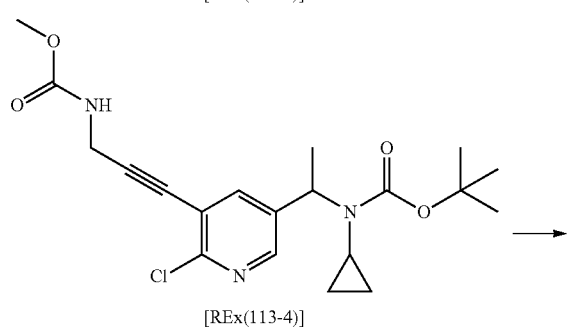 | | 277.4018 | O | 278 | [M + H]+ |
Ref Ex. No.: Reference Example Number
a: Salt
b: Molecular weight
d: MS Results APCI
e: Ion species
O: Oil
c: Properties
Reference Example 113
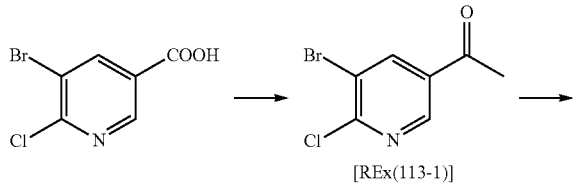
[REx(113-1)]
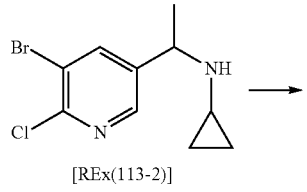
[REx(113-2)]
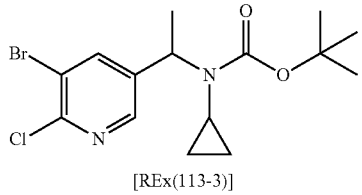
[REx(113-3)]
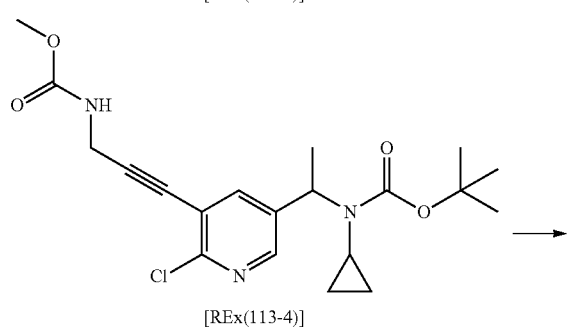
[REx(113-4)]
-continued
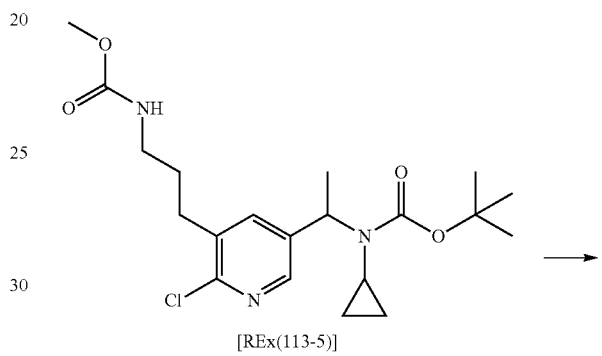
[REx(113-5)]
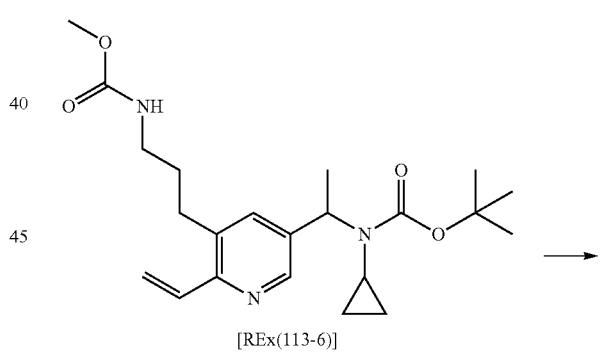
[REx(113-6)]
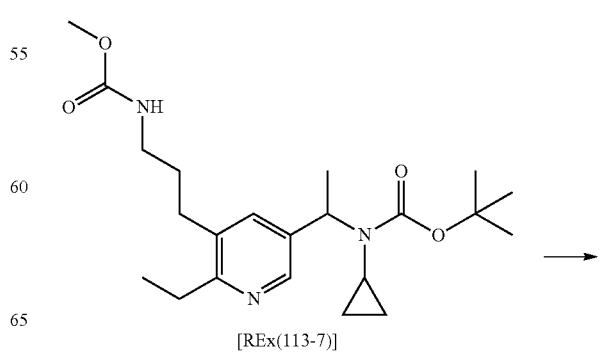
[REx(113-7)]

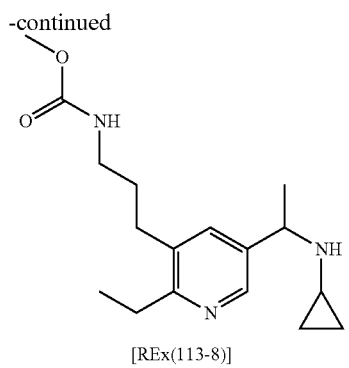

[REx(113-8)]

1) 5-Bromo-6-chloronicotinic acid and N,O-dimethylhydroxyamine hydrochloride were treated in the similar manner to Reference Example 7(5), and then the resulting compound and methylmagnesium bromide were treated in the similar manner to Reference Example 7(6) to give 1-(5-bromo-6-chloropyridin-3-yl)ethanone [REx(113-1)] as a colorless powder.
APCI-MS m/z: 234/236 [M+H]+.

2) 1-(5-Bromo-6-chloropyridin-3-yl)ethanone and cyclopropylamine were treated in the similar manner to Reference Example 6(6) to give N-[1-(5-bromo-6-chloropyridin-3-yl)ethyl]cyclopropylamine [REx(113-2)] as a pale yellow oil.
APCI-MS m/z: 275/277 [M+H]+.

3) To a solution of N-[1-(5-bromo-6-chloropyridin-3-yl)ethyl]cyclopropylamine (2.47 g) in ethyl acetate (15 mL)-tetrahydrofuran (15 mL)-water (15 mL) were added sodium hydrogen carbonate (3.78 g) and di-tert-butyl dicarbonate (3.94 g), and the mixture was stirred at room temperature for 41 hours. To the reaction solution was added water, and then the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=4/1→4/1) to give tert-butyl [1-(5-bromo-6-chloropyridin-3-yl)ethyl]cyclopropylcarbamate [REx(113-3)] (2.6 g) as a pale yellow oil.

4) To a solution of t-butyl [1-(5-bromo-6-chloropyridin-3-yl)ethyl]cyclopropylcarbamate (530 mg) in N,N-dimethylformamide (8 mL) were added methyl prop-2-yn-1-ylcarbamate (384 mg), triethylamine (1.96 mL), dichlorobis(triphenylphosphine)palladium (II) (69 mg) and copper (I) iodide (40 mg), and the mixture was stirred at 60° C. for 2 hours. The reaction solution was cooled, and then diluted with ethyl acetate, and an insoluble was filtered off. The filtrate was sequentially washed with water and saturated saline, dried over sodium sulfate, and then concentrated under reduced pressure. The resulting residue was purified by silica gel column chromatography (eluent: n-hexane/ethyl acetate=4/1→1/1) to give methyl [3-(5-{1-[(tert-butoxycarbonyl)(cyclopropyl)amino]ethyl}-2-chloropyridin-3-yl)prop-2-yn-1-yl]carbamate [REx(113-4)] (362 mg) as a pale yellow oil.
APCI-MS m/z: 408/410 [M+H]+.

5) Methyl [3-(5-{1-[(tert-butoxycarbonyl)(cyclopropyl)amino]ethyl}-2-chloropyridin-3-yl)prop-2-yn-1-yl]carbamate was reduced in the similar manner to Example 296(5) to give methyl [3-(5-{1-[(tert-butoxycarbonyl)(cyclopropyl)amino]ethyl}-2-chloropyridin-3-yl)propyl]carbamate [REx(113-5)] as a pale yellow oil.
APCI-MS m/z: 412/414 [M+H]+.

6) To a solution of methyl [3-(5-{1-[(tert-butoxycarbonyl)(cyclopropyl)amino]ethyl}-2-chloropyridin-3-yl)propyl]carbamate (380 mg) in dimethoxyethane (8 mL) were added vinyl boronic acid pinacol ester (235 μL), 2M sodium carbonate (1.38 mL) and dichlorobis(triphenylphosphine)palladium (II) (65 mg), and the mixture was stirred at 85° C. for 17 hours. The reaction solution was cooled, and then an insoluble was filtered off through Celite, and to the filtrate was added water, and the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=3/1→4/4) to give methyl [3-(5-{1-[(tert-butoxycarbonyl)(cyclopropyl)amino]ethyl}-2-vinylpyridin-3-yl)propyl]carbamate [REx(113-6)] (282 mg) as a pale yellow oil.
APCI-MS m/z: 404[M+H]+.

7) To a solution of methyl [3(5-{1-[(tert-butoxycarbonyl)(cyclopropyl)amino]ethyl}-2-vinylpyridin-3-yl)propyl]carbamate (280 mg) in methanol (10 mL) was added 10% palladium on carbon (140 mg), and the mixture was stirred under hydrogen for 2 hours. An insoluble was filtered off, and then the filtrate was concentrated under reduced pressure. The resulting residue was purified by silica gel column chromatography (eluent: chloroform→chloroform/methanol=4/1) to give methyl [3-(5-{1-[(tert-butoxycarbonyl)(cyclopropyl)amino]-ethyl}-2-ethylpyridin-3-yl)propyl]carbamate [REx(113-7)] (210 mg) as a pale yellow oil.
APCI-MS m/z: 406 [M+H]+.

8) To a solution of methyl [3-(5-{1-[(tert-butoxycarbonyl)(cyclopropyl)amino]ethyl}-2-ethylpyridin-3-yl)propyl]carbamate (204 mg) in dichloromethane (1.5 mL) was added trifluoroacetic acid (1.5 mL) under ice-cooling, and the mixture was stirred at room temperature for 1 hour. The reaction solution was poured into ice-cooled aqueous saturated sodium hydrogen carbonate solution, and extracted with chloroform. The organic layer was washed with saturated saline, dried over sodium sulfate, and then concentrated under reduced pressure. The resulting residue was purified by NH-silica gel column chromatography (eluent: chloroform→chloroform/methanol=20/1) to give methyl (3-{5-[1-(cyclopropylamino)ethyl]-2-ethylpyridin-3-yl}propyl)carbamate [REx(113-8)] (142 mg) as a pale yellow oil.
APCI-MS m/z: 306 [M+H]+.

Reference Example 114

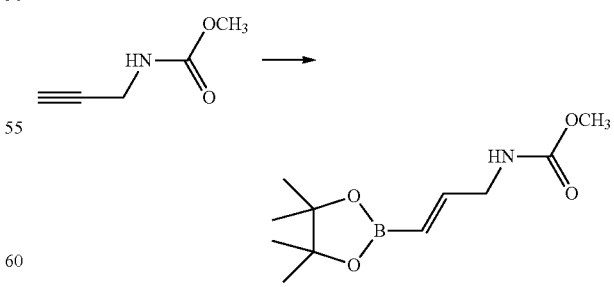

To a solution of (−)-α-pinene (3.64 mL) in tetrahydrofuran (5 mL) was added dropwise borane-dimethyl sulfide complex (1.09 mL) under ice-cooling, and the mixture was stirred at room temperature for 15 hours. To the reaction solution was added dropwise a solution of methyl prop-2- yn-1-ylcarbamate (1.0 g) in tetrahydrofuran (3 mL) under ice-cooling, and then the mixture was stirred at room temperature for 17 hours. To the reaction solution was added dropwise acetaldehyde (5 mL) under ice-cooling, and the mixture was stirred at room temperature for 3 hours. The reaction solution was concentrated under reduced pressure, and the resulting residue was dissolved in diethyl ether (15 mL). To the solution was added pinacol (1.56 g), and the mixture was stirred at room temperature for 2 hours. The reaction solution was washed with water, and then dried over magnesium sulfate and concentrated under reduced pressure. The resulting residue was purified by silica gel column chromatography (eluent: n-hexane/ethyl acetate=10/1→3/2) to give methyl [(2E)-3-(4,4,5,5-tetramethyl-1,3,2-dioxaboran-2-yl)prop-2-en-1-yl]carbamate (1.18 g) as a pale yellow oil.

APCI-MS m/z: 242 $[M+H]^+$.

Test Example

Inhibitory Activity Against Human Renin

A substrate of synthetic peptide (Nma-KHPFH LVIHK (Dnp)-$NH_2$) and test compound were mixed, and fluorescence intensity was assayed using a fluorophotometer before starting an enzymatic reaction (exciting wavelength: 340 nm, measuring wavelength: 460 nm). Recombinant human renin was added and the mixture was incubated at 37° C. for 1 hour, and the fluorescence intensity was measured after the reaction using a fluorophotometer (exciting wavelength: 340 nm, measuring wavelength: 460 nm). Renin activity was evaluated on the ground of fluorescence intensity which was obtained by deduction of the intensity before the reaction from the intensity after the reaction, and 50% inhibitory concentration (IC50) was calculated from renin activities under the existence of various concentration of the test compound. Example compounds herein showed the following values.

Test Result 1

TABLE 91

| Example | IC50 (nM) |
| --- | --- |
| 6 | 13 |
| 7 | 13 |
| 8 | 490 |
| 9 | 7.3 |
| 10 | 1.2 |
| 12 | 73 |
| 17 | 210 |
| 18 | 44 |
| 19 | 10 |
| 21 | 8.4 |
| 22 | 270 |
| 24 | 240 |
| 25 | 19 |
| 26 | 320 |
| 27 | 300 |
| 28 | 1.4 |
| 29 | 5.9 |
| 30 | 30 |
| 31 | 580 |
| 35 | 6.8 |
| 36 | 0.5 |
| 37 | 6.6 |
| 38 | 3.7 |
| 39 | 1.4 |
| 40 | 14 |
| 41 | 2.3 |
| 42 | 1.5 |
| 43 | 1.6 |

TABLE 91-continued

| Example | IC50 (nM) |
| --- | --- |
| 44 | 30 |
| 45 | 8.5 |
| 46 | 17 |
| 49 | 89 |
| 52 | 4.2 |
| 53 | 72 |
| 54 | 31 |
| 55 | 1.9 |
| 56 | 35 |
| 57 | 0.4 |
| 58 | 16 |
| 59 | 2.1 |
| 60 | 7 |
| 61 | 14 |
| 62 | 12 |
| 63 | 800 |
| 64 | 0.9 |
| 65 | 6.4 |
| 66 | 2.4 |
| 67 | 1.5 |
| 68 | 140 |
| 69 | 21 |
| 70 | 0.6 |
| 71 | 21 |
| 75 | 78 |
| 76 | 37 |
| 78 | 1 |
| 79 | 1.1 |
| 80 | 8.4 |
| 81 | 25 |
| 82 | 16 |
| 83 | 330 |
| 85 | 11 |
| 86 | 16 |
| 87 | 7 |
| 88 | 52 |
| 89 | 3.9 |
| 90 | 71 |
| 91 | 15 |
| 92 | 62 |
| 93 | 41 |
| 94 | 120 |
| 97 | 0.7 |
| 98 | 4.4 |
| 99 | 7.3 |
| 100 | 41 |
| 101 | 29 |
| 102 | 290 |
| 103 | 2.4 |
| 104 | 89 |

Test Result 2

TABLE 92

| Example | IC50 (nM) |
| --- | --- |
| 105 | 8.1 |
| 106 | 530 |
| 109 | 500 |
| 110 | 67 |
| 113 | 540 |
| 114 | 4.1 |
| 115 | 87 |
| 116 | 16 |
| 122 | 19 |
| 123 | 42 |
| 124 | 3.2 |
| 125 | 12 |
| 126 | 6.6 |
| 127 | 15 |
| 128 | 3.3 |
| 129 | 42 |
| 132 | 16 |
| 133 | 20 |
| 134 | 250 |

TABLE 92-continued

| Example | IC50 (nM) |
|---|---|
| 135 | 11 |
| 136 | 33 |
| 137 | 6.3 |
| 138 | 12 |
| 139 | 2.5 |
| 140 | 10 |
| 141 | 4 |
| 142 | 17 |
| 143 | 58 |
| 144 | 4.8 |
| 145 | 63 |
| 146 | 28 |
| 147 | 16 |
| 149 | 13 |
| 150 | 8.7 |
| 151 | 34 |
| 152 | 1.2 |
| 153 | 46 |
| 268 | 3.6 |
| 269 | 6.6 |
| 270 | 0.4 |
| 271 | 3.7 |
| 276 | 2.5 |
| 280 | 0.9 |
| 281 | 6.7 |
| 284 | 0.5 |
| 285 | 6.1 |
| 286 | 3 |
| 287 | 35 |

Test Result 3

TABLE 93

| Example | IC50 (nM) |
|---|---|
| 299 | 1.6 |
| 301 | 3.3 |
| 304 | 1.3 |
| 305 | 12 |
| 306 | 230 |

INDUSTRIAL APPLICABILITY

The compound [I] of the present invention or a pharmaceutically acceptable salt thereof has renin inhibitory activity and may be useful for treatment and/or prophylaxis of hypertension, cardiac failure, diabetic nephropathy and the like. Furthermore, the compound [II] is useful as a synthetic intermediate for preparing the compound [I].

The invention claimed is:

1. An isolated stereoisomer of a compound of the formula $I^{c2}$:

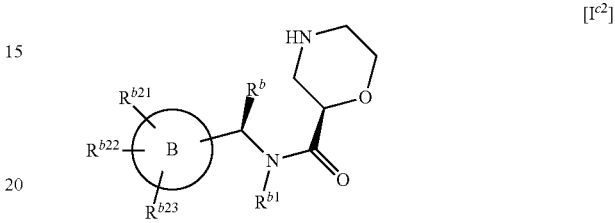

[$I^{c2}$]

wherein $R^b$ is lower alkyl,
$R^{b1}$ is cycloalkyl or alkyl,
the ring B is selected from
  1) a tetrahydronaphthyl group, or
  2) a pyridyl group, and
$R^{b21}$ to $R^{b23}$ are the same or different, and a group selected from 1) hydrogen, 2) halogen, 3) alkyl optionally substituted with a group selected from halogen, alkoxy and alkoxycarbonylamino, 4) alkoxy optionally substituted with a group selected from alkoxy and alkoxycarbonylamino, 5) cyano, 6) carbamoyl optionally substituted with alkyl, or 7) oxo,
or a pharmaceutically acceptable salt thereof.

2. A pharmaceutical composition comprising the isolated stereoisomer according to claim 1.

3. A pharmaceutical composition for use in the treatment of hypertension, cardiac failure, or diabetic nephropathy, comprising the isolated stereoisomer according to claim 1, or a pharmaceutically acceptable salt thereof.

* * * * *